(12) United States Patent
Garner et al.

(10) Patent No.: US 10,500,192 B2
(45) Date of Patent: Dec. 10, 2019

(54) COMBINATORIAL METHODS TO IMPROVE THE THERAPEUTIC BENEFIT OF BISANTRENE AND ANALOGS AND DERIVATIVES THEREOF

(71) Applicant: Race Oncology Ltd., Melbourne (AU)

(72) Inventors: William J. Garner, San Francisco, CA (US); Amie Franklin, Pacifica, CA (US); John Rothman, Lebanon, NJ (US)

(73) Assignee: RACE ONCOLOGY LTD., Melbourne (AU)

( * ) Notice: Subject to any disclaimer, the term of this patent is extended or adjusted under 35 U.S.C. 154(b) by 0 days.

(21) Appl. No.: 15/979,041

(22) Filed: May 14, 2018

(65) Prior Publication Data

US 2018/0256549 A1   Sep. 13, 2018

Related U.S. Application Data

(62) Division of application No. 14/907,729, filed as application No. PCT/US2014/048137 on Jul. 25, 2014, now Pat. No. 9,974,774.

(60) Provisional application No. 61/858,729, filed on Jul. 26, 2013.

(51) Int. Cl.

| A61K 31/4178 | (2006.01) |
| A61K 45/06 | (2006.01) |
| A61K 31/4168 | (2006.01) |
| A61K 31/473 | (2006.01) |
| A61K 47/54 | (2017.01) |
| A61K 47/50 | (2017.01) |

(52) U.S. Cl.
CPC ...... *A61K 31/4178* (2013.01); *A61K 31/4168* (2013.01); *A61K 31/473* (2013.01); *A61K 45/06* (2013.01); *A61K 47/50* (2017.08); *A61K 47/54* (2017.08)

(58) Field of Classification Search
CPC ................................................ A61K 31/4178
See application file for complete search history.

(56) References Cited

U.S. PATENT DOCUMENTS

| 4,258,181 A * | 3/1981 | Murdock ................ C07C 17/32 540/467 |
| 4,261,989 A | 4/1981 | Sasaki et al. |
| 4,515,954 A | 5/1985 | Lang, Jr. et al. |
| 4,784,845 A | 11/1988 | Desai et al. |
| 4,816,247 A | 3/1989 | Desai et al. |
| 4,900,838 A | 2/1990 | Murdock |
| 5,000,886 A | 3/1991 | Lawter et al. |
| 5,070,082 A | 12/1991 | Murdock et al. |
| 5,077,282 A | 12/1991 | Murdock et al. |
| 5,077,283 A | 12/1991 | Murdock et al. |
| 5,116,827 A | 5/1992 | Murdock et al. |
| 5,143,661 A | 9/1992 | Lawter et al. |
| 5,212,291 A | 5/1993 | Murdock et al. |
| 5,378,456 A | 1/1995 | Tsou |
| 5,387,584 A | 2/1995 | Schnur et al. |
| 5,436,243 A | 7/1995 | Sachs et al. |
| 5,550,149 A | 8/1996 | Powell et al. |
| 5,561,141 A | 10/1996 | Powell et al. |
| 5,573,781 A | 11/1996 | Brown et al. |
| 5,609,867 A | 3/1997 | Tsou |
| 5,639,887 A | 6/1997 | Powell et al. |
| 5,786,344 A | 7/1998 | Ratain et al. |
| 5,994,130 A | 11/1999 | Shyjan |
| 6,011,069 A | 1/2000 | Inomata et al. |
| 6,054,437 A | 4/2000 | Eilon et al. |
| 6,238,687 B1 | 5/2001 | Mao et al. |
| 6,245,790 B1 | 6/2001 | Hattori et al. |
| 6,306,897 B1 | 10/2001 | Uckun et al. |
| 6,368,598 B1 | 4/2002 | D'Amico et al. |
| 6,428,968 B1 | 8/2002 | Molnar-Kimber et al. |
| 6,443,898 B1 | 9/2002 | Unger et al. |
| 6,495,582 B1 | 12/2002 | Hale et al. |
| 6,610,677 B2 | 8/2003 | Davies et al. |
| 6,638,926 B2 | 10/2003 | Davies et al. |
| 6,649,640 B2 | 11/2003 | Hale et al. |
| 6,653,301 B2 | 11/2003 | Bebbington et al. |
| 6,660,731 B2 | 12/2003 | Bebbington et al. |
| 6,664,247 B2 | 12/2003 | Bebbington et al. |
| 6,670,167 B1 | 12/2003 | Chen et al. |
| 6,743,791 B2 | 6/2004 | Cao et al. |
| 6,753,348 B2 | 6/2004 | Uckun et al. |
| 6,872,715 B2 | 3/2005 | Santi et al. |

(Continued)

FOREIGN PATENT DOCUMENTS

| BE | 872309 | 5/1979 |
| BE | 872309 A | 5/1979 |

(Continued)

OTHER PUBLICATIONS

Cowan et al. J. Natl Cancer Inst, 1991, 83(15): 1077-84.*
SQ et al. L. Pharm Pharmacol, 2008, 60(2)213-9 (abstract).*
Gellert et al., Breast Cancer Res Treat, 2006, 96(1):73-81 (abstract).*
Rao et al. Oncology Reports, 15, 2006, 15:179-185.*
Nabholtz et al., Expert Opin Pharmacother, 2005, 6(7): 1073-94 (abstract).*
D.S. Alberts et al., "In Vitro Cytotoxicity Against Fresh Human Tumors and P388 Leukemia Predicts the Differential in Vivo Activity of a Series of Anthracene Anticancer Drugs," *Anti-Cancer Drugs* 2: 69-77 (1991) (abstract only).
M. Folini et al., "Remarkable Interference with Telomeric Function by a G-Quadruplex Selective Bisantrene Regioisomer," *Biochem. Pharmacol.* 79: 1781-1790 (2010).
D. Tormo et al., "Targeted Activation of Innate Immunity for Therapeutic Induction of Autophagy and Apoptosis in Melanoma Cells," *Cancer Cell* 16: 103-114 (2009).

(Continued)

*Primary Examiner* — Rei Tsang Shiao
(74) *Attorney, Agent, or Firm* — Ditthavong & Steiner P.C.

(57) ABSTRACT

The present invention describes methods and compositions for improving the therapeutic efficacy of therapeutic agents previously limited by suboptimal therapeutic performance by either improving efficacy as monotherapy or reducing side effects. Such methods and compositions are particularly applicable to bisantrene or derivatives, analogs, or prodrugs thereof.

5 Claims, No Drawings

(56) References Cited

U.S. PATENT DOCUMENTS

| | | |
|---|---|---|
| 6,875,863 B1 | 4/2005 | Tian et al. |
| 6,887,993 B1 | 5/2005 | Tian et al. |
| 6,903,116 B2 | 6/2005 | Yokota et al. |
| 6,967,198 B2 | 11/2005 | Benedict et al. |
| 6,989,385 B2 | 1/2006 | Bebbington et al. |
| 7,008,948 B2 | 3/2006 | Bebbington et al. |
| 7,041,687 B2 | 5/2006 | Binch et al. |
| 7,067,506 B2 | 6/2006 | Keegan et al. |
| 7,087,603 B2 | 8/2006 | Bebbington et al. |
| 7,091,213 B2 | 8/2006 | Metcalf, III et al. |
| 7,094,798 B1 | 8/2006 | Booth et al. |
| 7,098,330 B2 | 8/2006 | Bebbington et al. |
| 7,101,576 B2 | 9/2006 | Hovey et al. |
| 7,115,619 B2 | 10/2006 | Stevens et al. |
| 7,115,739 B2 | 10/2006 | Bebbington et al. |
| 7,129,244 B2 | 10/2006 | Kasibhatla et al. |
| 7,132,533 B2 | 11/2006 | Benedict et al. |
| 7,148,211 B2 | 12/2006 | Mazess et al. |
| 7,160,867 B2 | 1/2007 | Abel et al. |
| 7,169,817 B2 | 1/2007 | Pan et al. |
| 7,202,244 B2 | 4/2007 | Boyle et al. |
| 7,250,409 B2 | 7/2007 | Boger |
| 7,253,187 B2 | 8/2007 | Cao et al. |
| 7,304,061 B2 | 12/2007 | Hale et al. |
| 7,311,901 B2 | 12/2007 | Seo et al. |
| 7,318,931 B2 | 1/2008 | Okumu et al. |
| 7,345,054 B2 | 3/2008 | Hale et al. |
| 7,354,919 B2 | 4/2008 | Hale et al. |
| 7,390,815 B2 | 6/2008 | Davies et al. |
| 7,402,556 B2 | 7/2008 | Trouet et al. |
| 7,405,295 B2 | 7/2008 | Currie et al. |
| 7,410,988 B2 | 8/2008 | Dickson, Jr. et al. |
| 7,445,897 B2 | 11/2008 | Ho et al. |
| 7,446,122 B2 | 11/2008 | Chao et al. |
| 7,449,477 B2 | 11/2008 | Barda et al. |
| 7,462,713 B2 | 12/2008 | Benedict et al. |
| 7,470,709 B2 | 12/2008 | Barsanti et al. |
| 7,485,649 B2 | 2/2009 | Brnardic et al. |
| 7,501,435 B2 | 3/2009 | Arrington et al. |
| 7,504,397 B2 | 3/2009 | Hummersone et al. |
| 7,514,444 B2 | 4/2009 | Honigberg et al. |
| 7,531,556 B2 | 5/2009 | Green |
| 7,550,477 B2 | 6/2009 | Brnardic et al. |
| 7,560,462 B2 | 7/2009 | Gaudino et al. |
| 7,608,618 B2 | 10/2009 | Kesicki et al. |
| 7,625,890 B2 | 12/2009 | Heerding et al. |
| 7,625,913 B2 | 12/2009 | Bebbington et al. |
| 7,648,996 B2 | 1/2010 | Beckman et al. |
| 7,652,027 B2 | 1/2010 | Lee et al. |
| 7,652,135 B2 | 1/2010 | Binch et al. |
| 7,655,673 B2 | 2/2010 | Zhang et al. |
| 7,659,274 B2 | 2/2010 | Crew et al. |
| 7,691,853 B2 | 4/2010 | Bebbington et al. |
| 7,700,594 B2 | 4/2010 | Chen et al. |
| 7,728,042 B2 | 6/2010 | Eros et al. |
| 7,732,454 B2 | 6/2010 | Verner |
| 7,741,330 B1 | 6/2010 | Chen et al. |
| 7,745,446 B2 | 6/2010 | Maier et al. |
| 7,763,658 B2 | 7/2010 | Koya et al. |
| 7,781,580 B2 | 8/2010 | Lee et al. |
| 7,795,290 B2 | 9/2010 | Dickson, Jr. et al. |
| 7,807,630 B2 | 10/2010 | Dang et al. |
| 7,807,705 B2 | 10/2010 | Chen et al. |
| 7,816,398 B2 | 10/2010 | Swindell et al. |
| 7,820,797 B2 | 10/2010 | Boons |
| 7,825,129 B2 | 11/2010 | Pelliciari et al. |
| 7,825,132 B2 | 11/2010 | Cai et al. |
| 7,837,993 B2 | 11/2010 | Conboy et al. |
| 7,879,853 B2 | 2/2011 | Stadlwieser et al. |
| 7,897,608 B2 | 3/2011 | Wilkinson et al. |
| 7,897,623 B2 | 3/2011 | Riedl et al. |
| 7,901,876 B2 | 3/2011 | Di Fiore et al. |
| 7,902,194 B2 | 3/2011 | Dewdney et al. |
| 7,906,509 B2 | 3/2011 | Kennedy-smith et al. |
| 7,910,742 B2 | 3/2011 | Wendt et al. |
| 7,923,555 B2 | 4/2011 | Chen et al. |
| 7,928,105 B2 | 4/2011 | Gangloff et al. |
| 7,943,618 B2 | 5/2011 | Dewdney et al. |
| 7,943,767 B2 | 5/2011 | Chen et al. |
| 7,951,820 B2 | 5/2011 | Bebbington et al. |
| 7,956,064 B2 | 6/2011 | Chua et al. |
| 7,959,923 B2 | 6/2011 | You et al. |
| 7,982,037 B2 | 7/2011 | Bebbington et al. |
| 7,998,977 B2 | 8/2011 | Joseph et al. |
| 8,008,281 B2 | 8/2011 | Prendergast et al. |
| 8,008,318 B2 | 8/2011 | Beckmann et al. |
| 8,008,491 B2 | 8/2011 | Jiang et al. |
| 8,012,976 B2 | 9/2011 | Wang et al. |
| 8,026,355 B2 | 9/2011 | Hansen et al. |
| 8,067,395 B2 | 11/2011 | Jankowski et al. |
| 8,067,412 B2 | 11/2011 | Winssinger et al. |
| 8,088,760 B2 | 1/2012 | Chu et al. |
| 8,093,050 B2 | 1/2012 | Cho et al. |
| 8,093,244 B2 | 1/2012 | Diaz et al. |
| 8,097,622 B2 | 1/2012 | Nakayama et al. |
| 8,101,623 B2 | 1/2012 | Luke et al. |
| 8,114,870 B2 | 2/2012 | Xiao et al. |
| 8,119,366 B2 | 2/2012 | Stylianou |
| 8,119,654 B2 | 2/2012 | Jagtap et al. |
| 8,119,689 B2 | 2/2012 | Ebenstien et al. |
| 8,124,630 B2 | 2/2012 | Riedl et al. |
| 8,129,371 B2 | 3/2012 | Zask et al. |
| 8,133,857 B2 | 3/2012 | Aikawa |
| 8,148,393 B2 | 4/2012 | van Dalen et al. |
| 8,158,616 B2 | 4/2012 | Rodgers et al. |
| 8,158,638 B2 | 4/2012 | Ohsuki et al. |
| 8,163,755 B2 | 4/2012 | Jin et al. |
| 8,168,651 B2 | 5/2012 | Chua et al. |
| 8,178,125 B2 | 5/2012 | Wen et al. |
| 8,178,131 B2 | 5/2012 | Le Huerou et al. |
| 8,178,527 B2 | 5/2012 | Chen et al. |
| 8,183,249 B2 | 5/2012 | Cheng et al. |
| 8,183,250 B2 | 5/2012 | Penning et al. |
| 8,183,342 B2 | 5/2012 | Matsuyama |
| 8,188,103 B2 | 5/2012 | Van Der Aa et al. |
| 8,202,876 B2 | 6/2012 | Albaugh et al. |
| 8,207,195 B2 | 6/2012 | Navratil et al. |
| 8,211,054 B2 | 7/2012 | Guzi et al. |
| 8,211,669 B2 | 7/2012 | Reed et al. |
| 8,217,070 B2 | 7/2012 | Zhu et al. |
| 8,227,605 B2 | 7/2012 | Shipps, Jr. et al. |
| 8,227,807 B2 | 7/2012 | Gallagher et al. |
| 8,231,898 B2 | 7/2012 | Oshlack et al. |
| 8,232,277 B2 | 7/2012 | Chen et al. |
| 8,232,280 B2 | 7/2012 | Honigberg et al. |
| 8,236,802 B2 | 8/2012 | Xu et al. |
| 8,236,812 B2 | 8/2012 | Honigberg et al. |
| 8,242,103 B2 | 8/2012 | Lewis et al. |
| 8,242,147 B2 | 8/2012 | Dumas et al. |
| 8,242,270 B2 | 8/2012 | Lajeunesse et al. |
| 8,252,740 B2 | 8/2012 | Raucher et al. |
| 8,252,795 B2 | 8/2012 | Fink et al. |
| 8,252,930 B2 | 8/2012 | Stoit et al. |
| 8,258,132 B2 | 9/2012 | Bosch et al. |
| 8,263,357 B2 | 9/2012 | Reed |
| 8,268,819 B2 | 9/2012 | Jin et al. |
| 8,268,827 B2 | 9/2012 | Branca et al. |
| 8,273,782 B2 | 9/2012 | Seefeld et al. |
| 8,277,807 B2 | 10/2012 | Gallagher et al. |
| 8,299,077 B2 | 10/2012 | Berthel et al. |
| 8,299,088 B2 | 10/2012 | Matteucci et al. |
| 8,299,256 B2 | 10/2012 | Vialard et al. |
| 8,309,546 B2 | 11/2012 | Nakayama et al. |
| 8,309,573 B2 | 11/2012 | Fujio et al. |
| 8,314,060 B2 | 11/2012 | Gengrinovitch |
| 8,314,108 B2 | 11/2012 | Farouz et al. |
| 8,314,111 B2 | 11/2012 | Chen et al. |
| 8,318,719 B2 | 11/2012 | Dewdney et al. |
| 8,318,735 B2 | 11/2012 | Shipps, Jr. et al. |
| 8,318,740 B2 | 11/2012 | Wu |
| 8,318,815 B2 | 11/2012 | Huang et al. |
| 8,324,211 B2 | 12/2012 | Dewdney et al. |
| 8,324,226 B2 | 12/2012 | Collins et al. |
| 8,324,262 B2 | 12/2012 | Yuan et al. |

(56) References Cited

U.S. PATENT DOCUMENTS

| | | |
|---|---|---|
| 8,324,282 B2 | 12/2012 | Gerson et al. |
| 8,329,179 B2 | 12/2012 | Ni et al. |
| 8,329,701 B2 | 12/2012 | Mitchell et al. |
| 8,329,709 B2 | 12/2012 | Banka et al. |
| 8,334,309 B2 | 12/2012 | Klein et al. |
| 8,338,434 B2 | 12/2012 | Seefeld et al. |
| 8,338,477 B2 | 12/2012 | Duncan et al. |
| 8,343,913 B1 | 1/2013 | Cowen et al. |
| 8,343,923 B2 | 1/2013 | Long et al. |
| 8,344,007 B2 | 1/2013 | Tang et al. |
| 8,362,075 B2 | 1/2013 | Lewis et al. |
| 8,362,241 B2 | 1/2013 | D'Angelo et al. |
| 8,372,842 B2 | 2/2013 | Blake et al. |
| 8,377,886 B2 | 2/2013 | Susztak et al. |
| 8,377,946 B1 | 2/2013 | Chen et al. |
| 8,389,697 B2 | 3/2013 | Beria et al. |
| 8,394,818 B2 | 3/2013 | Gray et al. |
| 8,399,426 B2 | 3/2013 | Kim et al. |
| 8,410,158 B2 | 4/2013 | Seefeld et al. |
| 8,410,279 B2 | 4/2013 | Gazzard et al. |
| 8,420,678 B2 | 4/2013 | Mahadevan et al. |
| 8,420,690 B2 | 4/2013 | Seefeld et al. |
| 8,435,970 B2 | 5/2013 | Curry et al. |
| 8,436,012 B2 | 5/2013 | Ohtsuka et al. |
| 8,440,662 B2 | 5/2013 | Smith et al. |
| 8,445,198 B2 | 5/2013 | Knudsen |
| 8,445,271 B2 | 5/2013 | Lebedeva et al. |
| 8,445,509 B2 | 5/2013 | Miyamoto et al. |
| 8,450,305 B2 | 5/2013 | Winssinger et al. |
| 8,455,471 B2 | 6/2013 | Wisdom et al. |
| 8,455,488 B2 | 6/2013 | Odagami et al. |
| 8,461,157 B2 | 6/2013 | Cai et al. |
| 8,518,371 B2 | 8/2013 | Lee et al. |
| 8,535,655 B2 | 9/2013 | O'Shea et al. |
| 8,664,220 B2 | 3/2014 | Clark et al. |
| 8,673,914 B2 | 3/2014 | Chen et al. |
| 2001/0049349 A1 | 12/2001 | Chinery et al. |
| 2002/0156015 A1 | 10/2002 | Rabindran et al. |
| 2003/0125287 A1 | 7/2003 | Kandimalla et al. |
| 2004/0023290 A1 | 2/2004 | Griffin et al. |
| 2005/0043381 A1 | 2/2005 | Johnson et al. |
| 2005/0148643 A1 | 7/2005 | Rui et al. |
| 2005/0245525 A1 | 11/2005 | Keegan et al. |
| 2005/0256157 A1 | 11/2005 | Gesner et al. |
| 2006/0040883 A1 | 2/2006 | You et al. |
| 2006/0229277 A1 | 10/2006 | Laxminarayan |
| 2007/0009535 A1 | 1/2007 | Sikic et al. |
| 2007/0179161 A1 | 8/2007 | Parratt et al. |
| 2007/0196360 A1 | 8/2007 | Jensen et al. |
| 2007/0207952 A1 | 9/2007 | Silva et al. |
| 2008/0207738 A1 | 8/2008 | Kiss |
| 2008/0279961 A1 | 11/2008 | Burger |
| 2009/0131470 A1 | 5/2009 | Walmsley et al. |
| 2009/0143357 A1 | 6/2009 | Diaz et al. |
| 2009/0202539 A1 | 8/2009 | You et al. |
| 2009/0274713 A1 | 11/2009 | Chari et al. |
| 2009/0304695 A1 | 12/2009 | He et al. |
| 2009/0312280 A1 | 12/2009 | Anderes et al. |
| 2010/0022635 A1 | 1/2010 | Rajewski |
| 2010/0056523 A1 | 3/2010 | Heerding et al. |
| 2010/0069423 A1 | 3/2010 | Pommier et al. |
| 2010/0093824 A1 | 4/2010 | Frydman et al. |
| 2010/0105683 A1 | 4/2010 | Keegan et al. |
| 2010/0137338 A1 | 6/2010 | Seefeld et al. |
| 2010/0143332 A1 | 6/2010 | Parry et al. |
| 2010/0190749 A1 | 7/2010 | Ren et al. |
| 2010/0196354 A1 | 8/2010 | Morrell et al. |
| 2010/0222283 A1 | 9/2010 | Susztak et al. |
| 2010/0226917 A1 | 9/2010 | Brown et al. |
| 2010/0260868 A1 | 10/2010 | Humphries et al. |
| 2010/0267759 A1 | 10/2010 | Seefeld et al. |
| 2010/0267801 A1 | 10/2010 | Lewis et al. |
| 2010/0291025 A1 | 11/2010 | Rao et al. |
| 2010/0292165 A1 | 11/2010 | Clevers et al. |
| 2010/0303719 A1 | 12/2010 | Huang et al. |
| 2011/0009415 A1 | 1/2011 | Wu |
| 2011/0021498 A1 | 1/2011 | Stokes et al. |
| 2011/0053968 A1 | 3/2011 | Zhang et al. |
| 2011/0053972 A1 | 3/2011 | Seefeld et al. |
| 2011/0059096 A1 | 3/2011 | Dang et al. |
| 2011/0071182 A1 | 3/2011 | Seefeld et al. |
| 2011/0092423 A1 | 4/2011 | Rouse et al. |
| 2011/0092459 A1 | 4/2011 | Odagami et al. |
| 2011/0098221 A1 | 4/2011 | Lin et al. |
| 2011/0118230 A1 | 5/2011 | Chen et al. |
| 2011/0118298 A1 | 5/2011 | Fritz et al. |
| 2011/0124654 A1 | 5/2011 | Chen et al. |
| 2011/0129455 A1 | 6/2011 | Lin et al. |
| 2011/0160255 A1 | 6/2011 | Rouse et al. |
| 2011/0160256 A1 | 6/2011 | Rouse et al. |
| 2011/0178046 A1 | 7/2011 | Ross et al. |
| 2011/0183933 A1 | 7/2011 | Guzi et al. |
| 2011/0183938 A1 | 7/2011 | Dyke et al. |
| 2011/0195066 A1 | 8/2011 | Zhang |
| 2011/0196009 A1 | 8/2011 | Rouse et al. |
| 2011/0201592 A1 | 8/2011 | Collins et al. |
| 2011/0206661 A1 | 8/2011 | Zhang et al. |
| 2011/0223183 A1 | 9/2011 | Kitajewski et al. |
| 2011/0245230 A1 | 10/2011 | Mitchell et al. |
| 2011/0294814 A1 | 12/2011 | Kowalczyk-Prezewloka et al. |
| 2011/0318393 A1 | 12/2011 | Ladouceur et al. |
| 2012/0022026 A1 | 1/2012 | Krawczyk et al. |
| 2012/0071657 A1 | 3/2012 | Bebbington et al. |
| 2012/0088770 A1 | 4/2012 | Odagami et al. |
| 2012/0108574 A1 | 5/2012 | Ashwell et al. |
| 2012/0114765 A1 | 5/2012 | Cao et al. |
| 2012/0122724 A1 | 5/2012 | Zhou et al. |
| 2012/0149684 A1 | 6/2012 | Beight et al. |
| 2012/0184505 A1 | 7/2012 | Popovici-Muller et al. |
| 2012/0190707 A1 | 7/2012 | Ronai et al. |
| 2012/0201822 A1 | 8/2012 | Polakis et al. |
| 2012/0232082 A1 | 9/2012 | Wu |
| 2012/0245186 A1 | 9/2012 | Blackman et al. |
| 2012/0288879 A1 | 11/2012 | Altiok |
| 2012/0328603 A1 | 12/2012 | Ashkenazi et al. |
| 2012/0328608 A1 | 12/2012 | Siebel |
| 2012/0329791 A1 | 12/2012 | Ashwell et al. |
| 2012/0329793 A1 | 12/2012 | Ashwell et al. |
| 2013/0012528 A1 | 1/2013 | Cheng |
| 2013/0029972 A1 | 1/2013 | Hipskind et al. |
| 2013/0034598 A1 | 2/2013 | Cheng et al. |
| 2013/0039930 A1 | 2/2013 | Alitalo et al. |
| 2013/0040973 A1 | 2/2013 | Vannucchi et al. |
| 2013/0045286 A1 | 2/2013 | Le Huerou et al. |
| 2013/0064832 A1 | 3/2013 | Aikawa et al. |
| 2013/0079303 A1 | 3/2013 | Andrews et al. |
| 2013/0137752 A1 | 5/2013 | Brown et al. |
| 2013/0142758 A1 | 6/2013 | Verner et al. |
| 2013/0150433 A1 | 6/2013 | Bartz et al. |
| 2013/0183368 A1 | 7/2013 | Hutchison et al. |
| 2013/0210756 A1 | 8/2013 | Kim et al. |
| 2013/0216531 A1 | 8/2013 | Jain et al. |
| 2013/0217865 A1 | 8/2013 | Glover et al. |
| 2013/0224237 A1 | 8/2013 | Gilboa |
| 2013/0266570 A1 | 10/2013 | Weisbart et al. |
| 2013/0273080 A1 | 10/2013 | Elewaut et al. |
| 2013/0295121 A1 | 11/2013 | Johnson et al. |
| 2014/0018383 A1 | 1/2014 | Wald |
| 2014/0023664 A1 | 1/2014 | Lowman et al. |
| 2014/0038836 A1 | 2/2014 | Higgins et al. |
| 2014/0046030 A1 | 2/2014 | Thanos et al. |
| 2014/0065162 A1 | 3/2014 | Lipson et al. |
| 2014/0073604 A1 | 3/2014 | Bourdelais et al. |
| 2014/0094439 A1 | 4/2014 | Marathi et al. |
| 2014/0094526 A1 | 4/2014 | Marathi et al. |

FOREIGN PATENT DOCUMENTS

| | | |
|---|---|---|
| CH | 681780 | 5/1993 |
| CH | 681780 A | 5/1993 |
| DE | 3825374 | 2/1990 |
| DE | 3825374 A1 | 2/1990 |
| EP | 0338372 | 10/1989 |
| EP | 0338372 A2 | 10/1989 |

(56) References Cited

FOREIGN PATENT DOCUMENTS

| | | |
|---|---|---|
| EP | 0214501 | 9/1992 |
| EP | 0214501 B1 | 9/1992 |
| EP | 0616813 | 9/1994 |
| EP | 0616813 A2 | 9/1994 |
| EP | 1332755 | 8/2003 |
| EP | 1332755 A1 | 8/2003 |
| EP | 1464336 | 10/2004 |
| EP | 1464336 A1 | 10/2004 |
| WO | 97/039768 A1 | 10/1997 |
| WO | WO 97/039768 | 10/1997 |
| WO | 01/080843 A2 | 11/2001 |
| WO | 01/080884 A1 | 11/2001 |
| WO | WO 01/080843 | 11/2001 |
| WO | WO 01/080884 | 11/2001 |
| WO | 02/22577 A2 | 3/2002 |
| WO | WO 02/22577 | 3/2002 |
| WO | 2003/070823 A2 | 8/2003 |
| WO | WO 2003/070823 | 8/2003 |
| WO | 2004/064734 A2 | 8/2004 |
| WO | WO 2004/064734 | 8/2004 |
| WO | 2007/058850 A2 | 5/2007 |
| WO | WO 2007/058850 | 5/2007 |
| WO | 2008/070016 A2 | 6/2008 |
| WO | WO 2008/070016 | 6/2008 |
| WO | 2009/106549 A2 | 9/2009 |
| WO | WO 2009/106549 | 9/2009 |
| WO | 2010/096732 A1 | 8/2010 |
| WO | WO 2010/096732 | 8/2010 |
| WO | 2012/024367 A2 | 2/2012 |
| WO | WO 2012/024367 | 2/2012 |
| WO | 2012/129353 A1 | 9/2012 |
| WO | WO 2012/129353 | 9/2012 |
| WO | 2013/006706 A1 | 1/2013 |
| WO | WO 2013/006706 | 1/2013 |
| WO | 2013/033271 A2 | 3/2013 |
| WO | WO 2013/029180 | 3/2013 |
| WO | WO 2013/033271 | 3/2013 |
| WO | 2013/056092 A1 | 4/2013 |
| WO | WO 2013/056092 | 4/2013 |
| WO | 2013/064684 A1 | 5/2013 |
| WO | 2013/066903 A1 | 5/2013 |
| WO | WO 2013/064684 | 5/2013 |
| WO | WO 2013/066903 | 5/2013 |
| WO | 2013/086260 A2 | 6/2013 |
| WO | WO 2013/086260 | 6/2013 |
| WO | 2013/106824 A1 | 7/2013 |
| WO | WO 2013/106824 | 7/2013 |
| WO | WO 2013/138666 | 9/2013 |
| WO | 2013/174997 A1 | 11/2013 |
| WO | WO 2013/174997 | 11/2013 |
| WO | 2013/188750 A2 | 12/2013 |
| WO | WO 2013/188750 | 12/2013 |
| WO | 2014/006020 A1 | 1/2014 |
| WO | WO 2014/006020 | 1/2014 |
| WO | 2013/029180 A1 | 3/2014 |
| WO | 2014/036492 A1 | 3/2014 |
| WO | WO 2014/036492 | 3/2014 |
| WO | 2014/052462 A2 | 4/2014 |
| WO | 2014/059429 A2 | 4/2014 |
| WO | WO 2014/052462 | 4/2014 |
| WO | WO 2014/059429 | 4/2014 |
| WO | 2014/071231 A1 | 5/2014 |
| WO | 2014/080251 A1 | 5/2014 |
| WO | 2014/081732 A1 | 5/2014 |
| WO | WO 2014/071231 | 5/2014 |
| WO | WO 2014/080251 | 5/2014 |
| WO | WO 2014/081732 | 5/2014 |
| WO | 2013/138666 A1 | 9/2019 |

OTHER PUBLICATIONS

D.S. Alberts et al., "Phase I Clinical Investigation of 9,10-Anthracenedicarboxaldehyde bis[(4,5-dihydro-1H-imidazol-2-yl)hydrazone] Dihydrochloride with Correlative in Vitro Human Tumor Clonogenic Assay," Cancer Res. 42: 1170-1175 (1982).

B.S. Wang et al., "Activation of Tumor-Cytostatic Macrophages with the Antitumor Agent 9,10-Anthracenedicarboxaldehyde Bis[(4,5-dihydro-1H-imidazole-2-yl)hydrazine Dihydrochloride (Bisantrene)," Cancer Res. 44: 2363-2367 (1984).

C. Sissi et al., "DNA-Binding Preferences of Bisantrene Analogues: Relevance to the Sequence Specificity of Drug-Mediated Topoisomerase II Poisoning," Mol. Pharmacol. 54: 1036-1045 (1998).

M. Pennati et al., "Targeting Survivin in Cancer Therapy: Fulfilled Promises and Open Questions," Carcinogenesis 28: 1133-1139 (2007).

T. Utsugi et al., "Synergistic Antitumor Effects of Topoisomerase Inhibitors and Natural Cell-Mediated Cytotoxicity," Cancer Res. 49: 1429-1433 (1989).

G. Capranico et al., "Mapping Drug Interactions at the Covalent Topoisomerase II-DNA Complex by Bisantrene/Amsacrine Congeners," J. Biol. Chem. 273: 12732-12739 (1998).

G.T. Bowden et al., "Comparative Molecular Pharmacology in Leukemic L1210 Cells of the Anthracene Anticancer Drugs Mitoxantrone and Bisantrene,". Cancer Res. 45: 4915-4920 (1985).

C.K. Osborne et al., "Bisantrene, an Active Drug in Patients with Advanced Breast Cancer," Cancer Treat. Rep. 68: 357-360 (1984).

Y.M. Peng et al., "In Vivo and in Vitro Metabolism of the New Anticancer Drug Bisantrene," Cancer Chemother. Pharmacol. 14: 15-20 (1984).

G. Powis & J. S. Kovach, "Deposition of Bisantrene in Humans and Rabbits: Evidence for Intravascular Deposition of Drug as a Cause of Phlebitis," Cancer Res. 43: 925-929 (1983).

J. Rothman & Y. Paterson, "Live-Attenuated Listeria-Based Immunotherapy," Expert Rev. Vaccines 12: 493-504 (2013).

A. Spadea et al., "Bisantrene in Relapsed and Refractory Acute Myelogenous Leukemia," Leukemia Lymphoma 9: 217-220 (1993).

R.J. Spiegel et al., "Phase I Clinical Trial of 9,10-Anthracene Dicarboxaldehyde (Bisantrene) Administered in a Five-Day Schedule," Cancer Res. 42: 354-358 (1982).

D.D. Von Hoff et al., Phase I Clinical Investigation of 10-Anthracenedicarboxaldehyde bis[( 4,5-dihydro-1H-imidazol-2-yl)hydrazine]dihydrochloride (CL216,942), Cancer Res. 3118-3121 (1981).

T.P. Wunz et al., "New Antitumor Agents Containing the Anthracene Nucleus," J. Med. Chem. 30: 1313-1321 (1987).

A.S. Yang & J.-P. J. Issa, "Mitoxantrone: A Hypomethylating Agent," Cancer Biol. Ther. 2: 364-365 (2003).

B.-S. Yap et al., Phase I Clinical Evaluation of 9,10-Anthracenedicarboxy-aldehyde[bis(4,5-dihydro-1H-imidazol-2-yl]hydrazone]dihydrochloride (Bisantrene), Cancer Treat. Rep. 66: 1517-1520 (1982).

H.-Y. Yap et al., "Bisantrene, an Active New Drug in the Treatment of Metastatic Breast Cancer," Cancer Res. 43: 1402-1404 (1983).

K. Lee et al., "Anthracycline Chemotherapy Inhibits HIF-1 Transcriptional Activity and Tumor-Induced Mobilization of Circulating Angiogenic Cells," Proc. Natl. Acad. Sci. 106: 2353-2358 (2009).

B.S. Wang et al., "Immunotherapy of a Murine Lymphoma by Adoptive Transfer of Syngeneic Macrophages Activated by Bisantrene," Cancer Res. 46: 503-506 (1986).

A. Constantinou et al., "Novobiocin- and Phorbol-12-Myristate-13-Acetate-Induced Differentiation of Human Leukemia Cells Associates with a Reduction in Topoisomerase II Activity," Cancer Res. 49: 1110-1117 (1989).

M. Kamiwatari et al., "Correlation Between Reversing of Multidrug Resistance and Inhibiting of [$^3$H]Azidopine Photolabeling of P-Glycoprotein by Newly Synthesized Dihydropyridine Analogues in a Human Cell Line," Cancer Res. 49: 3190-3195 (1989).

A publication, K.-I. Miyamoto et al., "Inhibition of Multidrug Resistance by a New Staurosporine Derivative, NA-382, in Vitro and in Vivo," Cancer Res. 53: 1555-1559. (1993).

J.A. Locke et al., "Androgen Levels Increase by Intratumoral De Novo Steroidogenesis During Progression of Castration-Resistant Prostate Cancer," Cancer Res. 68: 6407-6415 (2008).

B.S. Iyengar et al., "1,4-Disubstituted Anthracene Antitumor Agents," J. Med. Chem. 40: 3734-3738 (1997).

(56) References Cited

OTHER PUBLICATIONS

R.S. Gupta et al., "Cross Resistance Pattern Towards Anticancer Drugs of a Human Carcinoma Multidrugs-Resistant Cell Line," Br. J. Cancer 58: 441-447 (1988).
E. Hernandez & N.B. Rosenshein, "Interaction Between Bisantrene and Radiation," Int. J. Radiation Oncol. Biol. Phys. 1395-1399 (1985).
Alberts et al., "In Vitro Cytotoxicity Against Fresh Human Tumors and P388 Leukemia Predicts the Differential in Vivo Activity of a Series of Anthracene Anticancer Drugs", published in Anti-Cancer Drugs 2: 69-77 (1991) (abstract only), 1 page.
Folini et al., "Remarkable Interference with Telomeric Function by a G-Quadruplex Selective Bisantrene Regioisomer", published in Biochem. Pharmacol. 79: 1781-1790 (2010), 10 pages.
Tormo et al., "Targeted Activation of Innate Immunity for Therapeutic Induction of Autophagy and Apoptosis in Melanoma Cells", published in Cancer Cell 16: 103-114 (2009), 12 pages.
Alberts et al., "Phase I Clinical Investigation of 9,10-Anthracenedicarboxaldehyde bis[(4,5-dihydro-1H-imidazol-2-yl) hydrazone] Dihydrochloride with Correlative in Vitro Human Tumor Clonogenic Assay",published in Cancer Res. 42: 1170-1175 (1982), 7 pages.
Wang et al.,, "Activation of Tumor-Cytostatic Macrophages with the Antitumor Agent 9,10-Anthracenedicarboxaldehyde Bis[(4,5-dihydro-1H-imidazole-2-yl)hydrazine Dihydrochloride (Bisantrene)", published in Cancer Res. 44: 2363-2367 (1984), 6 pages.
Sissi et al., "DNA-Binding Preferences of Bisantrene Analogues: Relevance to the Sequence Specificity of Drug-Mediated Topoisomerase II Poisoning," published in Mol. Pharmacol. 54: 1036-1045 (1998), 10 pages.
Pennati et al., "Targeting Survivin in Cancer Therapy: Fulfilled Promises and Open Questions," published in Carcinogenesis 28: 1133-1139 (2007), 7 pages.
Utsugi et al., "Synergistic Antitumor Effects of Topoisomerase Inhibitors and Natural Cell-Mediated Cytotoxicity,"published in Cancer Res. 49: 1429-1433 (1989), 6 pages.
Capranico et al., "Mapping Drug Interactions at the Covalent Topoisomerase II-DNA Complex by Bisantrene/Amsacrine Congeners," published in J. Biol. Chem. 273: 12732-12739 (1998), 10 pages.
Bowden et al., "Comparative Molecular Pharmacology in Leukemic L1210 Cells of the Anthracene Anticancer Drugs Mitoxantrone and Bisantrene," published in Cancer Res. 45: 4915-4920 (1985), 10 pages.
Osborne et al., "Bisantrene, an Active Drug in Patients with Advanced Breast Cancer," published in Cancer Treat. Rep. 68: 357-360 (1984), abstract, 1 page.
Peng et al., "In Vivo and in Vitro Metabolism of the New Anticancer Drug Bisantrene," published in Cancer Chemother. Pharmacol. 14: 15-20 (1985), abstract, 1 page.
Powis et al., Deposition of Bisantrene in Humans and Rabbits: Evidence for Intravascular Deposition of Drug as a Cause of Phlebitis, published in Cancer Res. 43: 925-929 (1983), 6 pages.

Rothman et al., "Live-Attenuated Listeria-Based Immunotherapy," published in Expert Rev. Vaccines 12: 493-504 (2013),12 pages.
Spadea et al., "Bisantrene in Relapsed and Refractory Acute Myelogenous Leukemia," published in Leukemia Lymphoma 9: 217-220 (1993), 4 pages.
Spiegel et al., "Phase I Clinical Trial of 9,10-Anthracene Dicarboxaldehyde (Bisantrene) Administered in a Five-Day Schedule," published in Cancer Res. 42: 354-358 (1982) 6 pages.
Von Hoff et al., Phase I Clinical Investigation of 10-Anthracenedicarboxaldehyde bis[( 4,5-dihydro-1H-imidazol-2-yl) hydrazine]dihydrochloride (CL216,942), published in Cancer Res. 3118-3121 (1981), 5 pages.
Wunz et al., "New Antitumor Agents Containing the Anthracene Nucleus,", published in J. Med. Chem. 30: 1313-1321 (1987), 1 page.
Yang et al., "Mitoxantrone: A Hypomethylating Agent," published in Cancer Biol. Ther. 2: 364-365 (2003), 2 pages.
Yap et al., 'Phase I Clinical Evaluation of 9,10-Anthracenedicarboxy-aldehyde[bis(4,5-dihydro-1H-imidazol-2-yl] hydrazone]dihydrochloride (Bisantrene), published in Cancer Treat. Rep. 66: 1517-1520 (1982), 4 pages.
Yap et al., "Bisantrene, an Active New Drug in the Treatment of Metastatic Breast Cancer," published in Cancer Res. 43: 1402-1404 (1983), 4 pages.
Lee et al., "Anthracycline Chemotherapy Inhibits HIF-1 Transcriptional Activity and Tumor-Induced Mobilization of Circulating Angiogenic Cells," published in Proc. Natl. Acad. Sci. 106: 2353-2358 (2009), 6 pages.
Wang et al., "Immunotherapy of a Murine Lymphoma by Adoptive Transfer of Syngeneic Macrophages Activated by Bisantrene," published in Cancer Res. 46: 503-506 (1986), 5 pages.
Constantinou et al., "Novobiocin- and Phorbol-12-Myristate-13-Acetate-Induced Differentiation of Human Leukemia Cells Associates with a Reduction in Topoisomerase II Activity," published in Cancer Res. 49: 1110-1117 (1989), 9 pages.
Kamiwatari et al., "Correlation Between Reversing of Multidrug Resistance and Inhibiting of [3H]Azidopine Photolabeling of P-Glycoprotein by Newly Synthesized Dihydropyridine Analogues in a Human Cell Line," published in Cancer Res. 49: 3190-3195 (1989), 7 pages.
Miyamoto et al., "Inhibition of Multidrug Resistance by a New Staurosporine Derivative, NA-382, in Vitro and in Vivo,"published in Cancer Res. 53: 1555-1559 (1993), 6 pages.
Locke et al., "Androgen Levels Increase by Intratumoral De Novo Steroidogenesis During Progression of Castration-Resistant Prostate Cancer," published in Cancer Res. 68: 6407-6415 (2008), 10 pages.
Iyengar et al., "1,4-Disubstituted Anthracene Antitumor Agents,", published in J. Med. Chem. 40: 3734-3738 (1997), 6 pages.
Gupta et al., "Cross Resistance Pattern Towards Anticancer Drugs of a Human Carcinoma Multidrug-Resistant Cell Line,"published in Br. J. Cancer 58: 441-447 (1988), 8 pages.
Hernandez et al., "Interaction Between Bisantrene and Radiation," published in Int. J. Radiation Oncol. Biol. Phys. 11: 1395-1399 (1985), 6 pages.

\* cited by examiner

COMBINATORIAL METHODS TO IMPROVE THE THERAPEUTIC BENEFIT OF BISANTRENE AND ANALOGS AND DERIVATIVES THEREOF

CROSS-REFERENCE TO RELATED APPLICATIONS

This application is a divisional application of U.S. patent application Ser. No. 14/907,729 by W. J. Garner et al., filed on Jan. 26, 2016 and entitled "Combinatorial Methods to Improve the Therapeutic Benefit of Bisantrene and Analogs and Derivatives Thereof," which was a United States national stage application under 35 U.S.C. § 371 of Patent Cooperation Treaty Application Serial No. PCT/US2014/048137 by W. J. Garner et al., filed on Jul. 25, 2014 and entitled "Combinatorial Methods to Improve the Therapeutic Benefit of Bisantrene and Analogs and Derivatives Thereof," which in turn claimed the benefit of U.S. Provisional Patent Application Ser. No. 61/858,729 by W. J. Garner et al., filed on Jul. 26, 2013 and entitled "Compositions and Methods to Improve the Therapeutic Benefit of Bisantrene and Analogs and Derivatives Thereof." The contents of these three prior applications are hereby incorporated in their entirety by this reference.

FIELD OF THE INVENTION

The present invention is directed to methods and compositions to improve the therapeutic benefit of bisantrene and analogs and derivatives thereof, particularly in the treatment of malignancies.

BACKGROUND OF THE INVENTION

The search for and identification of cures for many life-threatening diseases that plague humans still remains an empirical and sometimes serendipitous process. While many advances have been made from basic scientific research to improvements in practical patient management, there still remains tremendous frustration in the rational and successful discovery of useful therapies particularly for life-threatening diseases such as cancer, inflammatory conditions, infection, and other conditions.

Since the "War on Cancer" began in the early 1970's by the United States National Cancer Institute (NCI) of the National Institutes of Health (NIH), a wide variety of strategies and programs have been created and implemented to prevent, diagnose, treat and cure cancer. One of the oldest and arguably most successful programs has been the synthesis and screening of small chemical entities (<1500 MW) for biological activity against cancer. This program was organized to improve and streamline the progression of events from chemical synthesis and biological screening to preclinical studies for the logical progression into human clinical trials with the hope of finding cures for the many types of life-threatening malignant tumors. The synthesis and screening of hundreds of thousands of chemical compounds from academic and industrial sources, in addition to the screening of natural products and extracts from prokaryotes, invertebrate animals, plant collections, and other sources from all over the world has been and continues to be a major approach for the identification of novel lead structures as potential new and useful medicines. This is in addition to other programs including biotherapeutics designed to stimulate the human immune system with vaccines, therapeutic antibodies, cytokines, lymphokines, inhibitors of tumor blood vessel development (angiogenesis) or gene and antisense therapies to alter the genetic make-up of cancer cells, and other biological response modifiers.

The work supported by the NCI, other governmental agencies both domestic and foreign in academic or industrial research and development laboratories has resulted in an extraordinary body of biological, chemical and clinical information. In addition, large chemical libraries have been created, as well as highly characterized in vitro and in vivo biological screening systems that have been successfully used. However, from the tens of billions of dollars spent over the past thirty years supporting these programs both preclinically and clinically, only a small number of compounds have been identified or discovered that have resulted in the successful development of useful therapeutic products. Nevertheless, the biological systems both in vitro and in vivo and the "decision trees" used to warrant further animal studies leading to clinical studies have been validated. These programs, biological models, clinical trial protocols, and other information developed by this work remain critical for the discovery and development of any new therapeutic agent.

Unfortunately many of the compounds that have successfully met the preclinical testing and federal regulatory requirements for clinical evaluation were either unsuccessful or disappointing in human clinical trials. Many compounds were found to have untoward or idiosyncratic side-effects that were discovered during human clinical Phase I dose-escalation studies used to determine the maximum tolerated dose (MTD) and side-effect profile. In some cases, these toxicities or the magnitude of their toxicity were not identified or predicted in preclinical toxicology studies. In other cases, chemical agents where in vitro and in vivo studies suggested a potentially unique activity against a particular tumor type, molecular target or biological pathway were not successful in human Phase II clinical trials where specific examination of particular cancer indications/types were evaluated in government sanctioned (e.g., U.S. FDA), IRB approved clinical trials. In addition, there are those cases where potential new agents were evaluated in randomized Phase III clinical trials where a significant clinical benefit could not be demonstrated; such cases have also been the cause of great frustration and disappointment. Finally, a number of compounds have reached commercialization but their ultimate clinical utility has been limited by poor efficacy as monotherapy (<25% response rates) and untoward dose-limiting side-effects (Grade III and IV) (e.g., myelosuppression, neurotoxicity, cardiotoxicity, gastrointestinal toxicities, or other significant side effects).

In many cases, after the great time and expense of developing and moving an investigational compound into human clinical trials and where clinical failure has occurred, the tendency has been to return to the laboratory to create a better analog, look for agents with different structures but potentially related mechanisms of action, or try other modifications of the drug. In some cases, efforts have been made to try additional Phase I or II clinical trials in an attempt to make some improvement with the side-effect profile or therapeutic effect in selected patients or cancer indications. In many of those cases, the results did not realize a significant enough improvement to warrant further clinical development toward product registration. Even for commercialized products, their ultimate use is still limited by suboptimal performance.

With so few therapeutics approved for cancer patients and the realization that cancer is a collection of diseases with a multitude of etiologies and that a patient's response and survival from therapeutic intervention is complex with many factors playing a role in the success or failure of treatment including disease indication, stage of invasion and metastatic spread, patient gender, age, health conditions, previous therapies or other illnesses, genetic markers that can either promote or retard therapeutic efficacy, and other factors, the opportunity for cures in the near term remains elusive. Moreover, the incidence of cancer continues to rise with an approximate 4% increase predicted for 2003 in the United States by the American Cancer Society such that over 1.3 million new cancer cases are estimated. In addition, with advances in diagnosis such as mammography for breast cancer and PSA tests for prostate cancer, more patients are being diagnosed at a younger age. For difficult to treat cancers, a patient's treatment options are often exhausted quickly resulting in a desperate need for additional treatment regimens. Even for the most limited of patient populations, any additional treatment opportunities would be of considerable value. This invention focuses on inventive compositions and methods for improving the therapeutic benefit of sub-optimally administered chemical compounds including substituted hexitols such as bisantrene and analogs and derivatives thereof.

Relevant literature includes Foye, W. O., "Cancer Chemotherapeutic Agents," American Chemical Society, 1995, and Dorr, R. T., and Von Hoff, D. D., "Cancer Chemotherapy Handbook," Appleton and Lange, 1994.

Therefore, there is a need for compositions and methods including bisantrene or analogs or derivatives thereof that improve the therapeutic benefit of these compounds, particularly for the treatment of malignancies. There is a particular need for combinatorial methods to improve the therapeutic benefit of these compounds.

SUMMARY OF THE INVENTION

This invention relates to novel compositions and methods to improve the utility of chemical agents with suboptimal performance in patients suffering with immunological disease, metabolic disease, infection, or hyperproliferative diseases including cancer. The invention describes novel improvements, pharmaceutical ingredients, dosage forms, excipients, solvents, diluents, drug delivery systems, preservatives, more accurate drug administration, improved dose determination and schedules, toxicity monitoring and amelioration, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches. The invention also relates to the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some case, the use of these suboptimal therapeutics in conjunction with radiation or other conventional chemotherapeutic agents or biotherapeutic agents such as antibodies, vaccines, cytokines, lymphokines, gene and antisense therapies, or other biotherapeutic agents, would provide novel approaches and significant improvement.

In the inventive compositions and methods, the term suboptimal therapy includes agents where Phase I toxicity precluded further human clinical evaluation. It also includes those agents from Phase II trials where limited or no significant tumor responses were identified. Also, suboptimal therapy includes those agents, the subject of Phase III clinical trials the outcome of which was either medically or statistically not significant to warrant regulatory submission or approval by government agencies for commercialization or commercialized agents whose clinical performance (i.e. response rates) as a monotherapy are less than 25%, or whose side-effects are severe enough to limit wide utility. More specifically, the inventive methods and compositions also focus on improvements for bisantrene and derivatives or analogs thereof, including, but not limited to, the derivatives and analogs described below.

One aspect of the present invention is a method to improve the efficacy and/or reduce the side effects of sub-optimally administered drug therapy comprising the steps of:

(1) identifying at least one factor or parameter associated with the efficacy and/or occurrence of side effects of the drug therapy; and (2) modifying the factor or parameter to improve the efficacy and/or reduce the side effects of the drug therapy; wherein the drug therapy comprises administration of bisantrene or a derivative or analog thereof.

In one alternative, the drug therapy comprises administration of bisantrene. In another alternative, the drug therapy comprises a derivative or analog of bisantrene.

The derivative or analog of bisantrene can be selected from the group consisting of:

(a) the bisantrene analog of Formula (II)

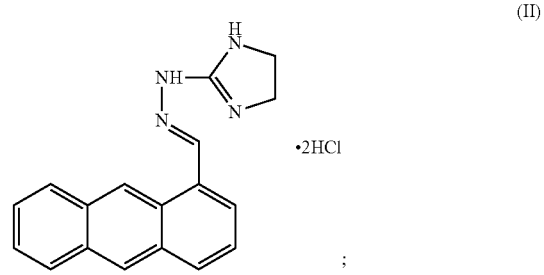 [SMILES: C(=N\NC1=NCCN1)/c1cccc2cc3ccccc3cc12]

(b) the bisantrene analog of Formula (III)

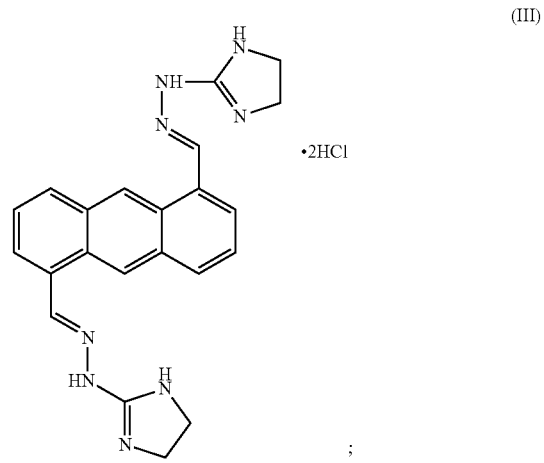 [SMILES: C(=N\NC1=NCCN1)/c1cccc2cc3c(/C=N/NC4=NCCN4)cccc3cc12]

(c) the bisantrene analog of Formula (IV)

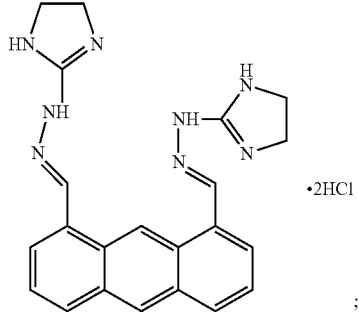

(d) the bisantrene analog of Formula (V)

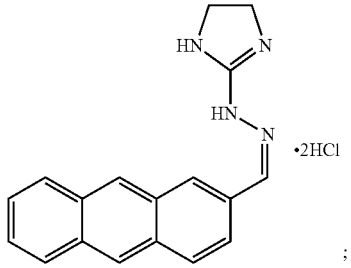

(e) the bisantrene analog of Formula (VI)

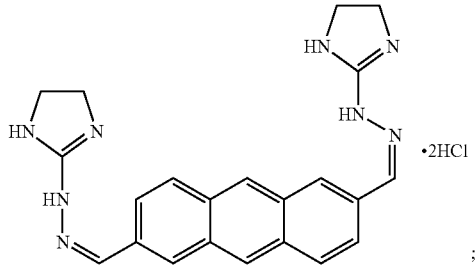

(f) the bisantrene analog of Formula (VII)

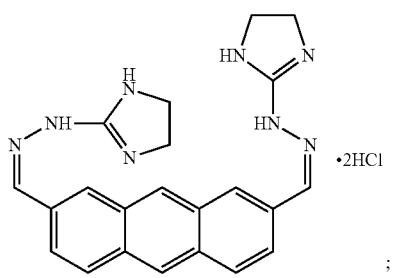

(g) the bisantrene analog of Formula (VIII)

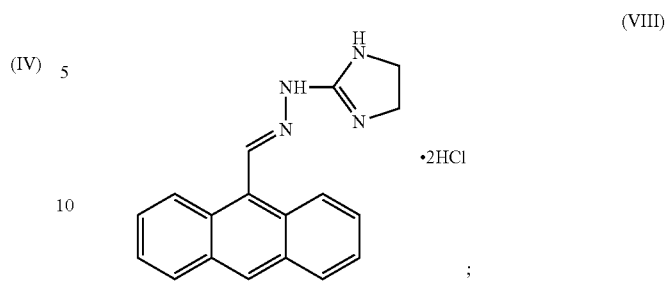

(h) the bisantrene analog anthracen-9-ylmethylene-[2-methoxyethoxymethylsulfanyl]-5-pyridin-3-yl-[1,2,4]triazol-4-amine;

(i) the bisantrene analog of Formula (X)

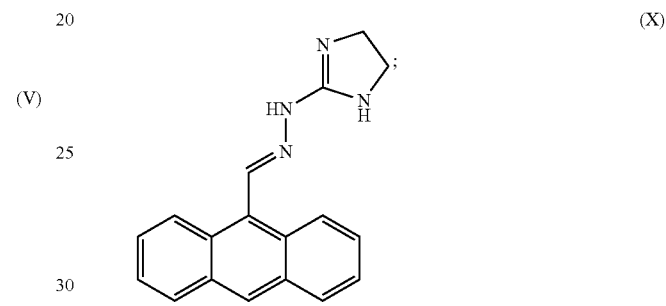

(j) the bisantrene analog of Formula (XI)

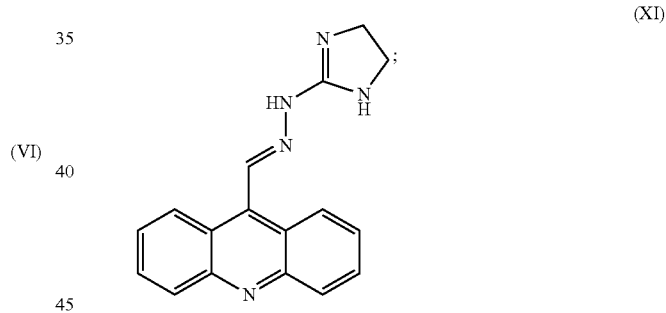

(k) the bisantrene analog of Formula (XII)

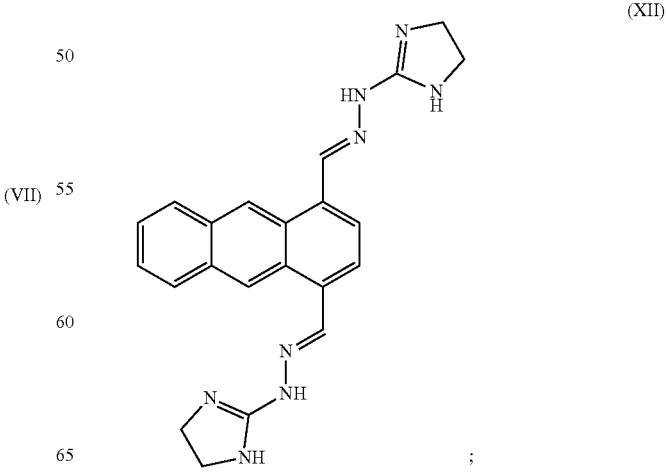

(l) the bisantrene analog of Formula (XIII)

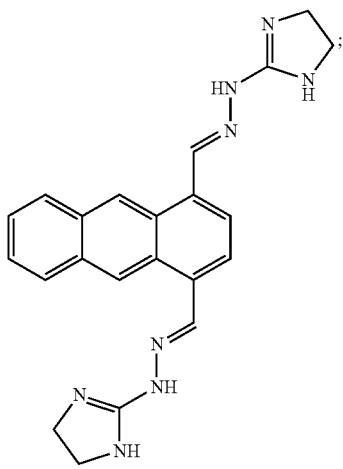

(XIII)

(m) bisantrene analogs of Formula (XIV)

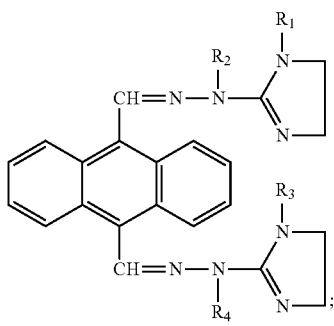

(XIV)

wherein $R_1$ and $R_3$ are the same or different and are hydrogen, $C_1$-$C_6$ alkyl, —C(O)—$R_5$, wherein $R_5$ is hydrogen, $C_1$-$C_6$ alkyl, phenyl, mono-substituted phenyl (wherein the substituent can be ortho, meta, or para and is fluoro, nitro, $C_1$-$C_6$ alkyl, $C_1$-$C_3$ alkoxy, or cyano), pentafluorophenyl, naphthyl, furanyl,

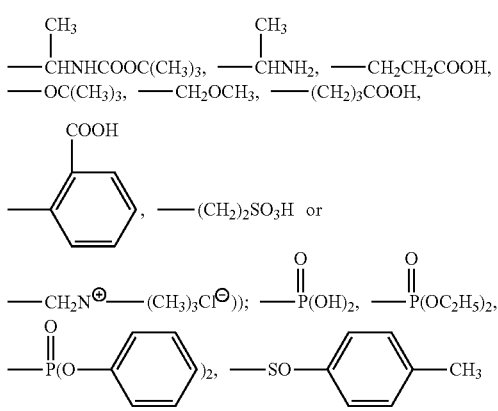

or
—SO$_3$H; wherein only one of $R_1$ and $R_3$ may be hydrogen or $C_1$-$C_6$ alkyl; $R_2$ and $R_4$ are the same or different and are: hydrogen, $C_1$-$C_4$ alkyl or —C(O)—$R_6$, where $R_6$ is hydrogen, $C_1$-$C_6$ alkyl, phenyl, mono-substituted phenyl (wherein the substituent may be in the ortho, meta, or para position and is fluoro, nitro, $C_1$-$C_6$ alkyl, $C_1$-$C_3$ alkoxy, or cyano), pentafluorophenyl, naphthyl, furanyl, or —CH$_2$OCH$_3$. The compounds can have the schematic structure $B(Q)_n$, wherein B is the residue formed by removal of a hydrogen atom from one or more basic nitrogen atoms of an amine, amidine, guanidine, isourea, isothiourea, or biguanide-containing pharmaceutically active compound, and Q is hydrogen or A, wherein A is

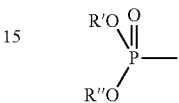

such that R' and R" are the same or different and are R (where R is $C_1$-$C_6$ alkyl, aryl, aralkyl, heteroalkyl, NC—CH$_2$CH$_2$—,

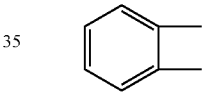

Cl$_3$C—CH$_2$—, or $R_7$OCH$_2$CH$_2$—, where $R_7$ is hydrogen or $C_1$-$C_6$ alkyl, hydrogen, or a pharmaceutically acceptable cation or R' and R" are linked to form a —CH$_2$CH$_2$— group or a

[benzene ring structure]

group, and n is an integer representing the number of primary or secondary basic nitrogen atoms in the compound such that at least one Q is A;

(n) the bisantrene analog 9,10-bis[(2-hydroxyethyl)iminomethyl]anthracene;

(o) the bisantrene analog 9,10-bis{[2-(-2-hydroxyethylamino)ethyl]iminomethyl}anthracene;

(p) the bisantrene analog 9,10-bis{[2-(-2-hydroxyethylamino)ethyl]iminomethyl}anthracene;

(q) the bisantrene analog 9,10-bis{[2-(morpholin-4-yl)ethyl]iminomethyl}anthracene;

(r) the bisantrene analog 9,10-bis[(2-hydroxyethyl)aminomethyl]anthracene;

(s) the bisantrene analog 9,10-bis{[2-(2-hydroxyethylamino)ethyl]aminomethyl}anthracene tetrahydrochloride;

(t) the bisantrene analog 9,10-bis{[2-(piperazin-1-yl)ethyl]aminomethyl}anthracene hexahydrochloride;

(u) the bisantrene analog 9,10-bis{[2-(morpholin-4-yl)ethyl]aminomethyl}anthracene tetrahydrochloride;

(v) N,N'-bis[2-(dimethylamino)ethyl]-9,10-anthracene-bis(methylamine);

(w) N,N'-bis(1-ethyl-3-piperidinyl)-9,10-anthracene-bis(methylamine); and (x) derivatives and salt forms of the compounds of (a)-(u).

Typically, the factor or parameter is selected from the group consisting of:

(1) dose modification;

(2) route of administration;

(3) schedule of administration;

(4) indications for use;
(5) selection of disease stage;
(6) other indications;
(7) patient selection;
(8) patient/disease phenotype;
(9) patient/disease genotype;
(10) pre/post-treatment preparation;
(11) toxicity management;
(12) pharmacokinetic/pharmacodynamic monitoring;
(13) drug combinations;
(14) chemosensitization;
(15) chemopotentiation;
(16) post-treatment patient management;
(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action;
(33) selective target cell population therapeutics;
(34) use with an agent enhancing its activity;
(35) use to modulate DNA methylation;
(36) use to inhibit telomerase or induce telomere dysfunction;
(37) use to activate macrophages or innate immunity;
(38) use to inhibit expression of survivin or with survivin inhibitors or modulators;
(39) use with multidrug resistance reversal agents;
(40) use in combinatorial regimes;
(41) use with directed antibody conjugates; and
(42) use with adjuvants.

Another aspect of the invention is a composition to improve the efficacy and/or reduce the side effects of suboptimally administered drug therapy comprising an alternative selected from the group consisting of:

(a) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;

(b) a composition comprising:
(i) a therapeutically effective quantity of a therapeutic agent, a modified therapeutic agent or a derivative, analog, or prodrug of a therapeutic agent or modified therapeutic agent; and
(ii) at least one additional therapeutic agent, therapeutic agent subject to chemosensitization, therapeutic agent subject to chemopotentiation, diluent, excipient, solvent system, drug delivery system, or agent for enhancing the activity or efficacy of the therapeutic agent, the modified therapeutic agent or the derivative, analog, or prodrug of a therapeutic agent or modified therapeutic agent of (a), wherein the composition possesses increased therapeutic efficacy or reduced side effects as compared with an unmodified therapeutic agent;

(c) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;

(d) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent;

(e) a therapeutically effective quantity of a therapeutic agent, a modified therapeutic agent, or a derivative, analog, or prodrug of a therapeutic agent or modified therapeutic agent that is subjected to a bulk drug product improvement;

(f) a therapeutically effective quantity of a therapeutic agent or a derivative, analog, or prodrug of a therapeutic agent, wherein the therapeutic agent or the derivative, analog, or prodrug of the therapeutic agent is optimized for increasing an immunologic response; and (g) a composition comprising:
(i) a therapeutically effective quantity of a therapeutic agent or a derivative, analog, or prodrug of a therapeutic agent; and
(ii) at least one immune adjuvant for stimulating an immune response;

wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent; wherein the unmodified therapeutic agent is bisantrene or a derivative or analog of bisantrene, the modified therapeutic agent is a modification of bisantrene or a derivative or analog of bisantrene, and the derivative, analog, or prodrug is a derivative, analog, or prodrug of bisantrene or of a derivative or analog of bisantrene.

Accordingly, as described in further detail below, one aspect of the present invention is a method to improve the efficacy and/or reduce the side effects of suboptimally administered drug therapy comprising the steps of:

(a) identifying at least one factor or parameter associated with the efficacy and/or occurrence of side effects of the drug therapy, wherein the factor or parameter is additionally associated with at least one of: (i) the specific disease or condition being treated; (ii) the stage of the disease or condition being treated; (iii) selection of an appropriate patient for treatment; (iv) selection of an appropriate phenotype of the patient or the disease or condition being treated; and (v) selection of an appropriate phenotype of the patient or the disease or condition being treated; and (b) modifying the factor or parameter to improve the efficacy and/or reduce the side effects of the drug therapy; wherein the drug therapy comprises administration of bisantrene or a derivative or analog thereof.

As described in further detail below, another aspect of the present invention is a method to improve the efficacy and/or reduce the side effects of suboptimally administered drug therapy comprising the steps of:

(a) identifying at least one factor or parameter associated with the efficacy and/or occurrence of side effects of the drug therapy, wherein the factor or parameter is additionally associated with at least one of: (i) the chemical composition of the drug being administered; (ii) the physical form of the drug being administered or a pharmaceutical composition including the drug being administered; (iii) the makeup of a pharmaceutical composition including the drug being administered; (iv) the specific use of the drug being administered; (v) the target cell, organ, or receptor targeted by the drug being administered; or (vi) additional agents administered with the drug being administered; and (b) modifying the factor or parameter to improve the efficacy and/or reduce the side effects of the drug therapy; wherein the drug therapy comprises administration of bisantrene or a derivative or analog thereof.

As described in further detail below, yet another aspect of the present invention is a method to improve the efficacy and/or reduce the side effects of suboptimally administered drug therapy comprising the steps of:

(a) identifying at least one factor or parameter associated with the efficacy and/or occurrence of side effects of the drug therapy; and (b) modifying the factor or parameter to improve the efficacy and/or reduce the side effects of the drug therapy; wherein the drug therapy comprises administration of bisantrene or a derivative or analog thereof;
and wherein the factor or parameter is use of bisantrene or a derivative or analog thereof in a combinatorial regime.

DETAILED DESCRIPTION OF THE INVENTION

Bisantrene is an unusual agent with direct cytotoxic action as well as genomic and immunologic methods of action. The chemical name for bisantrene is 9, 10-anthracenedicarboxaldehyde-bis [(4, 5-dihydro-1H-imidazole-2-yl) hydrazine] dihydrochloride, and it was originally classed as an anthracycline chemotherapeutic agent. These are drugs with planar structures based around a resonant aromatic ring structure that intercalates within the helices of DNA and disrupt various functions, including replication, presumably due to a strong inhibitory effect on the enzyme topoisomerase II. It was found that, like other anthracyclines, it could kill tumor cells in clonogenic assays and intercalate with DNA, where it inhibits both DNA and RNA synthesis. The primary chemotherapeutic mechanism for bisantrene is its preferential binding to A-T rich regions where it effects changes to supercoiling and initiates strand breaks in association with DNA associated proteins. This results from the inhibition of the enzyme topoisomerase II, which relaxes DNA coiling during replication. It was found that while inactive orally, intravenously (i.v.), intraperitoneally (i.p.), or subcutaneously (s.c.), the drug was effective in cancer models using colon 26, Lewis lung, Ridgway osteosarcoma, B16, Lieberman plasma cell, P388 or L1210 cancer cells. Activity in clonogenic assays from 684 patients was seen in breast, small cell lung, large cell lung, squamous cell lung, ovarian, pancreatic, renal, adrenal, head and neck, sarcoma, gastric, lymphoma and melanoma tumor cells, but not in colorectal cancer. Importantly, a lack of cross resistance with adriamycin and mitoxantrone was found.

Toxicity studies in dogs and monkeys revealed that at high doses leukopenia, anorexia, diarrhea, injection site necrosis, enterocolitis, muscle degeneration, and pulmonary edema were observed. Although anthracyclines, despite their clinical utility, are known to be cardiotoxic, the toxicity of bisantrene was observed to be less than that of the anthracycline doxorubicin.

Because of its lack of aqueous solubility at physiologic pH bisantrene precipitates in the body have been observed in studies of rabbits and calves. Deposition of drug into the tissues has been associated with phlebitis, and deposition has also been explored as a mechanism for the delivery of high tissue concentrations of the drug.

Bisantrene may have immunologic and/or genomic properties that might be responsible for some of its activities, and which may make this agent a useful tool in the combinatorial treatment of cancer in conjunction with newer immunotherapeutic agents. Subsequent to treatment with bisantrene, treated with bisantrene, and for 4 weeks thereafter, macrophages could be isolated from peritoneal exudate that had cytostatic anti-proliferative functionality in cultures of P815 (mastocytoma) tumor cells. Moreover, the supernatants from bisantrene activated macrophages also had a protective cytostatic effect in the tumor cell cultures. Further work revealed that macrophages activated with bisantrene and adoptively transferred to mice with EL-4 lymphomas more than doubled their median survival time, with 7 of 10 mice in the group being cured. Multiple administrations of activated macrophages were more effective than a single administration.

There is also evidence that the survivin inhibitors research that looked at the effect of bisantrene on survivin reported an interaction; one paper did find that the survivin inhibitors NSC80467 and YM155 acted in a manner that correlated with the known mechanism of DNA expression inhibition of bisantrene.

Bisantrene has also been found to have non-immunologic telomeric effects. Bisantrene binds to DNA at a site called a G-quadruplex, in which 4 guanines are associated by folding. Stabilization of the G-quadruplex can interfere with telomere-telomerase interaction and thus inhibit the activity of telomerase in various ways, including the displacement of telomerase binding proteins. Since the level of topoisomerase II inhibition does not always correlate with cytotoxic efficacy, alternative mechanisms may play a role in the actions of bisantrene. Analogs of bisantrene have been made in an attempt to improve upon the anti-telomerase activity; these analogs are described further below. Human melanoma (SK-Mel5) and colon cancer (LoVo) tumor cells were observed to lose their proliferative ability in the presence of these agents. Apoptosis was not observed, however a loss of immortality was seen, with treated cells reacquiring the ability to become senescent, age, and die.

Several clinical trials have investigated the pharmacokinetics of bisantrene in humans. In one trial of patients given a 90 min infusion at 260 mg/m$^2$ a biphasic elimination with an initial half-life of 65±15 min, a terminal half-life of 1142±226 min, and a steady state volume of distribution (Vdss) of 1845 L/m$^2$. Plasma clearance in this trial was 735 mL/min/m$^2$, with 11.3% of the administered dose excreted unchanged in the urine in 24 hr. In another trial, doses of 80-250 mg/m$^2$ were assessed, and the initial and terminal half-lives were 0.6 hr and 24.7 hr, respectively, with a clearance of 1045.5±51.0 mL/kg/hr and a calculated volume of distribution of 42.1±5.9 L/kg. In this study only 3.4±1.1% of the administered dose was found in the urine over 96 hr. In three other single dose studies triphasic elimination was reported, one with t½α, β, and γ of 3.44 min, 1.33 hr and 26.13 hr, respectively, another was 3 min, 1 hr, and 8 hr respectively, and the last revealed clearances of 0.1 hr, 1.9 hr and 43.9 hr, respectively. In one report a large volume of distribution (687 L/m$^2$) was interpreted as tissue sequestration of the drug with a subsequent depot effect. In a 72-hr infusion study, a plasma concentration of 12±6 ng/mL was observed at a dose of 56 mg/m$^2$, while a dose of 260 mg/m$^2$ resulted in a plasma concentration of 55±8 ng/mL. In this trial plasma clearance was 1306±179 mL/min/m$^2$ with urinary excretion of 4.6% of the dose in 24 hr. Finally, in another study, a 5 day schedule of 60 min infusions revealed a t½α and β of 0.9 and 9.7 hr, respectively with 7.1% of the dose excreted in the urine.

In phase 1 trials toxicity consisting of myelosuppression, phlebitis, erythema and edema was observed in patients with melanoma, hypernephroma, renal cell, hepatoma, bladder, or lung adenoma. A phase I pediatric study at doses between 10-120 mg/m$^2$/d×5 q3W observed leukopenia, neutropenia, minor LFT elevations, transient BP fluctuation during infusion, transient edema at injection site, and phlebitis. A phase I study found the MTD to be 300 mg/m$^2$ over 72 h with doses over 156 mg/m$^2$ requiring a central line due to phlebitis. Allergic reactions, fever, dyspnea, and chest pain were observed. Another study found IA infusions to be of no benefit over IV administration. In another study, with phase I doses between 190-430 mg/m$^2$ q3w, neutropenia was found to be the DLT, and phlebitis was observed. In phase II trials, the trials included patients with breast, colon, gastric, head and neck, hepatoma, NSCLC, SCLC, melanoma, leukemia, Hodgkin's and NHL lymphoma, multiple myeloma, ovarian, pancreas, prostate, renal, bladder, sarcoma, and a variety of pediatric cancers. Most patients had been previously treated. Adverse events (AE) were similar to that observed in phase I. In a phase III trial, it was found that bisantrene was less cardiotoxic than mitoxantrone or doxorubicin. Also, it is worth noting that in a number of clinical trials in which central venous administration was used that toxicity was noted to be considerably less than with peripheral venous administration.

Prior trials, concerned with a toxic chemotherapeutic mechanism of action in which the clinical dose was defined by tolerance, a model not suitable for the development of immunotherapies. The maximum tolerated dose model for the development of bisantrene was attended by toxicities that prompted investigators to co-administer hydrocortisone to limit potential acute inflammatory and allergic reactions which may have negatively impacted the then unrecognized immunologic aspects of the drug. These prior trials typically reported objective response rates, usually predicated on the RECIST scale (Response Evaluation Criteria In Solid Tumors), but not survival, performance status, or other measures of response. The methodology of such trials was derived from agents having a chemotherapeutic mechanism of action exclusively, not best suited for agents with immunological or genomic effects such as bisantrene, as it is now known that immune therapies can have salutary effects on survival independent of tumor responses, and that even minor responses of the type not reported in the older studies can be attended by a favorable overall outcome in terms of performance status and survival.

Cancer drug development in the 1980's, especially anthracycline development, was predicated upon a maximum tolerated dose (MTD) model. That is, since the drug is a toxin and the objective is to kill cells (hopefully more cancer cells than healthy normal cells) that the way to determine the most effective dose was to see how much drug could be given before doing irreparable damage to the patient. In this model, deaths due to drug overdose were an unfortunate but accepted aspect of treatment. Immunotherapy was in its infancy, and immunologic efficacy was not a consideration in the development of anti-cancer agents of the day. Today we know that a maximum tolerated dose is not necessarily the maximum immune-efficient dose, and that immune efficacy results from the summation of many disparate events which may be under-stimulated or over-stimulated at any given time. Further, many of the bisantrene studies reported in the 1980's used a classical RECIST reporting schema that quantified objective responses, but did not look at overall survival (OS). It is now known that different therapies can increase survival significantly, even in the absence of objective responses. Therefore, the clinical models and reporting structures used at the time of bisantrene development were not sufficient to understand the potential mechanisms of action of the drug or to capture all of the important clinical outcomes.

The development of an agent that has both cytotoxic and anti-tumor immune stimulating properties is a novel paradigm for which no clinical models exist. However, at a time in which a considerable effort is being given to understanding how to integrate the newer immunotherapies with the existing battery of effective chemotherapeutic agents, bisantrene may be poised to become a useful tool to develop methods for integrating these two disparate therapeutic modalities.

The structure of bisantrene hydrochloride is shown in Formula (I)

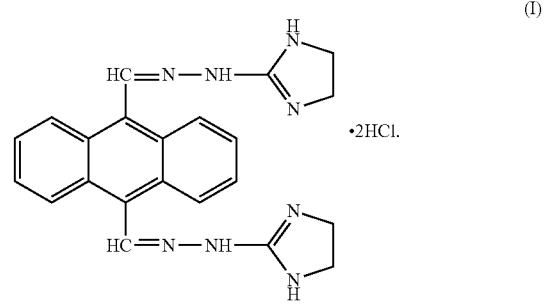

Bisantrene is a tricyclic aromatic compound with the chemical name, 9,10-anthracenedicarboxaldehyde bis[(4,5-dihydro-1H-imidazol-2-yl)hydrazine] dihydrochloride. The molecular formula is $C_{22}H_{22}N_8$.2HCl and the molecular weight, 471.4. The alkylimidazole side chains are very basic and, at physiologic pH, are positively charged. This is believed to facilitate electrostatic attractions to negatively charged ribose phosphate groups in DNA.

Bisantrene has shown antitumor activity in murine tumor models including P-388 leukemia and B-16 melanoma (R. V. Citarella et al., "Anti-Tumor Activity of CL-216942: 9,10-Anthracenedicarboxaldehyde bis (4,5-dihydro-1H-imidazol-2-yl)hydrazone)]dihydrochloride (Abstract #23) in *Abstracts of the 20$^{th}$ Interscience Conference on Antimicrobial Agents and Chemotherapy (Bethesda, Md., American Society for Microbiology* 1980)). Human tumor cells that were sensitive to bisantrene as assessed by in vitro colony-forming assays include breast cancer, ovarian cancer, renal cancer, small cell and non-small cell lung cancer, lymphoma, acute myelogenous leukemia, melanoma, gastric cancer, adrenal cancer, and head and neck cancer (D. D. Von Hoff et al, "Activity of 9,10-Anthracenedicarboxaldehyde bis[(4,5-dihydro-1H-imidazol-2-yl)hydrazine]dihydrochloride (CL216,942) in a human tumor cloning system," *Cancer Chemother. Pharmacol.* 6: 141-144 (1981) ("Von Hoff et al. (1981a)"). In phase I clinical trials bisantrene showed activity in hepatocellular cancer and hypernephroma (one patient each) (D. D. Von Hoff et al., "Phase I Clinical Investigation of 10-Anthracenedicarboxaldehyde bis[(4,5-dihydro-1H-imidazol-2-yl)hydrazine]dihydrochloride (CL216,942)," *Cancer Res.* 3118-3121 (1981) ("Von Hoff et al. (1981b)") and in lymphoma, myeloma, melanoma, renal cancer, and tumors of the bladder and lung (D. S. Alberts et al., "Phase I Clinical Investigation of 9,10-Anthracenedicarboxaldehyde bis[(4,5-dihydro-1H-imidazol-2-yl)hydrazone] Dihydrochloride with Correlative in Vitro Human Tumor Clonogenic Assay," *Cancer Res.* 42: 1170-1175 (1982)). Phase I activity was also observed in two other hypernephroma patients (R. J. Spiegel et al., "Phase I Clinical Trial of 9,10-Anthracene Dicarboxaldehyde (Bisantrene) Administered in a Five-Day Schedule, "*Cancer Res.* 42: 354-358 (1982)). Bisantrene was inactive in human colon cancer tested in vitro or in vivo (M. C. Perry et al. "Phase II Trial of Bisantrene in Advanced Colorectal Cancer: A Cancer and Leukemia Group B Study," *Cancer Treat. Rep.* 66: 1997-1998 (1982); Von Hoff et al. (1981a); Von Hoff et al. (1981b). It was also inactive in refractory malignant melanoma (D. S. Alberts et al., "Phase II Evaluation of Bisantrene Hydrochloride in Refractory Malignant Melanoma," *Invest. New Drugs* 5: 289-292 (1987)).

In Phase II clinical trials, bisantrene was active in patients with metastatic breast cancer (H.-Y. Yap et al., "Bisantrene, an Active New Drug in the Treatment of Metastatic Breast Cancer," *Cancer Res.* 43: 1402-1404 (1983)). Partial response rates were observed in heavily pretreated patients with metastatic breast cancer. However, the study was terminated because of significant local toxicity observed.

The mechanism of action for bisantrene has been studied. Bisantrene has been shown to induce altered DNA supercoiling indicative of DNA intercalation (G. T. Bowden et al., "Comparative Molecular Pharmacology in Leukemic L1210 cells of the Anthracene Anticancer Drugs Mitoxantrone and Bisantrene, *Cancer Res.* 45: 4915-4920 (1985)). In L-1210 leukemia cells bisantrene was also shown to induce protein-associated DNA strand breaks typical of drug-induced inhibition of DNA topoisomerase II enzymes (Bowden et al., 1985). Both cytotoxicity and the DNA strand breaks appear to be reduced in hypoxic conditions (C. U. Ludwig et al., "Reduced Bisantrene-Induced Cytotoxicity and Protein-Associated DNA Strand Breaks Under Hypoxic Condition," *Cancer Treat. Rep.* 68: 367-372 (1984)). The noncovalent binding of bisantrene to DNA appears to comprise two types of interactions: (1) intercalation of the planar anthracene moiety between DNA base pairs, and (2) electrostatic binding between negatively charged ribose phosphates of DNA and positively charged basic nitrogens on the alkyl side chains of the drug. This is reflected in the biphasic DNA dissociation curves for bisantrene in calf thymus DNA in vitro (W. O. Foye et al., "DNA-Binding Abilities of Bisguanylhydrazones of anthracene-9,10-dicarboxaldehyde," *Anti-Cancer Drug Design* 1: 65-71 (1986)).

In one alternative, bisantrene vials have been reconstituted with 2 to 5 mL of Sterile Water for Injection, USP, and then diluted with approximately 0.1 to 0.5 mg/mL in D5W (5% dextrose in water). Bisantrene is incompatible with saline and unstable in light (G. Powis et al., "Pharmacokinetic Study of ADAH in Humans and Sensitivity of ADAH to Light" (Abstract #C-74)," *ASCO Proc.* 1: 19 (1982).

Because of severe local venous toxicity, bisantrene doses have been infused via central venous access devices over 1 hour (Van Hoff et al., 1981b). Bisantrene has been infused through peripheral veins over 2 hours, and has been "piggybacked" into a running dextrose infusion in an attempt to lessen delayed swelling in the arm used for infusion.

To reduce venous irritation, hyperpigmentation, drug extravasation, and anaphylactoid reactions, patients have been given hydrocortisone (50 mg IV) and the antihistamine diphenhydramine (50 mg IM) immediately prior to bisantrene (Alberts et al. (1982)), supra). Bisantrene is known to stain the skin orange.

Maximally tolerated doses in several bisantrene phase I schedules include: (1) 200 mg/m$^2$ weekly×3 (150 mg/mg$^2$ for patients with poor bone marrow reserve (e.g., those patients who have received radiotherapy or extensive chemotherapy regimens) (Alberts et al. (1982), supra); (2) 150 mg/m$^2$ weekly×3 (repeat every 4-5 week) (B.-S. Yap et al., "Phase I Clinical Evaluation of 9,10-Anthracenedicarboxaldehyde[bis(4,5-dihydro-1H-imidazol-2-yl)hydrazone]dihydrochloride (Bisantrene)," *Cancer Treat. Rep.* 66: 1517-1520 (1982)) (3) 260 mg/m$^2$ monthly (every 3-4 week) (240 mg/mg$^2$ for patients with poor bone marrow reserve (e.g., those patients who have received radiotherapy or extensive chemotherapy regimens) (Von Hoff et al., 1981b); and (4) 80 mg/m$^2$ daily×5 (repeat every 4 weeks) (R. J. Spiegel et al. (1982), supra).

More than 95% of bisantrene is bound to plasma proteins and the drug has a long terminal plasma half-life. There appeared to be three phases of elimination: an initial distributive phase of 6 minutes, a beta phase of approximately 1.5 hours, and a final gamma elimination phase of 23 to 54 hours (Alberts et al. (1983), supra). Typical areas under the plasma concentration× time curve are 4.4 to 5.7 mg·h/mL following intravenous doses of 260 to 340 mg/m$^2$, respectively (Alberts et al. 1983, supra). Less than 7% of a bisantrene dose is excreted in the urine and the majority of the drug is eliminated by the hepatobiliary route. The drug may be metabolized to some extent in vivo. In vitro bisantrene is a substrate for hepatic microsomal enzymes but specific metabolites have not been identified. Preclinical drug distribution studies showed that the tissues with the highest concentration (in descending order) are kidney, liver, gallbladder, spleen, lung, and heart. Brain levels were extremely low. The drug did distribute to lymph nodes and bone marrow (W. H. Wu & G. Nicolau, "Disposition and Metabolic Profile of a New Antitumor Agent, CL 216,942 (Bisantrene) in Laboratory Animals," *Cancer Treat Rep.* 66: 1173-1185 (1982)).

The major dose-limiting toxic effect of bisantrene is leukopenia (Von Hoff et al. 1981b; Alberts et al. 1982, supra; Spiegel et al. 1982, supra; Yap et al 1982, supra)). On a schedule of every 3 to 4 weeks, the nadir for myelosuppression was 9 days with recovery by 19 days (Von Hoff et al. 1981b). Thrombocytopenia was mild although bisantrene can also inhibit platelet aggregation (M. E. Rybak et al., "The Effects of Bisantrene on Human Platelets," *Invest. New Drugs* 4: 119-125 (1986)). Anemia and cumulative myelosuppressive toxic effects were not encountered with this drug.

In addition to myelosuppression, bisantrene produced severe phlebitis along peripheral veins used for drug infusion (Von Hoff et al. 1981b; Alberts et al. 1982). This may have been caused by drug precipitation in veins which has been documented in experimental models (G. Powis & J. S. Kovach 1983). The drug is a potent vesicant and produces severe local tissue necrosis if inadvertently extravasated (Von Hoff et al 1981b). Severe arm swelling, hyperpigmented veins, and punctate perivenous orange discolorations have been occasionally observed following bisantrene infusions given through peripheral veins. The arm swelling appeared to be the result of a localized capillary leak syndrome in the arm used for infusion. In an experimental mouse skin model, extravasation necrosis was blocked with a local injection of sodium bicarbonate which physically decomposes bisantrene (R. T. Dorr et al., "Bisantrene Solubility and Skin Toxicity Studies: Effect of Sodium Bicarbonate as a Local Ulceration Antidote," *Invest. New Drugs* 2: 351-357 (1984)).

Up to 10% of patients experienced anaphylactoid reactions following a bisantrene infusion (J. W. Myers et al., "Anaphylactoid Reactions Associated with Bisantrene Infusions," *Invest. New Drugs* 1: 85-88 (1983)). Symptoms included chills, chest pain, shortness of breath, flushing, and pruritus. These effects may be caused by drug-induced histamine release. Hypotension is also reported with bisantrene, and prolongation of the infusion was recommended to reduce this complication (Von Hoff et al., 1981b). In addition, a few patients experienced diaphoresis and palpitations, usually near the end of a bisantrene infusion (Von Hoff et al., 1981b). The drug was not cardiotoxic in animals and use in the clinic has confirmed less cardiotoxicity than other agents in its class. No patients experienced electrocardiographic changes while receiving the drug and radioangiocardiographic monitoring demonstrated no decrease in ejection fraction or any other significant change in cardiac function (J. W. Myers et al., "Radioangiocardiographic Monitoring in Patients Receiving Bisantrene," *Am. J. Clin. Oncol.* 7: 129-130 (1984), incorporated herein by this reference).

Bisantrene has been reported to produce very little nausea or vomiting. Alopecia (hair loss) is also less intense with bisantrene compared with doxorubicin (J. D. Cowan et al., "Randomized Trial of Doxorubicin, Bisantrene, and Mitoxantrone in Advanced Breast Cancer: A Southwest Oncology Group Study," *J. Nat'l Cancer Inst.* 83: 1077-1084 (1991)). However, bisantrene can produce a mild fever in some patients and malaise may be particularly common. This was reported by up to one-half of patients studied (Yap et al. (1982), supra).

Therefore, because of the range and severity of potential side effects, particularly the existence of local venous reactions and anaphylactoid reactions, development of bisantrene had been halted. However, the results suggest a reevaluation of the use of bisantrene for antineoplastic use and for other indications, despite the prior halt of development.

Various formulations suitable for use in the administration of bisantrene or derivatives or analogs thereof are known in the art. U.S. Pat. No. 4,784,845 to Desai et al., incorporated herein by this reference, discloses a composition of matter for delivery of a hydrophobic drug (i.e., bisantrene or a derivative or analog thereof) comprising: (i) the hydrophobic drug; (ii) an oleaginous vehicle or oil phase that is substantially free of butylated hydroxyanisole (BHA) or butylated hydroxytoluene (BHT); (iii) a co-surfactant or emulsifier; (iv) a co-surfactant or auxiliary emulsifier; and (v) benzyl alcohol as a co-solvent. U.S. Pat. No. 4,816,247 by Desai et al., incorporated herein by this reference, discloses a composition of matter for delivery by intravenous, intramuscular, or intraarticular routes of hydrophobic drugs (such as bisantrene or a derivative or analog thereof) comprising: (i) the hydrophobic drug; (ii) a pharmaceutically acceptable oleaginous vehicle or oil selected from the group consisting of: (a) naturally occurring vegetable oils and (b) semisynthetic mono-, di-, and triglycerides, wherein the oleaginous vehicle or oil is free of BHT or BHA; (iii) a surfactant or emulsifier; (iv) a co-surfactant or emulsifier; (v) an ion-pair former selected from $C_6$-$C_{20}$ saturated or unsaturated aliphatic acids when the hydrophobic drug is basic and a pharmaceutically acceptable aromatic amine when the hydrophobic drug is acidic; and (vi) water. U.S. Pat. No. 5,000,886 to Lawter et al. and U.S. Pat. No. 5,143,661 to Lawter et al., both incorporated herein by this reference, disclose compositions for delivery of pharmaceutical agents such as bisantrene or a derivative or analog thereof comprising a microcapsule, wherein the microcapsule includes a hardening agent that is a volatile silicone fluid. U.S. Pat. No. 5,070,082 to Murdock et al., U.S. Pat. No. 5,077,282 to Murdock et al., and U.S. Pat. No. 5,077,283 to Murdock et al., all incorporated herein by this reference, disclose prodrug forms of poorly soluble hydrophobic drugs, including bisantrene and derivatives and analogs, that are salts of a phosphoramidic acid. U.S. Pat. No. 5,116,827 to Murdock et al. and U.S. Pat. No. 5,212,291 to Murdock et al., both incorporated herein by this reference, disclose prodrug forms of poorly soluble hydrophobic drugs, including bisantrene and derivatives and analogs, that are quinolinecarboxylic acid derivatives. U.S. Pat. No. 5,378,456 to Tsou, incorporated herein by this reference, includes compositions containing an anthracene antitumor agent, such as bisantrene or a derivative or analog thereof, in which the bisantrene or derivative or analog thereof is conjugated to or admixed with a divinyl ether-maleic acid (MVE) copolymer. U.S. Pat. No. 5,609,867 to Tsou, incorporated herein by this reference, discloses polymeric 1,4-bis derivatives of bisantrene and copolymers of bisantrene and another monomer, such as a dianhydride.

The present application, therefore, provides improved methods and compositions for the use of bisantrene and analogs or derivatives thereof for the treatment of malignancies while avoiding the side effects described above and improving the therapeutic efficacy of the drug.

As detailed above, in addition to direct antineoplastic effects related to the activity of bisantrene as a DNA intercalator, bisantrene also possesses other mechanisms of action, including immunopotentiation. These mechanisms are described in: (i) N. R. West et al., "Tumor-Infiltrating Lymphocytes Predict Response to Anthracycline-Based Chemotherapy in Estrogen-Resistant Breast Cancer," *Breast Canc. Res.* 13: R126 (2011), which concludes that the level of tumor-infiltrating lymphocytes is correlated with a response to the administration of anthracycline-based agents; the markers associated with tumor-infiltrating lymphocytes (TIL) include CD19, CD3D, CD48, GZMB, LCK, MS4A1, PRF1, and SELL; (ii) L. Zitvogel et al., "Immunological Aspects of Cancer Chemotherapy," *Nature Rev. Immunol.* 8: 59-73 (2008), which states that DNA damage, such as that produced by intercalating agents such as bisantrene, induces the expression of NKG2D ligands on tumor cells in an ATM-dependent and CHK1-dependent (but p53-independent) manner; NKG2D is an activating receptor that is involved in tumor immunosurveillance by NK cells, NKT cells, yO T cells and resting (in mice) and/or activated (in humans) $CD8^+$ T cells, and also states that anthracycline-based agents may act as immunostimulators, particularly in combination with IL-12; such agents also promote HMGB1 release and activate T cells; (iii) D. V. Krysko et al., "TLR2 and TLR9 Are Sensors of Apoptosis in a Mouse Model of Doxorubicin-Induced Acute Inflammation," *Cell Death Different.* 18: 1316-1325 (2011), which states that anthracycline-based antibiotics induce an immunogenic form of apoptosis that has immunostimulatory properties mediated by MyD88, TLR2, and TLR9; (iv) C. Ferraro et al., "Anthracyclines Trigger Apoptosis of Both G0-G1 and Cycling Peripheral Blood Lymphocytes and Induce Massive Deletion of Mature T and B Cells," *Cancer Res.* 60: 1901-1907 (2000), which stated that anthracyclines induce apoptosis and ceramide production, as well as activate caspase-3 in resting and cycling cells; the apoptosis induced is independent from CD95-L/CD95 and TNF/TNF-R; and (v) K. Lee et al., "Anthracycline Chemotherapy Inhibits HIF-1 Transcriptional Activity and Tumor-Induced Mobilization of Circulating Angiogenic Cells," *Proc. Natl. Acad. Sci. USA* 106: 2353-2358 (2009), which provides another antineoplastic mechanism for anthracycline-based antibiotics, namely inhibition of HIF-1 mediated gene transcription, which, in turn, inhibits transcription of VEGF required for angiogenesis; HIF-1 also activates transcription of genes encoding glucose transporter GLUT1 and hexokinases HK1 and HK2, which are required for the high level of glucose uptake and phosphorylation that is observed in metastatic cancer cells, and pyruvate dehydrogenase kinase 1 (PDK1), which shunts pyruvate away from the mitochondria, thereby increasing lactate production; patients with HIF-1α overexpression based on immunohistochemical results were suggested to be good candidates for treatment with anthracycline-based antibiotics.

Among the types of cancer for which a response to bisantrene has been seen are bladder carcinoma, multiple myeloma, lung adenocarcinoma, melanoma, and renal cell carcinoma (Alberts et al. (1982), supra), as well as breast cancer (Bowden et al. (1985), supra) and acute myelogenous leukemia, especially relapsed or refractory acute myeloid leukemia (A. Spadea et al., "Bisantrene in Relapsed and Refractory Myelogenous Leukemia," *Leukemia Lymphoma* 9: 217-220 (1993).

Bisantrene has been reported as activating tumor-cytostatic macrophages (B. S. Wang et al., "Activation of Tumor-Cytostatic Macrophages with the Antitumor Agent 9,10-Anthracenedicarboxaldehyde Bis[(4,5-dihydro-1H-imidazole-2-yl)hydrazine Dihydrochloride (Bisantrene)," *Cancer Res.* 44: 2363-2367 (1984)), incorporated herein by this reference. The minimal effective in vivo dose of bisantrene appeared to be 25 mg/kg, with peak activation being achieved at doses of 50 to 100 mg/kg. A number of macrophage activators are known, including *Bacillus* Calmette-Guérin, *Corynebacterium parvum*, endotoxins, muramyl dipeptide, pI:pC copolymer, pyran copolymer, lymphokines, Adriamycin, cyclophosphamide, and mitomycin C. The efficacy of bisantrene in allogeneic macrophage transplants and with supernatants of macrophages activated by bisantrene has been shown in B. S. Wang et al., "Immunotherapy of a Murine Lymphoma by Adoptive Transfer of Syngeneic Macrophages Activated by Bisantrene," *Cancer Res.* 46: 503-506 (1986), incorporated herein by this reference. Specifically, the active cells were obtained from peritoneal exudate. Bisantrene-activated macrophages were shown to be highly cytostatic to tumor cells. Repeated treatments with activated macrophages were shown to be more effective in protecting animals inoculated with tumors. This represents immunotherapy by adoptive transfer of immunocompetent cells. Culture supernatants of activated macrophages were also found to have antiproliferative effects on tumor cells, indicating that a cytostatic factor or factors were produced by these macrophages. (B. S. Wang et al., "Activation of Tumor-Cytostatic Macrophages with the Antitumor Agent 9,10-Anthracenedicarboxaldehyde Bis[(4,5-dihydro-1H-imidazole-2-yl)hydrazine] Dihydrochloride (Bisantrene)," *Cancer Res.* 44: 2363-2367 (1984)).

Bisantrene and analogs thereof have been reported as inhibiting telomerase activity, especially by stabilizing G-quadruplex DNA structures as disclosed in M. Folini et al., "Remarkable Interference with Telomeric Function by a G-Quadruplex Selective Bisantrene Regioisomer," *Biochem. Pharmacol.* 79: 1781-1790 (2010). The bisantrene analogs used are those of Formulas (II), (III), (IV), (V), (VI), (VII), and (VIII):

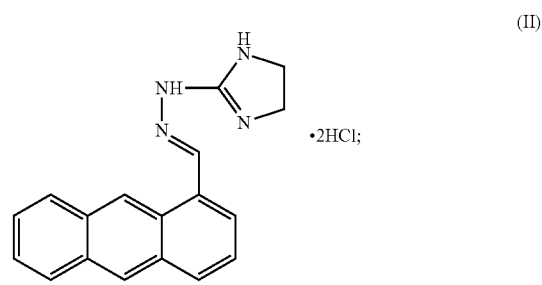

(II)

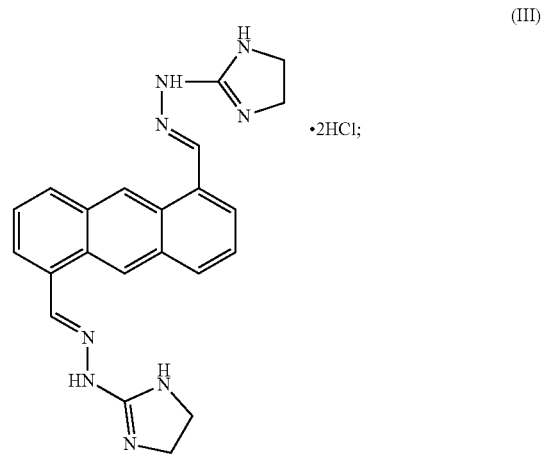

(III)

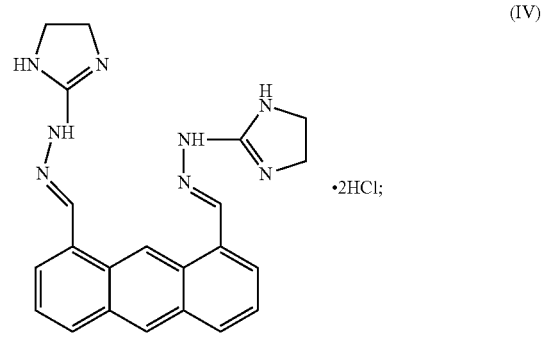

(IV)

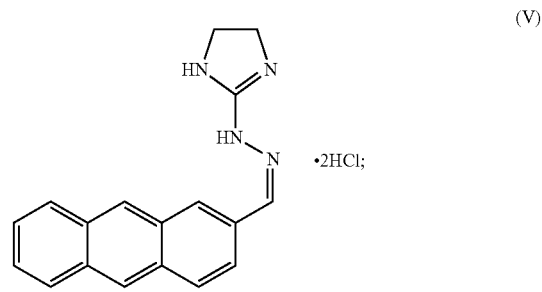 [SMILES: C(=N/NC1=NCCN1)/c1ccc2cc3ccccc3cc2c1]

(V)

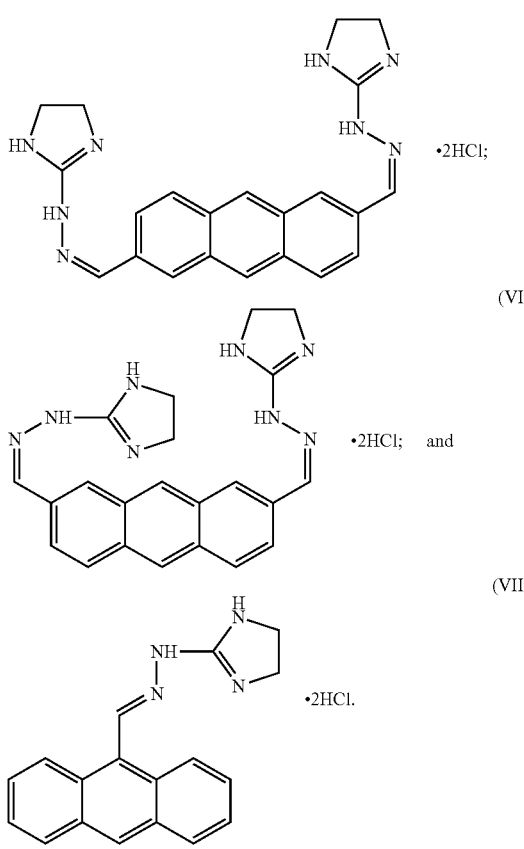

Telomerase is a ribonucleoprotein reverse transcriptase responsible for maintenance of telomere length. Its expression is associated with cell immortalization and tumorigenesis since it is expressed in most human tumor cells but is not active in most normal somatic cells. Telomerase machinery inhibitors have been evaluated as potential anticancer agents, including nucleotide analogs such as 7-deaza-2'-deoxyguanosine, BIBR1532, antisense oligonucleotides, GRN163L, and other agents. For such agents, a number of different pathways are involved in inhibition of telomerase activity. Generally, inhibition of telomerase activity results in cellular senescence or apoptosis in a time-dependent manner that correlates with the initial telomere length in the cells in which telomerase is inhibited. When telomere architecture collapses or is disrupted, a signaling cascade comparable to that produced by DNA damage is activated and cell cycle arrest (accelerated senescence) or cell death through apoptosis is induced.

Telomerase substrates are the telomeres, double-stranded DNA portions with a 3' protruding overhang (100-200 bases long), formed by a repeating noncoding sequence (TTAGGG (SEQ ID NO: 1) in humans). In analogy to other G-rich sequences, the single-stranded portion can fold into a structure called G-quadruplex. These folding results of overlapping planar regions were identified by four Hoogsteen-paired guanines. Hoogsteen base-pairing is between the N7 position of the purine base as a hydrogen-bond acceptor and the C6 amino group of the pyrimidine base as a donor. By recognizing and stabilizing this abnormal DNA base-pairing arrangement, selected ligands impair telomere-telomerase interaction thus interfering with the telomere elongation step catalyzed by the enzyme. Additionally, they can displace the telomere binding proteins (i.e., TRF2 and hPOT1) involved in telomere capping, thereby allowing recognition of the free terminal sequence as a DNA damage region. Several compounds able to interact with and stabilize G-quadruplex structures formed by G-rich single-stranded overhangs of telomeres have been identified, including anthraquinones, fluorenones, acridines, triazine, cationic porphyrins, and perylenes, as well as other compounds. These compounds share a general consensus structural motif based on a large flat aromatic surface linked to protonatable side chains. DNA binding occurs mainly through stacking on a terminal G-tetrad, whereas side chains contribute to the stability of the complex by hydrophobic/ionic interactions into the DNA grooves.

Since similar basic features characterize intercalation and base stacking, the scaffolds of classical intercalating agents are commonly used as starting structures to produce G-quadruplex recognition. Literature data have proven that, by working on the number, the length and the position of the charged side chains bound to a "classical" intercalator, it is possible to preferentially direct drug binding towards G-quadruplex forms. Indeed, such an approach has led to the identification of effective G-quadruplex binders such as the tri-substituted acridine BRACO 19 and the 2,6 or 2,7 bis-substituted amido-anthraquinones. These binders are characterized by poor cytotoxicity and are able to induce a reduction in telomere length upon long-term drug exposure. Bisantrene shares the structural "consensus motif" characteristic of effective G-quadruplex binders.

At least two side chains with amine groups protonatable at physiological pH are required for G-quadruplex binding. This includes bisantrene. Bisantrene is believed to intercalate between adjacent base pairs of double-stranded DNA through π-π stacking, with side chains located in either groove (threading mode), which grants affinity constants well above $10^6$ $M^{-1}$ under physiological conditions. For the analogs described above, the fact that the most efficient G-quadruplex binders are substituted on two distinct aromatic rings with side chains pointing in opposite directions with reference to the long axis of the aromatic system likely suggests formation of additional specific interactions between the 4,5-dihydro-1H-imidazol-2-yl hydrazone groups and the G-quadruplex structure.

At least one of the bisantrene analogs, Formula (III), has the ability to act both at the telomerase level, by interfering with substrate recognition (hence suppressing its catalytic activity), and at the telomere level, by modifying its structural organization. This compound affects telomere function not only in telomerase-expressing cells but also in ALT-positive cell lines, since it consistently provokes a DNA damage response, as evidenced by the formation of γH2AX foci that partially co-localize at the telomere, in agreement with results reported for telomestatin. For this compound, such a DNA damage response, together with the absence of apoptosis and the induction of cell cycle impairment (mainly G2M phase arrest), suggest a drug-mediated activation of a senescence pathway.

Additional bisantrene analogs have been described in T. P. Wunz et al., "New Antitumor Agents Containing the Anthracene Nucleus," *J. Med. Chem.* 30: 1313-1321 (1987), incorporated herein by this reference, including N,N'-bis[2-(dimethylamino)ethyl]-9,10-anthracene-bis(methylamine) and N,N'-bis(1-ethyl-3-piperidinyl)-9,10-anthracene-bis(methylamine).

Another bisantrene analog is the compound known as HL-37 and described in S. Q. Xie et al., "Anti-Tumour Effects of HL-37, a Novel Anthracene Derivative, In-Vivo and In-Vitro," *J. Pharm. Pharmacol.* 60: 213-219 (2008), incorporated herein by this reference. HL-37 is anthracen-9-ylmethylene-[2-methoxyethoxymethylsulfanyl]-5-pyridin-3-yl-[1,2,4]triazol-4-amine and has the structure shown below as Formula (IX):

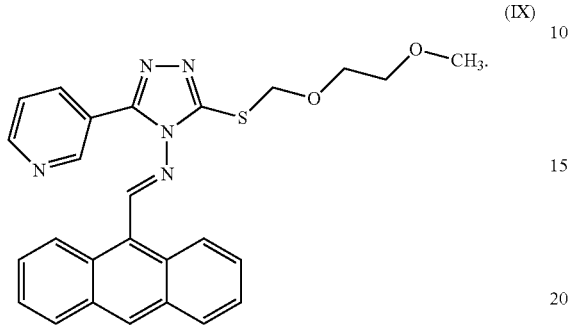

(IX)

Other bisantrene analogs and derivatives are known in the art, including the bisantrene analogs disclosed in J. A. Elliott et al., "Interaction of Bisantrene Anti-Cancer Agents with DNA: Footprinting, Structural Requirements for DNA Unwinding, Kinetics and Mechanism of Binding and Correlation of Structural and Kinetic Parameters with Anti-Cancer Activity," *Anticancer Drug Dis.* 3: 271-282 (1989), incorporated herein by this reference. C. Sissi et al., "DNA-Binding Preferences of Bisantrene Analogs: Relevance to the Sequence Specificity of Drug-Mediated Topoisomerase II Poisoning," *Mol. Pharmacol.* 54: 1036-1045 (1998), incorporated herein by this reference, discloses additional analogs, including an aza-bioisostere that can be considered a bisantrene-amsacrine hybrid. Still other bisantrene analogs and derivatives are disclosed in G. Zagotto et al., "Synthesis, DNA-Damaging and Cytotoxic Properties of Novel Topoisomerase II-Directed Bisantrene Analogues," *Bioorg. Med. Chem. Lett.* 20: 121-126 (1998), incorporated herein by this reference. T. L. Fields et al., "The Synthesis of Heterocyclic Analogs of Bisantrene," *J. Heterocyclic Chem.* 25: 1917-1918 (1988), incorporated herein by this reference, discloses bisguanylhydrazones of anthracene-9,10-dicarboxaldehyde as bisantrene analogs. Bisantrene-amsacrine hybrids are also disclosed in G. Capranico et al., "Mapping Drug Interactions at the Covalent Topoisomerase II-DNA Complex by Bisantrene/Amsacrine Congeners," *J. Biol. Chem.* 273: 12732-12739 (1998), incorporated herein by this reference. These compounds are depicted below as Formulas (X), (XI), (XII), and (XIII):

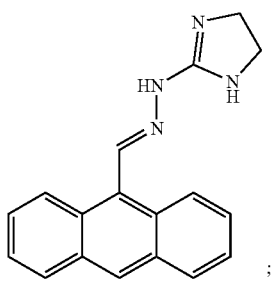

(X)

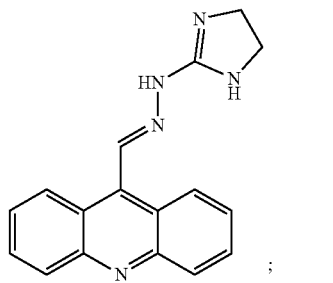

(XI)

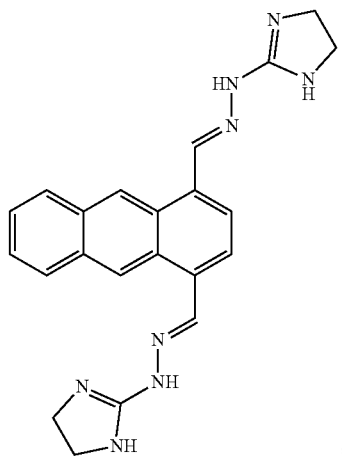

(XII)

; and

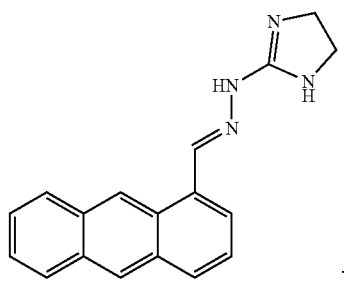

(XIII)

Additional derivatives and analogs of bisantrene include the diphosphoramidic and monophosphoramidic derivatives of bisantrene, disclosed in U.S. Pat. No. 4,900,838 to Murdock and U.S. Pat. No. 5,212,191 to Murdock et al., both of which are incorporated herein by this reference. These compounds are compounds of Formula (XIV):

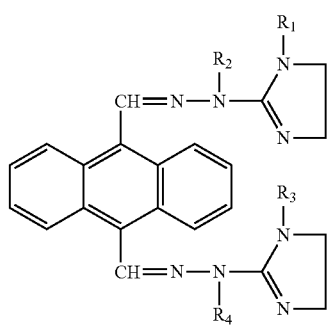

(XIV)

wherein $R_1$ and $R_3$ are the same or different and are hydrogen, $C_1$-$C_6$ alkyl, —C(O)—$R_5$, wherein $R_5$ is hydrogen, $C_1$-$C_6$ alkyl, phenyl, mono-substituted phenyl (wherein the substituent can be ortho, meta, or para and is fluoro, nitro, $C_1$-$C_6$ alkyl, $C_1$-$C_3$ alkoxy, or cyano), pentafluorophenyl, naphthyl, furanyl,

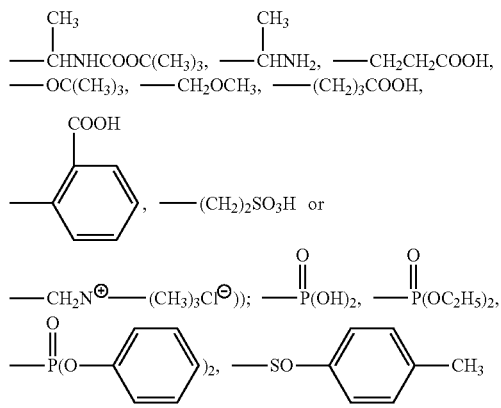

or
—$SO_3H$; wherein only one of $R_1$ and $R_3$ may be hydrogen or $C_1$-$C_6$ alkyl; $R_2$ and $R_4$ are the same or different and are: hydrogen, $C_1$-$C_4$ alkyl or —C(O)—$R_6$, where $R_6$ is hydrogen, $C_1$-$C_6$ alkyl, phenyl, mono-substituted phenyl (wherein the substituent may be in the ortho, meta, or para position and is fluoro, nitro, $C_1$-$C_6$ alkyl, $C_1$-$C_3$ alkoxy, or cyano), pentafluorophenyl, naphthyl, furanyl, or —$CH_2OCH_3$. The compounds can have the schematic structure $B(Q)_n$, wherein B is the residue formed by removal of a hydrogen atom from one or more basic nitrogen atoms of an amine, amidine, guanidine, isourea, isothiourea, or biguanide-containing pharmaceutically active compound, and Q is hydrogen or A, wherein A is

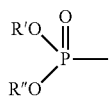

such that R' and R'' are the same or different and are R (where R is $C_1$-$C_6$ alkyl, aryl, aralkyl, heteroalkyl, NC—$CH_2CH_2$—,

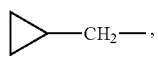

$Cl_3C$—$CH_2$—, or $R_7OCH_2CH_2$—, where $R_7$ is hydrogen or $C_1$-$C_6$ alkyl, hydrogen, or a pharmaceutically acceptable cation or R' and R'' are linked to form a —$CH_2CH_2$— group or a

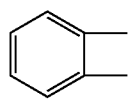

group, and n is an integer representing the number of primary or secondary basic nitrogen atoms in the compound such that at least one Q is A.

Additional bisantrene analogs are disclosed in M. Kozurková et al., "DNA Binding Properties and Evaluation of Cytotoxic Activity of 9,10-Bis-N-Substituted (Aminomethyl)anthracenes," *Int. J. Biol. Macromol.* 41: 415-422 (2007), incorporated herein by this reference. These compounds include 9,10-bis[(2-hydroxyethyl)iminomethyl]anthracene; 9,10-bis{[2-(-2-hydroxyethylamino)ethyl]iminomethyl}anthracene; 9,10-bis{[2-(morpholin-4-yl)ethyl]iminomethyl}anthracene; 9,10-bis[(2-hydroxyethyl)aminomethyl]anthracene; 9,10-bis{[2-(2-hydroxyethylamino)ethyl]aminomethyl}anthracene tetrahydrochloride; 9,10-bis{[2-(piperazin-1-yl)ethyl]aminomethyl}anthracene hexahydrochloride; and 9,10-bis{[2-(morpholin-4-yl)ethyl]aminomethyl}anthracene tetrahydrochloride.

Other analogs and derivatives are known in the art, including derivatives and salt forms of the compounds described above.

This invention relates to novel compositions and methods to improve the utility of chemical agents including bisantrene and derivatives and analogs thereof, as described above, with suboptimal performance for patients with cancer and with other diseases and conditions, including metabolic diseases, immunological diseases, and infectious diseases. The invention describes the novel development of improved pharmaceutical ingredients, dosage forms, excipients, solvents, diluents, drug delivery systems, preservatives, more accurate drug administrations, improved dose determination and schedules, toxicity monitoring and amelioration, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches, the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some cases, the inventive examples include the use of these sub-optimal therapeutics in conjunction with radiation or other conventional chemotherapeutic agents or biotherapeutic agents such as antibodies, vaccines, cytokines, lymphokines, gene and antisense therapies, or other biotherapeutic agents.

By definition, the term "suboptimal therapy" includes agents where Phase I toxicity precluded further human clinical evaluation. It also includes those agents from Phase II trials where inadequate tumor responses were identified. In addition, it also includes those agents, the subject of Phase III clinical trials, whose outcome was either medically or statistically not sufficiently significant to warrant submission or approval by regulatory agencies for commercialization or commercialized agents whose response rates as a monotherapy are inadequate or whose side-effects are severe enough to limit wider utility. Agents with suboptimal activity include but are not limited to the following: bisantrene and analogs and derivatives thereof. More specifically, the inventive methods and compositions also focus on improvements for bisantrene or analogs or derivatives thereof, as described above.

The activity of bisantrene has been described above.

Bisantrene and its analogs and derivatives possess antineoplastic activity through several mechanisms, including, but not necessarily limited to, intercalation in DNA, inhibition of the enzyme topoisomerase II, immune stimulation, and inhibition of telomerase. These activities are described above. Also, as described above, bisantrene and its analogs and derivatives also can activate macrophages.

As used herein, the term "derivative" as applied to bisantrene refers to a compound that has the same carbon skeleton as bisantrene, including the tricyclic aromatic nucleus and the two side chains attached to the tricyclic aromatic nucleus but has one or more substituents as described below that replace at least one hydrogen present in bisantrene with another moiety. As used herein, the term "analog" as applied to bisantrene applies to a compound related structurally to bisantrene but altering one or more of the tricyclic aromatic nucleus or one or more of the side chains, for example, by replacing one or more carbons in the tricyclic aromatic nucleus with nitrogens or by removing or moving one or both of the side chains. Some analogs are described above; others are known to one of skill in the art.

In summary, bisantrene and its derivatives or analogs can be expected to have antineoplastic activity against the following cancers: acute myelogenous leukemia (AML, also called acute non-lymphocytic leukemia, ANLL), lymphoma, ovarian cancer, and breast cancer, especially refractory AML or breast cancer.

Derivatives of bisantrene include, but are not limited to: (1) derivatives of bisantrene in which at least one of the hydrogen atoms bound to the carbon atoms that are directly bound to the tricyclic aromatic nucleus is replaced with lower alkyl; (2) derivatives of bisantrene in which at least one of the hydrogen atoms in the N=NH moiety is replaced with lower alkyl; or (3) derivatives of bisantrene in which at least one of the hydrogen atoms bound to the nitrogens of the five-membered rings are replaced with lower alkyl. Other derivatives of bisantrene are described below.

Analogs of bisantrene include, but are not limited to compounds described above as Formulas (II)-(XIV), as well as additional compounds described above and their derivatives.

As described above, and as detailed more generally below, derivatives and analogs of bisantrene can be optionally substituted with one or more groups that do not substantially affect the pharmacological activity of the derivative or analog. These groups are generally known in the art. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl and naphthyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicyclic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, =O, —$OZ^b$, —$SZ^b$, =S—, —$NZ^cZ^c$, =$NZ^b$, =N—$OZ^b$, trihalomethyl, —$CF_3$, —CN, —OCN, —SCN, —NO, —$NO_2$, =$N_2$, —$N_3$, —$S(O)_2Z^b$, —$S(O)_2NZ^b$, —$S(O)_2O$—, —$S(O_2)OZ^b$, —$OS(O_2)OZ^b$, —$OS(O_2)O$—, —$OS(O_2)OZ^b$, —$P(O)(O^-)_2$, —$P(O)(OZ^b)$ ($O^-$), —$P(O)(OZ^b)(OZ^b)$, —$C(O)Z^b$, —$C(S)Z^b$, —$C(NZ^b)$ $Z^b$, —C(O)O—, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —OC(O)O—, —$OC(O)OZ^b$, —$OC(S)OZ^b$, —$NZ^bC(O)Z^b$, —$NZ^bC(S)Z^b$, —$NZ^bC(O)O^-$, —$NZ^bC(O)OZ^b$, —$NZ^bC(S)OZ^b$, —$NZ^bC$ $(O)NZ^cZ$, —$NZ^bC(NZ^b)Z^b$, —$NZ^bC(NZ^b)NZ^cZ^c$, wherein $Z^a$ is selected from the group consisting of alkyl, cycloalkyl, heteroalkyl, cycloheteroalkyl, aryl, arylalkyl, heteroaryl and heteroarylalkyl; each $Z^b$ is independently hydrogen or $Z^a$; and each $Z^c$ is independently $Z^b$ or, alternatively, the two $Z^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —$NZ^cZ^c$ is meant to include —$NH_2$, —NH-alkyl, —N-pyrrolidinyl, and —N-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-C(O)$OZ^b$, -alkylene-C(O)$NZ^bZ^b$, and —$CH_2$—$CH_2$—C(O)—$CH_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —$Z^a$, halo, —$O^-$, —$OZ^b$, —$SZ^b$, —S—, —$NZ^cZ^c$, trihalomethyl, —$CF_3$, —CN, —OCN, —SCN, —NO, —$NO_2$, —$N_3$, —$S(O)_2Z^b$, —$S(O_2)O$—, —$S(O_2)OZ^b$, —$OS(O_2)OZ^b$, —$OS(O_2)O$—, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —C(O)O—, —C(O) $OZ^b$, —$C(S)OZ^b$, —$C(O)NZ^cZ^c$, —$C(NZ^b)NZ^cZ^c$, —OC (O)$Z^b$, —$OC(S)Z^b$, —OC(O)O—, —$OC(O)OZ^b$, —OC(S) $OZ^b$, —$NZ^bC(O)OZ^b$, —$NZ^bC(S)OZ^b$, —$NZ^bC(O)NZ^cZ$, —$NZ^bC(NZ^b)Z^b$, and —$NZ^bC(NZ^b)NZ^cZ^c$, wherein $Z^a$, $Z^b$, and $Z^c$ are as defined above.

Similarly, substituent groups useful for substituting nitrogen atoms in heteroalkyl and cycloheteroalkyl groups include, but are not limited to, —$Z^a$, halo, —O—, —$OZ^b$, —$SZ^b$, —S—, —$NZ^cZ^c$, trihalomethyl, —$CF_3$, —CN, —OCN, —SCN, —NO, —$NO_2$, —$S(O)_2Z^b$, —$S(O_2)O$—, —$S(O_2)OZ^b$, —$OS(O_2)OZ^b$, —$OS(O_2)O$—, —$P(O)(O^-)_2$, —$P(O)(OZ^b)(O^-)$, —$P(O)(OZ^b)(OZ^b)$, —$C(O)Z^b$, —C(S) $Z^b$, —$C(NZ^b)Z^b$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)OZ^b$, —$OC(S)OZ^b$, —$NZ^bC(O)Z^b$, —$NZ^bC(S)Z^b$, —$NZ^bC(O)$ $OZ^b$, —$NZ^bC(S)OZ^b$, —$NZ^bC(O)NZ^cZ$, —$NZ^bC(NZ^b)Z^b$, and —$NZ^bC(NZ^b)NZ^cZ^c$, wherein $Z^a$, $Z^b$, and $Z^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other stereoisomeric forms) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is a "hydrate." Examples of hydrates include, but are not limited to, hemihydrate, monohydrate, dihydrate, trihydrate, hexahydrate, and other hydrated forms. It should be understood by one of ordinary skill in the art that the pharmaceutically acceptable salt and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolyzable esters of the present compounds are the compounds whose carboxyls are present in the form of hydrolyzable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two double bonds, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. The general term "alkylene" encompasses more specific examples such as "ethylene," wherein n is 2, "propylene," wherein n is 3, and "butylene," wherein n is 4. The hydrocarbyl groups of the alkylene can be optionally substituted as described above.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —$NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the general term "carbocyclyl" encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur, although, in some contexts, "heteroatom" can refer to phosphorus, selenium, or other atoms other than carbon or hydrogen. When it is part of the backbone or skeleton of a chain or ring, a heteroatom must be at least divalent, and will typically be selected from N, O, P, and S.

As used herein, the term "alkanoyl" refers to an alkyl group covalently linked to a carbonyl (C=O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Alk_2$ and -$Alk_1$-N($Alk_2$)(Alk3), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —$S(O)_2$—Ar wherein Ar refers to an aryl group as described above. The term "aryloxyalkylsulfonyl" refers to a group of the structure —$S(O)_2$-Alk-O—Ar, where Alk is an alkyl group as described above and Ar is an aryl group as described above. The term "arylalkylsulfonyl" refers to a group of the structure —$S(O)_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is $CH_3CH_2OC(O)$—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al., incorporated herein by this reference. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

Accordingly, methods and compositions according to the present invention encompass bisantrene derivatives and analogs including one or more optional substituents as defined above, provided that the optionally substituted bisantrene derivative or analog possesses substantially equivalent pharmacological activity to amonafide as defined in terms of either or both topoisomerase II inhibition and DNA intercalation. Methods for determination of topoisomerase II inhibition are known in the art and are described, for example, in A. Constantinou et al., "Novobiocin- and Phorbol-12-Myristate-13-Acetate-Induced Differentiation of Human Leukemia Cells Associates with a Reduction in Topoisomerase II Activity," *Cancer Res.* 49: 1110-1117 (1989), incorporated herein by this reference. Methods for determination of DNA intercalation are known in the art and are described, for example, in H. Zipper et al., "Investigations on DNA Intercalation and Surface Binding by SYBR Green I, Its Structure Determination and Methodological Implications," *Nucl. Acids. Res.* 32(12): e103 (2004), incorporated herein by this reference.

Accordingly, as described in further detail below, one aspect of the present invention is a method to improve the efficacy and/or reduce the side effects of suboptimally administered drug therapy comprising the steps of:

(a) identifying at least one factor or parameter associated with the efficacy and/or occurrence of side effects of the drug therapy, wherein the factor or parameter is additionally associated with at least one of: (i) the specific disease or condition being treated; (ii) the stage of the disease or condition being treated; (iii) selection of an appropriate patient for treatment; (iv) selection of an appropriate phenotype of the patient or the disease or condition being treated; and (v) selection of an appropriate phenotype of the patient or the disease or condition being treated; and (b) modifying the factor or parameter to improve the efficacy and/or reduce the side effects of the drug therapy; wherein the drug therapy comprises administration of bisantrene or a derivative or analog thereof.

As described in further detail below, another aspect of the present invention is a method to improve the efficacy and/or reduce the side effects of suboptimally administered drug therapy comprising the steps of:

(a) identifying at least one factor or parameter associated with the efficacy and/or occurrence of side effects of the drug therapy, wherein the factor or parameter is additionally associated with at least one of: (i) the chemical composition of the drug being administered; (ii) the physical form of the drug being administered or a pharmaceutical composition including the drug being administered; (iii) the makeup of a pharmaceutical composition including the drug being administered; (iv) the specific use of the drug being administered; (v) the target cell, organ, or receptor targeted by the drug being administered; or (vi) additional agents administered with the drug being administered; and (b) modifying the factor or parameter to improve the efficacy and/or reduce the side effects of the drug therapy; wherein the drug therapy comprises administration of bisantrene or a derivative or analog thereof.

As described in further detail below, yet another aspect of the present invention is a method to improve the efficacy and/or reduce the side effects of suboptimally administered drug therapy comprising the steps of:

(a) identifying at least one factor or parameter associated with the efficacy and/or occurrence of side effects of the drug therapy; and (b) modifying the factor or parameter to improve the efficacy and/or reduce the side effects of the drug therapy; wherein the drug therapy comprises administration of bisantrene or a derivative or analog thereof; and wherein the factor or parameter is use of bisantrene or a derivative or analog thereof in a combinatorial regime.

(I) Suboptimal Therapeutics

In general, examples of compounds with suboptimal therapeutic activity may include antimetabolites, DNA/nucleic acid binding/reactive agents, topoisomerase inibitors, anti-tubulin agents, signal transduction inhibitors, protein synthesis inhibitors, inhibitors of DNA transcribing enzymes, DNA/RNA intercalating agents, DNA minor groove binders, drugs that block steroid hormone action, photochemically active agents, immune modifying agents, hypoxia selective cytotoxins, chemical radiation sensitizers and protectors, antisense nucleic acids, oligonucleotide and polynucleotide therapeutic agents, immune modifying agents, antitumor antibiotics, and other classes of therapeutic agents having antineoplastic, antiproliferative, or immune-system-modulating activity. Specific examples include: fluoropyrimidines, thiopurines, inhibitors of nucleoside diphosphate reductase, 2'-deoxyribonucleoside analogs, nucleosides, folic acid analogs, methotrexate, 6-diazo-5-oxo-norleucine, L-asparaginase, N-(phosphoacetyl)-L-aspartic acid, nitrogen mustard, mechlorethamine, chlorambucil, melphalan, cyclophosphamide, estramustine, platinum complexes, nitrosoureas, BCNU, CCNU, streptozotocin, alkyl sulfonates, busulfan, clomesone, triazenylimidazoles and related triazenes, mitozolomide, temozolomide, aziridines, tris(1-aziridinyl)phosphine sulfide, aziridinylphosphines, 3,6,-diaziridinyl-2,5-bis(carboethoxyamino)-1,4-benzoquinone (diaziquone) (AZQ), AZQ analogs, procarbazine, hexamethylamine, topoisomerase I inhibitors, camptothecin, camptothecin analogs, topoisomerase II inhibitors, anthracyclines, doxorubicin, epirubicin, etoposide, DNA intercalating agents, amsacrine, CI-921, 1'-carbamate analogs of amsacrine, 9-aminoacridine-4-carboxamides, acridine carboxamide, tricyclic carboxamides, 1-nitroacridine, acridine derivatives, diacridines, triacridines, podophyllotoxins, ellipticine, merbarone, benzisoquinolinediones, etoposide, teniposide, aminoanthraquinones, inhibitors of DNA-transcribing enzymes, transcription inhibitors, replication inhibitors, RNA replication inhibitors, polymerase inhibitors, rifamycins, actinomycins, DNA minor groove binding compounds, Hoechst 33258, mitomycins, CC-1065, mithramycins, chloromycins, olivomycins, phthalanilides, anthramycins, antimitotic agents, vinca alkaloids, vinblastine and analogs, vincristine and analogs, navelbine, colchicine and analogs, bleomycin and analogs, estramustine, aromatase inhibitors, tamoxifen, LHRH antagonists and analogs, porfimer, hematoporphyrins, electron-affinic oxygen mimetics, nitoaromatics, nitroheterocyclics, nitroimidizaoles, tirapazamine, mitomycins, menadione and analogs, napthoquinones, aziridoquinones, amine oxides, N-oxides, bioreductive agents, bioreductive alkylating agents, metal complexes, radiation sensitizers, radiation protectors, antisense agents, antigene agents, transcription factor inhibitors, ODN complexes, ribozymes, double stranded RNA, antitumor antibiotics, acivicin, aclararubicin, acodazole, acronycine, adozelesin, alanosine, allopurinol, altretamine, aminoglutethimide, amonafide, amsacrine, androgens, anguidine, aphidicolin glycinate, asaley, 5-azacitidine, azathioprine, Baker's Antifol, deoxythioguanosine, bisantrene HCl, bleomycin sulfate, busulfan, buthionine sulfoximine (BSO), BWA 773U82, BW 502U83 HCl, BW 7U85 mesylate, caracemide, carbetimer, carboplatin, carmustine, chlorambucil, chloroquinoxaline sulfonamide, chlorozotocin, chromomycin A3, cisplatin, cladribine, carboplatin, oxaliplatin, rhodamine compounds, corticosteroids, CPT-11, cristanol cyclocytidine, cyclophosphamide, cytarabine, cytembena, dabis maleate, dacarbazine, dactinomycin, daunorubicin HCl, deazauridine, dexrazoxane, dianhydrogalactitol (DAG), dibromodulcitol, didemnin B, diethyldithiocarbamate, diglycoaldehyde, dihydro-5-azacytidine, doxorubicin, echinomycin, edatrexate, edelfosine, eflornithine, elsamitrucin, epirubicin, esorubicin, estramustine phosphate, estrogens, etanidazole, ethiofos, etoposide, fadrazole, fazarabine, fenretinide, finasteride, flavone acetic acid, floxuridine, fludarabine phosphate, 5-fluorouracil, flutamide, gallium nitrate, gemcitabine, goserelin acetate, hepsulfam, hexamethylene bisacetamide, amonafide, hydrazine sulfate, 4-hydroxyandrostenedione, hydroxyurea, idarubicin HCl, ifosfamide, 4-ipomeanol, iproplatin, isotretinoin, leuproloide acetate, levamisole, liposomal daunorubicin, liposomal doxorubicin, lomustine, lonidamine, maytansine, mechloethamine hydrochloride, melphalan, menogaril, 6-mercaptopurine, mesna, methotrexate, N-methylformamide, mifepristone, mitoguazone, mitomycin C, mitotane, mitoxantrone hydrochloride, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, plicamycin, porfimer sodium, predimustine, procarbazine, progestins, pyrazofurin, razoxane, sargramostim, semustine, spirogermanium, streptonigrin, streptozocin, sulofenur, suramin sodium, tamoxifen, taxotere, tegafur, teniposide, terephthalamidine, teroxirone, thioguanine, thiotepa, thymidine, tiazofurin, topotecan, tormifene, treinoin, trifluoroperazine hydrochloride, trifluridine, trimetrexate, uracil mustard, vinblastine sulfate, vincristine sulfate, vindesine, vinorelbine, vinzolidine, Yoshi 864, zorubicin, 2-CI-2'-deoxyadenosine, 3-deazauridine, 4-nitroestrone, 6-methylmercaptopurine riboside, 9-aminocamptothecin, nitrocamptothecin, irinotecan, CPT-11, acivicin, acodazole HCl, ADR-529, ICRF-187, amasacrine, aminothiadiazole, ADTA, antibiotic FR901228, aphidicolin glycinate, azacytidine, AZT, bizelesin, brefeldins, wortmannins, canthardins, bromodeoxyuridines, bryostatin, BSO, CAI, caracemide, carboplatin, chlorosulfaquinoxaline, sulfonamide, cisplatin, clomesone, cyclocytidine HCl, cyclodisone, cyclopentenylcytosine, deoxyspergualin, DHAC, didemnin B, dideoxy-β-fluorouracil, dideoxyadenosine, dideoxyinosine, dihydrotriazine benzene sulfonyl fluoride, dolastatin 10, ecteinascidin 743, etanidazole, ethiofos (WR-2721), fazarabine, flavopiridol, fludarabine phosphate, fostriecin, gallium nitrate, genistein, hepsulfam, HMBA, hydrazine sulfate, iododeoxyuridine, ipomeanol, KNI-272, leucovorin calcium, levamisole, melphalan, menogaril, merbarone, methotrexate, misonidazole, mitoguazone, mitoxantrone HCl, mitozolomide, N-methylformamide, 06-benzylguanine, PALA, pancratistatin, penclomedine, pentamethylmelamine HCl, pentamidine isethionate, pentostatin, perillyl alcohol, phyllanthoside, pibenzimole HCl, piroxantrone, pyrazine diazohydroxide, pyrazoloacridine, quinocarmycins, rebeccamycins, rhizoxin, semustine (methyl CCNU), Taxol, terephthalamidine, teroxirone, thioguanine, thymidine, tiazofurin, TMCA, 5-fluorouracil, methotrexate, cyclophosphamide, ras inhibitors, farnesylation inhibitors, bromodeoxyuridine, tetracycline compounds, arsenic trioxide, combretastatins, 2-methoxyestradiol, thalidomide and analogs, cephalotaxine derivatives, gleevec, stributyrin, triciribine phosphate, trimetrexate, UCN-01, 7-hydroxystaurosporine, uridine, lycurium, ritrosulfan, artemisinin, artesunate, lonidamine, mesna, bromomannitol, hydrazine sulfate, pipobroman, phenesterin, pyrazine diazohydroxide, cytembena, spirogermanium, terephthalamidine, bufalin, dibromodulcitol, gemcitabine, FMDC, colchicine, thiocolchicine, colchicine analogs, LHRH analogs, paclitaxel, MGBG, meisoindigo, indarubin analogs, metformin, phlorizin, and other compounds, including homoharringtonine (HHT).

In particular, this invention is directed to bisantrene and derivatives and analogs thereof as described above.

(II) Dose Modification

Improvements for suboptimal chemotherapeutics including bisantrene and analogs and derivatives thereof are made by alterations to the time that the compound is administered, the use of dose-modifying agents that control the rate of metabolism of the compound, normal tissue protective agents, and other alterations. General examples include: variations of infusion schedules (e.g., bolus i.v. versus continuous infusion), the use of lymphokines (e.g., G-CSF, M-CSF, GM-CSF, EPO) to increase leukocyte count for improved immune response or for preventing anemia caused by myelosuppressive agents, or the use of rescue agents such as leucovorin for 5-FU or thiosulfate for cisplatin treatment. Specific inventive examples for bisantrene and analogs and derivatives thereof include: continuous i.v. infusion for hours to days; biweekly administration; doses greater than 5 mg/m$^2$/day; progressive escalation of dosing from 1 mg/m$^2$/day based on patient tolerance; doses less than 1 mg/m$^2$ for greater than 14 days; use of caffeine to modulate metabolism; use of isoniazid to modulate metabolism; selected and intermittent boost dose administrations; bolus single and multiple doses of 1-5 mg/m$^2$; oral dosing including multiple daily dosing; micro dosing, immediate release dosing; slow release dosing; or controlled release dosing.

(III) Route of Administration

Improvements for suboptimal chemotherapeutics including bisantrene and analogs and derivatives thereof are made by alterations in the route by which the compound is administered. General examples include: changing route from oral to intravenous administration and vice versa; or the use of specialized routes such as subcutaneous, intramuscular, intra-arterial, intraperitoneal, intralesional, intralymphatic, intratumoral, intrathecal, intravesicular, intracranial. Specific inventive examples for bisantrene and analogs and derivatives thereof include: central venous administration; intraperitoneal administration; intravenous administration; intravesicular administration for bladder cancer; intrathecal administration; intra-arterial administration; continuous infusion; or intermittent infusion. Particularly significant routes of administration for bisantrene and analogs and derivatives thereof include central venous administration, intraperitoneal administration, and intravenous administration.

(IV) Schedule of Administration

Improvements for suboptimal chemotherapeutics including bisantrene and analogs and derivatives thereof are made by alterations to the time that the compound is administered. General examples include: changing from a monthly administration to a weekly or daily dosing or variations of the schedule. Specific inventive examples for bisantrene and analogs and derivatives thereof include: administration to avoid anaphylaxis; daily administration; weekly administration for three weeks; weekly administration for two weeks; biweekly administration; biweekly administration for three weeks with a 1-2 week rest period; intermittent boost dose administration; or administration daily for one week then once per week for multiple weeks. Particularly significant schedules of administration for bisantrene and analogs and derivatives thereof include a schedule of administration to avoid anaphylaxis.

(V) Indications for Use

Improvements for suboptimal chemotherapeutics including bisantrene and analogs and derivatives thereof are made by alterations in the types of disease or the clinical stage of disease for which the compound is administered. General examples include: the use of solid tumor agents for leukemias and vice versa, the use of antitumor agents for the treatment of benign hyperproliferative disease such as psoriasis or benign prostate hypertrophy, metabolic diseases, immunological diseases or infection. Specific inventive examples for bisantrene and analogs and derivatives thereof include: use for the treatment of refractory breast cancer; use for the treatment of triple-negative breast cancer; use for the treatment of acute leukemias, including, but not limited to, acute myelocytic leukemia (AML); use for treatment of acute leukemias of childhood, including acute myelocytic leukemia (AML) and acute lymphocytic leukemia (ALL); use for treatment of myelodysplastic syndrome; use for treatment of chronic myelocytic leukemia (CML), either subsequent to or in combination with the administration of tyrosine kinase inhibitors or homoharringtonine; use for treatment of chronic lymphocytic leukemia; use for treatment of ovarian cancer; use for treatment of lymphoma including Hodgkin's lymphoma and non-Hodgkin's lymphoma; use for treatment of mycosis fungoides; use for treatment of prostate cancer, especially androgen-resistant prostate cancer; use for treatment of lung small-cell carcinoma, either subsequent to or in combination with the administration of EGFR inhibitors such as erlotinib (Tarceva) or gefitinib (Iressa), wherein the lung small cell carcinoma is characterized by either wild-type or mutated EGFR; use for treatment of lung non-small cell carcinoma, subsequent to or in combination with EGFR inhibitors such as erlotinib or gefitinib, wherein the lung non-small cell carcinoma is characterized by either wild-type or mutated EGFR; use for treatment of breast cancer characterized by overexpressed Her-2-neu; use for treatment of glioblastoma that is resistant to one or both of the following therapeutic agents: temozolomide (Temodar) or bevacizumab (Avastin), or is characterized by EGFR variant III, either alone or in combination with other therapeutic agents; use for treatment of malignancies characterized by overexpressed topoisomerase II; or use for treatment of malignancies characterized by overexpressed and/or mutated EGFR. Particularly significant indications for use for bisantrene and analogs and derivatives thereof include refractory breast cancer, triple-negative breast cancer, acute myelocytic leukemia, and acute leukemias of childhood, including ALL and AML.

(VI) Disease Stages

Improvements for suboptimal chemotherapeutics including bisantrene and analogs and derivatives thereof are made by alterations in the stage of disease at diagnosis/progression that the compound is administered. General examples include: the use of chemotherapy for non-resectable local disease, prophylactic use to prevent metastatic spread or inhibit disease progression or conversion to more malignant stages. Specific inventive examples for bisantrene and analogs and derivatives thereof include: use for the treatment of localized polyp stage colon cancer; use for the treatment of leukoplakia in the oral cavity; use to induce angiogenesis inhibition to prevent or limit metastatic spread; or use against HIV with AZT, DDI, or reverse transcriptase inhibitors.

(VII) Other Indications

Improvements for suboptimal chemotherapeutics including bisantrene and analogs and derivatives thereof are made by using the compound for non-malignant diseases and conditions. General examples include: premalignant conditions, benign hyperproliferative conditions, treatment of infections, treatment of parasitic infections, usage to relieve pain, use for control of pleural effusions. Specific inventive examples for bisantrene and analogs and derivatives thereof include: use as an anti-infective agent; use as an antiviral agent; use as an antibacterial agent; use for control of pleural effusions; use as an antifungal agent; use as an antiparasitic agent; use for treatment of eczema; use for treatment of shingles; use for treatment of condylomata; use for treatment of human papilloma virus (HPV); or use for treatment of herpes simplex virus (HSV).

(VIII) Patient Selection

Improvements for suboptimal chemotherapeutics including bisantrene and analogs and derivatives thereof are made by alterations to the type of patient that would best tolerate or benefit from the use of the compound. General examples include: use of pediatric doses for elderly patients, altered doses for obese patients; exploitation of co-morbid disease conditions such as diabetes, cirrhosis, or other conditions that may uniquely exploit a feature of the compound. Specific inventive examples for bisantrene and analogs and derivatives thereof include: patients with disease conditions with high levels of metabolic enzymes such as histone deacetylase, protein kinases, ornithine decarboxylase; patients with disease conditions with low levels of metabolic enzymes such as histone deacetylase, protein kinases, or ornithine decarboxylase; patients with low or high susceptibility to thrombocytopenia or neutropenia; patients intolerant of GI toxicities; patients characterized by over- or under-expression of jun, GPCRs, signal transduction proteins, VEGF, prostate specific genes, protein kinases, or telomerase; patients selected by immune screening; patients selected by DNA methylation screening.

(IX) Patient/Disease Phenotype

Improvements for suboptimal chemotherapeutics including substituted naphthalimides such as bisantrene and analogs and derivatives thereof are made by more precise identification of a patient's ability to tolerate, metabolize and exploit the use of the compound. General examples include: use of diagnostic tools and kits to better characterize a patient's ability to process/metabolize a chemotherapeutic agent or the patient's susceptibility to toxicity caused by potential specialized cellular, metabolic, or organ system phenotypes. Specific inventive examples for bisantrene and analogs and derivatives thereof include: use of a diagnostic tool, a diagnostic technique, a diagnostic kit, or a diagnostic assay to confirm a patient's particular phenotype; use of a method for measurement of a marker selected from the group consisting of histone deacetylase, ornithine decarboxylase, VEGF, a protein that is a gene product of a prostate specific gene, a protein that is a gene product of jun, and a protein kinase; surrogate compound dosing; low dose pre-testing for enzymatic status; determination of the multidrug resistance activity of cells; determining expression or activation of a signaling or metabolic protein, where an alteration in the level of expression or activation of the signaling or metabolic protein indicates the therapeutic potential of a chemotherapeutic agent; detection or assay of expression of biomarkers indicating sensitivity to apoptosis-inducing agents; use of an in vitro human tumor clonal assay to determine patients with enhanced responses; or use of an immunohistochemical assay to determine overexpression of HIF-1α. Particularly significant patient/disease phenotypes for bisantrene and analogs and derivatives thereof include patients with an enhanced response in an in vitro human tumor clonal assay and the quantity or activity of topoisomerase 2β present in cardiac cells.

(X) Patient/Disease Genotype

Improvements for suboptimal chemotherapeutics including bisantrene and analogs and derivatives thereof are made by testing and analyzing a patient's genotype for unique features that may be of value to predict efficacy, toxicity, metabolism, or other parameters relevant to therapeutic use of the suboptimal therapeutic. General examples include: biopsy samples of tumors or normal tissues (e.g., white blood cells) may be taken and analyzed to specifically tailor or monitor the use of a particular drug against a gene target; analysis of unique tumor gene expression pattern, SNP's (single nucleotide polymorphisms), to enhance efficacy or to avoid particular drug-sensitive normal tissue toxicities. Specific inventive examples for bisantrene and analogs and derivatives thereof include: genetic tests to determine the absence or nonfunctionality of ABCG2; genetic tests to determine the presence or functionality of FABP7; diagnostic tools, techniques, kits and assays to confirm a patient's particular genotype; gene/protein expression chips and analysis; Single Nucleotide Polymorphisms (SNP's) assessment; SNP's for histone deacetylase, ornithine decarboxylase, GPCR's, protein kinases, telomerase, jun; identification and measurement of metabolism enzymes and metabolites; determination of the presence of one or more specific genetic variants of the MDR1 gene associated with increased efficacy of an antineoplastic drug transported by MDR1 protein; identification of one or more biomarkers associated with sensitivity or resistance to bisantrene, derivatives or analogs thereof, or other intercalating agents or topoisomerase II inhibitors; presence of single nucleotide polymorphisms rs229109 and rs72552784 associated with sensitivity to bisantrene; or genetic abnormalities associated with acute myeloid leukemia. Particularly significant examples of patient/disease genotypes for bisantrene and analogs and derivatives thereof include the absence or nonfunctionality of ABCG2; the presence or functionality of FABP7; the presence of single nucleotide polymorphisms rs229109 and rs72552784 associated with sensitivity to bisantrene; or genetic abnormalities associated with acute myeloid leukemia. Genetic abnormalities associated with acute myeloid leukemia are disclosed in C. C. Kumar, "Genetic Abnormalities and Challenges in the Treatment of Acute Myeloid Leukemia," Genes & *Cancer* 2: 95-107 (2011), incorporated herein by this reference, and include, but are not limited to, the following genomic abnormalities: (i) t(8; 21); (ii) t(15,17); (iii) inv(16); (iv) der(11q23); (v) t(9; 22); (vi) t(6; 9); (vii) t(1; 22); (viii) t(8,16); (ix) t(7; 11); (x) t(12,22); (xi) inv(3); and (xii) t(16,21), leading to the following oncofusion proteins: (i) AML1-ETO; (ii) PML-RARα; (iii) CBFβ-MYH11; (iv) MLL fusions; (v) BCR-ABL1; (vi) DEK-CAN; (vii) OTT-MAL; (viii) MOZ-CPA; (ix) NUP98-HOXA9; (x) MN1-TEL; (xi) RPN1-EVI1; and (xii) FUS-ERG. Additionally, gene mutations have been found to occur in AML, including, but not limited to, mutations in KIT, FLT3, NRAS, KRAS, MML, BAAL, WT-1, CEBPα, NPM1, DNMT3A, and IDH1.

(XI) Pre-/Post-Treatment Preparation

Improvements for suboptimal chemotherapeutics including bisantrene and analogs and derivatives thereof are made by specialized preparation of a patient prior to or after the use of a chemotherapeutic agent. General examples include: induction or inhibition of metabolizing enzymes, specific protection of sensitive normal tissues or organ systems. Specific inventive examples for bisantrene and analogs and derivatives thereof include: the use of colchicine or an analog thereof; the use of a uricosuric; the use of uricase; the non-oral use of nicotinamide; the use of a sustained-release form of nicotinamide; the use of an inhibitor of poly-ADP ribose polymerase; the use of caffeine; the use of leucovorin rescue; infection control; or the use of an anti-hypertensive agent.

(XII) Toxicity Management

Improvements for suboptimal chemotherapeutics including bisantrene and analogs and derivatives thereof are made by use of additional drugs or procedures to prevent or reduce potential side-effects or toxicities. General examples include: the use of anti-emetics, anti-nausea agents, hematological support agents to limit or prevent neutropenia, anemia, thrombocytopenia, vitamins, antidepressants, treatments for sexual dysfunction, or use of other agents or methods to reduce potential side effects or toxicities. Specific inventive examples for bisantrene and analogs and derivatives thereof include: the use of colchicine or analogs; the use of uricosurics such as probenecid; the use of diuretics; the use of uricase; non-oral use of nicotinamide; use of sustained release forms of nicotinamide; use of inhibitors of poly-ADP ribose polymerase; the use of caffeine; leucovorin rescue; the use of sustained release allopurinol; non-oral use of allopurinol; administration of bone marrow transplant stimulants, blood, platelet infusions, Neupogen, G-CSF; or GM-CSF; pain management; infection control; administration of anti-inflammatories; administration of fluids; administration of corticosteroids; administration of insulin control medications; administration of antipyretics; administration of anti-nausea treatments; administration of anti-diarrhea treatments; administration of antihistamines as pre-treatment to prevent anaphylaxis; administration of agents for reduction of gastric toxicity; administration of steroids as pre-treatment to prevent anaphylaxis; administration of sympathetomimetics as pre-treatment to prevent anaphylaxis; and administration of an agent to control or prevent chemotherapy-induced thrombocytopenia.

(XIII) Pharmacokinetic/Pharmacodynamic Monitoring

Improvements for suboptimal chemotherapeutics including bisantrene and analogs and derivatives thereof are made by the use of monitoring drug levels after dosing in an effort to maximize a patient's drug plasma level, to monitor the generation of toxic metabolites, or to monitor of ancillary medicines that could be beneficial or harmful in terms of drug-drug interactions. General examples include: the monitoring of drug plasma protein binding, the monitoring of specific metabolites or breakdown products, or other products of biotransformation. Specific inventive examples for bisantrene and analogs and derivatives thereof include: multiple determinations of drug plasma levels; multiple determinations of metabolites in the blood or urine; monitoring of immune function; use of ELISPOT to measure immune responses; determination of surface marker upregulation; or monitoring of checkpoint inhibition.

(XIV) Drug Combinations

Improvements for suboptimal chemotherapeutics including bisantrene and analogs and derivatives thereof are made by exploiting unique drug combinations that may provide a more than additive or synergistic improvement in efficacy or side-effect management. General examples include: alkylating agents with anti-metabolites, topoisomerase inhibitors with antitubulin agents. Specific inventive examples for bisantrene and analogs and derivatives thereof include: use with fraudulent nucleosides; use with fraudulent nucleotides; use with thymidylate synthetase inhibitors; use with signal transduction inhibitors; use with cisplatin or platinum analogs; use with alkylating agents; use with anti-tubulin agents; use with antimetabolites; use with berberine; use with apigenin; use with colchicine and analogs; use with genistein; use with etoposide; use with cytarabine; use with camptothecins; use with vinca alkaloids, including vinblastine; use with topoisomerase inhibitors; use with 5-fluorouracil; use with curcumin; use with rosmarinic acid; use with mitoguazone; use with meisoindigo; use with imatinib; use with dasatinib; use with nilotinib; use with epigenetic modulators; use with transcription factor inhibitors; use with taxol; use with homoharringtonine; use with pyridoxal; use with spirogermanium; use with caffeine; use with nicotinamide; use with methylglyoxalbisguanylhydrazone; use with epidermal growth factor receptor (EGFR) inhibitors; use with poly-ADP ribose polymerase (PARP) inhibitors; use with Bruton's tyrosine kinase (BTK) inhibitors; use with bis-[thio-hydrazide] amides; use with succinimide or maleimide derivatives as inhibitors of topoisomerase II; use with HDAC inhibitors; use with immunostimulants; use with inhibitors of telomerase; use with agents that inhibit the expression or activity of Her2; use with agents that inhibit the expression or activity of estrogen receptors; use with agents that inhibit the expression or activity of antigens associated with specific tumor targets, such as CT antigens; use with G-quadruplex ligands; use with polycyclic lysophosphatidic receptor antagonists; use with anti-CTGF agents; use with myeloid differentiation inducing agents; use with covalent diabodies binding to a tumor-associated antigen; use with bispecific antibodies that have a cell-penetrating determinant and an intracellular target-binding determinant; use with multidomain molecules that comprise a cell binding ligand that binds to cells in the tumor stroma such as endothelial cells, fibroblasts, or immune cells and an oligonucleotide that inhibits the nonsense-mediated decay pathway; use with tumor-specific antibodies binding to a portion of the CD44 protein or a binding protein derived from the light-chain or heavy-chain complementary-determining regions of such antibodies; use with inhibitors of CXCR4; use with pyruvate dehydrogenase kinase (PDK1) inhibitors; use with epherin receptor targeting agents; use with binding proteins for Axl; use with Wnt pathway inhibitors together with MAPK pathway inhibitors; use with TEC family kinase inhibitors; use with substituted macrocyclic compounds with proteasome activity; use with peptide-based PACE4 inhibitors; use with azaindole derivatives as JAK3 inhibitors; use with inhibitors of Myc; use with inhibitors of furin and other pro-protein convertases; use with GPBP-1 inhibitors, optionally together with a p21 inhibitor; or use with $PGE_2$ inhibitors. Particularly significant examples of drug combinations for bisantrene and analogs and derivatives thereof include the use with cytarabine in acute leukemias of childhood (AML and ALL); use with survivin inhibitors or modulators, described below; use with $PGE_2$ inhibitors; or use with activatable antibodies targeting tumor specific markers.

(XV) Chemosensitization

Improvements for suboptimal chemotherapeutics including bisantrene and analogs and derivatives thereof are made by exploiting them as chemosensitizers where no measureable activity is observed when used alone but in combination with other therapeutics a more than additive or synergistic improvement in efficacy is observed. General examples include: misonidazole with alkylating agents, tirapazamine with cisplatin. Specific inventive examples for bisantrene and analogs and derivatives thereof include: as a chemosensitizer in combination with topoisomerase inhibitors; as a chemosensitizer in combination with fraudulent nucleosides; as a chemosensitizer in combination with fraudulent nucleotides; as a chemosensitizer in combination with thymidylate synthetase inhibitors; as a chemosensitizer in combination with signal transduction inhibitors; as a chemosensitizer in combination with cisplatin or platinum analogs; as a chemosensitizer in combination with alkylating agents; as a chemosensitizer in combination with anti-tubulin agents; as a chemosensitizer in combination with antimetabolites; as a chemosensitizer in combination with berberine; as a chemosensitizer in combination with apigenin; as a chemosensitizer in combination with colchicine or analogs of colchicine; as a chemosensitizer in combination with genistein; as a chemosensitizer in combination with etoposide; as a chemosensitizer in combination with cytarabine; as a chemosensitizer in combination with camptothecins; as a chemosensitizer in combination with vinca alkaloids; as a chemosensitizer in combination with 5-fluorouracil; as a chemosensitizer in combination with curcumin; as a chemosensitizer in combination with rosmarinic acid; or as a chemosensitizer in combination with mitoguazone.

(XVI) Chemopotentiation

Improvements for suboptimal chemotherapeutics including bisantrene and analogs and derivatives thereof are made by exploiting them as chemopotentiators where minimal therapeutic activity is observed alone but in combination with other therapeutics a more than additive or synergistic improvement in efficacy is observed. General examples include: dibromodulcitol with fraudulent nucleosides or fraudulent nucleotides. Specific inventive examples for bisantrene and analogs and derivatives thereof include: as a chemopotentiator in combination with fraudulent nucleosides; as a chemopotentiator in combination with fraudulent nucleotides; as a chemopotentiator in combination with thymidylate synthetase inhibitors; as a chemopotentiator in combination with signal transduction inhibitors; as a chemopotentiator in combination with cisplatin or platinum analogs; as a chemopotentiator in combination with alkylating agents; as a chemopotentiator in combination with anti-tubulin agents; as a chemopotentiator in combination with antimetabolites; as a chemopotentiator in combination with berberine; as a chemopotentiator in combination with apigenin; as a chemopotentiator in combination with colchicine or analogs of colchicine; as a chemopotentiator in combination with genistein; as a chemopotentiator in combination with etoposide; as a chemopotentiator in combination with cytarabine; as a chemopotentiator in combination with camptothecins; as a chemopotentiator in combination with vinca alkaloids; as a chemopotentiator in combination with topoisomerase inhibitors; as a chemopotentiator in combination with 5-fluorouracil; as a chemopotentiator in combination with curcumin; as a chemopotentiator in combination with rosmarinic acid; or as a chemopotentiator in combination with mitoguazone.

(XVII) Post-Treatment Patient Management

Improvements for suboptimal chemotherapeutics including bisantrene and analogs and derivatives thereof are made by drugs, treatments and or diagnostics to allow for the maximum benefit to patients treated with a compound. General examples include: pain management, nutritional support, anti-emetics, anti-nausea therapies, anti-anemia therapy, anti-inflammatories, growth factors. Specific inventive examples for bisantrene and analogs and derivatives thereof include: use with therapies associated with pain management; nutritional support; anti-emetics; anti-nausea therapies; anti-anemia therapy; anti-inflammatories: antipyretics; immune stimulants; or growth factors.

(XVIII) Alternative Medicine/Therapeutic Support

Improvements for suboptimal chemotherapeutics including bisantrene and analogs and derivatives thereof are made by the use of unapproved/non-conventional therapeutics or methods to enhance effectiveness or reduce side effects. General examples include: hypnosis, acupuncture, meditation, herbal medications and extracts, applied kinesiology. Specific inventive examples for bisantrene and analogs and derivatives thereof include: hypnosis; acupuncture; meditation; herbal medications created either synthetically or through extraction including natural anti-inflammatories (including rhein or parthenolide); immunostimulants (such as those found in *Echinacea*); antimicrobials (such as berberine); flavonoids, isoflavones, and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); or applied kinesiology.

(XIX) Bulk Drug Product Improvements

Improvements for suboptimal chemotherapeutics including bisantrene and analogs and derivatives thereof are made by alterations in the pharmaceutical bulk substance. General examples include: salt formation, homogeneous crystalline structure, pure isomers. Specific inventive examples for bisantrene and analogs and derivatives thereof include: free base form; salt formation; homogeneous crystalline structure; amorphous structure; pure isomers; increased purity; or lower residual solvents and heavy metals.

(XX) Diluent Systems

Improvements for suboptimal chemotherapeutics including bisantrene and analogs and derivatives thereof are made by alterations in the diluents used to solubilize and deliver/present the compound for administration. General examples include: Cremophor-EL, cyclodextrins for poorly water soluble compounds. Specific inventive examples for bisantrene and analogs and derivatives thereof include: use of emulsions; dimethylsulfoxide (DMSO); N-methylformamide (NMF); dimethylformamide (DMF); dimethylacetamide (DMA); ethanol; benzyl alcohol; dextrose-containing water for injection; Cremophor; cyclodextrins; or PEG.

(XXI) Solvent Systems

Improvements for suboptimal chemotherapeutics including bisantrene and analogs and derivatives thereof are made by alterations in the solvents used or required to solubilize a compound for administration or for further dilution. General examples include: ethanol, dimethylacetamide (DMA). Specific inventive examples for bisantrene and analogs and derivatives thereof include: the use of emulsions; DMSO; NMF; DMF; DMA; ethanol; benzyl alcohol; dextrose-containing water for injection; Cremophor; PEG; or salt systems.

(XXII) Excipients

Improvements for suboptimal chemotherapeutics including bisantrene and analogs and derivatives thereof are made by alterations in the materials/excipients, buffering agents, or preservatives required to stabilize and present a chemical compound for proper administration. General examples include: mannitol, albumin, EDTA, sodium bisulfite, benzyl alcohol. Specific inventive examples for bisantrene and analogs and derivatives thereof include: the use of mannitol; the use of albumin; the use of EDTA; the use of sodium bisulfite; the use of benzyl alcohol; the use of carbonate buffers; the use of phosphate buffers; the use of polyethylene glycol (PEG); the use of vitamin A; the use of vitamin D; the use of vitamin E; the use of esterase inhibitors; the use of cytochrome P450 inhibitors; the use of multi-drug resistance (MDR) inhibitors; the use of organic resins; or the use of detergents.

(XXIII) Dosage Forms

Improvements for suboptimal chemotherapeutics are made by alterations in the potential dosage forms of the compound dependent on the route of administration, duration of effect, plasma levels required, exposure to normal tissues potentially resulting in side effects, and exposure to metabolizing enzymes. General examples include: tablets, capsules, topical gels, creams, patches, suppositories. Specific inventive examples for bisantrene or derivatives or analogs thereof include: the use of tablets; the use of capsules; the use of topical gels; the use of topical creams; the use of patches; the use of suppositories; the use of lyophilized dosage fills; the use of immediate-release formulations; the use of slow-release formulations; the use of controlled-release formulations; the use of liquid in capsules; or the use of liposomal formulations.

(XXIV) Dosage Kits and Packaging

Improvements for suboptimal chemotherapeutics including bisantrene and analogs and derivatives thereof are made by alterations in the dosage forms, container/closure systems, accuracy of mixing and dosage preparation and presentation. General examples include: amber vials to protect from light, or stoppers with specialized coatings. Specific inventive examples for bisantrene and analogs and derivatives thereof include: the use of amber vials to protect from light; and stoppers with specialized coatings to improve shelf-life stability. Other forms of dosage kits and packaging are also known in the art and can include, for example, vials, ampules, jars, intravenous bags, or other containers.

(XXV) Drug Delivery Systems

Improvements for suboptimal chemotherapeutics including bisantrene and analogs and derivatives thereof are made by the use of delivery systems to improve the potential attributes of a pharmaceutical product such as convenience, duration of effect, or reduction of toxicities. General examples include: nanocrystals, bioerodible polymers, liposomes, slow release injectable gels, microspheres. Specific inventive examples for bisantrene and analogs and derivatives thereof include: the use of oral dosage forms; the use of nanocrystals; the use of nanoparticles; the use of cosolvents; the use of slurries; the use of syrups; the use of bioerodible polymers; the use of liposomes; the use of slow release injectable gels; the use of microspheres; the use of amphiphilic block copolymer systems; the use of emulsion vehicles comprising an emulsion of α-tocopherol stabilized by biocompatible surfactants; the use of biodegradable polymer compositions containing phosphorus and desaminotyrosyl L-tyrosine linkages in the polymer backbone; the use of substantially anhydrous injectable semi-solid compositions comprising a water immiscible fatty acid matrix and a cytostatic agent; the use of lipophilic vehicles; the use of pH-dependent carriers that include a compound that includes at least one ionizable group; the use of pH-dependent carriers that include a monocarboxylic acid having at least 8 carbons and less than about 10% by weight of zwitterionic phospholipids; the use of liposomes comprising the bisantrene or the derivative or analog thereof followed by administration of a lipid nanoparticle comprising a triggering agent; or the use of nonpegylated liposomes.

(XXVI) Drug Conjugate Forms

Improvements for suboptimal chemotherapeutics including bisantrene and analogs and derivatives thereof are made by alterations to the parent molecule with covalent, ionic, or hydrogen bonded moieties to alter the efficacy, toxicity, pharmacokinetics, metabolism, or route of administration. General examples include: polymer systems such as polyethylene glycols, polylactides, polyglycolides, amino acids, peptides, multivalent linkers, albumin conjugates. Specific inventive examples for bisantrene and analogs and derivatives thereof include: the use of polymer systems such as polyethylene glycols; the use of polylactides; the use of polyglycolides; the use of amino acids; the use of peptides; the use of multivalent linkers; the use of conjugates to fatty acids; the use of conjugates to fatty alcohols; the use of conjugates to elastin-like peptide; the use of conjugates with polyclonal or monoclonal antibodies, proteins, or peptides; the use of conjugates with cell-binding agents through a charged or pro-charged cross-linker; the use of conjugates to antibodies targeted to tumor markers; the use of biodegradable polymer-bioactive moiety conjugates; the use of conjugates with 2-nitroimidazole compounds with a secondary basic nitrogen atom and a linker; the use of conjugates with ladder frame polyether compounds, including those derived from brevenal, brevisin, tamulamide, brevetoxins, hemibrevetoxins, gambierols, and gambieric acids; the use of conjugates to antibodies having one or more non-natural amino acid residues at specific positions in the heavy or light chains; the use of conjugates to a sialoadhesin binding moiety; the use of pheophorbide-α conjugates to bisantrene or a derivative or analog thereof; the use of conjugates to multi-component nanochains; the use of conjugates to activatable antibodies that include a masking moiety, a cleavable moiety, and an antibody binding specifically to interleukin-6; the use of conjugates including hydrophilic linkers; the use of conjugates to antibodies specific for p97; the use of conjugates including a modified amino acid incorporating an azido group; the use of albumin conjugates; or the use of conjugates to folate.

(XXVII) Compound Analogs

Improvements for suboptimal chemotherapeutics including bisantrene and analogs and derivatives thereof are made by alterations to the parent structure of a molecule with additional chemical functionalities that may alter efficacy, reduce toxicity, improve pharmacological performance, be compatible with a particular route of administration, or alter the metabolism of the therapeutic agent. General examples include: alteration of side chains to increase or decrease lipophilicity; additional chemical functionalities to alter reactivity, electron affinity, or binding capacity; salt forms; conjugates to albumin. Specific inventive examples for bisantrene and analogs and derivatives thereof include: alteration of side chains to increase or decrease lipophilicity; additional chemical functionalities to alter reactivity, electron affinity, or binding capacity; salt forms; conjugates to albumin.

(XXVIII) Prodrugs

Improvements for suboptimal chemotherapeutics including bisantrene and analogs and derivatives thereof are made by alterations to the molecule such that improved pharmaceutical performance is gained with a variant of the active molecule in that after introduction into the body a portion of the molecule is cleaved to reveal the preferred active molecule. General examples include: enzyme sensitive esters, dimers, Schiff bases. Specific inventive examples for bisantrene and analogs and derivatives thereof include: the use of enzyme sensitive esters; the use of dimers; the use of Schiff bases; the use of pyridoxal complexes; the use of caffeine complexes; the use of plasmin-activated prodrugs; the use of a drug targeting complex comprising a targeting carrier molecule that is selectively distributed to a specific cell type or tissue containing the specific cell type, a linker which is acted upon by a molecule that is present at an effective concentration in the environs of the specific cell type, and a therapeutically active agent to be delivered to the specific cell type; or the use of a prodrug molecule comprising a conjugate of bisantrene or a derivative or analog of bisantrene, a protease-specific cleavable peptide, and optionally, a targeting peptide, with the prodrug molecule being substantially inactive prior to degradation of the protease-specific cleavable peptide by a proteolytic enzyme within or in close proximity to the cancer cell.

(XXIX) Multiple Drug Systems

Improvements for suboptimal chemotherapeutics including bisantrene and analogs and derivatives thereof are made by the use of additional compounds, such as therapeutic or biological agents that when administered in the proper fashion, a unique and beneficial effect can be realized. General examples include: inhibitors of multi-drug resistance, specific drug resistance inhibitors, specific inhibitors of selective enzymes, signal transduction inhibitors, repair inhibition. Specific inventive examples for bisantrene and analogs and derivatives thereof include the use of bisantrene or analogs and derivatives thereof with: the use of inhibitors of multi-drug resistance; the use of specific drug resistance inhibitors; the use of specific inhibitors of selective enzymes; the use of signal transduction inhibitors; the use of meisoindigo; the use of imatinib; the use of hydroxyurea; the use of dasatinib; the use of capecitabine; the use of nilotinib; the use of repair inhibition; the use of topoisomerase inhibitors with non-overlapping side effects; PARP inhibitors; EGFR inhibitors; or HDAC inhibitors.

(XXX) Biotherapeutic Enhancement

Improvements for suboptimal chemotherapeutics including bisantrene and analogs and derivatives thereof are made by its use in combination as sensitizers/potentiators with biological response modifiers. General examples include: use in combination as sensitizers/potentiators with biological response modifiers, cytokines, lymphokines, therapeutic antibodies, antisense therapies, gene therapies. Specific inventive examples for bisantrene and analogs and derivatives thereof include: use in combination as sensitizers/potentiators with biological response modifiers; use in combination as sensitizers/potentiators with cytokines; use in combination as sensitizers/potentiators with lymphokines; use in combination as sensitizers/potentiators with therapeutic antibodies; use in combination as sensitizers/potentiators with antisense therapies; use in combination as sensitizers/potentiators with gene therapies; use in combination as sensitizers/potentiators with ribozymes; use in combination as sensitizers/potentiators with RNA interference; use in combination with vaccines (cellular or non-cellular); or use in combination with stem cells.

(XXXI) Biotherapeutic Resistance Modulation

Improvements for suboptimal chemotherapeutics including bisantrene and analogs and derivatives thereof are made by exploiting their selective use to overcome developing or complete resistance to the efficient use of biotherapeutics. General examples include: tumors resistant to the effects of biological response modifiers, cytokines, lymphokines, therapeutic antibodies, antisense therapies, gene therapies. Specific inventive examples for bisantrene and analogs and derivatives thereof include: use against tumors resistant to the effects of biological response modifiers; use against tumors resistant to the effects of cytokines; use against tumors resistant to the effects of lymphokines; use against tumors resistant to the effects of therapeutic antibodies; use against tumors resistant to the effects of antisense therapies; use against tumors resistant to the effects of gene therapies; use against tumors resistant to the effects of ribozymes; or use against tumors resistant to the effects of RNA interference.

(XXXII) Radiation Therapy Enhancement

Improvements for suboptimal chemotherapeutics including bisantrene and analogs and derivatives thereof are made by exploiting their use in combination with ionizing radiation, phototherapies, heat therapies, radio-frequency generated therapies. General examples include: hypoxic cell sensitizers, radiation sensitizers/protectors, photosensitizers, radiation repair inhibitors. Specific inventive examples for bisantrene and analogs and derivatives thereof include: use with hypoxic cell sensitizers; use with radiation sensitizers/protectors; use with photosensitizers; use with radiation repair inhibitors; use with thiol depletion; use with vaso-targeted agents; use with radioactive seeds; use with radionuclides; use with radiolabeled antibodies; use with brachytherapy; or use with bioreductive alkylating agents.

(XXXIII) Novel Mechanisms of Action

Improvements for suboptimal chemotherapeutics including bisantrene and analogs and derivatives thereof are made by optimizing their utility by determining the various mechanisms of actions or biological targets of a compound for greater understanding and precision to better exploit the utility of the molecule. General examples include: imatinib (Gleevec) for chronic myelocytic leukemia (CML), arsenic trioxide for acute promyelocytic leukemia (APL), retinoic acid for APL. Specific inventive examples for bisantrene and analogs and derivatives thereof include: use with inhibitors of poly-ADP ribose polymerase; use with agents that affect vasculature; use with agents that promote vasodilation; use with oncogenic targeted agents; use with signal transduction inhibitors; use with agents inducing EGFR inhibition; use with agents inducing Protein Kinase C inhibition; use with agents inducing Phospholipase C downregulation; use with agents including jun down regulation; use with agents modulating expression of histone genes; use with agents modulating expression of VEGF; use with agents modulating expression of ornithine decarboxylase; use with agents modulating expression of jun D; use with agents modulating expression of v-jun; use with agents modulating expression of GPCRs; use with agents modulating expression of protein kinase A; use with agents modulating expression of protein kinases other than protein kinase A; use with agents modulating expression of telomerase; use with agents modulating expression of prostate specific genes; use with agents modulating expression of histone deacetylase; or use with agents modulating expression of CHK2 checkpoint kinase.

(XXXIV) Selective Target Cell Population Therapeutics

Improvements for suboptimal chemotherapeutics including bisantrene and analogs and derivatives thereof are made by more precise identification and exposure of the compound to those select cell populations where the compounds effect can be maximally exploited. General examples include: tirapazamine and mitomycin c for hypoxic cells, vinca alkaloids for cells entering mitosis. Specific inventive examples for bisantrene and analogs and derivatives thereof include: use against radiation sensitive cells; use against radiation resistant cells; use against energy depleted cells; use against endothelial cells.

(XXXV) Use with Agents to Enhance Activity

Improvements for suboptimal chemotherapeutics including bisantrene and analogs and derivatives thereof are made by use of agents to enhance activity of the amonafide or the derivative or analog of amonafide. General examples include: use with nicotinamide, caffeine, tetandrine, or berberine. Specific inventive examples for bisantrene and analogs and derivatives thereof include: use with nicotinamide; use with caffeine; use with tetandrine; or use with berberine.

(XXXVI) Use to Modulate DNA Methylation

Improvements for suboptimal chemotherapeutics including bisantrene and derivatives and analogs thereof are made by use of bisantrene or derivatives or analogs thereof to modulate DNA methylation. It is known that aberrant DNA methylation is associated with malignancy. Specific inventive examples for bisantrene and derivatives and analogs thereof include: use to promote gene silencing; or use with drugs that inhibit DNA methylation. The effect of demethylation is described in L. Suarez & S. D. Gore, "Demethylation Demystification," *Blood* 121: 1488-1489 (2011), incorporated herein by this reference. Drugs that inhibit DNA methylation are described in PCT Patent Application Publication No. WO 2009/106549 by Geroni et al., incorporated herein by this reference. Drugs that inhibit DNA methylation include, but are not limited to, 5'-azacytidine, 5-aza-2'-deoxycytidine, zebularine, L-methionine, apicidine, hydralazine, procainamide, and antisense oligonucleotides directed against mRNA for DNA methyltransferase. Additional drugs that inhibit DNA methylation include inhibitors of histone deacetylase (HDAC). These compounds include, but are not limited to, compounds disclosed in PCT Patent Application Publication No. WO 02/22577 by Bair et al., incorporated herein by this reference, including, but not limited to, N-hydroxy-3-[4-[[(2-hydroxyethyl)[2-(1H-indol-3-yl)ethyl]-amino]methyl]phenyl]-2E-2-propenamide, suberoylanilide hydroxamic acid, 4-(2-amino-phenylcarbamoyl)-benzyl]-carbamic acid pyridine-3-ylmethyl ester and derivatives thereof, butyric acid, pyroxamide, trichostatin A, oxamflatin, apicidin, depsipeptide, depudecin, trapoxin, HC toxin, and sodium phenylbutyrate.

(XXXVII) Use to Inhibit Telomerase or Induce Telomere Dysfunction

Improvements for suboptimal chemotherapeutics including bisantrene and derivatives or analogs thereof are made by use of bisantrene or derivatives or analogs thereof to inhibit telomerase or induce telomere dysfunction. It is known that the expression and activity of telomerase in maintaining telomere length is associated with cell immortalization and carcinogenesis; telomerase is active in most human tumor cells but generally inactive in most human somatic cells. Specific inventive examples for bisantrene and derivatives and analogs thereof include: use to inhibit telomerase; or use to induce telomere dysfunction.

The use of derivatives of bisantrene to interfere with telomeric function is disclosed in M. Folini et al., "Remarkable Interference with Telomeric Function by a G-Quadruplex Selective Bisantrene Regioisomer," *Biochem. Pharmacol.* 79: 1781-1790 (2010), incorporated herein by this reference. The enzyme telomerase is a ribonucleoprotein reverse transcriptase responsible for telomere length maintenance. Its expression is associated with cell immortalization and tumorigenesis, as it is expressed in most human tumor cells but is not active in most human somatic cells. Typically, inhibition of telomerase results in cellular senescence or apoptosis in a time-dependent manner correlating with initial telomere length. Alternatively, tumor cell crisis can be induced rapidly by promoting telomere dysfunction; this must be distinguished from the inhibition of telomerase activity. Many proteins are involved in preserving the complex telomere architecture. When the complex telomere architecture is disrupted or collapses, it activates a signaling cascade comparable to that promoted by DNA damage and leads to cell cycle arrest (accelerated senescence) or apoptosis. Telomerase substrates are telomeres in DNA. These are double-stranded DNA portions with a 3'-protruding overhang 100-200 bases in length formed by a repeated noncoding sequence, typically TTAGGG (SEQ ID NO: 1) in humans. In analogy to other guanine-rich structures, the single-stranded portion can fold into a structure called G-quadruplex, which includes four Hoogsten-paired guanine residues. Hoogsten base-pairing is an alternative for base-pairing in DNA to the conventional Watson-Crick base pairs. Certain ligands stabilize this unconventional DNA base-pairing arrangement and impair telomere-telomerase interaction, thus interfering with the catalysis of the telomere elongation step catalyzed by telomerase. Certain ligands also can displace the telomere binding proteins such as TRF2 and hPOT1 normally involved in telomere capping, thus allowing recognition of the free terminal sequence as a region of DNA damage. Bisantrene and derivatives and analogs thereof share a general consensus structural motif of compounds either inhibiting telomerase activity or disrupting telomere structure. This structural motif includes a large flat aromatic surface linked to protonatable side chains. In compounds with this structural motif, DNA binding occurs mainly through stacking on a terminal G-tetrad, whereas side chains contribute to the stability of the complex by hydrophobic/ionic interactions into the DNA grooves. The number and position of side chains affect anthracene/G-quadruplex interaction. Such derivatives can selectively stabilize G-quadruplex folding. Telomerase inhibition correlates with G-quadruplex recognition for such derivatives. At least some of these derivatives are capable of inducing antiproliferative effects and a DNA damage response at the telomeric level in telomerase-positive and ALT-positive tumor cells. This result is associated with the expression of the cyclin-dependent kinase inhibitor $p21^{waf1}$, which is known to be involved in a senescence pathway triggered by telomere dysfunction. There is also enhanced expression of trimethyl K9 histone H3, which is a marker suggestive of cellular senescence-associated changes in chromatin structure. The expression of senescence-associated β-galactosidase is also enhanced. These responses are associated with the occurrence of a DNA damage signal at the telomere level. The results with bisantrene analogs and derivatives suggest formation of additional specific interactions between the 4,5-dihydro-1H-imidazol-2-yl hydrazone groups and the G-quadruplex structure. These analogs and derivatives can act at both the telomerase level, by interfering with substrate recognition and thus suppressing its catalytic activity, and at the telomere level, by suppressing its organization. These results suggest a drug-mediated activation of a senescence pathway.

These results suggest that bisantrene analogs and derivatives can be used with other telomerase inhibitors, including BPPA (2,6-bis(3-piperidinopropionamido)anthraquinone), (−)-epigallocatechin gallate, H-7 (2,6-bis(3-piperidinopropionamido)anthraquinone), β-rubromycin, and BIBR1532 (2-[[(2E)-3-(2-naphthalenyl)-1-oxo-2-butenyl1-yl]amino] benzoic acid).

(XXXVIII) Use to Activate Macrophages or Innate Immunity

Improvements for suboptional chemotherapeutics including bisantrene and derivatives or analogs thereof are made by use of bisantrene or derivatives or analogs thereof to activate macrophages or induce innate immunity. Macrophages bridge innate and adaptive immunity. The role of macrophages is described in J. Rothman & Y. Patterson, "Live-Attenuated *Listeria*-Based Immunotherapy," *Exp. Rev.* 12: 493-504 (2013), incorporated herein by this reference, which shows the effectiveness of genetically engineered *Listeria* strains in promoting both innate and adaptive immune responses mediated by the activity of macrophages. Specific inventive examples for bisantrene and derivatives and analogs thereof include: use to activate macrophages; use to induce innate immunity; or use to induce adaptive immunity.

B. S. Wang et al., "Immunotherapy of a Murine Lymphoma by Adoptive Transfer of Syngeneic Macrophages Activated with Bisantrene," *Cancer Res.* 46: 503-506 (1986), and B. S. Wang et al., "Activation of Tumor-Cytostatic Macrophages with the Antitumor Agent 9,10-Anthracenedicarboxaldehyde Bis[4,5-dihydro-1H-imidazole-1-2yl)hydrazone] Dihydrochloride (Bisantrene)," *Cancer Res.* 44: 2363-2367 (1984), both of which are incorporated herein by this reference, disclose that macrophages can be activated with bisantrene and that such activated macrophages had an antineoplastic effect in vivo. These effects appear to involve adaptive immunity via the activation of tumor killing T cells directly, as allogeneic transplants of activated macrophages were shown to eliminate tumors in recipients, as well as through innate immunity, as the supernatants of bisantrene activated macrophages had a lesser, but still significant therapeutic effect on tumor bearing recipient mice. Additionally, there exist immune agents that have the effect of inducing apoptosis in cancer cells, and the use of such agents is described further below. This approach is described in D. Tormo et al., "Targeted Activation of Innate Immunity for Therapeutic Induction of Autophagy and Apoptosis in Melanoma Cells," *Cancer Cell* 16: 103-114 (2009), incorporated herein by this reference. These agents include polyinosine-polycytidylic acid, especially when complexed to polyethyleneimine.

(XXXIX) Use to Inhibit Expression of Survivin or with Survivin Inhibitors or Modulators Bisantrene analogs and derivatives also selectively inhibit gene promoter activity for survivin (BIRC5) and to downregulate survivin in vitro, leading to apoptosis (T. G. Glaros et al., "The 'Survivin Suppressants' NSC80467 and YM1155 Induce a DNA Damage Response," *Cancer Chemother. Pharmacol.* 70: 207-212 (2012), incorporated herein by this reference). Survivin is encoded by the BIRC5 gene and is a member of the inhibitor of apoptosis (IAP) family. The survivin protein functions to inhibit caspase activation and thereby leads to negative regulation of apoptosis. The survivin protein is frequently highly expressed in tumor cells. Survivin expression is highly regulated by the cell cycle and is only expressed in the G2/M phase. Survivin localizes to the mitotic spindle by interaction with tubulin during mitosis. Regulation of survivin is linked to the p53 protein and is a direct target of the Wnt pathway; it is also upregulated by β-catenin. Accordingly, survivin is a regulator of apoptosis and acts to counter apoptosis. As an anti-apoptotic protein, it is a potential target for drug therapy for cancer as its activity may promote resistance to antineoplastic therapeutic agents. Two major pathways of apoptosis have been identified in mammalian cells. A first pathway, designated the extrinsic pathway, is triggered by the binding of ligands to cell-surface trimeric membrane death receptors and leads to caspase-8 activation. A second pathway, designated the extrinsic pathway, involves mitochondria, which respond to pro-apoptotic signals by releasing cytochrome c, which in turn binds and activates the apoptotic protease-activating factor-1, causing assembly of a multiprotein caspase-activating complex (apoptosome) and leading to activation of caspase-9 and initiation of a protease cascade. The extrinsic and intrinsic pathways for apoptosis converge on downstream effector caspases involved in apoptosis. Some of these, such as caspase-3 and caspase-7, are targets of suppression by an endogenous family of anti-apoptotic proteins called inhibitor of apoptosis proteins (IAPs). Some members of this family also interfere with caspase-9 processing, the upstream initiation of the mitochondrial pathway of apoptosis. The human genome encodes eight IAP family members including X-linked inhibitor of apoptosis protein (X-IAP), cIAP1, cIAP2, ML-IAP (Livin; K-IAP), Naip, ILP2 (TS-IAP), Apollon/Bruce and survivin. The human survivin gene spans 14.7 kb on the telomeric position of chromosome 17 and is transcribed from a TATA-less, GC-rich promoter to generate the wild-type transcript and four different splice variant mRNA molecules. Wild-type human survivin is a 16.5 kD protein of 142 amino acids and is composed of a single baculovirus IAP repeat domain and an extended C-terminal α-helical coiled-coil domain; the survivin protein molecule does not contain the RING-finger domain found in other IAPs. There is considerable evidence pointing to a functional role of survivin in both apoptosis control and cell division. Survivin is a chromosomal passenger protein that localizes to kinetochores at metaphase, transfers to the central spindle midzone at anaphase and accumulates in mid-bodies at telophase. Physical interactions with the inner centromere protein, Aurora B and Borealin/Dasra B are required to target the complex to the kinetochore, to properly form the bipolar spindle and to complete cytokinesis. This function, involving preservation of genome fidelity and regulation of microtubule dynamics, requires close control of cell-cycle-dependent transcription of the survivin gene during the mitotic phase, as well as post-translational modifications of the protein including phosphorylation by the p34$^{cdc2}$ and Aurora B kinases and monoubiquitination through Lys48 and Lys63 linkages. This pathway may be dominant in normal, differentiated cells and may constitute the primary function of survivin in adult tissues. However, there is evidence that survivin is upregulated in $G_2$/M cell compartments in a number of cancer lines. Other non-cell-cycle-dependent mechanisms driving survivin gene transcription independent of mitosis have been described, which involve tissue patterning circuits (Wnt/(3-catenin), cytokine activation signal-transducer-and-activator-of-transcription-3, costimulatory messages such as those of OX-40, and pleiotropic signaling mechanisms such as v-akt murine thymoma viral oncogene homolog 1 or protein kinase B (AkT) and nuclear factor-KB that are typically operative during development and are upregulated in cancer cells. These non-cell-cycle-dependent pathways may be dominant in tumor cells. The fraction of survivin produced through these non-cell-cycle-dependent mechanisms mediates apoptosis inhibition through intermolecular cooperation with cofactors including the hepatitis B virus X-interacting protein, a target of the oncogenic viral hepatitis B virus X protein and X-IAP, leading to the formation of complexes that inhibit caspase-9 processing. Moreover, subcellular compartmentalization of survivin in mitochondria seems to play a role in the anti-apoptotic function of the protein. Specifically, the existence of a mitochondrial pool of survivin was recently reported, and it was found that in response to cell death stimulation, mitochondrial survivin is rapidly discharged and released into the cytosol, where it prevents caspase activation and inhibits apoptosis. Mitochondrial survivin may be exclusively associated with tumor transformation. It also has been found that survivin has a nuclear export signal and that in cancer cells the anti-apoptotic and mitotic roles of survivin can be separated through mutation of its nuclear export signal, which abrogates the cytoprotective activity of the protein but still allows mitosis to proceed. The stability and function of survivin require a physical interaction with the molecular chaperone heat shock protein 90 (Hsp90), which involves the Hsp90 ATPase domain and the survivin baculovirus IAP repeat domain. Although survivin is expressed in tissues that are characterized by self-renewal and proliferation, such as adult liver cells, gastrointestinal tract mucosal cells, T cells, and hematopoietic progenitor cells, its expression is significantly lower than in transformed cells. Global deregulation of the survivin gene may be mediated by oncogenes or loss of tumor suppressors such as wild-type p53 protein. There is also considerable evidence that survivin plays an important role in the drug-resistant phenotype of human cancer cells. For example, it has been shown that taxol-induced microtubule stabilization and mitotic arrest increase the expression of survivin, which engenders a cell survival pathway to counteract taxol-induced apoptosis. Other pathways may also be involved. For example, the mammalian target of rapamycin pathway, which constitutes a sensor network for stress conditions, may be involved in resistance to taxol by increasing survivin levels. Also, insulin-like growth factor-1-mediated mammalian target of rapamycin activation in prostate cancer cells can positively modulate survivin levels by favoring stabilization and translation of a survivin mRNA pool and that mammalian target of rapamycin inhibition with rapamycin, alone or in combination with taxol, can abolish survivin increase. Survivin may also mediate resistance to other anti-neoplastic therapeutic agents and to radiation. Therefore, agents that inhibit or block the expression or activity of survivin may be useful in treating malignancies, especially by preventing or reducing the development of resistance to chemotherapeutic agents or by promoting apoptosis.

Bisantrene or derivatives or analogs thereof can also be used with survivin inhibitors or modulators.

Survivin inhibitors include, but are not limited to, NSC80467 (2-methyl-1-(2-methylpropyl)-3-[2-(4-nitrophenyl)-2-oxoethyl]benzo[f]benzimidazol-3ium-4,9-dione bromide), YM1155 (1-(2-methoxyethyl)-2-methyl-4,9-dioxo-3-(pyrazin-2-ylmethyl)-4,9-dihydro-1H-naphtho[2,3-d]imidazolium bromide), SPC3042 (a locked antisense nucleic acid designed as an antisense 16-mer LNA gapmer (J. B. Hansen et al., "SPC3042: A Proapoptotic Survivin Inhibitor," *Mol. Cancer Ther.* 7: 2736-2745 (2008), incorporated herein by this reference), targeting the region comprising the stop codon of the open reading frame in exon 4 of the survivin transcript), NU6140 (4-(6-cyclohexylmethoxy-9H-purin-2-ylamino)-N,N-diethylbenzamide), toxoflavin, gambogic acid, LLP-3 (4-(3,5-bis(benzyloxy)phenyl)-6-(5-chloro-2-hydroxyphenyl)-2-oxo-1,2-dihydropyridine-3-carbonitrile) ISIS 23722, (6S,9S)—N-benzyl-6-(4-hydroxybenzyl)-2,9-dimethyl-4,7-dioxo-8-(quinolin-8-ylmethyl)octahydro-1H-pyrazino[2,1-c][1,2,4]triazine-1-carboxamide, 4-(((6S,9S)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen phosphate, tetra-O-methyl-nordi hydroguaiaretic acid, butane-bridge-modified tetra-O-methyl-nordihydroguaiaretic acids, including 1,4-bis[3,4-bis[3-(piperdin-1-yl)propoxy]phenyl]-butane, tetra-substituted nordihydroguaiaretic acid derivatives via ether bonds or carbamate bonds, tetraglycinyl nordihydroguaiaretic acid, LY2181308, dichloroacetic acid, and ICG-001 ((6S,9aS)-6-(4-hydroxybenzyl)-N-benzyl-8-(naphthalen-1-ylmethyl)-4,7-dioxo-hexahydro-2H-pyrazino[1,2-a]pyrimidine-1(6H)-carboxamide). Other survivin inhibitors and methods for inhibiting the expression of survivin are disclosed in U.S. Pat. No. 8,455,488 to Odagami et al., U.S. Pat. No. 8,318,815 to Huang et al., U.S. Pat. No. 8,232,277 to Chen et al., U.S. Pat. No. 8,178,527 to Chen et al., U.S. Pat. No. 7,959,923 to You et al., United States Patent Application Publication No. 20120088770 by Odagami et al., United States Patent Application Publication No. 20110263607 by Kouji et al., United States Patent Application Publication No. 20110092459 by Odagami et al., United States Patent Application Publication No. 20090304695 by He et al., United States Patent Application Publication No. 20090202539 by You et al., United States Patent Application Publication No. 20080267951 by You et al., United States Patent Application Publication No. 20060040883 by You et al., and United States Patent Application Publication No. 20030125287 by Kandimalla et al., all of which are incorporated herein by this reference.

Additional survivin inhibitors are disclosed in: U.S. Pat. No. 7,710,068 to Berezov et al., incorporated herein by this reference, and include compounds of Formula (A-1)

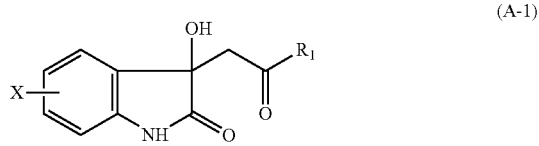

wherein: X is hydrogen, halogen, hydroxyl, alkoxy, or $C_1$-$C_4$ linear or branched alkyl; and $R_1$ is $C_1$-$C_6$ linear or branched alkyl or cycloalkyl optionally substituted with halogen, nitro, amine, or dioxole). Inhibitors or modulators or survivin are also disclosed in U.S. Pat. No. 8,026,355 to Hansen et al., incorporated herein by this reference (oligonucleotides, particularly antisense oligonucleotides, targeted to nucleic acids encoding survivin) and in U.S. Pat. No. 7,910,742 to Wendt et al., incorporated herein by this reference (a compound selected from the group consisting of tert-butyl 4-(((5-chloro-3-(4-(2-chloro-5-(trifluoromethyl)phenyl)-5-cyano-6-oxo-1,6-dihydropyridin-2-yl)-2-hydroxybenzyl)(methyl)amino)carbonyl)-1-piperidinecarboxylate; N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide; 1-acetyl-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N,4-dimethyl-4-piperidinecarboxamide; tert-butyl 4-(((5-chloro-3-(4-(2-chloro-5-(trifluoromethyl)phenyl)-5-cyano-6-oxo-1,6-dihydropyridin-2-yl)-2-hydroxybenzyl)(methyl)amino)carbonyl)-4-phenyl-1-piperidinecarboxylate; N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-phenyl-4-piperidinecarboxamide; N-(5-chloro-3-(4-(2-chloro-5-(trifluoromethyl)phenyl)-5-cyano-6-oxo-1,6-di hydropyridin-2-yl)-2-hydroxybenzyl)-N-methyl-1-(4-pyridinyl)-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-1-(4-cyanophenyl)-N-methyl-4-piperidinecarboxamide; 1-(4-acetylphenyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide; 1-acetyl-N-(5-chloro-3-(4-(2-chloro-5-(trifluoromethyl)phenyl)-5-cyano-6-oxo-1,6-di hydropyridin-2-yl)-2-hydroxybenzyl)-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-1-(methoxyacetyl)-N-methyl-4-piperidinecarboxamide; 1-butyryl-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-methyl butanoyl)-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4,4,4-trifluorobutanoyl)-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4,4,4-trifluorobutanoyl)-4-piperidinecarboxamide; N-(5-chloro-3-(4-(2-chloro-5-(trifluoromethyl)phenyl)-5-cyano-6-oxo-1,6-d ihydropyridin-2-yl)-2-hydroxybenzyl)-N-methyl-1-(tetrahydro-2-furanylcarbonyl)-4-piperidinecarboxamide; 1-(3-butynoyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(3-nitropropanoyl)-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-1-(cyclopropylcarbonyl)-N-methyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-1-(cyclopropylacetyl)-N-methyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-1-(cyclohexylcarbonyl)-N-methyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-propyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-phenylethyl)-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-(2,6,6-trimethyl-1-cyclohexen-1-yl)ethyl)-4-piperidinecarboxamide; 1-(2-(benzyloxy)ethyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide; N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(3-(5-methyl-2-furyl)butyl)-4-piperidinecarboxamide; 1-acetyl-N4(4'-chloro-5-(4-(2-chloro-5-(trifluoromethyl)phenyl)-5-cyano-6-oxo-1,6-dihydropyridin-2-yl)-4-hydroxy(1,1'-biphenyl)-3-Amethyl)-N-methyl-4-piperidinecarboxamide; and 1-acetyl-N-(3-(4-(2-chloro-5-(trifluoromethyl)phenyl)-5-cyano-6-oxo-1,6-dihydropyridin-2-yl)-5-cyclopentyl-2-hydroxybenzyl)-N-methyl-4-piperidinecarboxamide).

(XL) Use with Multidrug Resistance Reversal Agents

Improvements for suboptimal chemotherapeutics including bisantrene and derivatives or analogs thereof are made by use of bisantrene or derivatives or analogs thereof with multidrug resistance reversal agents. Multidrug resistance reversal agents include, but are not limited to, verapamil, N-myristoylated protein kinase C-α pseudo substrate peptides; dexverapamil (an enantiomer of verapamil); N-solanesyl-N,N'-bis(3,4-dimethylbenzyl)ethylenediamine, cepharanthine, quinidine, reserpine, chlorpromazine and trifluoperazine (S. Akiyama et al., "Most Drugs That Reverse Multidrug Resistance Also Inhibit Photoaffinity Labeling of P-Glycoprotein by a Vinblastine Analog," *Mol. Pharmacol.* 33: 144-147 1988, incorporated herein by this reference)); triazine derivatives (A. Dhainaut et al., "New Triazine Derivatives as Potent Modulators of Multidrug Resistance," *J. Med. Chem.* 35: 2481-2496 (1992), incorporated herein by this reference); terferadine; RU-486; dihydropyridine analogs (M. Kamiwatari et al., "Correlation Between Reversing of Multidrug Resistance and Inhibiting of [$^3$H]Azidopine Photolabeling of P-Glycoprotein by Newly Synthesized Dihydropyridine Analogues in a Human Cell Line," *Cancer Res.* 49: 3190-3195 (1989), incorporated herein by this reference); the staurosporine derivative NA-382 (K.A. Miyamoto et al., "Inhibition of Multidrug Resistance by a New Staurosporine Derivative, NA-382, in Vitro and in Vivo,"

*Cancer Res.* 53: 1555-1559 (1993), incorporated herein by this reference); ningalin B analogs (U.S. Pat. No. 7,250,409 to Boger, incorporated herein by this reference); other agents (U.S. Pat. No. 5,786,344 to Ratain et al, incorporated herein by this reference, including: cyclosporine A, verapamil, cefoperazone, N-ethoxycarbonyl-7-oxo-staurosporine (NA-382); nifedipine, nitrendipine, nicardipine and diltiazem; other dihydropyridines; tiapamil; nisoldipine; nimodipine; nitrendipine; phenothiazines; thioxanthenes; fluphenazine; chlorpromazine; triflupromazine; trifluoperazine; prochlorperazine; progesterone; metabolites of progesterone; tirilazad; vincristine; vinblastine; actinomycin D; colchicine; etoposide; daunorubicin; doxorubicin; taxotere; taxol; tamoxifen; reserpine; dipyramidole; chloroquine; propranolol; terfenadine; ivermectin; and quinidine. Additional multidrug resistance reversal agents are disclosed in U.S. Pat. No. 8,673,914 to Chen et al., incorporated herein by this reference; these multidrug resistance reversal agents are phosphodiesterase inhibitors, such as PDE5 inhibitors, and include sildenafil, vardenafil, tadalafil, lodenafil, udenafil, benzamidenafil, mirodenafil, avanafil, zaprinast, SLX-2101, UK-371,800, UK-122764, icariin, DA-8159, and 3-[4-(2-hydroxyethyl)piperazin-1-yl]-7-(6-methoxypyridin-3-yl)-1-(2-propoxyethyl)pyrido[3,4-N-pyrazin-2(1H)-one.

(XLI) Use in Combinatorial Regimes

Improvements for suboptimal chemotherapeutics including bisantrene and derivatives or analogs thereof are made by use of bisantrene or derivatives or analogs thereof in combinatorial regimes. A significant area of research is directed at methods for combining newer immunotherapies with older cytotoxic modalities. Specific inventive examples for bisantrene and derivatives or analogs thereof include: use in a combinatorial regime as a chemotherapeutic agent with at least one agent inducing immunoactivity; use in a combinatorial regime as a chemotherapeutic agent with at least one agent inducing macrophage activation; use in a combinatorial regime as a chemotherapeutic agent with at least one cytokine; use in a combinatorial regime as a chemotherapeutic agent with at least one agent inhibiting telomerase; use in a combinatorial regime as a chemotherapeutic agent with at least one agent inhibiting survivin; use in a combinatorial regime as a chemotherapeutic agent with at least one agent inducing demethylation; use in a combinatorial regime as a chemotherapeutic agent with at least one adjuvant; use in a combinatorial regime as a chemotherapeutic agent with at least one antibody; use in a combinatorial regime as a chemotherapeutic agent with at least one innate or adaptive immune stimulator; use in a combinatorial regime as a chemotherapeutic agent with at least one checkpoint inhibitor; use in a combinatorial regime as a chemotherapeutic agent with at least one mTOR antagonist; use in a combinatorial regime as a chemotherapeutic agent with at least one Akt inhibitor; use in a combinatorial regime as a chemotherapeutic agent with at least one notch inhibitor; use in a combinatorial regime as a chemotherapeutic agent with at least one HSP inhibitor; use in a combinatorial regime as a chemotherapeutic agent with at least one phosphatidylinositide 3-kinase inhibitor; use in a combinatorial regime as a chemotherapeutic agent with at least one kinase inhibitor; use in a combinatorial regime as a chemotherapeutic agent with cytarabine; use in a combinatorial regime as a chemotherapeutic agent with taxane; use in a combinatorial regime as a chemotherapeutic agent with taxol; use in a combinatorial regime as an agent inducing macrophage activation with at least one agent inducing telomerase inhibition; use in a combinatorial regime as an agent inducing macrophage activation with at least one cytokine; use in a combinatorial regime as an agent inducing macrophage activation with at least one agent inhibiting survivin; use in a combinatorial regime as an agent inducing macrophage activation with at least one agent inducing demethylation; use in a combinatorial regime as an agent inducing macrophage activation with at least one adjuvant; use in a combinatorial regime as an agent inducing macrophage activation with at least one antibody; use in a combinatorial regime as an agent inducing macrophage activation with at least one innate or adaptive immune stimulator; use in a combinatorial regime as an agent inducing macrophage activation with at least one checkpoint inhibitor; use in a combinatorial regime as an agent inducing macrophage activation with at least one mTOR antagonist; use in a combinatorial regime as an agent inducing macrophage activation with at least one Akt inhibitor; use in a combinatorial regime as an agent inducing macrophage activation with at least one notch inhibitor; use in a combinatorial regime as an agent inducing macrophage activation with at least one HSP inhibitor; use in a combinatorial regime as an agent inducing macrophage activation with at least one phosphatidylinositide 3-kinase inhibitor; use in a combinatorial regime as an agent inducing macrophage activation with at least one kinase inhibitor; use in a combinatorial regime as an agent inducing macrophage activation with cytarabine; use in a combinatorial regime as an agent inducing macrophage activation with taxane; or use in a combinatorial regime as an agent inducing macrophage activation with taxol.

(XLII) Use with Directed Antibody Conjugates

Improvements for suboptional chemotherapeutics including bisantrene and derivatives or analogs thereof are made by use of bisantrene or derivatives or analogs thereof with directed antibody conjugates.

(XLIII) Use with Adjuvants

Improvements for suboptional chemotherapeutics including bisantrene and derivatives or analogs thereof are made by use of bisantrene or derivatives or analogs thereof with adjuvants. The adjuvant can be, but is not limited to, GM-CSF, poly-ICLC (carboxymethylcellulose, polyinosinic-polycytidylic acid, and poly L-lysine), nanoparticles, microparticles, aluminum salts, squalene, QS-21 (a plant extract from *Quillaja saponaria* containing water-soluble triterpene glycosides), virosomes, IL-2, IL-7, IL-21, and type 1 interferons. Other adjuvants are known in the art.

Accordingly, one aspect of the present invention is a method to improve the efficacy and/or reduce the side effects of suboptimally administered drug therapy comprising the steps of:

(1) identifying at least one factor or parameter associated with the efficacy and/or occurrence of side effects of the drug therapy; and (2) modifying the factor or parameter to improve the efficacy and/or reduce the side effects of the drug therapy.

Typically, the factor or parameter is selected from the group consisting of:

(1) dose modification;
(2) route of administration;
(3) schedule of administration;
(4) indications for use;
(5) selection of disease stage;
(6) other indications;
(7) patient selection;
(8) patient/disease phenotype;
(9) patient/disease genotype;
(10) pre/post-treatment preparation
(11) toxicity management;
(12) pharmacokinetic/pharmacodynamic monitoring;

(13) drug combinations;
(14) chemosensitization;
(15) chemopotentiation;
(16) post-treatment patient management;
(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action;
(33) selective target cell population therapeutics;
(34) use with an agent enhancing its activity;
(35) use to modulate DNA methylation;
(36) use to inhibit telomerase or induce telomere dysfunction;
(37) use to activate macrophages or innate immunity;
(38) use to inhibit expression of survivin or with survivin inhibitors or modulators;
(39) use with multidrug resistance reversal agents;
(40) use in combinatorial regimes;
(41) use with directed antibody conjugates; and
(42) use with adjuvants.

The suboptimally administered drug therapy can comprise administration of bisantrene or of a derivative or analog of bisantrene, as described above.

Typically, when the suboptimally administered drug therapy is used to treat a hyperproliferative disease, the hyperproliferative disease is cancer. Methods according to the present invention and compositions according to the present invention suitable for use in those methods are applicable to many forms of cancer, including, but not limited to: (A) breast cancer, including: (1) ductal carcinoma, including ductal carcinoma in situ (DCIS) (comedocarcinoma, cribriform, papillary, micropapillary), infiltrating ductal carcinoma (IDC), tubular carcinoma, mucinous (colloid) carcinoma, papillary carcinoma, metaplastic carcinoma, and inflammatory carcinoma; (2) lobular carcinoma, including lobular carcinoma in situ (LCIS) and invasive lobular carcinoma; (3) Paget's disease of the nipple; (4) Her2/neu$^+$ tumors; (5) ER$^+$ tumors; and (6) triple negative tumors; (B) cancers of the female reproductive system, including: (1) cancers of the cervix uteri, including cervical intraepithelial neoplasia (Grade I), cervical intraepithelial neoplasia (Grade II), cervical intraepithelial neoplasia (Grade III) (squamous cell carcinoma in situ), keratinizing squamous cell carcinoma, nonkeratinizing squamous cell carcinoma, verrucous carcinoma, adenocarcinoma in situ, adenocarcinoma in situ, endocervical type, endometrioid adenocarcinoma, clear cell adenocarcinoma, adenosquamous carcinoma, adenoid cystic carcinoma, small cell carcinoma, and undifferentiated carcinoma; (2) cancers of the corpus uteri, including endometrioid carcinoma, adenocarcinoma, adenocanthoma (adenocarcinoma with squamous metaplasia), adenosquamous carcinoma (mixed adenocarcinoma and squamous cell carcinoma, mucinous adenocarcinoma, serous adenocarcinoma, clear cell adenocarcinoma, squamous cell adenocarcinoma, and undifferentiated adenocarcinoma; (3) cancers of the ovary, including serous cystadenoma, serous cystadenocarcinoma, mucinous cystadenoma, mucinous cystadenocarcinoma, endometrioid tumor, endometrioid adenocarcinoma, clear cell tumor, clear cell cystadenocarcinoma, and unclassified tumor; (4) cancers of the vagina, including squamous cell carcinoma and adenocarcinoma; and (5) cancers of the vulva, including vulvar intraepithelial neoplasia (Grade I), vulvar intraepithelial neoplasia (Grade II), vulvar intraepithelial neoplasia (Grade III) (squamous cell carcinoma in situ); squamous cell carcinoma, verrucous carcinoma, Paget's disease of the vulva, adenocarcinoma (NOS), basal cell carcinoma (NOS), and Bartholin's gland carcinoma; (C) cancers of the male reproductive system, including: (1) cancers of the penis, including squamous cell carcinoma; (2) cancers of the prostate, including adenocarcinoma, sarcoma, and transitional cell carcinoma of the prostate; (3) cancers of the testis, including seminomatous tumor, nonseminomatous tumor, teratoma, embryonal carcinoma, yolk sac tumor, and choriocarcinoma; (D) cancers of the cardiac system, including sarcoma (angiosarcoma, fibrosarcoma, rhabdomyosarcoma, liposarcoma), myxoma, rhabdomyoma, fibroma, lipoma and teratoma; (E) cancers of the respiratory system, including squamous cell carcinoma of the larynx, primary pleural mesothelioma, and squamous cell carcinoma of the pharynx; (F) cancers of the lung, including squamous cell carcinoma (epidermoid carcinoma), variants of squamous cell carcinoma, spindle cell carcinoma, small cell carcinoma, carcinoma of other cells, carcinoma of intermediate cell type, combined oat cell carcinoma, adenocarcinoma, acinar adenocarcinoma, papillary adenocarcinoma, bronchiolo-alveolar carcinoma, solid carcinoma with mucus formation, large cell carcinoma, giant cell carcinoma, clear cell carcinoma, and sarcoma; (G) cancers of the gastrointestinal tract, including: (1) cancers of the ampulla of Vater, including primary adenocarcinoma, carcinoid tumor, and lymphoma; (2) cancers of the anal canal, including adenocarcinoma, squamous cell carcinoma, and melanoma; (3) cancers of the extrahepatic bile ducts, including carcinoma in situ, adenocarcinoma, papillary adenocarcinoma, adenocarcinoma, intestinal type, mucinous adenocarcinoma, clear cell adenocarcinoma, signet-ring cell carcinoma, adenosquamous carcinoma, squamous cell carcinoma, small cell (oat) carcinoma, undifferentiated carcinoma, carcinoma (NOS), sarcoma, and carcinoid tumor; (4) cancers of the colon and rectum, including adenocarcinoma in situ, adenocarcinoma, mucinous adenocarcinoma (colloid type; greater than 50% mucinous carcinoma), signet ring cell carcinoma (greater than 50% signet ring cell), squamous cell (epidermoid) carcinoma, adenosquamous carcinoma, small cell (oat cell) carcinoma, undifferentiated carcinoma, carcinoma (NOS), sarcoma, lymphoma, and carcinoid tumor; (5) cancers of the esophagus, including squamous cell carcinoma, adenocarcinoma, leiomyosarcoma, and lymphoma; (6) cancers of the gallbladder, including adenocarcinoma, adenocarcinoma, intestinal type, adenosquamous carcinoma, carcinoma in situ, carcinoma (NOS), clear cell adenocarcinoma, mucinous adenocarcinoma, papillary adenocarcinoma, signet-ring cell carcinoma, small cell (oat cell) carcinoma, squamous cell carcinoma, and undifferentiated carcinoma; (7) cancers of the lip and oral cavity, including squamous cell carcinoma; (8) cancers of the liver, including hepatoma (hepatocellular carcinoma), cholangiocarcinoma, hepatoblastoma, angiosarcoma, hepatocellular adenoma, and hemangioma; (9) cancers of the exocrine pancreas, including duct cell carcinoma, pleomorphic giant cell carcinoma, giant cell carcinoma, osteoclastoid type, adenocarcinoma, adenosquamous carcinoma, mucinous (colloid) carcinoma, cystadenocarcinoma, acinar cell carcinoma, papillary carcinoma, small cell (oat cell) carcinoma, mixed cell typed, carcinoma (NOS), undifferentiated carcinoma, endocrine cell tumors arising in the islets of Langerhans, and carcinoid; (10) cancers of the salivary glands, including acinic (acinar) cell carcinoma, adenoid cystic carcinoma (cylindroma), adenocarcinoma, squamous cell carcinoma, carcinoma in pleomorphic adenoma (malignant mixed tumor), mucoepidermoid carcinoma (well differentiated or low grade), and mucoepidermoid carcinoma (poorly differentiated or high grade); (11) cancers of the stomach, including adenocarcinoma, papillary adenocarcinoma, tubular adenocarcinoma, mucinous adenocarcinoma, signet ring cell carcinoma, adenosquamous carcinoma, squamous cell carcinoma, small cell carcinoma, undifferentiated carcinoma, lymphoma, sarcoma, and carcinoid tumor; and (12) cancers of the small intestine, including adenocarcinoma, lymphoma, carcinoid tumors, Kaposi's sarcoma, leiomyoma, hemangioma, lipoma, neurofibroma, and fibroma; (H) cancers of the urinary system, including: (1) cancers of the kidney, including renal cell carcinoma, carcinoma of Bellini's collecting ducts, adenocarcinoma, papillary carcinoma, tubular carcinoma, granular cell carcinoma, clear cell carcinoma (hypernephroma), sarcoma of the kidney, and nephroblastoma; (2) cancers of the renal pelvis and ureter, including transitional cell carcinoma, papillary transitional cell carcinoma, squamous cell carcinoma, and adenocarcinoma; (3) cancers of the urethra, including transitional cell carcinoma, squamous cell carcinoma, and adenocarcinoma; and (4) cancers of the urinary bladder, including carcinoma in situ, transitional urothelial cell carcinoma, papillary transitional cell carcinoma, squamous cell carcinoma, adenocarcinoma, undifferentiated; (I) cancers of muscle, bone, and soft tissue, including: (1) cancers of bone, including: (a) bone-forming: osteosarcoma; (b) cartilage-forming: chondrosarcoma and mesenchymal chondrosarcoma; (c) giant cell tumor, malignant; (d) Ewing's sarcoma; (e) vascular tumors: hemangioendothelioma, hemangiopericytoma, and angiosarcoma; (f) connective tissue tumors: fibrosarcoma, liposarcoma, malignant mesenchymoma, and undifferentiated sarcoma; and (g) other tumors: chordoma and adamantinoma of long bones; (2) cancers of soft tissues, including: alveolar soft-part sarcoma, angiosarcoma, epithelioid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, rhabdomyosarcoma, synovial sarcoma, and sarcoma (NOS); (3) cancers of the nervous system, including cancers of the skull (osteoma, hemangioma, granuloma, xanthoma, osteitis deformans), cancers of the meninges (meningioma, meningiosarcoma, gliomatosis), cancers of the brain (astrocytoma, medulloblastoma, glioma, ependymoma, germinoma (pilealoma), glioblastoma multiforme, oligodendroglioma, schwannoma, retinoblastoma, congenital tumors), and cancers of the spinal cord neurofibroma, meningioma, glioma, sarcoma); (4) hematologic cancers, including myeloid leukemia (acute and chronic), acute lymphoblastic leukemia, chronic lymphocytic leukemia, myeloproliferative diseases, multiple myeloma; myelodysplastic syndrome), Hodgkin's disease, and non-Hodgkin's lymphoma (malignant lymphoma); (5) cancers of the endocrine system, including: (a) cancers of the thyroid gland, including papillary carcinoma (including those with follicular foci), follicular carcinoma, medullary carcinoma, and undifferentiated (anaplastic) carcinoma; and (b) neuroblastomas, including sympathicoblastoma, sympathicogonioma, malignant ganglioneuroma, gangliosympathicoblastoma, and ganglioneuroma; (6) cancers of the skin, including squamous cell carcinoma, spindle cell variant of squamous cell carcinoma, basal cell carcinoma, adenocarcinoma developing from sweat or sebaceous gland, and malignant melanoma; (7) cancers of the eye, including: (a) cancers of the conjunctiva, including carcinoma of the conjunctiva; (b) cancers of the eyelid, including basal cell carcinoma, squamous cell carcinoma, melanoma of the eyelid, and sebaceous cell carcinoma; (c) cancers of the lacrimal gland, including adenocarcinoma, adenoid cystic carcinoma, carcinoma in pleomorphic adenoma, mucoepidermoid carcinoma, and squamous cell carcinoma; (d) cancers of the uvea, including spindle cell melanoma, mixed cell melanoma, and epithelioid cell melanoma; (e) cancers of the orbit, including sarcoma of the orbit, soft tissue tumor, and sarcoma of bone; and (f) retinoblastoma. In particular, methods according to the present invention and compositions according to the present invention are particularly suitable for the treatment of the following types of cancers: (1) melanoma; (2) colon cancer; (3) chronic lymphocytic leukemia; (4) skin cancer; (5) lung cancer, including small-cell lung cancer and non-small-cell lung cancer; (6) throat cancer; (7) stomach cancer; (8) salivary gland cancer; (9) breast cancer, including triple-negative breast cancer and breast cancer characterized by overexpression of Her-2-neu; (10) prostate cancer, including androgen-resistant prostate cancer; (11) pancreatic cancer; (12) ovarian cancer; (13) uterine cancer; (14) endometrial cancer; (15) other leukemias; (16) renal cell carcinoma; (17) multiple myeloma; (18) liver cancer; (19) pituitary gland cancer; (20) acute myeloid leukemia; (21) oophoroma; (22) glioma; (23) head and neck cancer; (23) colorectal cancer; (24) bladder cancer; (25) HPV-induced papilloma; (26) Hodgkin's lymphoma; (27) non-Hodgkin's lymphoma; (28) chronic myelocytic leukemia; (29) mycosis fungoides; and (30) myelodysplastic syndrome. In addition, methods according to the present invention and compositions according to the present invention are also particularly suitable for treatment of several non-malignant proliferative conditions, including psoriasis and HSV-induced shingles.

The following improvements all apply either to bisantrene itself or derivatives or analogs of bisantrene as described above indicated with respect to the specific improvement indicated below, unless either bisantrene or derivatives or analogs of bisantrene are specifically indicated.

When the improvement is made by dose modification, the dose modification can be, but is not limited to, at least one dose modification selected from the group consisting of:

(a) continuous i.v. infusion for hours to days;
(b) biweekly administration;
(c) doses greater than 5 mg/m$^2$/day;
(d) progressive escalation of dosing from 1 mg/m$^2$/day based on patient tolerance;
(e) doses less than 1 mg/m$^2$ for greater than 14 days;
(f) use of caffeine to modulate metabolism;
(g) use of isoniazid to modulate metabolism;
(h) selected and intermittent boost dose administrations;
(i) bolus single and multiple doses of 1-5 mg/m$^2$;
(j) oral dosing including multiple daily dosing;
(k) micro-dosing;
(l) immediate release dosing;
(m) slow release dosing; and
(n) controlled release dosing.

When the improvement is made by route of administration, the route of administration can be, but is not limited to, a route of administration selected from the group consisting of:
- (a) central venous administration;
- (b) intraperitoneal administration;
- (c) intravenous administration;
- (d) intravesicular administration for bladder cancer;
- (e) intrathecal administration;
- (f) intra-arterial administration;
- (g) continuous infusion; and
- (h) intermittent infusion.

When the improvement is made by schedule of administration, the schedule of administration can be, but is not limited to, a schedule of administration selected from the group consisting of:
- (a) administration to avoid anaphylaxis;
- (b) daily administration;
- (c) weekly administration for three weeks;
- (d) weekly administration for two weeks;
- (e) biweekly administration;
- (f) biweekly administration for three weeks with a 1-2 week rest period;
- (g) intermittent boost dose administration; and
- (h) administration daily for one week then once per week for multiple weeks.

When the improvement is made by an indication for use, the indication for use can be, but is not limited to, an indication for use selected from the group consisting of:
- (a) use for treatment of refractory breast cancer;
- (b) use for treatment of triple-negative breast cancer;
- (c) use for treatment of acute leukemias, including acute myelocytic leukemia (AML);
- (d) use for treatment of acute leukemias of childhood, including acute myelocytic leukemia (AML) and acute lymphocytic leukemia (ALL);
- (e) use for treatment of myelodysplastic syndrome;
- (f) use for treatment of chronic myelocytic leukemia (CML), either subsequent to or in combination with the administration of tyrosine kinase inhibitors or homoharringtonine;
- (g) use for treatment of chronic lymphocytic leukemia;
- (h) use for treatment of Hodgkin's lymphoma;
- (i) use for treatment of non-Hodgkin's lymphoma;
- (j) use for treatment of mycosis fungoides;
- (k) use for treatment of prostate cancer, especially androgen-resistant prostate cancer;
- (l) use for treatment of lung small-cell carcinoma, either subsequent to or in combination with the administration of EGFR inhibitors such as erlotinib (Tarceva) or gefitinib (Iressa), wherein the lung small-cell carcinoma is characterized by either wild-type or mutated EGFR;
- (m) use for treatment of lung non-small cell carcinoma, subsequent to or in combination with EGFR inhibitors such as erlotinib or gefitinib, wherein the lung non-small cell carcinoma is characterized by either wild-type or mutated EGFR;
- (n) use for treatment of breast cancer characterized by overexpressed Her-2-neu;
- (o) use for treatment of glioblastoma that is resistant to one or both of the following therapeutic agents: temozolomide (Temodar) or bevacizumab (Avastin), or is characterized by EGFR variant III, either alone or in combination with other therapeutic agents;
- (p) use for treatment of malignancies characterized by overexpressed topoisomerase II; and
- (q) use for treatment of malignancies characterized by overexpressed and/or mutated EGFR.

Triple-negative breast cancer is a form of breast cancer that is characterized by tumors that do not express estrogen receptor (ER), progesterone receptor (PR), or HER-2 genes. This form of breast cancer represents an important clinical challenge because these cancers do not respond to endocrine therapy or a number of targeted agents. Current treatment strategies for triple-negative breast cancer include many chemotherapy agents, such as the anthracyclines, taxanes, ixabepilone, and platinum agents, as well as selected biologic agents and possibly anti-EGFR drugs.

Tyrosine kinase inhibitors used for treatment of chronic myelocytic leukemia (CML) include, but are not limited to, imatinib, bosutinib, nilotinib, dasatinib, erlotinib, afatinib, and dacomitinib. Additional tyrosine kinase inhibitors are known in the art. For example, the use of tyrosine kinase inhibitors is described in United States Patent Application Publication No. 2011/0206661 by Zhang et al., incorporated herein by this reference, which is directed to trimethoxyphenyl inhibitors of tyrosine kinase, and in United States Patent Application Publication No. 2011/0195066 by Zhang, incorporated herein by this reference, which is directed to quinolone inhibitors of tyrosine kinase, both of which are incorporated herein by this reference. The use of tyrosine kinase inhibitors is also described in United States Patent Application Publication No. 2011/053968 by Zhang et al., incorporated herein by this reference, which is directed to aminopyridine inhibitors of tyrosine kinase. The use of tyrosine kinase inhibitors is also described in United States Patent Application Publication No. 2010/0291025 by Rao et al., incorporated herein by this reference, which is directed to indazole inhibitors of tyrosine kinase. The use of tyrosine kinase inhibitors is also described in United States Patent Application Publication No. 2010/0190749 by Ren et al., incorporated herein by this reference; these tyrosine kinase inhibitors are benzoxazole compounds; compounds of this class can also inhibit mTOR and lipid kinases such as phosphoinositide 3-kinases. The use of tyrosine kinase inhibitors is also described in U.S. Pat. No. 8,242,270 by Lajeunesse et al., incorporated herein by this reference; these tyrosine kinase inhibitors are 2-aminothiazole-5-aromatic carboxamides. Still other tyrosine kinase inhibitors are known in the art or are under development, and are described in B. J. Druker & N. B. Lydon, "Lessons Learned from the Development of an Abl Tyrosine Kinase Inhibitor for Chronic Myelogenous Leukemia," *J. Clin. Invest.* 105: 3-7 (2000), incorporated herein by this reference.

Homoharringtonine (omacetaxine mepesuccinate) has the structure shown below:

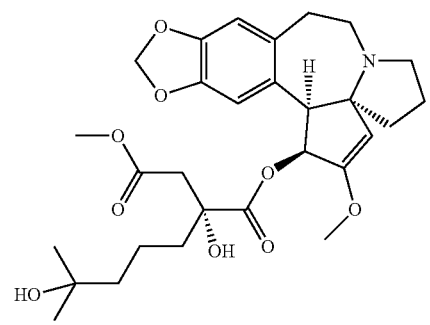

and is a protein translation inhibitor. Homoharringtonine inhibits protein translation by preventing the initial elongation step of protein synthesis. It interacts with the ribosomal A-site and prevents the correct positioning of amino acid side chains of incoming aminoacyl-tRNAs.

Androgen-resistant prostate cancer, also known as castration-resistant prostate cancer, is characterized by reactivation of androgen-regulated processes and is detectable by an increase in prostate-specific antigen (PSA) despite the administration of androgen deprivation therapy; it has been suggested that sufficient androgens remain available even subsequent to the administration of androgen deprivation therapy through reactions employing progesterone as a starting material for the synthesis of dihydrotestosterone (J. A. Locke et al., "Androgen Levels Increase by Intratumoral De Novo Steroidogenesis During Progression of Castration-Resistant Prostate Cancer," *Cancer Res.* 68: 6407-6415 (2008), incorporated herein by this reference).

EGFR inhibitors include, but are not limited to, erlotinib (Tarceva) and gefitinib (Iressa). These EGFR inhibitors specifically inhibit the EGFR tyrosine kinase. Mutations in the EGFR gene may affect the sensitivity of EGFR to EGFR inhibitors such as erlotinib and gefitinib. At least some of these mutations may increase sensitivity to EGFR inhibitors (J. G. Paez et al., "EGFR Mutations in Lung Cancer: Correlation with Clinical Response to Gefitinib Therapy," *Science* 304: 1497-1500 (2004), incorporated herein by this reference; R. Sordella et al., "Gefitinib-Sensitizing EGFR Mutations in Lung Cancer Activate Anti-Apoptotic Pathways," *Science* 305: 1163-1167 (2005), incorporated herein by this reference). However, relapses are frequent; at least some relapses are associated with a mutation at amino acid 790 of EGFR in which threonine is changed to methione (T790M) (S. Kobayashi et al., "EGFR Mutation and Resistance of Non-Small-Cell Lung Cancer to Gefitinib," *New Engl. J. Med.* 352: 786-792 (2005), incorporated herein by this reference).

Other EGFR inhibitors are known in the art. EGFR inhibitors include, but are not limited to, erlotinib, gefitinib, lapatinib, lapatinib ditosylate, afatinib, canertinib, neratinib, (E)-2-methoxy-N-(3-(4-(3-methyl-4-(6-methylpyridin-3-yloxy)phenylamino)quinazolin-6-yl)allyl)acetamide (CP-724,714), 2-[(3,4-dihydroxyphenyl)methylene]-propanedinitrile (AG 18), 2-bromo-4-[(6,7-dimethoxy-4-quinazolinyl)amino]-phenol (WHI-P154), N-(2-(4-(3-chloro-4-(3-(trifluoromethyl)phenoxy)phenylamino)-5H-pyrrolo[3,2-d]pyrimidin-5-yl)ethyl)-3-hydroxy-3-methylbutanamide (TAK-285), N-[4-[[3-chloro-4-[(3-fluorophenyl)methoxy]phenyl]amino]-6-quinazolinyl]-2-propenamide 4-methylbenzenesulfonate (AST-1306), (R)—N4-(3-chloro-4-(thiazol-2-ylmethoxy)phenyl)-N6-(4-methyl-4,5-dihydrooxazol-2-yl)quinazoline-4,6-diamine (ARRY334543), icotinib, N-(3-chlorophenyl)-6,7-dimethoxyquinazolin-4-amine (AG-1478), 2-[[3,5-bis(1,1-dimethylethyl)-4-hydroxyphenyl]methylene]-propanedinitrile (SF 6847), dacomitinib, desmethyl erlotinib, 2-(4-(3-ethynylphenylamino)-7-(2-methoxyethoxy)quinazolin-6-yloxy)ethanol hydrochloride (OSI-420), N-(3-(5-chloro-2-(4-(4-methylpiperazin-1-yl)phenylamino)pyrimidin-4-ylthio)phenyl)acrylamide (WZ-8040), N-(3-(5-chloro-2-(2-methoxy-4-(4-methylpiperazin-1-yl)phenylamino)pyrimidin-4-yloxy)phenyl)acrylamide (WZ4002), N-(3-(5-chloro-2-(4-(4-methylpiperazin-1-yl)phenylamino)pyrimidin-4-yloxy)phenyl)acrylamide (WZ3146), (E)-N-benzyl-2-cyano-3-(3,4-dihydroxyphenyl)acrylamide (AG-490), N-(3,4-dichloro-2-fluorophenyl)-6-methoxy-7-(((3aR,5r,6aS)-2-methyl-octahydrocyclopenta[c]pyrrol-5-yl)methoxy)quinazolin-4-amine (XL647), N-(3-bromophenyl)-6,7-dimethoxyquinazolin-4-amine hydrochloride (PD153035), and (S)-morpholin-3-ylmethyl 4-(1-(3-fluorobenzyl)-1H-indazol-5-ylamino)-5-methylpyrrolo[1,2-f][1,2,4]triazin-6-ylcarbamate (BMS-599626). Still other EGFR inhibitors are known in the art, including monoclonal antibodies and derivatives thereof. Such monoclonal antibodies and derivatives thereof include cetuximab, panitumumab, matuzumab, nimotuzumab, trastuzumab, zalutumumab, and zatuximab. In addition, such monoclonal antibodies and derivatives thereof can be conjugated to therapeutic agents such as toxins or radionuclides. The conjugation of monoclonal antibodies to radionuclides is described in K. K. Bhargava & S. A. Acharya, "Labeling of Monoclonal Antibodies with Radionuclides," *Semin. Nucl. Med.* 19: 187-201 (1989), incorporated herein by this reference. The conjugation of monoclonal antibodies to non-radionucleotide therapeutic agents is described in P. Chames et al., "Therapeutic Antibodies: Successes, Limitations, and Hopes for the Future," *Br. J. Pharmacol.* 157: 220-233 (2009), incorporated herein by this reference. The non-radionuclide therapeutic agents can include, a fragment of *Pseudomonas* exotoxin, diphtheria toxin, the A chain of ricin, *Staphylococcus aureus* enterotoxin, mertansine, a calicheamicin cytotoxic agent, interleukin-2, and other agents known in the art. Monoclonal antibodies can also be fused to effector proteins and membrane proteins. As used herein in this context, the term "monoclonal antibodies" includes, but is not limited to, chimeric antibodies, humanized antibodies, antibody fragments such as scFv fragments, diabodies, heavy chain antibodies (HcAbs), and single-domain antibodies (sdAbs). Such monoclonal antibodies are not necessarily produced as the result of cell fusion between B cells and myeloma cells, and can be produced in other eukaryotic cells or even bacterial cells according to methods known in the art.

Additional EGFR inhibitors, including derivatives of erlotinib and salts thereof, are described in United States Patent Application Publication No. 2013/0012528 by Cheng, incorporated herein by this reference.

Overexpression of Her-2-neu, particularly in breast cancer, is associated in some cases with advanced disease and relative resistance to conventional chemotherapy. In such cases, the use of cisplatin plus a recombinant humanized anti-p185HER2 monoclonal antibody has been suggested (M. D. Pegram et al., "Phase II Study of Receptor-Enhanced Chemosensitivity Using Recombinant Humanized Anti-p185HER2/neu Monoclonal Antibody Plus Cisplatin in Patients with HER2/neu Overexpressing Metastatic Breast Cancer Refractory to Chemotherapy Treatment," *J. Clin. Oncol.* 16: 2659-2671 (1998), incorporated herein by this reference). The overexpression of Her-2-neu is also associated with changes in the regulation of a number of genes, including proline 4-hydroxylase, galectin 1, galectin 3, fibronectin 1, p-cadherin, which are genes involved in cell-matrix interactions, and genes involved with cell proliferation and transformation. A number of genes associated with MYC signaling were also differentially expressed (A. Mackay et al., "cDNA Microarray Analysis of Genes Associated with ERBB2 (HER2/neu) Overexpression in Human Mammary Luminal Epithelial Cells," *Oncogene* 22: 2680-2688 (2003), incorporated herein by this reference).

EGFR variant III is a variant of EGFR that does not respond to gefitinib; cells possessing the variant do not show reduction of phosphorylation subsequent to treatment with gefitinib. Additionally, although such cells may show a degree of reduction of phosphorylation of EGFR after more extended treatment with gefitinib, these cells continue to be resistant to the antineoplastic effects of gefitinib, possibly because the phosphorylation of Akt is unaffected in cells with variant III while being inhibited in EGFR-expressing cells after treatment with gefitinib (C. A. Learn, "Resistance to Tyrosine Kinase Inhibition by Mutant Epidermal Growth Factor Receptor Variant III Contributes to the Neoplastic Phenotype of Glioblastoma Multiforme," *Clin. Cancer Res.* 10: 3216-3224 (2004), incorporated herein by this reference). Conventional treatments for glioblastoma include temozolomide, frequently administered with radiotherapy, bevacizumab (Avastin), and the protein therapeutic APG101.

When the improvement is made by selection of disease stage, the selection of disease stage can be, but is not limited to, at least one selection of disease stage selected from the group consisting of:
 (a) use for the treatment of localized polyp stage colon cancer;
 (b) use for the treatment of leukoplakia in the oral cavity;
 (c) use to induce angiogenesis inhibition to prevent or limit metastatic spread;
 (d) use against HIV with AZT, DDI, or reverse transcriptase inhibitors;
 (e) use for recurrent leukemia, including AML; and
 (f) use for recurrent breast cancer, including Her/neu$^+$, ER$^+$ or triple negative breast cancer.

When the improvement is made by other indications, the other indications can be, but are not limited to, at least one other indication selected from the group consisting of:
 (a) use as an anti-infective agent;
 (b) use as an antiviral agent;
 (c) use as an antibacterial agent;
 (d) use for control of pleural effusions;
 (e) use as an antifungal agent;
 (f) use as an antiparasitic agent;
 (g) use for treatment of eczema;
 (h) use for treatment of shingles;
 (i) use for treatment of condylomata;
 (j) use for treatment of human papilloma virus (HPV); and
 (k) use for treatment of herpes simplex virus (HSV).

When the improvement is made by patient selection, the patient selection can be, but is not limited to, a patient selection carried out by a criterion selected from the group consisting of:
 (a) selecting patients with a disease condition characterized by a high level of a metabolic enzyme selected from the group consisting of histone deacetylase, protein kinases, and ornithine decarboxylase;
 (b) selecting patients with a disease condition characterized by a low level of a metabolic enzyme selected from the group consisting of histone deacetylase, protein kinases, and ornithine decarboxylase;
 (c) selecting patients with a low or high susceptibility to a condition selected from the group consisting of thrombocytopenia and neutropenia;
 (d) selecting patients intolerant of GI toxicities;
 (e) selecting patients characterized by over- or under-expression of a gene selected from the group consisting of jun, GPCRs, signal transduction proteins, VEGF, prostate specific genes, protein kinases, and telomerase;
 (f) selecting patients as the result of immune screening;
 (g) selecting patients as the result of DNA methylation screening;
 (h) selecting patients with recurrent disease characterized by the duration of their initial response;
 (i) selecting patients without mutations in p53; and
 (j) selecting for patients without extensive prior treatment, especially with agents that induce multidrug resistance.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, β$_3$-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

When the improvement is made by analysis of patient or disease phenotype, the analysis of patient or disease phenotype can be, but is not limited to, a method of analysis of patient or disease phenotype carried out by a method selected from the group consisting of:
 (a) use of a diagnostic tool, a diagnostic technique, a diagnostic kit, or a diagnostic assay to confirm a patient's particular phenotype;
 (b) use of a method for measurement of a marker selected from the group consisting of histone deacetylase, ornithine decarboxylase, VEGF, a protein that is a gene product of a prostate specific gene, a protein that is a gene product of jun, and a protein kinase;
 (c) surrogate compound dosing;
 (d) low dose pre-testing for enzymatic status;
 (e) determination of the multi-drug resistance activity of cells;
 (f) determining expression or activation of a signaling or metabolic protein, where an alteration in the level of expression or activation of the signaling or metabolic protein indicates the therapeutic potential of a chemotherapeutic agent;

(g) detection or assay of expression of biomarkers indicating sensitivity to apoptosis-inducing agents;
(h) use of an in vitro human tumor clonal assay to determine patients with enhanced responses;
(i) use of an immunohistochemical assay to determine overexpression of HIF-1α;
(j) assessment of p53 mutation; and
(k) determination of the quantity or activity of topoisomerase 213 in cardiac cells.

Processes and kits for determination of the multi-drug resistance of cells are described in U.S. Pat. No. 8,445,271 to Lebedeva et al., incorporated herein by this reference. The processes measure the transport of at least one xanthene compound that is transportable across a cell membrane by one or more of MDR1, MRP, or BCRP in the presence or absence of one or more membrane transporter inhibitors. Preferably, the xanthene compound has the structure:

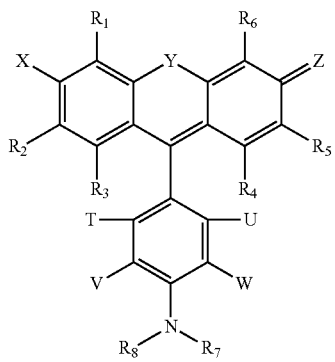

wherein: (i) $R^1$-$R^6$ are each independently hydrogen, halo, carboxyl, alkoxy, aryloxy, thiol, alkylthiol, arylthiol, azido, nitro, nitroso, cyano, amino, hydroxyl, phosphonyl, sulfonyl, carbonyl, boronic acid, aryl, heteroaryl, or alkyl or alkoxy optionally substituted with one or more of halo, amino, hydroxy, phosphonyl, sulfonyl, carbonyl, boronic acid, aryl, or heteroaryl; (ii) heteroatom Y is independently selected from the group consisting of O, S, Se, $NR^9$, and $CR^{10}R^{11}$; (iii) X is independently selected from the group consisting of $OR^{12}$, $NR^{12}R^{13}$; (iv) Z is independently selected from the group consisting of O and $R^{16}R^{17}$; (v) each $R^9$, $R^{10}$, $R^{11}$, $R^{12}$, $R^{13}$, $R^{16}$, and $R^{17}$ is independently hydrogen, $C_1$-$C_{12}$ alkyl, carboxyalkyl, substituted or nonsubstituted aminoalkyl, or alkylsulfonate; (vi) T and U are independently hydrogen, $C_1$-$C_{12}$ alkyl, $C_1$-$C_{12}$ alkoxy, aryloxy, amino, halo, cyano, carboxy, carboxyalkyl, acetoxymethylcarbonyl, carbonyl, sulfonyl, phosphonyl, boronic acid, aryl, and heteroaryl; and (vii) V and W are each independently selected from $OR^{14}$, $SR^{15}$, or $NR^{12}R^{13}$, such that at least one of V or W, in combination with $NR^7R^8$, forms a metal chelator, where each $R^7$, $R^8$, $R^{12}$, $R^{13}R^{14}$, and $R^{15}$ are independently hydrogen, $C_1$-$C_{12}$ alkyl, carboxyalkyl, alkoxy, or aryloxy. The membrane transporter inhibitors can comprise general inhibitors, specific inhibitors, or a combination of general and specific inhibitors. General inhibitors include, but are not limited to, cyclosporin A, biricodar, tariquidar, plant polyphenols, curcumin, tRA98006, and imatinib mesylate. Specific inhibitors include, but are not limited to, valspodar, verapamil, vanadate, PAK-104P, MK-571, FTC, Ko134, elacridar, novobiocin, probenecid, BIB-E, disulfuram, indomethacin, furosemide, Penicillin G, sulfinpirazole, laniquidar, zosuquidar, ontogen, isothiocyanates, phytoestrogens, TAG-139, flavonoids, MS-209, NSAIDs, mitotane, PK11195, cyclosporine D, anthranilamide, pipecolinate, quinoline, OC-144-093, diallyl sulfide, amooranin, agosterol A, siRNA, rifampicin, amiodarone, quinidine, quinine, nifedipine, dexniguldipin, LY455776, V-104, tricyclic izoxazoles, pluronic L61, and fumitremorgin C. Verapamil acts as a reversal agent and acts to bind and inhibit the activity of P-glycoprotein. This blocks the efflux of antineoplastic agents such as bisantrene and thereby kills resistant cells. Verapamil has specifically been shown to reverse resistance to bisantrene mediated by P-glycoprotein and thus resensitize cells to bisantrene; bisantrene is a substrate for P-glycoprotein (X. P. Zhang et al., "P-Glycoprotein Mediates Profound Resistance to Bisantrene," *Oncol. Res.* 6: 291-301 (1994), incorporated herein by this reference). Another method of determining patient phenotype for expression of the P-glycoprotein membrane transporter is described in United States Patent Application Publication No. 2007/0009535 by Sikic et al., incorporated herein by this reference. The degree of the expression of the P-glycoprotein membrane can be determined by antibody assay. A method of determining expression or activation of a signaling or metabolic protein, where an alteration in the level of expression or activation of the signaling or metabolic protein indicates the therapeutic potential of a chemotherapeutic agent is described in United States Patent Application Serial No. 2012/0288879 by Altiok, incorporated herein by this reference. Phosphorylation status or protein acetylation can be assessed. Methods for detection or assay of expression of biomarkers indicating sensitivity to apoptosis-inducing agents are described in United States Patent Application Publication No. 2012/0328603, incorporated herein by this reference. The biomarkers can include certain fucosyltransferases, including fucosyltransferase 3 and fucosyltransferase 6, as well as sialyl Lewis A and/or X antigens. The use of an immunohistochemical assay to determine overexpression of HIF-1α as a marker for sensitivity to anthracycline and anthracycline derivatives and analogs, including bisantrene and derivatives and analogs thereof, is disclosed in K. Lee et al., "Anthracycline Chemotherapy Inhibits HIF-1 Transcriptional Activity and Tumor-Induced Mobilization of Circulating Angiogenic Cells," *Proc. Natl. Acad. Sci.* 106: 2353-2358 (2009), incorporated herein by this reference. Topoisomerase 2β activity in cardiac cells, such as cardiomyocytes, has been shown to be associated with development of cardiotoxicity as a consequence of administration of anthracyclines and other therapeutic agents. Although bisantrene is considered less cardiotoxic than other anthracycline analogs or derivatives, cardiotoxicity may still exist. Topoisomerase 213 has been shown to be required for anthracycline to induce DNA double-strand breaks and changes in the transcriptome, leading to mitochondrial dysfunction and generation of reactive oxygen species. Therefore, the quantity or activity of topoisomerase 2β can be used as a biomarker to predict risk of cardiotoxicity before administration of bisantrene or an analog or derivative thereof (P. Vejpongsa & E. T. Yeh, "Topoisomerase 2β: A Promising Molecular Target for Primary Prevention of Anthracycline-Induced Cardiotoxicity," *Clin. Pharmacol. Ther.* 95: 45-52 (2014), incorporated herein by this reference).

When the improvement is made by analysis of patient or disease genotype, the analysis of patient or disease genotype can be, but is not limited to, a method of analysis of patient or disease genotype carried out by a method selected from the group consisting of:
(a) genetic tests to determine the absence or nonfunctionality of ABCG2;

(b) genetic tests to determine the presence or functionality of FABP7;
(c) use of a diagnostic tool, a diagnostic technique, a diagnostic kit, or a diagnostic assay to confirm a patient's particular genotype;
(d) use of a gene chip;
(e) use of gene expression analysis;
(f) use of single nucleotide polymorphism (SNP) analysis;
(g) measurement of the level of a metabolite or a metabolic enzyme;
(h) determination of the presence of one or more specific genetic variants of the MDR1 gene associated with increased efficacy of an antineoplastic drug transported by MDR1 protein;
(i) identification of one or more biomarkers associated with sensitivity or resistance to bisantrene, derivatives or analogs thereof, or other intercalating agents or topoisomerase II inhibitors; and
(j) determination of the presence or absence of the single nucleotide polymorphisms (SNPs) rs229109 and/or 72552784 associated with sensitivity to bisantrene.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference).

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference.

Specific genetic variants of the MDR1 gene encoding the MDR protein associated with increased therapeutic efficacy of an anticancer drug are disclosed in U.S. Pat. No. 7,445,897 to Ho et al., incorporated herein by this reference, which also discloses hybridization methods with probes incorporating these variants to detect their presence.

Methods for identification of one or more biomarkers associated with sensitivity or resistance to chemotherapeutic agents are described in U.S. Pat. No. 8,445,198 to Knudsen, incorporated herein by this reference. These biomarkers can be genes or microRNA; a change in the level of expression of the gene or microRNA indicates that the cell is sensitive or resistant to a specific chemotherapeutic agent. The gene can be one or more of ACTB, ACTN4, ADA, ADAM9, ADAMTS1, ADD1, AF1Q, AIF1, AKAP1, AKAP13, AKR1C1, AKT1, ALDH2, ALDOC, ALG5, ALMS1, ALOX15B, AMIGO2, AMPD2, AMPD3, ANAPC5, ANP32A, ANP32B, ANXA1, AP1G2, APOBEC3B, APRT, ARHE, ARHGAP15, ARHGAP25, ARHGDIB, ARHGEF6, ARL7, ASAH1, ASPH, ATF3, ATIC, ATP2A2, ATP2A3, ATPSD, ATP5G2, ATP6V1B2, BC008967, BCAT1, BCHE, BCL11B, BDNF, BHLHB2, BIN2, BLMH, BMI1, BNIP3, BRDT, BRRN1, BTN3A3, C11orf2, C14orf139, C15orf25, C18orf10, C1orf24, C1orf29, C1orf38, C1QR1, C22orf18, C6orf32, CACNA1G, CACNB3, CALM1, CALML4, CALU, CAP350, CASP2, CASP6, CASP7, CAST, CBLB, CCNA2, CCNB1IP1, CCND3, CCR7, CCR9, CD1A, CD1C, CD1D, CD1E, CD2, CD28, CD3D, CD3E, CD3G, CD3Z, CD44, CD47, CD59, CD6, CD63, CD8A, CD8B1, CD99, CDC10, CDC14B, CDH11, CDH2, CDKLS, CDKN2A, CDW52, CECR1, CENPB, CENTB1, CENTG2, CEP1, CG018, CHRNA3, CHS1, CIAPIN1, CKAP4, CKIP-1, CNP, COL4A1, COL5A2, COL6A1, CORO1C, CRABP1, CRK, CRY1, CSDA, CTBP1, CTSC, CTSL, CUGBP2, CUTC, CXCL1, CXCR4, CXorf9, CYFIP2, CYLD, CYR61, DATF1, DAZAP1, DBN1, DBT, DCTN1, DDX18, DDXS, DGKA, DIAPH1, DKC1, DKFZP434J154, DKFZP564C186, DKFZP564G2022, DKFZp564J157, DKFZP564K0822, DNAJC10, DNAJC7, DNAPTP6, DOCK10, DOCK2, DPAGT1, DPEP2, DPYSL3, DSIPI, DUSP1, DXS9879E, EEF1B2, EFNB2, EHD2, EIFSA, ELK3, ENO2, EPAS1, EPB41L4B, ERCC2, ERG, ERP70, EVER1, EVI2A, EVL, EXT1, EZH2, F2R, FABPS, FAD104, FAM46A, FAU, FCGR2A, FCGR2C, FER1L3, FHL1, FHOD1, FKBP1A, FKBP9, FLJ10350, FLJ10539, FLJ10774, FLJ12270, FLJ13373, FLJ20859, FLJ21159, FLJ22457, FLJ35036, FLJ46603, FLNC, FLOT1, FMNL1, FNBP1, FOLH1, FOXF2, FSCN1, FTL, FYB, FYN, GOS2, G6PD, GALIG, GALNT6, GATA2, GATA3, GFPT1, GIMAPS, GIT2, GJA1, GLRB, GLTSCR2, GLUL, GMDS, GNAQ, GNB2, GNBS, GOT2, GPR65, GPRASP1, GPSM3, GRP58, GSTM2, GTF3A, GTSE1, GZMA, GZMB, H1F0, H1FX, H2AFX, H3F3A, HA-1, HEXB, HIC, HIST1H4C, HK1, HLA-A, HLA-B, HLA-DRA, HMGA1, HMGN2, HMMR, HNRPA1, HNRPD, HNRPM, HOXA9, HRMT1L1, HSA9761, HSPA5, HSU79274, HTATSF1, ICAM1, ICAM2, IER3, IFI16, IFI44, IFITM2, IFITM3, IFRG28, IGFBP2, IGSF4, IL13RA2, IL21R, IL2RG, IL4R, IL6, IL6R, IL6ST, IL8, IMPDH2, INPP5D, INSIG1, IQGAP1, IQGAP2, IRS2, ITGA5, ITM2A, JARID2, JUNB, K-ALPHA-1, KHDRBS1, KIAA0355, KIAA0802, KIAA0877, KIAA0922, KIAA1078, KIAA1128, KIAA1393, KIFC1, LAIR1, LAMB1, LAMB3, LAT, LBR, LCK, LCP1, LCP2, LEF1, LEPRE1, LGALS1, LGALS9, LHFPL2, LNK, L0054103, L0055831, LOC81558, LOC94105, LONP, LOX, LOXL2, LPHN2, LPXN, LRMP, LRP12, LRRC5, LRRN3, LST1, LTB, LUM, LY9, LY96, MAGEB2, MAL, MAP1B, MAP1LC3B, MAP4K1, MAPK1, MARCKS, MAZ, MCAM, MCL1, MCM5, MCM7, MDH2, MDN1, MEF2C, MFNG, MGC17330, MGC21654, MGC2744, MGC4083, MGC8721, MGC8902, MGLL, MLPH, MPHOSPH6, MPP1, MPZL1, MRP63, MRPS2, MT1E, MT1K, MUF1, MVP, MYB, MYL9, MYO1B, NAP1L1, NAP1L2, NARF, NASP, NCOR2, NDN, NDUFAB1, NDUFS6, NFKBIA, NID2, NIPA2, NME4, NME7, NNMT, NOL5A, NOL8, NOMO2, NOTCH1, NPC1, NQO1, NR1D2, NUDC, NUP210, NUP88, NVL, NXF1, OBFC1, OCRL, OGT, OXA1L, P2RX5, P4HA1, PACAP, PAF53, PAFAH1B3, PALM2-AKAP2, PAX6, PCBP2, PCCB, PFDN5, PFN1, PFN2, PGAM1, PHEMX, PHLDA1, PIM2, PITPNC1, PLACE, PLAGL1, PLAUR, PLCB1, PLEK2, PLEKHC1, PLOD2, PLSCR1, PNAS-4, PNMA2, POLR2F, PPAP2B, PRF1, PRG1, PRIM1, PRKCH, PRKCQ, PRKD2, PRNP, PRP19, PRPF8, PRSS23, PSCDBP, PSMB9, PSMC3, PSME2, PTGER4, PTGES2, PTOV1, PTP4A3, PTPN7, PTPNS1, PTRF, PURA, PWP1, PYGL, QKI, RAB3GAP, RAB7L1, RAB9P40, RAC2, RAFTLIN, RAG2, RAP1B, RASGRP2, RBPMS, RCN1, RFC3, RFC5, RGC32, RGS3, RHOH, RIMS3, RIOK3, RIPK2, RIS1, RNASE6, RNF144, RPL10, RPL10A, RPL12, RPL13A, RPL17, RPL18, RPL36A, RPLPO, RPLP2, RPS15, RPS19, RPS2, RPS4X, RPS4Y1, RRAS, RRAS2, RRBP1, RRM2, RUNX1, RUNX3, S100A4, SART3, SATB1, SCAP1, SCARB1, SCN3A, SEC31L2, SEC61G, SELL, SELPLG, SEMA4G, SEPT10, SEPT6, SERPINA1, SERPINB1, SERPINB6, SFRS5, SFRS6, SFRS7, SH2D1A, SH3GL3, SH3TC1, SHD1, SHMT2, SIAT1, SKB1, SKP2, SLA, SLC1A4, SLC20A1, SLC25A15, SLC25A5, SLC39A14, SLC39A6, SLC43A3, SLC4A2, SLC7A11, SLC7A6, SMAD3, SMOX, SNRPA, SNRPB, SOD2, SOX4, SP140, SPANXC, SPI1, SRF, SRM, SSA2, SSBP2, SSRP1, SSSCA1, STAG3, STAT1, STAT4, STAT5A, STC1, STC2, STOML2, T3JAM, TACC1, TACC3, TAF5, TALI, TAP1, TARP, TBCA, TCF12, TCF4, TFDP2, TFPI, TIMM17A, TIMP1, TJP1, TK2, TM4SF1, TM4SF2, TM4SF8, TM6SF1, TMEM2, TMEM22, TMSB10, TMSNB, TNFAIP3, TNFAIP8, TNFRSF10B, TNFRSF1A, TNFRSF7, TNIK, TNPO1, TOB1, TOMM20, TOX, TPK1, TPM2, TRA@, TRAl, TRAM2, TRB@, TRD@, TRIM, TRIM14, TRIM22, TRIM28, TRIP13, TRPV2, TUBGCP3, TUSC3, TXN, TXNDC5, UBASH3A, UBE2A, UBE2L6, UBE2S, UCHL1, UCK2, UCP2, UFD1L, UGDH, ULK2, UMPS, UNG, USP34, USP4, VASP, VAV1, VLDLR, VWF, WASPIP, WBSCR20A, WBSCR20C, WHSCl, WNT5A, ZAP70, ZFP36L1, ZNF32, ZNF335, ZNF593, ZNFN1A1, and ZYX. The microRNA can be one or more of ath-MIR180aNo2, Hcd102 left, Hcd111 left, Hcd115 left, Hcd120 left, Hcd142 right, Hcd145 left, Hcd148_HPR225 left, Hcd181 left, Hcd181 right, Hcd210_HPR205 right, Hcd213_HPR182 left, Hcd230 left, Hcd243 right, Hcd246 right, Hcd248 right, Hcd249 right, Hcd250 left, Hcd255 left, Hcd257 left, Hcd257 right, Hcd263 left, Hcd266 left, Hcd270 right, Hcd279 left, Hcd279 right, Hcd28_HPR391eft, Hcd28_HPR39 right, Hcd282PO right, Hcd289 left, Hcd294 left, Hcd318 right, Hcd323 left, Hcd330 right, Hcd338 left, Hcd340 left, Hcd350 right, Hcd355_HPR190 left, Hcd361 right, Hcd366 left, Hcd373 right, Hcd383 left, Hcd383 right, Hcd384 left, Hcd397 left, Hcd404 left, Hcd412 left, Hcd413 right, Hcd415 right, Hcd417 right, Hcd421 right, Hcd425 left, Hcd438 right, Hcd434 right, Hcd438 left, Hcd440_HPR257 right, Hcd444 right, Hcd447 right, Hcd448 left, Hcd498 right, Hcd503 left, Hcd511 right, Hcd512 left, Hcd514 right, Hcd517 left, Hcd517 right, Hcd530 right, Hcd536_HPR104 right, Hcd542 left, Hcd544 left, Hcd547 left, Hcd559 right, Hcd562 right, Hcd569 right, Hcd570 right, Hcd578 right, Hcd581 right, Hcd586 left, Hcd586 right, Hcd587 right, Hcd605 left, Hcd605 left, Hcd605 right, Hcd608 right, Hcd627 left, Hcd631 left, Hcd631 right, Hcd634 left, Hcd642 right, Hcd649 right, Hcd654 left, Hcd658 right, Hcd669 right, Hcd674 left, Hcd678 right, Hcd683 left, Hcd684 right, Hcd689 right, Hcd690 right, Hcd691 right, Hcd693 right, Hcd697 right, Hcd704 left, Hcd704 left, Hcd712 right, Hcd716 right, Hcd731 left, Hcd738 left, Hcd739 right, Hcd739 right, Hcd749 right, Hcd753 left, Hcd754 left, Hcd755 left, Hcd760 left, Hcd763 right, Hcd768 left, Hcd768 right, Hcd770 left, Hcd773 right, Hcd777 left, Hcd778 right, Hcd781 left, Hcd781 right, Hcd782 left, Hcd783 left, Hcd788 left, Hcd794 right, Hcd796 left, Hcd799 left, Hcd807 right, Hcd812 left, Hcd817 left, Hcd817 right, Hcd829 right, Hcd852 right, Hcd861 right, Hcd863PO right, Hcd866 right, Hcd869 left, Hcd873 left, Hcd886 right, Hcd889 right, Hcd891 right, Hcd892 left, Hcd913 right, Hcd923 left, Hcd923 right, Hcd938 left, Hcd938 right, Hcd939 right, Hcd946 left, Hcd948 right, Hcd960 left, Hcd965 left, Hcd970 left, Hcd975 left, Hcd976 right, Hcd99 right, HPR100 right, HPR129 left, HPR154 left, HPR159 left, HPR163 left, HPR169 right, HPR172 right, HPR181 left, HPR187 left, HPR199 right, HPR206 left, HPR213 right, HPR214 right, HPR220 left, HPR220 right, HPR227 right, HPR232 right, HPR233 right, HPR244 right, HPR262 left, HPR264 right, HPR266 right, HPR271 right, HPR76 right, hsa_mir.sub.-490_Hcd20 right, HSHELA01, HSTRNL, HUMTRAB, HUMTRF, HUMTRN, HUMTRS, HUMTRV1A, let-7f-2-prec2, mir-001b-1-prec1, mir-001b-2-prec, mir-007-1-prec, mir-007-2-precNo2, mir-010a-precNo2, mir-015b-precNo2, mir-016a-chr13, mir-016b-chr3, mir-017-precNot mir-017-precNo2, mir-018-prec, mir-019a-prec, mir-019b-1-prec, mir-019b-2-prec, mir-020-prec, mir-022-prec, mir-023a-prec, mir-023b-prec, mir-024-2-prec, mir-025-prec, mir-027b-prec, mir-029c-prec, mir-032-precNo2, mir-033b-prec, mir-033-prec, mir-034-precNo1, mir-034-precNo2, mir-092-prec-13=092-1No2, mir-092-prec-X=092-2, mir-093-prec-7.1=093-1, mir-095-prec-4, mir-096-prec-7No1, mir-096-prec-7No2, mir-098-prec-X, mir-099b-prec-19No1, mir-100-1/2-prec, mir-100No1, mir-101-prec-9, mir-102-prec-1, mir-103-2-prec, mir-103-prec-5=103-1, mir-106aNo1, mir-106-prec-X, mir-107No1, mir-107-prec-10, mir-122a-prec, mir-123-precNo1, mir-123-precNo2, mir-124a-1-prec1, mir-124a-2-prec, mir-124a-3-prec, mir-125b-1, mir-125b-2-precNo2, mir-127-prec, mir-128b-precNo1, mir-128b-precNo2, mir-133a-1, mir-135-2-prec, mir-136-precNo2, mir-138-1-prec, mir-140No2, mir-142-prec, mir-143-prec, mir-144-precNo2, mir-145-prec, mir-146bNo1, mir-146-prec, mir-147-prec, mir-148aNo1, mir-148-prec, mir-149-prec, mir-150-prec, mir-153-1-prec1, mir-154-prec1No1, mir-155-prec, mir-15aNo1, mir-16-1No1, mir-16-2No1, mir-181a-precNo1, mir-181b-1No1, mir-181b-2No1, mir-181b-precNo1, mir-181b-precNo2, mir-181c-precNo1, mir-181dNo1, mir-188-prec, mir-18bNo2, mir-191-prec, mir-192No2, mir-193bNo2, mir-194-2No1, mir-195-prec, mir-196-2-precNo2, mir-197-prec, mir-198-prec, mir-199a-1-prec, mir-199a-2-prec, mir-199b-precNo1, mir-200a-prec, mir-200bNo1, mir-200bNo2, mir-202*, mir-202-prec, mir-204-precNo2, mir-205-prec, mir-208-prec, mir-20bNo1, mir-212-precNo1, mir-212-precNo2, mir-213-precNo1, mir-214-prec, mir-215-precNo2, mir-216-precNo1, mir-219-2No1, mir-219-prec, mir-223-prec, mir-29b-1No1, mir-29b-2=102prec7.1=7.2, mir-321No1, mir-321No2, mir-324No1, mir-324No2, mir-328No1, mir-342No1, mir-361No1, mir-367No1, mir-370No1, mir-371No1, miR-373*No1, mir-375, mir-376aNo1, mir-379No1, mir-380-5p, mir-382, mir-384, mir-409-3p, mir-423No1, mir-424No2, mir-429No1, mir-429No2, mir-4323p, mir-4325p, mir-449No1, mir-450-1, mir-450-2No1, mir-483No1, mir-484, mir-487No1, mir-495No1, mir-499No2, mir-501No2, mir-503No1, mir-509No1, mir-514-1No2, mir-515-15p, mir-515-23p, mir-516-33p, mir-516-43p, mir-518e/526c, mir-519a-1/52, mir-519a-2No2, mir-519b, mir-519c/52, mir-520c/52, mir-526a-2No1, mir-526a-2No2, MPR103 right, MPR121 left, MPR121 left, MPR130 left, MPR130 right, MPR133 right, MPR141 left, MPR151 left, MPR156 left, MPR162 left, MPR174 left, MPR174 right, MPR185 right, MPR197 right, MPR203 left, MPR207 right, MPR215 left, MPR216 left, MPR224 left, MPR224 right, MPR228 left, MPR234 right, MPR237 left, MPR243 left, MPR244 right, MPR249 left, MPR254 right, MPR74 left, MPR88 right, and MPR95 left.

Analysis for the SNPs rs229109 and rs72552784, associated with sensitivity to bisantrene, is disclosed in United States Patent Application Publication No. 2014/0038836 by Higgins et al., incorporated herein by this reference.

When the improvement is made by pre-/post-treatment preparation, the method of pre-/post-treatment preparation can be, but is not limited to, a method of pre-treatment or post-treatment preparation selected from the group consisting of:
(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) infection control; and
(j) the use of an anti-hypertensive agent.

When the improvement is made by toxicity management, the method of toxicity management can be, but is not limited to, a method of toxicity management selected from the group consisting of:
(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) the use of sustained-release allopurinol;
(j) the non-oral use of allopurinol;
(k) the administration of bone marrow transplant stimulants, blood, platelet infusions, Neupogen, G-CSF; or GM-CSF;
(l) pain management;
(m) infection control; and
(n) administration of anti-inflammatories;
(o) administration of fluids;
(p) administration of corticosteroids;
(q) administration of insulin control medications;
(r) administration of antipyretics;
(s) administration of anti-nausea treatments;
(t) administration of anti-diarrhea treatment;
(u) administration of antihistamines as pre-treatment to prevent anaphylaxis;
(v) administration of agents for reduction of gastric toxicity;
(w) administration of steroids as pre-treatment to prevent anaphylaxis;
(x) administration of sympathetomimetics as pre-treatment to prevent anaphylaxis; and
(y) administration of an agent to control or prevent chemotherapy-induced thrombocytopenia.

Uricosurics include, but are not limited to, probenecid, benzbromarone, and sulfinpyrazone. A particularly preferred uricosuric is probenecid. Uricosurics, including probenecid, may also have diuretic activity.

Poly-ADP ribose polymerase inhibitors are described in G. J. Southan & C. Szabo, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs;

Inhibitors of the Synthesis and Actions of Adrenocortical Hormones" in *Goodman & Gilman's The Pharmacological Basis of Therapeutics* (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

Agents for reduction of gastric toxicity include, but are not limited to, ferruginol (C. Areche et al., "Gastroprotective Activity of Ferruginol in Mice and Rats: Effects on Gastric Secretion, Endogenous Prostaglandins and Non-Protein Sulfhydryls," *J. Pharm. Pharmacol.* 60: 245-251 (2008)), incorporated herein by this reference.

The use of an agent to control or prevent chemotherapy-induced thrombocytopenia is disclosed in U.S. Pat. No. 8,183,342 to Matsuyama, incorporated herein by this reference. The agent can be a Bax-inhibiting peptide of the following formula: $X^1PX^2LX^3X^4$ (SEQ ID NO: 2), wherein $X^1$ is an amino acid with a non-polar side chain, $X^2$ is an amino acid with a non-polar side chain; $X^3$ is an amino acid with a charged polar side chain, $X^4$ is an amino acid with a charged polar side chain, and either $X^1$ or $X^4$ may be absent. Preferred peptides include VPMLKE (SEQ ID NO: 3), VPMLK (SEQ ID NO: 4), PMLKE (SEQ ID NO: 5), PMLK (SEQ ID NO: 6), VPTLK (SEQ ID NO: 7), and VPALR (SEQ ID NO: 8).

When the improvement is made by pharmacokinetic/pharmacodynamic monitoring, the pharmacokinetic/pharmacodynamic monitoring can be, but is not limited to a method selected from the group consisting of:
(a) multiple determinations of blood plasma levels;
(b) multiple determinations of at least one metabolite in blood or urine;
(c) monitoring of immune function;
(d) use of ELISPOT to measure immune responses;
(e) determination of surface marker upregulation; and
(f) monitoring of checkpoint inhibition.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

Monitoring of immune function can be carried out by methods known in the art, including the use of the Cylex® Immune Cell Function Assay, as described in A. Zeevi et al., "Monitoring Immune Function During Tacrolimus Tapering in Small Bowel Transplant Recipients," *Transplant Immunol.* 15: 17-24 (2005), incorporated herein by this reference.

Immune function can also be monitored by assays for upregulation of Th-1 markers such as IL-la, TNF-α, IL-2, IL-12, IL-18 or IFN-γ. Immune function can also be monitored by assays for down regulation of Th-2 products such as IL-4 or IL-10. Similarly, T cell activation markers like CD25+, CD44+, CD62Llow, CD69+, CD71 and CD95 can be used. Macrophage activation is associated with upregulation of the markers CD-13, CD-14, and CD-169 (importantly the dendritic cell markers of CD-80 and CD-86) and the secretion of IFN-γ, IL-1β, IL-6, IL-8, IL-12, IL-18, IL-13, CSF-1, MCP-1, TNF α, iNOS, G-CSF, M-CSF, GM-CSF, CCl3, CCL4, CXCL2, CXCL9, CXCl0, CXCL11, CCR3, and CCR5, so that expression of these markers and molecules can be monitored by conventional methods, such as immunoassays or immunoabsorbent procedures, for the monitoring of immune function. The ELISPOT procedure, described below, can also be used. Other molecules assayed for the monitoring of immune function can include PPAR-γ, the co-stimulatory molecules CD80 and CD-86, IL-17 (to assess Th-17 cell activation and $T_{reg}$ reduction), as well as several Toll-like receptors, including TLR2, TLR4, TLR5, TLR7, and TLR9.

The ELISPOT, or enzyme-linked immunosorbent spot assay is another method known in the art suitable for the determination of immune function and described in C. Czerkinsky et al., "A Solid-Phase Enzyme-Linked Immunospot (ELISPOT) Assay for Enumeration of Specific Antibody-Secreting Cells," *J. Immunol. Meth.*, 65: 109-121 (1983), incorporated herein by this reference. In this assay, either a monoclonal or a polyclonal capture antibody is coated onto a PVDF (polyvinylidene fluoride) microplate. The antibody is chosen for its specificity for the antigen in question. The plate is then blocked, typically with a serum protein that is nonreactive with any of the antibodies in the assay. After this, cells of interest are plated out at varying densities, along with an antigen or a mitogen, and then placed in an incubator with appropriate conditions for the growth and proliferation of the cells. Cytokine (or another cell product to be detected) secreted by activated cells is captured locally by the antibody coated on the microplate. A biotinylated polyclonal antibody specific for the chosen analyte (i.e., the cytokine or other cell product to be detected) is added; this antibody is specific for a distinct epitope of the target cytokine or other cell product to be detected. The detected cytokine or other cell product is then visualized using streptavidin conjugated to an enzyme that produces a precipitable product, such as horseradish peroxidase or alkaline phosphatase, and a precipitating substrate. The colored end product, detectable as a spot, typically represents an individual cell producing the cytokine or other cell product to be detected. The spots can be counted manually or using an automated reader.

Methods for determination of surface marker upregulation are known in the art and are described in T. W. Kuijpers et al., "Membrane Surface Antigen Expression on Neutrophils: A Reappraisal of the Use of Surface Markers for Neutrophil Activation," *Blood* 78: 1105-1111 (1991), incorporated herein by this reference. For determination of surface marker upregulation, particularly of tumor cell markers, a number of surface markers can be monitored. The cancer testes (CT) antigens have all been used, including the MUC series (e.g. MUC1), the MAGE series (e.g. MAGE-A), NYESO-1, and others. HER-2/neu is a favorite can be monitored in breast cancer, as are estrogen receptors. The antiangiogenic markers like VEGF-1 or endoglin (CD-105) are also useful for monitoring. CA-125 has been used for colon cancer. Other cancer markers that can be monitored include, but are not limited to, CA-9 (a marker of tumor related hypoxia), SCCE, the DAM series (DAM-6, DAM-10, and others), ELF2, Ep-CAM, GP-100, h-TERT (human telomerase), the SART series (SART-1, SART-2, and SART-3), the MART series (MART-1, MART-2, and others), WT-1, mutated p53, and many other markers. In particular, for hematopoietic tumors, the following markers may be useful: NuSAP1, CD56, MAGE-A3, PRAME, ROPN1, SCP-1, SLLP1, and SPO11 for AML; as described in S. Anguille et al., "Leukemia-Associated Antigens and Their Relevance to the Immunotherapy of Acute Myeloid Leukemia," *Leukemia* 26: 2186-2196 (2012), incorporated herein by this reference. For lymphoma, the following markers may be useful: TCL-1, CD-20, HOX-11, and other markers.

Methods for monitoring checkpoint inhibition are known in the art and are described in V. Sudakin et al., "Checkpoint Inhibition of the APC/C in HeLa Cells Is Mediated by a Complex of BUBR1, BUB3, CDC20, and MAD2," *J. Cell Biol.* 154: 925-936 (2001), incorporated herein by this reference. Downregulation of CTLA-4, PD-1. OX-40 or many other checkpoint kinases known in the art can be monitored. Similarly, reduction of regulatory T cells ($T_{reg}$s), regulatory DC, and regulatory neutrophils are prima facie evidence of checkpoint blockade and these cells can be monitored for evidence of checkpoint inhibition by conventional immunoassay methods, such as immunoassay of cell surface markers. T cell activation is mediated by the presentation of antigen by dendritic cells; a differentiated myeloid cell considered by some a type of macrophage. Classical macrophages themselves can have antigen presentation capabilities. In the same way that tumor killing T cells are activated by antigen presentation, so are tumor protecting regulatory T cells and there are various subclasses of $T_{reg}$s now identified. Thus, changes in the manner in which antigens are presented by myeloid cells, and alterations in the T cell phenotypes mediated by cytokines produced by macrophages, can determine whether or not the predominant activated T cell phenotypes kill or protect tumor cells. Thus, a theoretical relationship exists between macrophage activation and killer vs regulatory T cell activation.

When the improvement is made by drug combination, the drug combination can be, but is not limited to, a drug combination selected from the group consisting of:
(a) use with fraudulent nucleosides;
(b) use with fraudulent nucleotides;
(c) use with thymidylate synthetase inhibitors;
(d) use with signal transduction inhibitors;
(e) use with cisplatin or platinum analogs;
(f) use with alkylating agents;
(g) use with anti-tubulin agents;
(h) use with antimetabolites;
(i) use with berberine;
(j) use with apigenin;
(k) use with colchicine or an analog thereof;
(l) use with genistein;
(m) use with etoposide;
(n) use with cytarabine;
(o) use with camptothecins;
(p) use with vinca alkaloids;
(q) use with topoisomerase inhibitors;
(r) use with 5-fluorouracil;
(s) use with curcumin;
(t) use with rosmarinic acid;
(u) use with mitoguazone;
(v) use with meisoindigo;
(w) use with imatinib;
(x) use with dasatinib;
(y) use with nilotinib;
(z) use with epigenetic modulators;
(aa) use with transcription factor inhibitors;
(ab) use with taxol;
(ac) use with homoharringtonine;
(ad) use with pyridoxal;
(ae) use with spirogermanium;
(af) use with caffeine;
(ag) use with nicotinamide;
(ah) use with methylglyoxalbisguanylhydrazone;
(ai) use with poly-ADP ribose polymerase (PARP) inhibitors;
(aj) use with EGFR inhibitors;
(ak) use with Bruton's tyrosine kinase (BTK) inhibitors;
(al) use with bis-[thio-hydrazide] amides;
(am) use with succinimide or maleimide derivatives as inhibitors of topoisomerase II;
(an) use with histone deacetylase (HDAC) inhibitors;
(ao) use with immunostimulants;
(ap) use with telomerase inhibitors;
(aq) use with agents that inhibit the expression or activity of Her2;
(ar) use with agents that inhibit the expression or activity of estrogen receptors;
(as) use with agents that inhibit the expression or activity of antigens associated with specific tumor targets;
(at) use with G-quadruplex ligands;
(au) use with polycyclic lysophosphatidic receptor antagonists;
(av) use with anti-CTGF agents;
(aw) use with myeloid differentiation inducing agents;
(ax) use with covalent diabodies binding to a tumor-associated antigen;
(ay) use with bispecific antibodies that have a cell-penetrating determinant and an intracellular target-binding determinant;
(az) use with multidomain molecules that comprise a cell binding ligand that binds to cells in the tumor stroma such as endothelial cells, fibroblasts, or immune cells and an oligonucleotide that inhibits the nonsense-mediated decay pathway;
(ba) use with tumor-specific antibodies binding to a portion of the CD44 protein or a binding protein derived from the light-chain or heavy-chain complementary-determining regions of such antibodies;
(bb) use with inhibitors of CXCR4;
(bc) use with pyruvate dehydrogenase kinase (PDK1) inhibitors;
(bd) use with epherin receptor targeting agents;
(be) use with binding proteins for Axl;
(bf) use with Wnt pathway inhibitors together with MAPK pathway inhibitors;
(bg) use with TEC family kinase inhibitors;
(bh) use with substituted macrocyclic compounds with proteasome activity;
(bi) use with peptide-based PACE4 inhibitors;
(bj) use with azaindole derivatives as JAK3 inhibitors;
(bk) use with inhibitors of Myc;
(bl) use with inhibitors of furin and other pro-protein convertases;
(bm) use with GPBP-1 inhibitors, optionally together with a p21 inhibitor;
(bn) use with $PGE_2$ inhibitors; and
(bo) use with activatable antibodies targeting tumor-specific markers.

Topoisomerase inhibitors include, but are not limited to, irinotecan, topotecan, camptothecin, lamellarin D, amsacrine, etoposide, etoposide phosphate, teniposide, doxorubicin, 4-[2-(3,5-dioxo-1-piperazinyl)-1-methylpropyl]piperazine-2,6-dione (ICRF-193), doxorubicin, daunorubicin, mitroxantrone, tenoposide, actinomycin-D, and Ofloxin.

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," Clin. Cancer Res. 9: 516s (2003), incorporated herein in its entirety by this reference.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, dianhydrogalactitol, dibromodulcitol, other substituted hexitols, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, trimelamol, and uramustine, as described in U.S. Pat. No. 7,446,122 by Chao et al., incorporated herein by this reference.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Colchicine is a tricyclic alkaloid that exerts its activity by binding to the protein tubulin. Analogs of colchicine include, but are not limited to, cholchiceinamide, N-desacetylthiocolchicine, demecolcine, N-acetyliodocolchinol, trimethylcolchicinie acid (TMCA) methyl ether, N-acetylcolchinol, TMCA ethyl ether, isocolchicine, isocolchiceinamide, iso-TMCA methyl ether, colchiceine, TMCA, N-benzoyl TMCA, colchicosamide, colchicoside, colchinol and colchinoic acid (M. H. Zweig & C. F. Chignell, "Interaction of Some Colchicine Analogs, Vinblastine and Podophyllotoxin with Rat Brain Microtubule Protein," Biochem. Pharmacol. 22: 2141-2150 (1973) and B. Yang et al., "Syntheses and Biological Evaluation of Ring C-Modified Colchicine Analogs," Bioorg. Med. Chem. Lett. 20: 3831-3833 (2010)), both of which are incorporated herein by this reference.

Genistein is an isoflavone with the systemic name 5,7-dihydroxy-3-(4-hydroxyphenyl)chromen-4-one. Genistein has a number of biological activities, including activation of PPARs, inhibition of several tyrosine kinases, inhibition of topoisomerase, antioxidative activity, activation of Nrf2 antioxidative response, activation of estrogen receptor beta, and inhibition of the mammalian hexose transporter GLUT2.

Etoposide is an anticancer agent that acts primarily as a topoisomerase II inhibitor. Etoposide forms a ternary complex with DNA and the topoisomerase II enzyme, prevents re-ligation of the DNA strands and thus induces DNA strand breakage and promotes apoptosis of the cancer cells.

Cytarabine is a nucleoside analog replacing the ribose with arabinose. It can be incorporated into DNA and also inhibits both DNA and RNA polymerases and nucleotide reductase. It is particularly useful in the treatment of acute myeloid leukemia and acute lymphocytic leukemia, Camptothecins include camptothecin, homocamptothecin, topotecan, irinotecan, DB 67, BNP 1350, exatecan, lurtotecan, ST 1481, and CKD 602. These compounds act as topoisomerase I inhibitors and block DNA synthesis in cancer cells.

Vinca alkaloids include vinblastine, vincristine, vindesine, and vinorelbine.

Topoisomerase inhibitors include topoisomerase I inhibitors and topoisomerase II inhibitors. Topoisomerase I inhibitors include the camptothecins and lamellarin D. Topoisomerase II inhibitors include, in addition to amonafide and derivatives and analogs thereof, etoposide, teniposide, doxorubicin, daunorubicin, mitoxantrone, amsacrine, ellipticines, and aurintricarboxylic acid. A number of plant-derived naturally-occurring phenolic compounds, such as genistein, quercetin, and resveratrol, exhibit inhibitory activity toward both topoisomerase I and topoisomerase II.

5-fluorouracil is a base analog that acts as a thymidylate synthase inhibitor and thereby inhibits DNA synthesis. When deprived of a sufficient supply of thymidine, rapidly dividing cancer cells die by a process known as thymineless death.

Curcumin is believed to have anti-neoplastic, anti-inflammatory, antioxidant, anti-ischemic, anti-arthritic, and anti-amyloid properties and also has hepatoprotective activity.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Meisoindigo is active via several, possibly novel mechanisms of action. It has cell cycle specific effects, including arrest in G(O)/G1 for AML cell lines and G2/M arrest for HT-29 colorectal cell lines. It also stimulates apoptosis through a number of mechanisms, including the upregulation of p21 and p27 and the downregulation of Bcl-2 in primary AML cells, as well as upregulation of Bak and Bax in AML cells (DKO insensitive to chemotherapy), and a novel caspase-dependent pathway in K562 cells. Meisoindigo also has effects on mitochondria, but with no change in Bcl-2, Bax, and Bid protein expression.

Meisoindigo also stimulates the cleavage of pro-caspase 3, 8, 9 and PARP in HL-60 myeloid cells. Meisoindigo also is directed to multiple cellular targets, which are possibly synergistic and complementary. For example, it promotes differentiation of human myeloblastic leukemic cells, accompanied by down regulation of c-myb gene expression. It also promotes inhibition of DNA and RNA synthesis in W256 cells, microtubule assembly, glycogen synthase kinase-3β (GSK-3β) (at 5-50 nM), CDK1/cyclin B, and CDK5/p25 (tau microtubule protein phosphorylation). Additionally, meisoindigo decreases β-catenin and c-myc (HL-60 cells, but not in K562), affects the Wnt pathway through inhibiting GSK-3β and down regulating β-catenin and c-myc protein expression. Meisoindigo also promotes upregulation of CD11b, promoting myeloid differentiation, and upregulation of Ahi-1 in Jurkat cells (inducing phosphorylation of c-Myb). Furthermore, meisoindigo exhibits antiangiogenic effects, including decreased VEGF protection, VCAM-1, tubule formulation in HUVEC, and ECV304 apoptosis.

Imatinib is an inhibitor of the receptor tyrosine kinase enzyme ABL and is used to treat chronic myelogenous leukemia, gastrointestinal stromal tumors, and other hyperproliferative disorders.

Dasatinib is an inhibitor of BCR/ABL and Src family tyrosine kinases and is used to treat chronic myelogenous leukemia and acute lymphoblastic leukemia.

Nilotinib is another tyrosine kinase inhibitor approved for the treatment of chronic myelogenous leukemia; it inhibits the kinases BCR/ABL, KIT, LCK, EPHA3, and a number of other kinases.

Epigenetic modulators include polyamine-based epigenetic modulators, such as the polyamine-based epigenetic modulators described in S. K. Sharma et al., "Polyamine-Based Small Molecule Epigenetic Modulators," *Med. Chem. Commun.* 3: 14-21 (2012), and L. G. Wang & J. W. Chiao, "Prostate Cancer Chemopreventive Activity of Phenethyl Isothiocyanate Through Epigenetic Regulation (Review), *Int. J. Oncol.* 37: 533-539 (2010), both incorporated herein by this reference.

Transcription factor inhibitors include 1-(4-hexaphenyl)-2-propane-1-one, 3-fluoro-4-[[2-hydroxy-2-(5,5,8,8-tetramethyl-5,6,7,8-tetrahydro-2-naphthalenyl)acetyl]amino]-benzoic acid (BMS 961), 4-[5-[8-(1-methylethyl)-4-phenyl-2-quinolinyl]-1H-pyrrolo-2-benzoic acid (ER-50891), 7-ethenyl-2-(3-fluoro-4-hydroxyphenyl)-5-benzoxazolol (ERB 041), and other compounds. Transcription factor inhibitors are described in T. Berg, "Inhibition of Transcription Factors with Small Organic Molecules," *Curr. Opin. Chem. Biol.* 12: 464-471 (2008), incorporated herein by this reference.

Tetrandrine has the chemical structure 6,6',7,12-tetramethoxy-2,2'-dimethyl-1 β-berbaman and is a calcium channel blocker that has anti-inflammatory, immunologic, and antiallergenic effects, as well as an anti-arrhythmic effect similar to that of quinidine. It has been isolated from *Stephania tetranda* and other Asian herbs.

VEGF inhibitors include bevacizumab (Avastin), which is a monoclonal antibody against VEGF, itraconazole, and suramin, as well as batimastat and marimastat, which are matrix metalloproteinase inhibitors, and cannabinoids and derivatives thereof.

Cancer vaccines are being developed. Typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, "Cancer Vaccines: Accomplishments and Challenges," *Crit. Rev. Oncol. Hematol.* 67: 93-102 (2008), incorporated herein by this reference.

The use of methylglyoxalbisguanylhydrazone in cancer therapy has been described in D. D. Von Hoff, "MGBG: Teaching an Old Drug New Tricks," *Ann. Oncol.* 5: 487-493 (1994), incorporated herein by this reference.

Poly-ADP ribose polymerase inhibitors are described in G. J. Southan & C. Szabo, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds. Poly-ADP ribose polymerase (PARP) inhibitors include, but are not limited to: (1) derivatives of tetracycline as described in U.S. Pat. No. 8,338,477 to Duncan et al.; (2) 3,4-dihydro-5-methyl-1(2H)-isoquinoline, 3-aminobenzamide, 6-aminonicotinamide, and 8-hydroxy-2-methyl-4(3H)-quinazolinone, as described in U.S. Pat. No. 8,324,282 to Gerson et al.; (3) 6-(5H)-phenanthridinone and 1,5-isoquinolinediol, as described in U.S. Pat. No. 8,324,262 by Yuan et al.; (4) (R)-3-[2-(2-hydroxymethylpyrrolidin-1-yl)ethyl]-5-methyl-2H-isoquinolin-1-one, as described in U.S. Pat. No. 8,309,573 to Fujio et al.; (5) 6-alkenyl-substituted 2-quinolinones, 6-phenylalkyl-substituted quinolinones, 6-alkenyl-substituted 2-quinoxalinones, 6-phenylalkyl-substituted 2-quinoxalinones, substituted 6-cyclohexylalkyl substituted 2-quinolinones, 6-cyclohexylalkyl substituted 2-quinoxalinones, substituted pyridones, quinazolinone derivatives, phthalazine derivatives, quinazolinedione derivatives, and substituted 2-alkyl quinazolinone derivatives, as described in U.S. Pat. No. 8,299,256 to Vialard et al.; (6) 5-bromoisoquinoline, as described in U.S. Pat. No. 8,299,088 to Mateucci et al.; (7) 5-bis-(2-chloroethyl)amino]-1-methyl-2-benzimidazolebutyric acid, 4-iodo-3-nitrobenzamide, 8-fluoro-5-(4-((methylamino)methyl)phenyl)-3,4-dihydro-2H-azepino[5,4,3-cd] indol-1(6H)-one phosphoric acid, and N-[3-(3,4-dihydro-4-oxo-1-phthalazinyl)phenyl]-4-morpholinebutanamide methanesulfonate, as described in U.S. Pat. No. 8,227,807 to Gallagher et al.; (8) pyridazinone derivatives, as described in U.S. Pat. No. 8,268,827 to Branca et al.; (9) 4-[3-(4-cyclopropanecarbonyl-piperazine-1-carbonyl)-4-fluorobenzyl]-2H-phthalazin-1-one, as described in U.S. Pat. No. 8,247,416 to Menear et al.; (10) tetraaza phenalen-3-one compounds, as described in U.S. Pat. No. 8,236,802 to Xu et al.; (11) 2-substituted-1H-benzimidazole-4-carboxamides, as described in U.S. Pat. No. 8,217,070 to Zhu et al.; (12) substituted 2-alkyl quinazolinones, as described in U.S. Pat. No. 8,188,103 to Van der Aa et al.; (13) 1H-benzimidazole-4-carboxamides, as described in U.S. Pat. No. 8,183,250 to Penning et al.; (13) indenoisoquinolinone analogs, as described in U.S. Pat. No. 8,119,654 to Jagtap et al.; (14) benzoxazole carboxamides, described in U.S. Pat. No. 8,088,760 to Chu et al; (15) diazabenzo[de] anthracen-3-one compounds, described in U.S. Pat. No. 8,058,075 to Xu et al.; (16) dihydropyridophthalazinones, described in U.S. Pat. No. 8,012,976 to Wang et al., (17) substituted azaindoles, described in U.S. Pat. No. 8,008,491 to Jiang et al.; (18)

fused tricyclic compounds, described in U.S. Pat. No. 7,956,064 to Chua et al.; (19) substituted 6a,7,8,9-tetrahydropyrido[3,2-e]pyrrolo[1,2-a]pyrazin-6(5H)-ones, described in U.S. Pat. No. 7,928,105 to Gangloff et al.; and (20) thieno[2,3-c]isoquinolines, described in U.S. Pat. No. 7,825,129 to Pellicciari et al., all of which are incorporated herein by this reference. Other PARP inhibitors are known in the art.

EGFR inhibitors, including both small molecules and monoclonal antibodies, are described above. Other EGFR inhibitors are known in the art.

Bruton's tyrosine kinase (BTK) is a kinase enzyme that plays a key role in the maturation of B cells and in mast cell activation through the high-affinity IgE receptor. Deficiencies in BTK activity are associated with the primary immunodeficiency disease X-linked agammaglobulinemia. The Btk gene is located on the X-chromosome. BTK contains a PH domain that binds phosphatidyl inositol (3,4,5)-triphosphate (PIP3). PIP3 induces BTK to phosphorylate phospholipase C, which in turn hydrolyzes phosphatidyl inositol diphosphate into two second messengers, inositol triphosphate and diacylglycerol, which in turn modulate the activity of downstream proteins in B cells. BTK inhibitors include, but are not limited to: LFM-A13 (α-cyano-β-hydroxy-β-methyl-N-(2,5-dibromophenyl)propenamide; terreic acid ((1R,6S)-3-hydroxy-4-methyl-7-oxabicyclo[4.1.0]hept-3-ene-2,5-dione); ibrutinib; pyrazolo[3,4-d]pyrimidine and pyrrolo[2,3-d]pyrimidine compounds as disclosed in U.S. Pat. No. 8,377,946 to Chen et al., incorporated herein by this reference; 2,4-disubstituted pyrimidines as disclosed in U.S. Pat. No. 8,338,439 to Singh et al., incorporated herein by this reference; 6-phenyl-imidazo[1,2-a]pyridine and 6-phenyl-imidazo[1,2-b]pyridazine derivatives, as disclosed in U.S. Pat. No. 8,324,211 to Dewdney et al., incorporated herein by this reference; 5-phenyl-1H-pyridin-2-one, 6-phenyl-2H-pyridazin-3-one, and 5-phenyl-1H-pyrazin-2-one derivatives, as disclosed in U.S. Pat. No. 8,318,719 to Dewdney et al. and U.S. Pat. No. 8,299,077 to Berthel et al., incorporated herein by this reference; 1-(3-(4-amino-3-(4-phenoxyphenyl)-1H-pyrazolo[3,4-d]pyrimidin-1-yl)piperidin-1yl)prop-2-en-1-one, (E)-1-(3-(4-amino-3-(4-phenoxyphenyl)-1H-pyrazolo[3,4-d]pyrimidin-1-yl)piperidin-1-yl)but-2-en-1-one, 1-(3-(4-amino-3-(4-phenoxyphenyl)-1H-pyrazolo[3,4-d]pyrimidin-1-yl)piperidin-1-yl)sulfonylethene, 1-(3-(4-amino-3-(4-phenoxyphenyl)-1H-pyrazolo[3,4-d]pyrimidin-1-yl)piperidin-1-yl)prop-2-yn-1-one, 1-(4-(4-amino-3-(4-phenoxyphenyl)-1H-pyrazolo[3,4-d]pyrimidin-1-yl)piperidin-1-yl)prop-2-en-1-one, N-((1s,4s)-4-(4-amino-3-(4-phenoxyphenyl)-1H-pyrazolo[3,4-d]pyrimidin-1-yl)cyclohexyl)acrylamide, 1-((R)-3-(4-amino-3-(4-phenoxyphenyl)-1H-pyrazolo[3,4-d]pyrimidin-1-yl)pyrrolidin-1-yl)prop-2-en-1-one, 1-((S)-3-(4-amino-3-(4-phenoxyphenyl)-1H-pyrazolo[3,4-d]pyrimidin-1-yl)pyrrolidin-1-yl)prop-2-en-1-one, 1-((R)-3-(4-amino-3-(4-phenoxyphenyl)-1H-pyrazolo[3,4-d]pyrimidin-1-yl)piperidin-1-yl)prop-2-en-1-one, 1-((S)-3-(4-amino-3-(4-phenoxyphenyl)-1H-pyrazolo[3,4-d]pyrimidin-1-yl)piperidin-1-yl)prop-2-en-1-one, and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one, as disclosed in U.S. Pat. No. 8,236,812 to Honigberg et al., incorporated herein by this reference; pyrazolo[3,4-d]pyrimidines, as disclosed in U.S. Pat. No. 8,232,280 to Honigberg et al., incorporated herein by this reference; 2-(4-fluoro-2-methylphenylamino)-1,6-dimethyl-7-[3-(4-methyl-4-oxo-4$\lambda^5$[1,4]azaphosphinan-1-yl)-propenyl]-1,8-dihydro-imidazo[4,5-h]isoquinolin-9-one, 2-(2,6-dichloro-phenylamino)-1,6-dimethyl-7-[3-(4-methyl-4-oxo-4$\lambda^5$[1,4]azaphosphinan-1-yl)-propenyl]-1,8-dihydro-imidazo[4,5-h]isoquinolin-9-one, 2-(4-fluoro-2-methylphenylamino)-1,6-dimethyl-7-[3-(4-oxo-4-phenyl-4$\lambda^5$[1,4]azaphosphinan-1-yl)-propenyl]-1,8-dihydro-imidazo[4,5-h]isoquinolin-9-one, 2-(3-fluoro-6-methylphenylamino)-1,6-dimethyl-7-[3-(4-oxo-4-phenyl-4$\lambda^5$[1,4]azaphosphinan-1-yl)-propenyl]-1,8-dihydro-imidazo[4,5-h]isoquinolin-9-one, 2-(2,6-dichlorophenylamino)-1,6-dimethyl-7-[3-(4-oxo-4-phenyl-4$\lambda^5$[1,4]azaphosphinan-1-yl)-propenyl]-1,8-dihydro-imidazo[4,5-h]isoquinolin-9-one, 2-(2,4-dichloro-6-methylphenylamino)-1,6-dimethyl-7-[3-(4-oxo-4-phenyl-4$\lambda^5$[1,4]azaphosphinan-1-yl)-propenyl]-1,8-dihydro-imidazo[4,5-h]isoquinolin-9-one, 2-(3-fluoro-6-methylphenylamino)-1,6-dimethyl-7-{2-[(4-oxo-4-phenyl-4$\lambda^5$[1,4]azaphosphinan-1-yl)-propenyl]-1,8-dihydro-imidazo[4,5-h]isoquinolin-9-one, 2-(2,4-dichloro-6-methylphenylamino)-1,6-dimethyl-7-[3-(4-oxo-4-phenyl-4$\lambda^5$-[1,4]azaphosphinan-1-yl)-propyl]-1,8-dihydro-imidazo[4,5-h]isoquinolin-9-one, 2-(4-fluoro-2-methylphenylamino)-1,6-dimethyl-7-[3-(4-oxo-4-phenyl-4$\lambda^5$-[1,4]azaphosphinan-1-yl)-propyl]-1,8-dihydro-imidazo[4,5-h]isoquinolin-9-one, 2-(4-fluoro-2-methylphenylamino)-1,6-dimethyl-7-[3-(4-oxo-4-(4-fluorophenyl)-4$\lambda^5$-[1,4]azaphosphinan-1-yl)-propenyl]-1,8-dihydro-imidazo[4,5-h] isoquinolin-9-one, 2-(3-fluoro-6-methylphenylamino)-1,6-dimethyl-7-[3-(4-oxo-4-(4-methoxyphenyl)-4$\lambda^5$-[1,4]azaphosphinan-1-yl)-propenyl]-1,8-dihydro-imidazo[4,5-h] isoquinolin-9-one, 2-(4-fluoro-2-methylphenylamino)-1,6-dimethyl-7-{3-[4-(4-fluorophenylmethyl)-4-oxo-4$\lambda^5$[1,4]azaphosphinan-1-yl]-propenyl}-1,8-dihydro-imidazo[4,5-h]isoquinolin-9-one, 2-(4-fluoro-2-methylphenylamino)-1,6-dimethyl-7-{3-[4-(cyclopropylmethyl)-4-oxo-4$\lambda^5$-[1,4]azaphosphinan-1-yl]-propenyl}-1,8-dihydro-imidazo[4,5-h]isoquinolin-9-one, 2-(4-fluoro-2-methylphenylamino)-1,6-dimethyl-7-{3-[4-(cyclopropyl)-4-oxo-4$\lambda^5$-[1,4]azaphosphinan-1-yl)-propenyl}-1,8-dihydro-imidazo[4,5-h]isoquinolin-9-one, 2-(4-fluoro-2-methylphenylamino)-1,6-dimethyl-7-{3-[(1-oxo-1-methyl-1$\lambda^5$-phosphinan-4-yl)-carbonylamino]propenyl}-1,8-dihydro-imidazo[4,5-h]isoquinolin-9-one, 2-(4-fluoro-2-methylphenylamino)-1,6-dimethyl-7-{3-[(1-oxo-1-trans-phenyl-1$\lambda^5$-phosphinan-4-yl)-carbonylamino]propenyl}-1,8-dihydro-imidazo[4,5-h]isoquinolin-9-one, 2-(4-fluoro-2-methyl-phenylamino)-1,6-dimethyl-7-{3-[(1-oxo-1-cis-phenyl-1$\lambda^5$-phosphinan-4-yl)-carbonylamino]propenyl}-1,8-dihydro-imidazo[4,5-h]isoquinolin-9-one, dichlorophenylamino)-1,6-dimethyl-7-[3-(N-phenylpiperazin-1-yl)-propenyl]-1,8-dihydro-imidazo[4,5-h]isoquinolin-9-one, 2-(4-fluoro-2-methylphenylamino)-1,6-dimethyl-7-[3-(N-phenylpiperazin-1-yl)-propenyl]-1,8-dihydro-imidazo[4,5-h]isoquinolin-9-one, 2-(4-fluoro-2-methylphenylamino)-1,6-dimethyl-7-[3-(N-(4-chlorophenyl)-piperazin-1-yl)-propenyl]-1,8-dihydro-imidazo[4,5-h]isoquinolin-9-one, 2-(4-fluoro-2-methylphenylamino)-1,6-dimethyl-7-[3-(N-methylcarbonylpiperazin-1-yl)-propenyl]-1,8-dihydro-imidazo[4,5-h]isoquinolin-9-one, 2-(4-fluoro-2-methylphenylamino)-1,6-dimethyl-7-[3-(N-phenylcarbonylpiperazin-1-yl)-propenyl]-1,8-dihydro-imidazo[4,5-h]isoquinolin-9-one, 2-(4-fluoro-2-methylphenylamino)-1,6-dimethyl-7-[3-(N-methylsulfonylpiperazin-1-yl)-propenyl]-1,8-dihydro-imidazo[4,5-h]isoquinolin-9-one, 2-(3-fluoro-2-methylphenylamino)-1,6-dimethyl-7-[3-(N-methylsulfonylpiperazin-1-yl)-propenyl]-1,8-dihydro-imidazo[4,5-h]isoquinolin-9-one, 2-(4-fluoro-2-methylphenylamino)-1,6-dimethyl-7-[3-(N-(2,6-dichlorophenylmethyl)-piperazin-1-yl)-propenyl]-1,8-dihydro-imidazo[4,5-h]isoquinolin-9-one, 2-(4-fluoro-2-methylphenylamino)-1,6-dimethyl-7-[3-(N-phenylsulfonylpiperazin-1-yl)-propenyl]-1,8-dihydro-imidazo[4,5-h] isoquinolin-9-one, 2-(4-fluoro-2-methylphenylamino)-1,6- dimethyl-7-[3-(N-(4-fluorophenyl)-piperazin-1-yl)-propenyl]-1,8-dihydro-imidazo[4,5-h]isoquinolin-9-one, 2-(4-fluoro-2-methylphenylamino)-1,6-dimethyl-7-[3-(N-tert-butyloxycarbonylpiperazin-1-yl)-propenyl]-1,8-dihydro-imidazo[4,5-h]isoquinolin-9-one, 2-(4-fluoro-2-methylphenylamino)-1,6-dimethyl-7-[3-(N—(N,N-dimethylaminosulfonyl)-piperazin-1-yl)-propenyl]-1,8-dihydro-imidazo[4,5-h]isoquinolin-9-one, 2-(4-fluoro-2-methylphenylamino)-1,6-dimethyl-7-[3-(N-ethylcarbonylpiperazin-1-yl)-propenyl]-1,8-dihydro-imidazo[4,5-h]isoquinolin-9-one, 2-(4-fluoro-2-methylphenylamino)-1,6-dimethyl-7-[3-(N-(isopropylsulfonyl)-piperazin-1-yl)-propenyl]-1,8-dihydro-imidazo[4,5-h]isoquinolin-9-one, 2-(4-fluoro-2-methylphenylamino)-1,6-dimethyl-7-[3-(N-(ethylsulfonyl)-piperazin-1-yl)-propenyl]-1,8-dihydro-imidazo[4,5-h]isoquinolin-9-one, and 2-(4-fluoro-2-methylphenylamino)-1,6-dimethyl-7-[3-(N-isopropylcarbonylpiperazin-1-yl)-propenyl]-1,8-dihydro-imidazo[4,5-h]isoquinolin-9-one, as disclosed in U.S. Pat. No. 8,067,395 to Jankowski et al., incorporated herein by this reference; 4-tert-butyl-N-(2-methyl-3-{1-methyl-5-[5-(morpholine-4-carbonyl)-pyridin-2-ylamino]-6-oxo-1,6-dihydro-pyridazin-3-yl}-phenyl)-benzamide, 4-tert-butyl-N-(2-methyl-3-{1-methyl-5-[5-(4-methyl-piperazine-1-carbonyl)pyridin-2-ylamino]-6-oxo-1,6-dihydro-pyridazin-3-yl}-phenyl)-benzamide, 4-tert-butyl-N-{2-methyl-3-[1-methyl-6-oxo-5-(pyridin-2-ylamino)-1,6-dihydropyridazin-3-yl]-phenyll-benzamide, 4-tert-butyl-N-{2-methyl-3-[1-methyl-6-oxo-5-(pyrimidin-4-ylamino)-1,6-dihydropyridazin-3-yl]-phenyl}-benzamide, 4-(1-hydroxy-1-methyl-ethyl)-N-(2-methyl-3-1-methyl-5-[5-(4-methyl-piperazine-1-carbonyl)-pyridin-2-ylamino]-6-oxo-1,6-dihydro-pyridazin-3-yl}-phenyl)benzamide, 4-tert-butyl-piperazine-1-carboxylic acid (2-methyl-3-{1-methyl-5-(morpholine-4-carbonyl)-pyridin-2-ylamino]-6-oxo-1,6-dihydro-pyridazin-3-yl}-phenyl)-amide, 4-tert-butyl-2-methoxy-N-(2-methyl-3-{1-methyl-5-[5-(morpholine-4-carbonyl)pyridin-2-ylamino]-6-oxo-1,6-dihydro-pyridazin-3-yl}-phenyl)-benzamide, 7-tert-butyl-3-(2-methyl-3-1-methyl-5-[5-(morpholine-4-carbonyl)-pyridin-2-ylamino]-6-oxo-1,6-dihydro-pyridazin-3-yl]-phenyl)-3H-quinazolin-4-one, 6-{6-[3-(4-tert-butyl-benzoylamino)-2-methyl-phenyl]-2-methyl-3-oxo-2,3-dihydro-pyridazin-4-ylamino}-nicotinic acid methyl ester, 3-tert-butoxy-azetidine-1-carboxylic acid (2-methyl-3-{1-methyl-5-[5-(morpholine-4-carbonyl)-pyridin-2-ylamino]-6-oxo-1,6-dihydro-pyridazin-3-yl}-phenyl)-amide, 4-tert-butyl-N-(2-methyl-3-{1-methyl-5-[2-(4-methyl-piperazin-1-yl)-pyrimidin-4-ylamino]-6-oxo-1,6-dihydro-pyridazin-3-yl}-phenyl)-benzamide, 4-tert-butyl-N-{2-methyl-3-[1-methyl-5-(2-methylsulfanyl-pyrimidin-4-ylamino)-6-oxo-1,6-dihydro-pyridazin-3-yl]-phenyl}-benzamide, 4-tert-butyl-N-{3-[5-(2-methanesulfonyl-pyrimidin-4-ylamino)-1-methyl-6-oxo-1,6-dihydropyridazin-3-yl]-2-methyl-phenyl}-benzamide, 4-tert-butyl-N-{2-methyl-3-[1-methyl-5-(2-morpholin-4-yl-pyrimidin-4-ylamino)-6-oxo-1,6-dihydro-pyridazin-3-yl]-phenyl}-benzamide, 4-(1-hydroxy-1-methyl-ethyl)-N-(2-methyl-3-{1-methyl-5-[5-(morpholine-4-carbonyl)pyridin-2-ylamino]-6-oxo-1,6-dihydro-pyridazin-3-yl}-phenyl)-benzamide, 4-(1-hydroxy-1-methyl-ethyl)-N-(3-{1-methyl-5-[5-(morpholine-4-carbonyl)pyridin-2-ylamino]-6-oxo-1,6-dihydro-pyridazin-3-yl}-phenyl)-benzamide, 4-tert-butyl-N-{3-[5-(2-methoxy-pyrimidin-4-ylamino)-1-methyl-6-oxo-1,6-dihydropyridazin-3-yl]-2-methyl-phenyl}-benzamide; 4-tert-butyl-N-(3-{5-[2-(2-dimethylamino-ethoxy)-pyrimidin-4-ylamino]-1-methyl-6-oxo-1,6-dihydro-pyridazin-3-yl}-2-methyl-phenyl)-benzamide, 4-tert-butyl-N-(2-methyl-3-{1-methyl-6-oxo-5-[2-(pyrrolidin-3-ylmethoxy)-pyrimidin-4-ylamino]-1,6-dihydro-pyridazin-3-yl}-phenyl)-benzamide, 4-tert-butyl-N-(3-{5-[2-(3-hydroxymethyl-pyrrolidin-1-yl)-pyrimidin-4-ylamino]-1-methyl-6-oxo-1,6-dihydro-pyridazin-3-yl}-2-methyl-phenyl)-benzamide, 4-tert-butyl-N-{2-methyl-3-[1-methyl-6-oxo-5-(2-pyrrolidin-1-yl-pyrimidin-4-ylamino)-1,6-dihydro-pyridazin-3-yl]-phenyl}-benzamide, 4-tert-butyl-N-(3-{5-[2-(3-hydroxy-pyrrolidin-1-yl)-pyrimidin-4-ylamino]-1-methyl-6-oxo-1,6-dihydro-pyridazin-3-yl}-2-methyl-phenyl)-benzamide, 4-tert-butyl-N-{2-methyl-3-[1-methyl-5-(3-methyl-ureido)-6-oxo-1,6-dihydro-pyridazin-3-yl]-phenyl}-benzamide, 4-tert-butyl-N-(2-methyl-3-{1-methyl-5-[4-(morpholine-4-carbonyl)-phenylamino]-6-oxo-1,6-dihydro-pyridazin-3-yl}-phenyl)-benzamide, 4-tert-butyl-N-(3-{1-methyl-5-[5-(morpholine-4-carbonyl)-pyridin-2-ylamino]-6-oxo-1,6-dihydro-pyridazin-3-yl}-phenyl)-benzamide, 4-tert-butyl-N-(3-{5-[4-(4-hydroxy-piperidine-1-carbonyl)-phenylamino]-1-methyl-6-oxo-1,6-dihydro-pyridazin-3-yl}-2-methyl-phenyl)-benzamide, 4-tert-butyl-N-{3-[5-ethyl-ureido)-1-methyl-6-oxo-1,6-dihydro-pyridazin-3-2-methylphenyl}-benzamide; 4-dimethylamino-N-(3-{5-[5-(4-hydroxy-piperidine-1-carbonyl)-pyridin-2-ylamino]-1-methyl-6-oxo-1,6-dihydro-pyridazin-3-yl}-2-methyl-phenyl)-benzamide, N-(3-hydroxy-4,4-dimethyl-pentyl)-2-(3-{1-methyl-5-[5-(morpholine-4-carbonyl)-pyridin-2-ylamino]-6-oxo-1,6-dihydro-pyridazin-3-yl}-phenyl)-acetamide, 4-tert-butyl-2-hydroxy-N-(2-methyl-3-{1-methyl-5-[5-(morpholine-4-carbonyl)-pyridin-2-ylamino]-6-oxo-1,6-dihydro-pyridazin-3-yl}-phenyl)-benzamide, 6-{3-[2-(1,3-dihydro-isoindol-2-yl)-2-oxo-ethyl]-phenyl}-4-[5-(4-hydroxypiperidine-1-carbonyl)-pyridin-2-ylamino]-2-methyl-2H-pyridazin-3-one, 7-tert-butyl-3-(2-methyl-3-{1-methyl-5-[5-(morpholine-4-carbonyl)-pyridin-2-ylamino]-6-oxo-1,6-dihydro-pyridazin-3-yl}-phenyl)-2,3-dihydro-1H-quinazolin-4-one, 6-{3-[2-(2-Isopropoxy-azetidin-1-yl)-2-oxo-ethyl]-phenyl}-2-methyl-4-[5-(morpholine-4-carbonyl)-pyridin-2-ylamino]-2H-pyridazin-3-one, 6-{3-[2-(4-tert-butyl-phenyl)-2-oxo-ethyl]-phenyl}-2-methyl-4-[5-(morpholine-4-carbonyl)pyridin-2-ylamino]-2H-pyridazin-3-one, 6-{3-[2-(4-tert-butyl-piperazin-1-yl)-2-oxo-ethyl]-phenyl}-2-methyl-4-[5-(morpholine-4-carbonyl)-pyridin-2-ylamino]-2H-pyridazin-3-one, 6-{3-[2-(3-tert-butoxy-azetidin-1-yl)-2-oxo-ethyl]-phenyl}-2-methyl-4-[5-(morpholine-4-carbonyl)-pyridin-2-ylamino]-2H-pyridazin-3-one, 6-{3-[2-(1,3-dihydro-isoindol-2-yl)-2-oxo-ethyl]-phenyl}-2-methyl-4-[5-(morpholine-4-carbonyl)-pyridin-2-ylamino]-2H-pyridazin-3-one, 6-{3-[2-(4-Isopropyl-piperazin-1-yl)-2-oxo-ethyl]-phenyl}-2-methyl-4-[5-(morpholine-4-carbonyl)-pyridin-2-ylamino]-2H-pyridazin-3-one, 6-{3-[2-(4-tert-butyl-piperidin-1-yl)-2-oxo-ethyl]-phenyl}-2-methyl-4-[5-(morpholine-4-carbonyl)-pyridin-2-ylamino]-2H-pyridazin-3-one, N-(3,3-dimethyl-butyl)-2-(3-{1-methyl-5-[5-(morpholine-4-carbonyl)-pyridin-2-ylamino]-6-oxo-1,6-dihydro-pyridazin-3-yl}-phenyl)-acetamide, 6-{3-[2-(4-acetyl-piperazin-1-yl)-2-oxo-ethyl]-phenyl}-2-methyl-4-[5-(morpholine-4-carbonyl)-pyridin-2-ylamino]-2H-pyridazin-3-one, 4-cyclopropyl-N-{2-hydroxymethyl-3-[1-methyl-5-(1-methyl-1H-pyrazol-3-ylamino)-6-oxo-1,6-dihydro-pyridazin-3-yl]-phenyl}-benzamide, and 4-cyclopropyl-N-(2-hydroxymethyl-3-1-methyl-5-[5-(morpholine-4-carbonyl)pyridin-2-ylamino]-6-oxo-1,6-dihydro-pyridazin-3-yl}-phenyl)-benzamide, as disclosed in U.S. Pat. No. 7,943,618 to Dewdney et al., incorporated herein by this reference; 6-dimethylamino-2-(3-{1-methyl-5-[5-(morpholine-4-carbonyl)-pyridin-2-ylamino]-6-oxo-1,6-dihydro-pyridazin-3-yl}-phenyl)-2H-isoquinolin-1-one, 6-dimethylamino-2-(2-methyl-3-{1-methyl-5-[5-(morpholine-4-carbonyl)-pyridin-2-ylamino]-6-oxo-1, 6-dihydro-pyridin-3-yl}-phenyl)-2H-isoquinolin-1-one, 6-dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one, 6-dimethylamino-2-{2-hydroxymethyl-3-[1-methyl-5-(1-methyl-1H-pyrazol-3-ylamino)-6-oxo-1,6-dihydro-pyridin-3-yl]-phenyl}-2H-isoquinolin-1-one, 1-{5-[3-(6-dimethylamino-1-oxo-1H-isoquinolin-2-yl)-2-hydroxymethyl-phenyl]-1-methyl-2-oxo-1,2-dihydro-pyridin-3-yl}-3-ethyl-urea, 2-(2-hydroxymethyl-3-{1-methyl-5-[5-(morpholine-4-carbonyl)-pyridin-2-ylamino]-6-oxo-1,6-dihydropyridin-3-yl}-phenyl)-6-(1-methyl-cyclopropyl)-2H-isoquinolin-1-one, 2-{2-hydroxymethyl-3-[1-methyl-5-(5-morpholin-4-ylmethyl-pyridin-2-ylamino)-6-oxo-1,6-dihydro-pyridin-3-yl]-phenyl}-6-(1-methyl-cyclopropyl)-2H-isoquinolin-1-one, 2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-6-(1-methyl-cyclopropyl)-2H-isoquinolin-1-one, 6-cyclopropyl-2-{2-hydroxymethyl-3-[1-methyl-5-(5-morpholin-4-ylmethyl-pyridin-2-ylamino)-6-oxo-1,6-dihydro-pyridin-3-yl]-phenyl}-2H-isoquinolin-1-one, 6-cyclopropyl-2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-2H-isoquinolin-1-one, 6-cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one, 6-cyclopropyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one, 6-cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3-methyl-2H-isoquinolin-1-one, 2-{2-hydroxymethyl-3-[1-methyl-5-(5-morpholin-4-yl-pyridin-2-ylamino)-6-oxo-1,6-dihydro-pyridin-3-yl]-phenyl}-6-(1-methyl-cyclopropyl)-2H-isoquinolin-1-one, 6-dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one, 6-tert-butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one, 6-cyclopropyl-3-hydroxymethyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one, 6-cyclopropyl-3-hydroxymethyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one, 6-cyclopropyl-3-dimethylaminomethyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one, 3-tert-butoxymethyl-6-cyclopropyl-2-{3-[5-(6-fluoro-pyridin-2-ylamino)-1-methyl-6-oxo-1,6-dihydro-pyridin-3-yl]-2-hydroxymethyl-phenyl}-2H-isoquinolin-1-one, 6-dimethylamino-2-{2-hydroxymethyl-3-[1-methyl-5-(6-methylamino-pyridin-2-ylamino)-6-oxo-1,6-dihydro-pyridin-3-yl]-phenyl}-2H-isoquinolin-1-one, 6-dimethylamino-2-(2-hydroxymethyl-3-{1-methyl-5-[6-(4-methyl-piperazin-1-yl)-pyridin-2-ylamino]-6-oxo-1,6-dihydro-pyridin-3-yl}-phenyl)-2H-isoquinolin-1-one, 2-{3-[5-(6-amino-pyridin-2-ylamino)-1-methyl-6-oxo-1,6-dihydro-pyridin-3-yl]-2-hydroxymethyl-phenyl}-6-dimethylamino-2H-isoquinolin-1-one, 2-(6-{5-[3-(6-dimethylamino-1-oxo-1H-isoquinolin-2-yl)-2-hydroxymethyl-phenyl]-1-methyl-2-oxo-1,2-dihydro-pyridin-3-ylamino}-pyridin-3-yloxy)-N-methyl-acetamide; 2-{3-[5-(5,6-dimethoxy-pyridin-2-ylamino)-1-methyl-6-oxo-1,6-dihydro-pyridin-3-yl]-2-hydroxymethyl-phenyl}-6-dimethylamino-2H-isoquinolin-1-one, 6-dimethylamino-2-(2-hydroxymethyl-3-{5-[5-methoxy-6-(2-methoxy-ethoxy)-pyridin-2-ylamino]-1-methyl-6-oxo-1,6-dihydro-pyridin-3-yl}-phenyl)-2H-isoquinolin-1-one, 6-dimethylamino-2-(2-hydroxymethyl-3-{5-[6-methoxy-5-(2-methoxy-ethoxy)-pyridin-2-ylamino]-1-methyl-6-oxo-1,6-dihydro-pyridin-3-yl}-phenyl)-2H-isoquinolin-1-one, 2-(3-{5-[5,6-bis-(2-methoxy-ethoxy)-pyridin-2-ylamino]-1-methyl-6-oxo-1,6-dihydro-pyridin-3-yl}-2-hydroxymethyl-phenyl)-6-dimethylamino-2H-isoquinolin-1-one, 6-dimethylamino-2-{2-hydroxymethyl-3-[1-methyl-5-(2-morpholin-4-yl-pyrimidin-4-ylamino)-6-oxo-1,6-dihydro-pyridin-3-yl]-phenyl}-2H-isoquinolin-1-one, 6-dimethylamino-2-(2-hydroxymethyl-3-{1-methyl-5-[2-(4-methyl-piperazin-1-yl)-pyrimidin-4-ylamino]-6-oxo-1,6-dihydro-pyridin-3-yl}-phenyl)-2H-isoquinolin-1-one; 2-[4-(6-{5-[3-(6-dimethylamino-1-oxo-1H-isoquinolin-2-yl)-2-hydroxymethyl-phenyl]-1-methyl-2-oxo-1,2-dihydropyridin-3-ylamino}-pyridin-3-yl)-piperazin-1-yl]-isobutyramide, 2-(3-{5-[6-(4-acetyl-piperazin-1-yl)-pyridin-2-ylamino]-1-methyl-6-oxo-1,6-dihydropyridin-3-yl}-2-hydroxymethyl-phenyl)-6-dimethylamino-2H-isoquinolin-1-one, 6-dimethylamino-2-{3-[5-(5-ethyl-1H-pyrazol-3-ylamino)-1-methyl-6-oxo-1,6-dihydro-pyridin-3-yl]-2-hydroxymethyl-phenyl}-2H-isoquinolin-1-one, 6-dimethylamino-2-(3-{5-[5-(2-hydroxy-ethoxy)-6-(2-methoxy-ethoxy)-pyridin-2-ylamino]-1-methyl-6-oxo-1,6-dihydro-pyridin-3-yl}-2-hydroxymethyl-phenyl)-2H-isoquinolin-1-one, 6-cyclopropyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one, and 2-(2-hydroxymethyl-3-{1-methyl-5-[5-(morpholine-4-carbonyl)-pyridin-2-ylamino]-6-oxo-1,6-dihydro-pyridazin-3-yl}-phenyl)-6-(1-methyl-cyclopropyl)-2H-isoquinolin-1-one, as disclosed in U.S. Pat. No. 7,906,509 to Kennedy-Smith et al., incorporated herein by this reference; 6-dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-phthalazin-1-one, 6-dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-phthalazin-1-one, 6-dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-2H-phthalazin-1-one, 6-tert-butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-phthalazin-1-one, 6-tert-butyl-2-{hydroxymethyl-3-[1-methyl-5-(5-morpholin-4-yl-pyridin-2-ylamino)-6-oxo-1,6-dihydro-pyridin-3-yl]-phenyl}-2H-phthalazin-1-one, 6-tert-butyl-2-[2-hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-2H-phthalazin-1-one, 6-dimethylamino-2-[2-hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-2H-phthalazin-1-one, 6-dimethylamino-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-phthalazin-1-one, 2-(3-{5-[5-(4-acetyl-piperazin-1-yl)-pyridin-2-ylamino]-1-methyl-6-oxo-1,6-dihydro-pyridin-3-yl}-2-hydroxymethyl-phenyl)-6-tert-butyl-2H-phthalazin-1-one, 2-(3-{5-[5-(4-acetyl-piperazin-1-yl)-pyridin-2-ylamino]-1-methyl-6-oxo-1,6-dihydro-pyridin-3-yl}-2-hydroxymethyl-phenyl)-6-dimethylamino-2H-phthalazin-1-one, 6-tert-butyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-phthalazin-1-one, 6-tert-butyl-2-(3-{5-[5-(4-ethylpiperazin-1-yl)-pyridin-2-ylamino]-1-methyl-6-oxo-1,6-dihydro-pyridin-3-yl}-2-hydroxymethyl-phenyl)-2H-phthalazin-1-one, 6-tert-butyl-2-{2-hydroxymethyl-3-[1-methyl-6-oxo-5-(5-piperazin-1-yl-pyridin-2-ylamino)-1,6-dihydro-pyridin-3-yl]-phenyl}-2H-phthalazin-1-one, and 4-(6-{5-[3-(6-tert-butyl-1-oxo-1H-phthalazin-2-yl)-2-hydroxymethyl-phenyl]-1-methyl-2-oxo-1,2-dihydro-pyridin-3-ylamino}-pyridin-3-yl)-piperazine-1-carboxylic acid tert-butyl ester, as disclosed in U.S. Pat. No. 7,902,194 to Dewdney et al., incorporated herein by this reference; pyrazolopyrimidines, as disclosed in U.S. Pat. No. 7,741,330 to Chen et al., incorporated herein by this reference; imidazo[1,5-f][1,2,4]triazines, as disclosed in U.S. Pat. No. 7,732,454 to Verner, incorporated herein by this reference; 1-(3-(4-amino-3-(4-phenoxyphenyl)-1H-pyrazolo[3,4-d]pyrimidin-1-yl)piperidin-1-yl)prop-2-en-1-one, (E)-1-(3-(4-amino-3-(4-phenoxyphenyl)-1H-pyrazolo[3,4-d]pyrimidin-1-yl)piperidin-1-yl)but-2-en-1-one, 1-(3-(4-amino-3-(4-phenoxyphenyl)-1H-pyrazolo[3,4-d]pyrimidin-1-yl)piperidin-1-yl)sulfonylethene, 1-(3-(4-amino-3-(4-phenoxyphenyl)-1H-pyrazolo[3,4-d]pyrimidin-1-yl)piperidin-1-yl)prop-2-yn-1-one, 1-(4-(4-amino-3-(4-phenoxyphenyl)-1H-pyrazolo[3,4-d]pyrimidin-1-yl)piperidin-1-yl)prop-2-en-1-one, N-((1 S,4S)-4-(4-amino-3-(4-phenoxyphenyl)-1H-pyrazolo[3,4-d]pyrimidin-1-yl)cyclohexyl)acrylamide, 1-((R)-3-(4-amino-3-(4-phenoxyphenyl)-1H-pyrazolo[3,4-d]pyrimidin-1-yl)pyrrolidin-1-yl)prop-2-en-1-one, 1-((S)-3-(4-amino-3-(4-phenoxyphenyl-1H-pyrazolo[3,4-d]pyrimidin-1-yl)pyrrolidin-1-yl)prop-2-en-1-one, 1-((R)-3-(4-amino-3-(4-phenoxyphenyl)-1H-pyrazolo[3,4-d]pyrimidin-1-yl)piperidin-1-yl)prop-2-en-1-one, 1-((S)-3-(4-amino-3-(4-phenoxyphenyl)-1H-pyrazolo[3,4-d]pyrimidin-1-yl)piperidin-1-yl)prop-2-en-1-one, and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one, disclosed in U.S. Pat. No. 7,514,444 to Honigberg et al., incorporated herein by this reference; imidazo[1,2-a]pyrazin-8-ylamines, disclosed in U.S. Pat. No. 7,405,295 to Currie et al., incorporated herein by this reference; α-cyano-p-hydroxy-β-methyl-N-(2,5-dibromophenyl)-propenamide, α-cyano-p-hydroxy-β-methyl-N-[4-(methylsulfonyl)phenyl]-propenamide, α-cyano-p-hydroxy-β-methyl-N-[3-methylsulfonyl)phenyl]-propenamide, α-cyano-p-hydroxy-β-methyl-N-[3-bromo-4-(trifluoromethoxy)-phenyl]propenamide, α-cyano-p-hydroxy-β-methyl-N-(2,4-dibromophenyl)-propenamide, α-cyano-p-hydroxy-β-methyl-N-(2,4-dichlorophenyl)-propenamide, α-cyano-p-hydroxy-β-methyl-N-(2,5-dichlorophenyl)-propenamide, α-cyano-p-hydroxy-β-methyl-N-(3,4-didichlorophenyl)-propenamide, or pharmaceutically acceptable salts thereof, as disclosed in U.S. Pat. No. 6,753,348 to Uckun et al., incorporated herein by this reference; and calanolides, as disclosed in U.S. Pat. No. 6,306,897 to Uckun et al., incorporated herein by this reference. Other inhibitors of BTK are known in the art.

Bis-[thio-hydrazide] amides, such as $N^{r1},N^{r3}$-dimethyl-$N^{r1},N^{r3}$-di(phenylcarbonothioyl)malonohydrazide, are disclosed as a compound that can be used with other antineoplastic agents, especially in the treatment of MDR-resistant malignancies, in U.S. Pat. No. 7,763,658 to Koya et al., incorporated herein by this reference. Other bis-[thio-hydrazide] amides are also disclosed.

Use with succinimide or maleimide derivatives as Topoisomerase II inhibitors is disclosed in United States Patent Application Publication 2007/0196360 by Jensen et al., incorporated herein by this reference.

HDAC inhibitors include, but are not limited to, compounds disclosed in PCT Patent Application Publication No. WO 02/22577 by Bair et al., incorporated herein by this reference, including, but not limited to, N-hydroxy-3-[4-[[(2-hydroxyethyl)[2-(1H-indol-3-yl)ethyl]-amino]methyl]phenyl]-2E-2-propenamide, suberoylanilide hydroxamic acid, 4-(2-amino-phenylcarbamoyl)-benzyl]-carbamic acid pyridine-3-ylmethyl ester and derivatives thereof, butyric acid, pyroxamide, trichostatin A, oxamflatin, apicidin, depsipeptide, depudecin, trapoxin, HC toxin, and sodium phenylbutyrate.

Immunostimulants include, but are not limited to, deoxycholic acid, tetrachlorodecaoxide, imiquimod, and resiquimod.

Agents that inhibit the expression or activity of Her2 include, but are not limited to, lapatinib ditosylate, afatinib, lapatinib, CP-724714 ((E)-2-methoxy-N-(3-(4-(3-methyl-4-(6-methylpyridin-3-yloxy)phenylamino)quinazolin-6-yl)allyl)acetamide), mubritinib, canertinib, CUDC-101 (7-(4-(3-ethynylphenylamino)-7-methoxyquinazolin-6-yloxy)-N-hydroxyheptanamide), Tyrphostin AG 879 (2-(2E)-3-[3,5-bis(1,1-dimethylethyl)-4-hydroxyphenyl]-2-cyano-2-propenethioamide), TAK-285 (N-(2-(4-(3-chloro-4-(3-(trifluoromethyl)phenoxy)phenylamino)-5H-pyrrolo[3,2-d]pyrimidin-5-yl)ethyl)-3-hydroxy-3-methylbutanamide), ARRY 380 (N-(4-([1,2,4]triazolo[1,5-a]pyridin-7-yloxy)-3-methylphenyl)-6-(5-((2-(methylsulfonyl)ethylamino)methyl)furan-2-yl)quinazolin-4-amine), AV412, AZD8931 (2-(4-(4-(3-chloro-2-fluorophenylamino)-7-methoxyquinazolin-6-yloxy)piperidin-1-yl)-N-methylacetamide), neratinib, AEE788 ((R)-6-(4-((4-ethylpiperazin-1-yl)methyl)phenyl)-N-(1-phenylethyl)-7H-pyrrolo[2,3-d]pyrimidin-4-amine), and BMS-599626 ((S)-morpholin-3-ylmethyl 4-(1-(3-fluorobenzyl)-1H-indazol-5-ylamino)-5-methylpyrrolo[1,2-f][1,2,4]triazin-6-ylcarbamate).

Agents that inhibit the expression or activity of estrogen receptors include, but are not limited to, fulvestrant.

Agents that inhibit the expression or activity of antigens associated with specific tumor targets include, but are not limited to: (i) agents that inhibit the binding of estrogen to the estrogen receptor, including tamoxifen, toremifene, and fulvestrant; (ii) aromatase inhibitors, including anastrozole, exemestane, and letrozole; (iii) tyrosine kinase inhibitors, including imatinib mesylate, dasatinib, nilotinib, and bosutinib; (iv) antibodies binding to HER-2 or blocking its activity, including trastuzumab and pertuzumab; (v) small-molecule agents that inhibit the tyrosine kinase activity of HER-2, including lapatinib; (vi) small-molecule agents that inhibit the tyrosine kinase activity of EGFR, including gefitinib and erlotinib; (vii) monoclonal antibodies binding to EGFR, including cetuximab and panitumumab; (viii) small-molecule agents that inhibit the serine/threonine kinase mTOR, including temsirolimus; (ix) small-molecule agents that bind to immunophilin FK-binding protein 12, including everolimus; (x) small-molecule agents that block the activity of multiple tyrosine kinase enzymes, including vandetanib; (xi) small-molecule agents that block the activity of an activated mutant form of the serine/threonine kinase BRAF, BRAF V600E, including vemafuranib; (xii) small-molecule agents that inhibit the tyrosine kinase activity of the EML4-ALK fusion protein, including crizotinib; (xiii) small-molecule agents that are inhibitors of histone deacetylase (HDAC) activity, including vorinostat and romidepsin; (xiv) small-molecule agents that modulate the activity of retinoic acid receptors, retinoid X receptors, or both, including bexarotene, alitretinoin, and tretinoin; (xv) small-molecule agents that are proteasome inhibitors, including bortezomib and carfilzomib; (xvi) small-molecule agents that are antifolates and selectively accumulate in cells expressing RFC-1, overexpressed in malignant cells, including pralatrexate; (xvii) monoclonal antibodies that bind to VEGF or block activity of proteins involved in VEGF signaling, including bevacizumab; (xviii) recombinant fusion proteins that bind to VEGF, including ziv-aflibercept; (xix) small-molecule agents that bind to VEGF or block activity of proteins involved in VEGF signaling, including sorafenib, sunitinib, pazopanib (which has other activities as well), regorafenib (which has other activities as well), and cabozanitib (which has other activities as well); and (xx) monoclonal antibodies binding to tumor markers that trigger an anti-neoplastic immune response, including rituximab (binding to CD20), alemtuzumab (binding to CD52), ofatumumab (binding to CD20), ipilimumab (binding to CTLA-4), tositumomab (binding to CD20; this monoclonal antibody can be conjugated to the radioisotope $^{131}$I), and ibritumomab (binding to CD20; this monoclonal antibody can be conjugated to $^{111}$In or $^{90}$Y).

Agents that are G-quadruplex ligands include, but are not limited to, 3,11-difluoro-6,8,13-trimethyl-8H-quino[4,3,2-kl] acridinium methosulfate, BRACO-19 (9-[4-(N,N-dimethylamino)phenylamino]-3,6-bis(3-pyrrolidino-propionamido)acridine), and telomestatin. These agents are described in United States Patent Application Publication No. 2008/0279961 by Burger, incorporated herein by this reference, and in U.S. Pat. No. 7,115,619 to Stevens et al., incorporated herein by this reference.

Polycyclic compounds that are lysophosphatidic receptor antagonists are disclosed in U.S. Pat. No. 8,664,220 to Clark et al., incorporated herein by this reference. The polycyclic lysophosphatidic receptor antagonist can be selected from the group consisting of 1-{4'-[4-(2-benzyl-cyclohexylamino)-3-methyl-isoxazol-5-yl]-biphenyl-4-yl}-cyclopropanecarboxylic acid; 1-{4'-[3-methyl-4-(4-o-tolyl-piperazine-1-carbonyl)-isoxazol-5-yl]-biphenyl-4-yl}-cyclopropanecarboxylic acid; 1-(4'-{4-[4-(3,4-dichloro-benzenesulfonyl)-piperazine-1-carbonyl]-3-methyl-isoxazol-5-yl}-biphenyl-4-yl)-cyclopropanecarboxylic acid; 1-{4'-[3-methyl-4-(3-phenethyl-oxiranyl)-isoxazol-5-yl]-biphenyl-4-yl}-cyclopropanecarboxylic acid; 1-{4'[3-methyl-4-(2-oxo-4-phenyl-pyrrolidin-1-ylmethyl)-isoxazol-5-yl]-biphenyl-4-yl}-cyclopropanecarboxylic acid; 1-{4'-[3-methyl-4-(4-phenyl-piperidin-1-ylmethyl)-isoxazol-5-yl]-biphenyl-4-yl}-cyclopropanecarboxylic acid; 1-{4'-[4-(2-imino-5-phenyl-[1,3,4]oxadiazol-3-ylmethyl)-3-methyl-isoxazol-5-yl]-biphenyl-4-yl}-cyclopropanecarboxylic acid; 1-{4'-[4 ((S)-4-benzyl-2-oxo-oxazolidin-3-ylmethyl)-3-methyl-isoxazol-5-yl]-biphenyl-4-yl}-cyclopropanecarboxylic acid; 1-{4'-[3-methyl-4((S)-2-oxo-4-phenyl-oxazolidin-3-ylmethyl)-isoxazol-5-yl]-biphenyl-4-yl}-cyclopropanecarboxylic acid; 1-{4'-[3-methyl-4R,5S)-4-methyl-2-oxo-5-phenyl-oxazolidin-3-ylmethyl)-isoxazol-5-yl]-biphenyl-4-yl}-cyclopropanecarboxylic acid; 1-{4'-[3-methyl-4-((4S,5R)-4-methyl-2-oxo-5-phenyl-oxazolidin-3-ylmethyl)-isoxazol-5-yl]-biphenyl-4-yl}-cyclopropanecarboxylic acid; 1-{4'-[3-methyl-4-(3-phenyl-pyrrolidin-1-ylmethyl)-isoxazol-5-yl]-biphenyl-4-yl}-cyclopropanecarboxylic acid; 1-{4'-[3-methyl-4-(3-phenyl-piperidin-1-ylmethyl)-isoxazol-5-yl]-biphenyl-4-yl}-cyclopropanecarboxylic acid; 1-{4'-[3-methyl-4-(2-oxo-5-phenyl-oxazolidin-3-ylmethyl)-isoxazol-5-yl]-biphenyl-4-yl}-cyclopropanecarboxylic acid; 1-[4'-(3-methyl-4-{2-[methyl-((R)-1-phenyl-ethyl)-carbamoyl]-cyclopropyl}-isoxazol-5-yl)-biphenyl-4-yl]-cyclopropanecarboxylic acid; 1-[4'-(3-methyl-4-{2-[methyl-((R)-1-phenyl-ethyl)-carbamoyl]-cyclopropyl}-isoxazol-5-yl)-biphenyl-4-yl]-cyclopropanecarboxylic acid; 1-{4-[4-(3-benzyl-2-oxo-oxazolidin-5-yl)-3-methyl-isoxazol-5-yl]-biphenyl-4-yl}-cyclopropanecarboxylic acid; [1-(4'-{4-[4-(4-benzyl-phenyl)-1-hydroxy-butyl]-3-methyl-isoxazol-5-yl}-biphenyl-4-yl)-cyclopropyl]-acetic acid; [1-(4'-{4-[1-hydroxy-4-(4-phenoxy-phenyl)-butyl]-3-methyl-isoxazol-5-yl}-biphenyl-4-yl)-cyclopropyl]-acetic acid; 1-{4'-[4-(1-benzyl-piperidin-4-ylamino)-3-methyl-isoxazol-5-yl]-biphenyl-4-yl}-cyclopropanecarboxylic acid; (1-{4'-[4-(1-benzyl-piperidin-4-ylamino)-3-methyl-isoxazol-5-yl]-biphenyl-4-yl}-cyclopropyl)-acetic acid; [1-(4'-{4-[hydroxy-(5-phenyl-[1,3,4]oxadiazol-2-yl)-methyl]-3-methyl-isoxazol-5-yl}-biphenyl-4-yl)-cyclopropyl]-acetic acid; [1-(4'-{3-methyl-4-[1-(3-phenyl-isoxazol-5-yl)-ethylamino]-isoxazol-5-yl}-biphenyl-4-yl)-cyclopropyl]-acetic acid; [1-(4'-{3-methyl-4-[1-(3-phenyl-isoxazol-5-yl)-ethylamino]-isoxazol-5-yl}-biphenyl-4-yl)-cyclopropyl]-acetic acid; {1-[4'-(3-methyl-4-{1-methyl-2-[4-(4-trifluoromethyl-benzyloxy)-phenyl]-ethylamino}-isoxazol-5-yl)-biphenyl-4-yl]-cyclopropyl}-acetic acid; 1-(4'-{4-[(1-benzyl-1H-[1,2,3]triazol-4-yl)-methanesulfonylamino-methyl]-3-methyl-isoxazol-5-yl}-biphenyl-4-yl)-cyclopropanecarboxylic acid; (4'-{4-[(1-benzyl-1H-[1,2,3]triazol-4-yl)-hydroxy-methyl]-3-methyl-isoxazol-5-yl}-biphenyl-4-yl)-acetic acid; 3-(4'-{4-[(1-benzyl-1H-[1,2,3]triazol-4-yl)-hydroxy-methyl]-3-methyl-isoxazol-5-yl}-biphenyl-4-yl)-propionic acid; [4'-(4-{hydroxy-[1-(3-trifluoromethyl-benzyl)-1H-[1,2,3]triazol-4-yl]-methyl}-3-methyl-isoxazol-5-yl)-biphenyl-4-yl]-acetic acid; 3-[4'-(4-{hydroxy-[1-(3-trifluoromethyl-benzyl)-1H-[1,2,3]triazol-4-yl]-methyl}-3-methyl-isoxazol-5-yl)-biphenyl-4-yl]-propionic acid; [1-(4'-{4-[(5-benzyl-[1,3,4]oxadiazol-2-yl)-hydroxy-methyl]-3-methyl-isoxazol-5-yl}-biphenyl-4-yl)-cyclopropyl]-acetic acid; [4'-(4-{[1-(3,4-dichloro-benzyl)-1H-[1,2,3]triazol-4-yl]-hydroxy-methyl}-3-methyl-isoxazol-5-yl)-biphenyl-4-yl]-acetic acid; 1-(4'-{3-methyl-4-[trans-1-(2-phenyl-cyclopropyl)-ethylamino]-isoxazol-5-yl}-biphenyl-4-yl)-cyclopropanecarboxylic acid; {4'-[3-methyl-4-(6-phenyl-pyridin-2-ylamino)-isoxazol-5-yl]-biphenyl-4-yl}-acetic acid; 1-{4'-[3-methyl-4-(6-phenoxy-pyridin-2-ylamino)-isoxazol-5-yl]-biphenyl-4-yl}-cyclopropanecarboxylic acid; 3-{4'-[3-methyl-4-(5-phenyl[1,3,4]oxadiazol-2-ylamino)-isoxazol-5-yl]-biphenyl-4-yl}-propionic acid; 1-{4'-[3-methyl-4-(3-phenoxy-phenylamino)-isoxazol-5-yl]-biphenyl-4-yl}-cyclopropanecarboxylic acid; 1-{4'-[4-(6'-ethoxy-[2,3']bipyridinyl-6-ylamino)-3-methyl-isoxazol-5-yl]-biphenyl-4-yl}-cyclopropanecarboxylic acid; 1-(4'-{4-[3-(2-methoxy-pyridin-3-yl)-phenylamino]-3-methyl-isoxazol-5-yl}-biphenyl-4-yl)-cyclopropanecarboxylic acid; 1-{4'-[4-(2'-methoxy-[2,3']bipyridinyl-6-ylamino)-3-methyl-isoxazol-5-yl]-biphenyl-4-yl}-cyclopropanecarboxylic acid; 1-{4'-[4-(6'-methoxy-[2,3']bipyridinyl-6-ylamino)-3-methyl-isoxazol-5-yl]-biphenyl-4-yl}-cyclopropanecarboxylic acid; 1-{4'-[4-([2,4']bipyridinyl-6-ylamino)-3-methyl-isoxazol-5-yl]-biphenyl-4-yl}-cyclopropanecarboxylic acid; 1-(4'-{4-[3-(6-methoxy-pyridin-3-yl)-phenylamino]-3-methyl-isoxazol-5-yl}-biphenyl-4-yl)-cyclopropanecarboxylic acid; 1-{4'-[3-methyl-4-(3-pyridin-3-yl-phenylamino)-isoxazol-5-yl]-biphenyl-4-yl}-cyclopropanecarboxylic acid; 1-(4'-{4-[3-(5-methoxypyridin-3-yl)-phenylamino]-3-methyl-isoxazol-5-yl}-biphenyl-4-yl)-cyclopropanecarboxylic acid; 1-(4'-{3-methyl-4-[6-(methyl-phenyl-amino)-pyridin-2-ylamino]-isoxazol-5-yl}-biphenyl-4-yl)-cyclopropanecarboxylic acid; 1-(4'-{3-methyl-4-[3-(methyl-phenyl-amino)-phenylamino]-isoxazol-5-yl}-biphenyl-4-yl)-cyclopropanecarboxylic acid; 1-(4'-{4-[bis-(6-benzyl-pyridin-2-yl)-amino]-3-methyl-isoxazol-5-yl}-biphenyl-4-yl)-cyclopropanecarboxylic acid; 1-(4'-{4-[(2'-dimethylaminomethyl-biphenyl-3-carbonyl)-amino]-3-methyl-isoxazol-5-yl}-biphenyl-4-yl)-cyclopropanecarboxylic acid; 1-{4'-[3-methyl-4-(6-pyrazol-1-yl-pyridin-2-ylamino)-isoxazol-5-yl]-biphenyl-4-yl}-cyclopropanecarboxylic acid; 1-{4'-[3-methyl-4-(6-morpholin-4-yl-pyridin-2-ylamino)-isoxazol-5-yl]-biphenyl-4-yl}-cyclopropanecarboxylic acid; 1-{4'-[4-(6-benzyloxy-pyridin-2-ylamino)-3-methyl-isoxazol-5-yl]-biphenyl-4-yl}-cyclopropanecarboxylic acid; 1-{4'-[3-methyl-4-(6-phenylsulfanyl-pyridin-2-ylamino)-isoxazol-5-yl]-biphenyl-4-yl}-cyclopropanecarboxylic acid; 1-{4'-[4-(6-benzenesulfinyl-pyridin-2-ylamino)-3-methyl-isoxazol-5-yl]-biphenyl-4-yl}-cyclopropanecarboxylic acid; 1-{4'-[4-(6-benzenesulfonyl-pyridin-2-ylamino)-3-methyl-isoxazol-5-yl]-biphenyl-4-yl}-cyclopropanecarboxylic acid; 3-{4'-[3-methyl-4-(6-phenyl-pyridin-2-ylamino)-isoxazol-5-yl]-biphenyl-4-yl}-propionic acid; 2-methyl-2-{4'-[3-methyl-4-(6-phenyl-pyridin-2-ylamino)-isoxazol-5-yl]-biphenyl-4-yl}-propionic acid; (1-{4'-[3-methyl-4-(6-phenyl-pyridin-2-ylamino)-isoxazol-5-yl]-biphenyl-4-yl}-cyclopropyl)-acetic acid; 1-{4'-[4-(6-cyclopentylethynyl-pyridin-2-ylamino)-3-methyl-isoxazol-5-yl]-biphenyl-4-yl}-cyclopropanecarboxylic acid; 1-(4'-{3-methyl-4-[6-(pyrrolidine-1-carbonyl)-pyridin-2-ylamino]-isoxazol-5-yl}-biphenyl-4-yl)-cyclopropanecarboxylic acid; 1-{4'-[4-(6-cyclopropylcarbamoyl-pyridin-2-ylamino)-3-methyl-isoxazol-5-yl]-biphenyl-4-yl}-cyclopropanecarboxylic acid; 1-{4'-[4-(6-cyclohexyloxy-pyridin-2-ylamino)-3-methyl-isoxazol-5-yl]-biphenyl-4-yl}-cyclopropanecarboxylic acid; 1-{4'-[4-(6-cyclobutoxy-pyridin-2-ylamino)-3-methyl-isoxazol-5-yl]-biphenyl-4-yl}-cyclopropanecarboxylic acid; 1-(4'-{4-[6-(1-cyclohexyl-ethoxy)-pyridin-2-ylamino]-3-methyl-isoxazol-5-yl}-biphenyl-4-yl)-cyclopropanecarboxylic acid; 1-{4'-[3-methyl-4-(6-phenethyloxy-pyridin-2-ylamino)-isoxazol-5-yl]-biphenyl-4-yl}-cyclopropanecarboxylic acid; 4'-[3-methyl-4-(5-phenyl-[1,3,4]oxadiazol-2-ylamino)-isoxazol-5-yl]-biphenyl-4-carboxylic acid; 1-(4'-{3-methyl-4-[6-(2-oxo-oxazolidin-3-yl)-pyridin-2-ylamino]-isoxazol-5-yl}-biphenyl-4-yl)-cyclopropanecarboxylic acid; 1-(4'-{4-[6-(3-carbamoyl-phenyl)-pyridin-2-ylamino]-3-methyl-isoxazol-5-yl}-biphenyl-4-yl)-cyclopropanecarboxylic acid; 1-(4'-{3-methyl-4-[6-(2H-tetrazol-5-yl)-pyridin-2-ylamino]-isoxazol-5-yl}-biphenyl-4-yl)-cyclopropanecarboxylic acid; and 1-{4'-[4-(6-cyclopropylmethoxy-pyridin-2-ylamino)-3-methyl-isoxazol-5-yl]-biphenyl-4-yl}-cyclopropanecarboxylic acid.

Anti-CTGF agents are disclosed in United States Patent Application Publication No. 2014/0065162 by Lipson et al., incorporated herein by this reference. Anti-CTGF (connective tissue growth factor) agents include, but are not limited to, anti-CTGF antibody, anti-CTGF antibody fragment, anti-CTGF antibody mimetic or anti-CTGF oligonucleotide; the anti-CTGF oligonucleotide can be an antisense oligonucleotide, siRNA, shRNA or miRNA.

Myeloid differentiation inducing agents are disclosed in United States Patent Application Publication No. 2014/0018383 by Wald, incorporated herein by this reference, including, but not limited to, securinine and securinine analogs.

Covalent diabodies binding to a tumor-associated antigen are disclosed in United States Patent Application Publication No. 2013/0295121 by Johnson et al. The diabody can comprise a first polypeptide chain and a second polypeptide chain: (1) which first polypeptide chain comprises: (i) a first domain comprising a binding region of a light chain variable domain of a first immunoglobulin (VL1) specific for a first epitope; and (ii) a second domain comprising a binding region of a heavy chain variable domain of a second immunoglobulin (VH2) specific for a second epitope; and which first domain and second domains are covalently linked such that the first domain and second domain do not associate to form an epitope binding site; (II) which second polypeptide chain comprises: (i) a fourth domain comprising a binding region of a light chain variable domain of the second immunoglobulin (VL2); and (ii) a fifth domain comprising a binding region of a heavy chain variable domain of the first immunoglobulin (VH1), and which fourth domain and fifth domain are covalently linked such that the fourth domain and fifth domain do not associate to form an epitope binding site; wherein: (A) the first domain and the fifth domain associate to form a first binding site (VL1)(VH1) that binds the first epitope; (B) said second domain and said fourth domain associate to form a second binding site (VL2)(VH2) that binds the second epitope; (C) at least one of said first or said second polypeptide chains of said diabody additionally comprises an E-coil or a K-coil separator; and (D) wherein when said separator of said first or second polypeptide is an E-coil, said separator of said serum-protein binding polypeptide is a K-coil, and when said separator of said first or second polypeptide is an K-coil, said separator of said serum-protein binding polypeptide is an E-coil.

Bispecific antibodies that have a cell-penetrating determinant and an intracellular target-binding determinant are disclosed in United States Patent Application Publication No. 2013/0266570 by Weisbart et al, incorporated herein by this reference. In one alternative, the bispecific antibodies have Fv fragments with a cell-penetrating determinant and a second Fv fragment with an intracellular target-binding determinant. In one embodiment, the intracellular target-binding determinant is an E3 ubiquitin-protein ligase, or tumor suppressor-interacting protein, such as MDM2. In one embodiment, the intracellular target-binding determinant may target an oncoprotein such as a myc or ras oncoprotein. In another embodiment, the intracellular target-binding determinant may target DNA repair proteins such as a RAD52 protein, ataxia telangiectasia mutated protein (ATM), CHK2 or CHK1 proteins, or BCL2 protein. Additional examples of proteins associated with DNA repair include but are not limited to BRCA1, MDC1, 53BP1, p53, ATR, and p21.

Multidomain molecules that comprise a cell binding ligand that binds to cells in the tumor stroma such as endothelial cells, fibroblasts, or immune cells and that are used with an oligonucleotide that inhibits the nonsense-mediated decay pathway are disclosed in United States Patent Application Publication No. 2013/0224237 by Gilboa, incorporated herein by this reference. The oligonucleotide can be a short interfering RNA (siRNA); a micro-interfering RNA (miRNA); antisense oligonucleotides; a small, temporal RNA (stRNA); a short, hairpin RNA (shRNA), or combinations thereof. Typically, the oligonucleotide inhibits the function or the expression of at least one factor associated with the NMD pathway comprising at least one of: RENT1, RENT2, eIF4A, UPF1, UPF2, UPF3B, RNPS1, Y14, MAGOH, NMD1, SMG, or combinations thereof. The target of the cell binding ligand can be vascular endothelial growth factor (VEGF), vascular endothelial growth factor receptor (VEGFR-2), Tie2; fibronectin, vitronectin, collagen, laminin, fibroblast antigens, fibroblast activation protein (FAP), glucose-regulated protein 78 (GRP78), stromal derived factor 1 (SDF-1), MCP-1, MIP-la, MIP-113 RANTES, exotaxin IL-8, C3α, P-selectin, E-selectin, LFA-1, VLA-4, VLA-5, CD44, MMP activation, VEGF, EGF, PDGF, VCAM, ECAM, G-CSF, GM-CSF, SCF, EPO, tenascin, neurophilin, MAdCAM-1, neuropilin-1, a4 integrins, a5 integrins, or beta defensins 3 and 4.

Tumor-specific antibodies binding to a portion of the CD44 protein or a binding protein derived from the light-chain or heavy-chain complementary-determining regions of such antibodies are disclosed in United States Patent Application Publication No. 2013/0217865 by Glover et al., incorporated herein by this reference.

Inhibitors of CXCR4 are disclosed in United States Patent Application Publication No. 2013/0216531 by Jain et al., incorporated herein by this reference. The CXCR4 inhibitor can be selected from the group consisting of 1,1'-[1,4-phenylene-bis(methylene)]-bis-1,4,8,11-tetraazacyclotetra-decane (AMD-3100); Mozobil; Plerixafor; NOXA12; CTCE-9908; ALX40-4C; T22; T140; Met-SDF-113; T134; AMD-3465; N'-(1-H-benzimidazol-2-ylmethyl)-N1-(5,6,7,8-tetrahydroquinoline-8-yl)-butane-1,4-diamine; CTCF-0214; CTCF-9908; CP-1221 (linear peptides, cyclic peptides, natural amino-acids, unnatural amino acids, and peptidomimetic compounds); 4F-benzoylTN24003; KRH-1120; KRH-1636; KRH-2731; polyphemusin analogue; ALX40-4C; T-140; T-140 analogs and derivatives; TN14003; TC14012; TE14011; and any combinations thereof. Additionally, the CXCR4 inhibitor can be used with a VEGF inhibitor, such as a VEGF inhibitor selected from the group consisting of ABT-869; AEE-788; AG-13736; AG-028262; Angiostatin; bevacizumab; AVE-8062; AZD-2171; sorafenib; BMS-387032; CEP-7055; CHIR-258; GFKI; CP-547632; CP-564959; E-7080; 786034; GW-654652; IMC-1C11; KRN-951; PKC-412; PTK-787; SU11248; SU-5416; SU-6668; AVE-0005; thalidomide; XL-647; XL-999; ZD-6474; ZK-304709; Pazopanib; CDP791; Enzastaurin; BIBF 1120; BAY 573952; BAY 734506; XL 184; IMC-1121B; CEP 701; SU 014813; SU 10944; SU 12662; OSI-930; BMS 582664; ZD-6126; Imatinib; Glivec; Gleevec; STI-571; CGP-57148; RAD-001; BMS-354825; Volociximab; CCI-779; 17-AAG; DMXAA; CI-1040; CI-1033; (5-[5-fluoro-2-oxo-1,2-dihydroindol (3Z)-ylidenemethyl]-2,4-dimethyl-1H-pyrrole-3-carboxylic acid [2-diethylaminoethyl]amide); 4TBPPAPC; AMG 706; Nexavar®; and PTK/ZK. In another alternative, the CXCR4 inhibitor can be used with a p38 MAPK inhibitor. The p38 MAPK inhibitor can be selected from the group consisting of antisense p38 MAPK nucleic acids and fragments thereof, antibodies that bind p38 MAPK and fragments thereof, EO-1428, SB239063, SB281832, VX-702, VX-745, ZM336372, RPR 200765A, N-(3-tert-butyl-1-methyl-5-pyrazolyl)-N'-(4-(4-pyridinylmethyl)phenyl)urea, SB203580, SB202190, PD169316, fr-167653, trans-1-(4-hydroxycyclohexyl)-4-(4-fluorophenyl)-5-(2 methoxypyrimidin-4-yl)imidazole, 2-(4-chlorophenyl)-4-)4-fluorophenyl)-5-pyridin-4-yl-1,2-dihydropyrazol-3-one, and any combinations thereof.

Pyruvate dehydrogenase kinase (PDK1) inhibitors are disclosed in PCT Patent Application Publication No. WO 2013/174997 by Villalba et al., incorporated herein by this reference, and include dichloroacetate, antisense RNA, small inhibitory RNA, short hairpin RNA, and ribozymes.

Epherin receptor targeting agents are disclosed in PCT Patent Application Publication No. WO 2013/106824 by Xiong et al., incorporated herein by this reference, and include peptide targeting agents such as TNYLFSPNGPIA (SEQ ID NO: 9) or TNYLFSPNGPIARAW (SEQ ID NO: 10), YSAYPDSVPMMS (SEQ ID NO: 11) or a cyclic peptide including a lactam bridge.

Binding proteins for Axl are disclosed in PCT Patent Application Publication No. WO 2013/064684 by Beau-Larvor et al., incorporated herein by this reference, and include monoclonal antibodies. The protein Axl binds to the ligand Gas6 and has been shown to regulate various cellular processes including cell proliferation, adhesion, migration and survival in a large variety of cells in vitro.

Wnt pathway inhibitors, used together with MAPK pathway inhibitors, are disclosed in PCT Patent Application Publication No. WO 2013/086260 by Hoey et al., incorporated herein by this reference. The Wnt pathway inhibitor can be an antibody that binds a frizzled (FZD) protein or a portion thereof. Alternatively, the Wnt pathway inhibitor can be a soluble receptor. The MAPK pathway inhibitor can be a MEK inhibitor, such as BAY 86-9766 (RDEA1 19), PD0325901, CI-1040, PD98059, PD318088, GSK1 120212 (JTP-74057), AZD8330 (ARRY-424704), AZD6244 (ARRY-142886), ARRY-162, ARRY-300, AS703026, U0126, CH4987655, or TAK-733, or a Raf inhibitor such as GDC-0879, PLX-4720, PLX-4032 (vemurafenib), RAF265, BAY 73-4506, BAY 43-9006 (sorafenib), SB590885, XL281 (BMS-908662), or GSK 21 18436436.

TEC family kinase inhibitors are disclosed in PCT Patent Application Publication WO 2014/071231 by Buggy et al. and in PCT Patent Application WO 2014/071231 by Buggy et al., both incorporated herein by this reference. Typically, the TEC family kinase inhibitor is a covalent inhibitor, such as ibrutinib.

Substituted macrocyclic compounds with proteasome activity are disclosed in PCT Patent Application Publication No. WO 2013/188750 by Pirrung et al., incorporated herein by this reference. The compounds can be structurally related to glidobactins.

Peptide-based PACE4 inhibitors are disclosed in PCT Patent Application Publication No. WO 2013/029180 by Day et al., incorporated herein by this reference.

Azaindole derivatives as JAK3 inhibitors are disclosed in PCT Patent Application Publication No. WO 2014/081732 by Goldstein et al., incorporated herein by this reference. The compounds can be N-(3-(7-pivaloyl-5H-pyrrolo[2,3-b]pyrazin-2-yl)phenyl)acrylamide; 2-(3-acrylamidophenyl)-N-(tert-butyl)-5H-pyrrolo[2,3-b]pyrazine-7-carboxamide; or N-(tert-butyl)-2-(3-(4-(dimethylamino)but-2-enamido)phenyl)-5H-pyrrolo[2,3-b]-pyrazine-7-carboxam ide.

Inhibitors of Myc are disclosed in PCT Patent Application Publication No. WO 2014/059429 by Gudkov et al., incorporated herein by this reference. The inhibitors can have the structure of Formula (A-2):

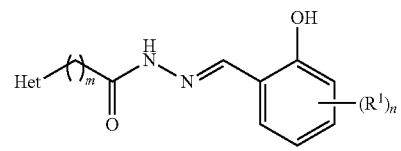

wherein: (i) $R^1$ is alkyl, hydroxyl, amino, alkoxy, aryl, alkenyl, alkynyl, or alkylenearyl; (ii) Het is heteroaryl; and (iii) m and n are each independently 0, 1, 2, 3, or 4.

Inhibitors of furin and other pro-protein convertases are disclosed in PCT Patent Application Publication No. WO 2013/138666 by Strongin et al., incorporated herein by this reference. The inhibitors can have the structure of Formula (A-3):

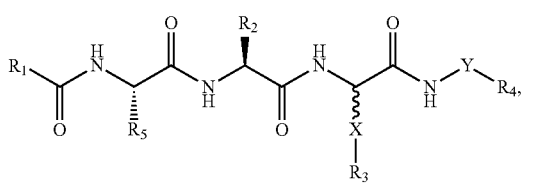
(A-3)

wherein: (i) $R_1$ is alkyl, cycloalkyl, heteroalicyclyl, aryl, or heteroaryl; (ii) $R_2$ is alkyl, cycloalkyl, or heteroalicyclyl; (iii) $R_3$ is —Z—guanidine or —Z—C(NH$_2$)=NH, wherein Z is aryl or heteroaryl; (iv) $R_4$ is —W—C(NH$_2$)=NR', wherein W is aryl, thiophenyl, furanyl, oxazolyl, pyrrolyl, or picolinyl, and wherein R' is hydrogen or hydroxyl; (v) $R_5$ is —U-guanidine, wherein U is alkyl, cycloalkyl, heteroalicyclyl, aryl, or heteroaryl; (vi) X is —CH$_2$—, —CH$_2$CH$_2$—, —CH$_2$NHC(=O)—, —CH$_2$CH$_2$C(=O)NH—, or —CH$_2$C(=O)NH—, and (vii) Y is —CH2, —S(=O)$_2$—, or —C(=O)—.

GPBP-1 inhibitors, which can optionally be used together with a p21 inhibitor, are disclosed in PCT Application Publication No. WO 2014/006020 by Saus et al., incorporated herein by this reference. The GPBP-1 inhibitors comprise three phenyl moieties linked by methylene linkages wherein the phenyl moieties are variously substituted. The p21 inhibitor can be, but is not limited to, p21-specific antibodies, p21-specific siRNA, p21-specific shRNA, p21-specific antisense nucleic acids, and p21 expression inhibitors. The p21 expression inhibitor can be, but is not limited to, flavopiridol, temsirolimus, roxithromyin, raloxifene hydrochloride, rifampicin, megestrol acetate, primaquine diphosphate, losartan potassium, valsartan, perhexiline maleate, or nisoldipine. An inhibitor of ATP-binding cassette transporter 7 (ABCC7) can also be used; the inhibitor of ABCC7 can be, but is not limited to, ABCC7-specific antibodies, ABCC7-specific siRNA, ABCC7-specific shRNA, ABCC7-specific antisense nucleic acids, and ABCC7 expression inhibitors. The ABCC7 expression inhibitor can be, but is not limited to, 3-[(3-trifluoromethyl)phenyl]-5-[(4-carboxyphenyl)methylene]-2-thioxo-4-thiazolidinone, 7,9-dimethyl-11-phenyl-6-(5-methylfuran-2-yl)-5,6-dihydro-pyrimido-[4',5'-3,4]pyrrolo[1,2-a]quinoxaline-8,10-(7H,9H)-dione, lonidamine, chromanol 293B, glibenclamide, and N-(2-naphthalenyl)-((3,5-dibromo-2,4-dihydroxyphenyl)methylene)glycine hydrazide.

PGE$_2$ inhibitors are disclosed in U.S. Pat. No. 6,245,790 to Hattori et al., incorporated herein by this reference, and include oxazole compounds, including compounds of Formula (A-4)

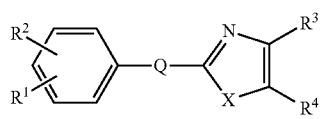
(A-4)

wherein:
(i) $R^1$ is: lower alkyl substituted with hydroxyl, carboxyl, or protected carboxyl; carboxyl; protected carboxyl; carbamoyl; a heterocyclic group; cyano; hydroxyl; halo-lower alkylsulfonyloxy; lower alkoxy optionally substituted with hydroxyl or carbamoyl; aryl substituted with carboxyl, protected carboxyl, carbamoyl, or heterocyclyl; or amino optionally substituted with protected carboxyl or lower alkylsulfonyl;
(ii) $R^2$ is hydrogen or lower alkyl;
(iii) $R^3$ is aryl optionally substituted with halogen;
(iv) $R^4$ is aryl optionally substituted with halogen;
(v) Q is a group of Subformula (A-4(a))

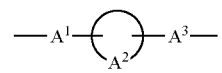
(A-4(a))

wherein: (A) -$A^1$- is a single bond or lower alkylene; (B) the moiety of Subformula (A-4(b))

(A-4(b))

is cyclo($C_5$-$C_9$)alkene, cyclo($C_3$-$C_9$)alkane, bicyclo($C_6$-$C_9$) alkene, or bicyclo($C_5$-$C_9$)alkane; and (C) -$A^3$- is a single bond or lower alkylene; and
(vi) X is O, NH, or S. Additional compounds include SC560; sulforaphane; curcumin; ketorolac; bromfenac; and nepafenac.

Activatable antibodies targeting tumor specific markers are disclosed in United States Patent Application Publication No. 2014/0023664 by Lowman et al., incorporated herein by this reference. The activatable antibody can be selected from the group consisting of activatable antibodies (i) an activatable antibody comprising: a non-binding steric moiety (NB); a cleavable linker (CL); and an antibody or antibody fragment (AB) that binds specifically to a target, wherein: the NB comprises a polypeptide that does not bind specifically to the AB; the CL is a polypeptide of up to 50 amino acids in length that comprises a substrate (S) for an enzyme; the CL is positioned in the activatable antibody such that in an uncleaved state, the NB interferes with binding of the AB to the target and in a cleaved state, the NB does not interfere with binding of the AB to the target; and the NB does not inhibit cleavage of the CL by the enzyme; (ii) an activatable antibody comprising: a non-binding steric moiety (NB); a cleavable linker (CL); and an antibody or antibody fragment (AB) that binds specifically to a target, wherein: the NB comprises a polypeptide that does not bind specifically to the AB; the CL is a polypeptide that comprises a substrate (S) for an enzyme; the CL is positioned in the activatable antibody such that in an uncleaved state, the NB interferes with binding of the AB to the target and in a cleaved state, the NB does not interfere with binding of the AB to the target; the NB does not inhibit cleavage of the CL by the enzyme; and the activatable antibody in the uncleaved state has the structural arrangement from N-terminus to C-terminus as follows: NB-CL-AB or AB-CL-NB; and (iii) an activatable antibody comprising: a binding partner (BP) for a non-binding steric moiety (NB); a cleavable linker (CL); and an antibody or antibody fragment (AB) that binds specifically to a target, wherein: the BP is a polypeptide that binds to the NB when exposed thereto; the NB does not bind specifically to the AB; the CL is a polypeptide that comprises a substrate (S) for an enzyme; the CL is positioned in the activatable antibody such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CL by the enzyme.

When the improvement is made by use of bisantrene or a bisantrene derivative or analog for chemosensitization, the chemosensitization can include, but is not limited to:
- (a) use as a chemosensitizer in combination with topoisomerase inhibitors;
- (b) use as a chemosensitizer in combination with fraudulent nucleosides;
- (c) use as a chemosensitizer in combination with fraudulent nucleotides;
- (d) use as a chemosensitizer in combination with thymidylate synthetase inhibitors;
- (e) use as a chemosensitizer in combination with signal transduction inhibitors;
- (f) use as a chemosensitizer in combination with cisplatin or platinum analogs;
- (g) use as a chemosensitizer in combination with alkylating agents;
- (h) use as a chemosensitizer in combination with anti-tubulin agents;
- (i) use as a chemosensitizer in combination with antimetabolites;
- (j) use as a chemosensitizer in combination with berberine;
- (k) use as a chemosensitizer in combination with apigenin;
- (l) use as a chemosensitizer in combination with colchicine or analogs of colchicine;
- (m) use as a chemosensitizer in combination with genistein;
- (n) use as a chemosensitizer in combination with etoposide;
- (o) use as a chemosensitizer in combination with cytarabine;
- (p) use as a chemosensitizer in combination with camptothecins;
- (q) use as a chemosensitizer in combination with vinca alkaloids;
- (r) use as a chemosensitizer in combination with 5-fluorouracil;
- (s) use as a chemosensitizer in combination with curcumin;
- (t) use as a chemosensitizer in combination with rosmarinic acid; and
- (u) use as a chemosensitizer in combination with mitoguazone.

When the improvement is made by use of bisantrene or a bisantrene analog or derivative for chemopotentiation, the chemopotentiation can include, but is not limited to:
- (a) use as a chemopotentiator in combination with topoisomerase inhibitors;
- (b) use as a chemopotentiator in combination with fraudulent nucleosides;
- (c) use as a chemopotentiator in combination with fraudulent nucleotides;
- (d) use as a chemopotentiator in combination with thymidylate synthetase inhibitors;
- (e) use as a chemopotentiator in combination with signal transduction inhibitors;
- (f) use as a chemopotentiator in combination with cisplatin or platinum analogs;
- (g) use as a chemopotentiator in combination with alkylating agents;
- (h) use as a chemopotentiator in combination with anti-tubulin agents;
- (i) use as a chemopotentiator in combination with antimetabolites;
- (j) use as a chemopotentiator in combination with berberine;
- (k) use as a chemopotentiator in combination with apigenin;
- (l) use as a chemopotentiator in combination with colchicine or analogs of colchicine;
- (m) use as a chemopotentiator in combination with genistein;
- (n) use as a chemopotentiator in combination with etoposide;
- (o) use as a chemopotentiator in combination with cytarabine;
- (p) use as a chemopotentiator in combination with camptothecins;
- (q) use as a chemopotentiator in combination with vinca alkaloids;
- (r) use as a chemopotentiator in combination with 5-fluorouracil;
- (s) use as a chemopotentiator in combination with curcumin;
- (t) use as a chemopotentiator in combination with rosmarinic acid; and
- (u) use as a chemopotentiator in combination with mitoguazone.

When the improvement is made by post-treatment management, the post-treatment management can be, but is not limited to, a method selected from the group consisting of:
- (a) a therapy associated with pain management;
- (b) nutritional support;
- (c) administration of an anti-emetic;
- (d) an anti-nausea therapy;
- (e) administration of an anti-inflammatory agent;
- (f) administration of an antipyretic agent;
- (g) administration of an immune stimulant; and
- (h) administration of a growth factor.

When the improvement is made by alternative medicine/post-treatment support, the alternative medicine/post-treatment support can be, but is not limited to, a method selected from the group consisting of:
- (a) hypnosis;
- (b) acupuncture;
- (c) meditation;
- (d) administration of a herbal medication created either synthetically or through extraction; and
- (e) applied kinesiology.

In one alternative, when the method is administration of a herbal medication created either synthetically or through extraction, the herbal medication created either synthetically or through extraction can be selected from the group consisting of:
- (a) a natural anti-inflammatory;
- (b) an immunostimulant;
- (c) an antimicrobial; and
- (d) a flavonoid, isoflavone, or flavone.

When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an anti-microbial, the anti-microbial can be berberine.

When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

When the improvement is made by a bulk drug product improvement, the bulk drug product can be, but is not limited to, a bulk drug product improvement selected from the group consisting of:
(a) preparation as a free base form;
(b) salt formation;
(c) preparation as a homogeneous crystalline structure;
(d) amorphous structure;
(e) preparation as a pure isomer;
(f) increased purity;
(g) preparation with lower residual solvent content; and
(h) preparation with lower residual heavy metal content.

When the improvement is made by use of a diluent, the diluent can be, but is not limited to, a diluent selected from the group consisting of:
(a) an emulsion;
(b) dimethylsulfoxide (DMSO);
(c) N-methylformamide (NMF)
(d) dimethylformamide (DMF)
(e) dimethylacetamide (DMA);
(f) ethanol;
(g) benzyl alcohol;
(h) dextrose-containing water for injection;
(i) Cremophor;
(j) cyclodextrins; and
(k) PEG.

When the improvement is made by use of a solvent system, the solvent system can be, but is not limited to, a solvent system selected from the group consisting of:
(a) an emulsion;
(b) DMSO;
(c) NMF;
(d) DMF;
(e) DMA;
(f) ethanol;
(g) benzyl alcohol;
(h) dextrose-containing water for injection;
(i) Cremophor;
(j) PEG; and
(k) salt systems.

When the improvement is made by use of an excipient, the excipient can be, but is not limited to, an excipient selected from the group consisting of:
(a) mannitol;
(b) albumin;
(c) EDTA;
(d) sodium bisulfite;
(e) benzyl alcohol;
(f) carbonate buffers;
(g) phosphate buffers;
(h) PEG;
(i) vitamin A;
(j) vitamin D;
(k) vitamin E;
(l) esterase inhibitors;
(m) cytochrome P450 inhibitors;
(n) multi-drug resistance (MDR) inhibitors;
(o) organic resins; and
(p) detergents.

Suitable esterase inhibitors include, but are not limited to, ebelactone A and ebelactone B.

Suitable cytochrome P450 inhibitors include, but are not limited to, 1-aminobenzotriazole, N-hydroxy-N'-(4-butyl-2-methylphenyl)formamidine, ketoconazole, methoxsalen, metyrapone, roquefortine C, proadifen, 2,3',4,5'-tetramethylstilbene, and troleandomycin.

Suitable MDR inhibitors include, but are not limited to, 5'-methoxyhydnocarpin, INF 240, INF 271, INF 277, INF 392, INF 55, reserpine, and GG918. MDR inhibitors are described in M. Zloh & S. Gibbons, "Molecular Similarity of MDR9 Inhibitors," *Int. J. Mol. Sci.* 5: 37-47 (2004), incorporated herein by this reference. Other MDR inhibitors, described therein as MDR reversal agents, suitable for use with bisantrene or a derivative or analog thereof, are disclosed in U.S. Pat. No. 5,550,149 to Powell et al., U.S. Pat. No. 5,561,141 to Powell et al., and U.S. Pat. No. 5,639,887 to Powell et al., all of which are incorporated herein by this reference; these compounds are bicyclic amines including, but not limited to, α-(3,4-dimethoxyphenyl)-1,3-dihydro-5,6-dimethoxy-α-[(4-methyl phenyl)thio]-2H-isoindole-2-heptanenitrile, 2-[7-(3,4-dimethoxyphenyl)-7-[(4-methylphenyl)thio]heptyl]-2,3-dihydro-5,6-dimethoxy-1H-isoindole, 5,6 dichloro-α-(3,4-dimethoxyphenyl)-1,3-dihydro-α-[(4-methylphenyl)thio]-2-H-isoindole-2-heptanenitrile, α-(3,4-dimethoxyphenyl)-1,3-dihydro-5-[2-(1H-imidazol-1-yl)ethoxy]-6-methoxy-α-[(4-methylphenyl)thio]-2H-isoindole-2-heptanenitrile dihydrochloride, α-(3,4-dimethoxyphenyl)-1,3-dihydro-5,6-dimethoxy-α-[(4-methylphenyl)thio]-2H-isoindole-2-heptanoic acid methyl ester, α-(cyclohexylthio)-α-(3,4-dimethoxyphenyl)-1,3-dihydro-5,6-dimethoxy-2(1H)-isoindoleheptanenitrile hydrochloride, α-(3,4-dimethoxyphenyl)-7,8-dihydro-α-[(4-methylphenyl)thio]-1,3-dioxolo[4,5-g]quinoline-6(5H)-heptanenitrile, α-(4-chlorobutyl)-3,4-dimethoxy-α-[(4-methylphenyl)-thio]benzeneacetonitrile, α-(3-chloro-2-methylpropyl)-3,4-dimethoxy-α-[(4-methyl-phenyl) thio]benzeneacetonitrile, α-(11-bromoundecyl)-3,4-dimethoxy-α-[(4-methylphenyl)-thio]benzeneacetonitrile, α-(5-chloropentyl)-3,4-dimethoxy-α-[(4-methylphenyl)-thio]benzeneacetonitrile, α-(5-bromooctyl)-3,4-dimethoxy-α-[(4-methylphenyl)-thio]benzeneacetonitrile, α-(5-iodopentyl)-3,4-dimethoxy-α-[(4-methylphenyl)-thio]benzeneacetonitrile, α-(5-aminopentyl)-3,4-dimethoxy-α-[(4-methylphenyl)-thio]benzeneacetonitrile, α-(5-chlorohexyl)-3,4-dimethoxy-α-[(4-methylphenyl)-thio]benzeneacetonitrile, 4-[4-chloro-1-[(4-methylphenyl)thio]butyl]-1,2-dimethoxybenzene, 4-[6-bromo-1-[(4-methylphenyl)thio]hexyl]-1,2-dimethoxybenzene, α-3,4-dimethoxyphenyl)-3-(hydroxymethyl)-α-[(4-methylphenyl)thio] benzenepropanenitrile, 3-(chloromethyl)-α-(dimethoxyphenyl)-α-[(4-methylphenyl)thio]benzenepropanenitrile, 4-[6-bromo-1-[(4-methylphenyl)thio]heptyl]-1,2-dimethoxybenzene, 5-[7-bromo-1-[(4-methylphenyl)thio]heptyl]-2-methoxy-phenoxy](1,2-dimethylethyl)dimethylsilane, α-(5-chloropentyl)-α-(cyclohexylthio)-3,4-dimethoxybenzeneacetonitrile, α-(5-aminopentyl)-α-(cyclohexylthio)-3,4-dimethoxybenzeneacetonitrile, 5-[6-bromo-1-[(4-methylphenyl)thio]hexyl-1,3-benzodioxole, 1-[6-bromo-1-[(methylphenyl)thio]hexyl]-4-(trifluoromethoxy)benzene, 1-[[6-bromo-1-(4-fluorophenyl)hexyl]thio]-4-methylbenzene, α-(5-bromopentyl)-3,4-dimethoxy-α-[(4-methylphenyl)-thio]benzeneacetonitrile, [(7-bromo-1-phenylheptyl)thio]benz- ene, α-(5-bromopentyl)-α-(cyclohexylthio)-3,4-dimethoxybenzeneacetonitrile, 7-bromo-2-(3,4-dimethoxyphenyl)-2-(2-pyridylthio)-heptanonitrile, and α-(5-hydroxypentyl)-3,4-dimethoxy-α-[(methylphenyl)-thio]benze neacetic acid methyl ester. U.S. Pat. No. 6,372,775 to Rabindran et al., incorporated herein by this reference, discloses the use of fumitremorgin A, B, and C and diketopiperazines as MDR inhibitors.

Suitable organic resins include, but are not limited to, a partially neutralized polyacrylic acid, as described in U.S. Pat. No. 8,158,616 to Rodgers et al., incorporated herein by this reference.

Suitable detergents include, but are not limited to, non-ionic detergents such as a polysorbate or a poloxamer, and are described in PCT Patent Application Publication No. WO/1997/039768 by Bjorn et al., incorporated herein by this reference.

When the improvement is made by use of a dosage form, the dosage form can be, but is not limited to, a dosage form selected from the group consisting of:
(a) tablets;
(b) capsules;
(c) topical gels;
(d) topical creams;
(e) patches;
(f) suppositories;
(g) lyophilized dosage fills;
(h) immediate-release formulations;
(i) slow-release formulations;
(j) controlled-release formulations;
(k) liquid in capsules; and
(l) liposomal formulations.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to dibromodulcitol and derivatives thereof, comprises the following steps:

(1) Dissolve the drug in water for injection precooled to below 10° C. Dilute to final volume with cold water for injection to yield a 40 mg/mL solution.

(2) Filter the bulk solution through an 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the pre-chilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

Immediate-release formulations are described in U.S. Pat. No. 8,148,393 to van Dalen et al., incorporated herein by this reference. Immediate-release formulations can include, for example, conventional film-coated tablets.

Slow-release formulations are described in U.S. Pat. No. 8,178,125 to Wen et al., incorporated herein by this reference. Slow-release formulations can include, for example, microemulsions or liquid crystals.

Controlled-release formulations are described in U.S. Pat. No. 8,231,898 to Oshlack et al., incorporated herein by this reference. Controlled-release formulations can include, for example, a matrix that includes a controlled-release material. Such a controlled-release material can include hydrophilic and/or hydrophobic materials, such as gums, cellulose ethers, acrylic resins, protein derived materials, waxes, shellac, and oils such as hydrogenated castor oil or hydrogenated vegetable oil. However, any pharmaceutically acceptable hydrophobic or hydrophilic controlled-release material which is capable of imparting controlled-release of the amonafide or derivative or analog thereof may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (e.g., hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polymethacrylate, polyacrylamide, poly(methacrylic acid anhydride), and glycidyl methacrylate copolymers.

A liposomal formulation suitable for bisantrene or a derivative or analog thereof comprises small unilamellar or multilamellar liposomes of size range between 0.01 and 100 μM, and between about 50-95% liposome-entrapped bisantrene, composed of hydrogenated soy phosphatidylcholine, distearoyl phosphatidylglycerol, and cholesterol of natural or synthetic origin lipids, in aqueous solution which can be reconstituted from a lyophilized form to an injectable liposome suspension. The composition is prepared by reconstituting a lyophilized bisantrene/liposome composition to a liposome concentrate, then diluting the concentrate for parenteral administration for the treatment of cancer.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability. Other forms of dosage kits and packaging are also known in the art and can include, for example, vials, ampules, jars, intravenous bags, or other containers.

When the improvement is made by use of a drug delivery system, the drug delivery system can be, but is not limited to, a drug delivery system selected from the group consisting of:

(a) oral dosage forms;
(b) nanocrystals;
(c) nanoparticles;
(d) cosolvents;
(e) slurries;
(f) syrups;
(g) bioerodible polymers;
(h) liposomes;
(i) slow-release injectable gels;
(j) microspheres;
(k) amphiphilic block copolymer systems;
(l) emulsion vehicles comprising an emulsion of α-tocopherol stabilized by biocompatible surfactants;
(m) biodegradable polymer compositions containing phosphorus and desaminotyrosyl L-tyrosine linkages in the polymer backbone;
(n) substantially anhydrous injectable semi-solid compositions comprising a water immiscible fatty acid matrix and a cytostatic agent;
(o) lipophilic vehicles;
(p) pH-dependent carriers that include a compound that includes at least one ionizable group;
(q) pH-dependent carriers that include a monocarboxylic acid having at least 8 carbons and less than about 10% by weight of zwitterionic phospholipids;
(r) liposomes comprising the bisantrene or the derivative or analog thereof followed by administration of a lipid nanoparticle comprising a triggering agent; and
(s) nonpegylated liposomes.

Nanocrystals are described in U.S. Pat. No. 7,101,576 to Hovey et al., incorporated herein by this reference.

Nanoparticles for drug delivery are described in U.S. Pat. No. 8,258,132 to Bosch et al., incorporated herein by this reference. Typically, such nanoparticles have an average particle size of the active ingredient of less than about 1000 nm, more preferably, less than about 400 nm, and most preferably, less than about 250 nm. The nanoparticles can be coated with a surface stabilizer, such as, but not limited to, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxes 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)), dioctyl sodium sulfosuccinate (DOSS), docusate sodium (Ashland Chem. Co., Columbus, Ohio); Duponol P®, which is a sodium lauryl sulfate (DuPont); Triton X-200®, which is an alkyl aryl polyether sulfonate (Rohm and Haas); Crodestas F-110®, which is a mixture of sucrose stearate and sucrose distearate (Croda Inc.); p-isononylphenoxy-poly-(glycidol), also known as Olin-IOG® or Surfactant 10-G® (Olin Chemicals, Stamford, Conn.); Crodestas SL-40® (Croda, Inc.); and SA9OHCO, which is $C_{18}H_{37}CH_2(CON(CH_3)-OCH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methyl-glucamide; n-heptyl-β-D-glucopyranoside; n-heptyl β-D-thioglucoside; n-hexyl β-D-glucopyranoside; nonanoyl-N-methylglucamide; n-nonanoyl β-D-glucopyranoside; octanoyl-N-methylglucamide; n-octyl β-D-glucopyranoside; and octyl β-D-thioglucopyranoside.

Pharmaceutically acceptable cosolvents are described in U.S. Pat. No. 8,207,195 to Navratil et al., incorporated herein by this reference, and include, but are not limited to, water, methanol, ethanol, 1-propanol, isopropanol, 1-butanol, isobutanol, t-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether.

Slurries for use in pharmaceutical formulations are described in United States Patent Application Publication No. 2006/0229277 by Laxminarayan, incorporated herein by this reference.

Syrups for use in pharmaceutical formulations are described in U.S. Pat. No. 8,252,930 to Stoit et al., incorporated herein by this reference. Such syrups can include the active ingredient and a syrup-forming component such as sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutyrate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly (alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference. Nonpegylated liposomes for drug delivery, specifically delivery of doxorubicin, are described in J. Baselga et al., "Phase III Trial of Nonpegylated Liposomal Doxorubicin in Combination with Trastuzumab and Paclitaxel in HER2-Positive Metastatic Breast Cancer," *Ann. Oncol.* 25: 592-598 (2014), incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000), incorporated herein by this reference.

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

Another drug delivery system potentially usable with bisantrene and analogs and derivatives thereof is the amphiphilic block copolymer system described in U.S. Pat. No. 7,311,901 to Seo et al., incorporated herein by this reference. In general, the amphiphilic block copolymer comprises a hydrophilic block and a hydrophobic block with a terminal hydroxyl group, wherein the terminal hydroxyl group of the hydrophobic block is substituted with a tocopherol or cholesterol group. U.S. Pat. No. 7,311,901 to Seo et al., incorporated herein by this reference, further describes polymeric compositions capable of forming stable micelles in an aqueous solution, comprising the amphiphilic block copolymer and a polylactic acid derivative wherein one or both ends of the polylactic acid derivative are covalently bound to at least one carboxyl group.

Yet another drug delivery system potentially useful with bisantrene and analogs and derivatives thereof is the emulsion vehicle described in U.S. Pat. No. 6,485,383 to Lambert et al., incorporated herein by this reference. In general, this emulsion vehicle comprises an emulsion of α-tocopherol stabilized by biocompatible surfactants. Also included in the emulsion is pegylated vitamin E. Pegylated α-tocopherol includes polyethylene glycol subunits attached by a succinic acid diester at the ring hydroxyl of vitamin E and serves as a primary surfactant and a stabilizer as well as a secondary solvent in emulsions of α-tocopherol.

Yet another drug delivery system potentially useful with bisantrene and analogs and derivatives thereof are the biodegradable polymer compositions described in U.S. Pat. No. 6,238,687 to Mao et al., incorporated herein by this reference. These polymers contain phosphorus and desaminotyrosyl L-tyrosine linkages in the polymer backbone.

Yet another drug delivery system potentially useful with bisantrene and analogs and derivatives thereof are the pharmaceutically acceptable substantially anhydrous injectable semi-solid compositions described in U.S. Pat. No. 5,573,781 to Brown et al., incorporated herein by this reference. The compositions comprise a water immiscible fatty acid matrix and a cytostatic agent, such as bisantrene or a derivative or analog thereof. Typically, the matrix material will be fatty acid ester compositions, having the desired flowable and viscosity characteristics, either as a natural characteristic or as a result of additives. Suitable lipid compositions will comprise fatty acid esters, either a single fatty acid ester or a mixture of fatty acid esters, which are biodegradable in the host, by themselves or in combination with one or more physiologically acceptable thickening agents, particularly fatty acid salts or synthetic and/or longer chain fatty acid esters, e.g. waxy esters. Suitable fatty acid ester compositions will comprise a single or mixture of fatty acid esters, and may comprise two or more different fatty acid esters, usually not more than ten different fatty acid esters. Suitable fatty acid esters include mono-, di- and tri-glycerides, as well as mono- and dibasic acid esters, e.g. ethyl oleate, isopropyl myristate, or other such esters, where the carboxylic acid group will usually have at least 6, more usually at least 8 carbon atoms, preferably at least about 12 carbon atoms, and may be saturated or unsaturated, usually having not more than 3 sites of ethylenic unsaturation per acid moiety, and the fatty acid esters will have at least 8 carbon atoms and not more than about 60 carbon atoms, usually not more than about 50 carbon atoms. Of particular interest are glycerides having fatty acids of from about 12 to 24 carbon atoms, saturated or unsaturated, naturally occurring or synthetic. The alcohols will usually have from about 1 to 6, usually 1 to 5, more usually 1 to 3 hydroxyl groups and not more than two ether groups and will usually be from 2 to 6, more usually 2 to 3 carbon atoms. The fatty acid esters of the subject invention will not include esters which are modified with additional functional groups which increase the water solubility properties of the esters, e.g. such as polyoxyethylated castor oil or other alkyleneoxy modified fatty acid esters. The fatty acid esters may be added as partially pure fractions or complex mixtures such as saturated or partially saturated glycerides, e.g. oils and fats. Any carboxylic acid ester oil which is physiologically acceptable can be employed as the matrix component, where the oil may be a single or combination of oils, which may or may not be partially hydrogenated. Specific physiologically acceptable oils of interest include vegetable oils, such as sesame, peanut, soybean, cottonseed, corn, olive, persic, castor, and the like.

Lipophilic vehicles are described in U.S. Pat. No. 7,148,211 to Mazess et al., incorporated herein by this reference. These lipophilic vehicles include polysorbate 20 as a nonionic solubilizer, butylated hydroxytoluene as a lipophilic antioxidant, optionally, ethanol, and an aqueous vehicle. Other alcohols or polyols can be used in place of or together with ethanol. Other non-ionic solubilizers can be used. Other lipophilic antioxidants can be used.

The use of pH-dependent carriers that include a compound that includes at least one ionizable group is disclosed in United States Patent Application Publication No. 2014/0094526 by Marathi et al. The at least one ionizable group can be a carboxylic acid group, hydroxy group, amino group, amide groups, or other similarly ionizable groups. The carriers are immiscible in water or soluble in oils, and, for weak acids, the ionizable groups have a pKa value greater than or equal to about pH 3.5.

The use of pH-dependent carriers that include a monocarboxylic acid having at least 8 carbons and less than about 10% by weight of zwitterionic phospholipids is disclosed in United States Patent Application Publication No. 2014/0094439 by Marathi et al.

The use of liposomes comprising the bisantrene or the derivative or analog thereof followed by administration of a lipid nanoparticle comprising a triggering agent is disclosed in PCT Patent Application Publication No. WO 2013/066903 by Yang et al., incorporated herein by this reference. The triggering agent can be non-ionic, such as TPGS or polyoxyethylene stearate.

When the improvement is made by use of a drug conjugate form, the drug conjugate form can be, but is not limited to, a drug conjugate form selected from the group consisting of:

(a) a polymer system;
(b) polylactides;
(c) polyglycolides;
(d) amino acids;
(e) peptides;
(f) multivalent linkers;
(g) conjugates to fatty acids;
(h) conjugates to fatty alcohols;
(i) conjugates to elastin-like peptide;
(j) conjugates with polyclonal or monoclonal antibodies, proteins, or peptides;
(k) conjugates with cell-binding agents through a charged or pro-charged cross-linker;
(l) conjugates to antibodies targeted to tumor markers;
(m) biodegradable polymer-bioactive moiety conjugates;
(n) conjugates with 2-nitroimidazole compounds with a secondary basic nitrogen atom and a linker;
(o) conjugates with ladder frame polyether compounds, including those derived from brevenal, brevisin, tamulamide, brevetoxins, hemibrevetoxins, gambierols, and gambieric acids;
(p) conjugates to antibodies having one or more non-natural amino acid residues at specific positions in the heavy or light chains;
(q) conjugates to a sialoadhesin binding moiety;
(r) pheophorbide-α conjugates;
(s) conjugates to multi-component nanochains;
(t) conjugates to activatable antibodies that include a masking moiety, a cleavable moiety, and an antibody binding specifically to interleukin-6;
(u) conjugates including hydrophilic linkers;
(v) conjugates to antibodies specific for p97;
(w) conjugates including a modified amino acid incorporating an azido group;
(x) conjugates to albumin; and
(y) conjugates to folate.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Conjugates to fatty acids are described in U.S. Pat. No. 7,235,538 to Webb et al., incorporated herein by this reference. The fatty acid is preferably a $C_8$-$C_{26}$ unbranched fatty acid such as caprylic acid, capric acid, lauric acid, myristic acid, palmitic acid, palmitoleic acid, stearic acid, oleic acid, vaccinic acid, linoleic acid, α-linolenic acid, eleostearic acid, p3-linolenic acid, gondoic acid, dihomo-γ-linolenic acid, arachidonic acid, eicopentaenoic acid, docosenoic acid, docosatetraenoic acid, docosapentaenoic acid, docosahexaenoic acid, and nervonic acid.

Conjugates to fatty alcohols are disclosed in U.S. Pat. No. 7,816,398 to Swindell et al., incorporated herein by this reference. The fatty alcohol conjugates have the general structure RO—C(O)—OX, where X is an antineoplastic agent moiety of an antineoplastic agent XOH, R is a $C_8$-$C_{26}$ fatty acid group of a fatty alcohol ROH wherein R is one of the following fatty acids: octanoic (caprylic); nonanoic (pelargonic); decanoic (capric); undecanoic (hendecanoic); dodecanoic (lauric); tridecanoic; tetradecanoic (myristic); pentadecanoic; hexadecanoic (palmitic); heptadecanoic (margaric); octadecanoic (stearic); 12-hydroxy stearic; nonadecanoic; eicosanoic (arachidic); heneicosanoic; docosanoic (behenic); tricosanoic; tetracosanoic (lignoceric); 10-undecenoic (hendecenoic); 11-dodecenoic; 12-tridecenoic; 9-tetradecenoic (myristoleic); 9-trans-tetradecenoic (myristelaidic); 10-pentadecenoic; 10-trans-pentadecenoic; 9-hexadecenoic (palmitoleic); 8-trans-hexadecenoic (palmitelaidic); 10-heptadecenoic; 10-trans-heptadecenoic; 6-octadecenoic (petroselinic); 6-trans-octadecenoic (petroselaidic); 8-octadecenoic (oleic); 9-11-octadecenoic (vaccenic); 11-trans-octadecenoic (transvaccenic); 9-cis-12 hydroxy-octadecenoic (ricinoleic); 9-trans-12-hydroxy-octadecenoic (ricinelaidic); 7-nonadecenoic; 7-trans-nonadecenoic; 10-nonadecenoic; 10-trans-nonadecenoic; 10-13-nonadecadienoic; 10-13-trans-nonadecadienoic; 8-12-octadecadienoic (linoleic); 9-trans-12-trans octadecadienoic (linoelaidic); octadecadienoic (conjugated); 9-12-15-octadecatrienoic (linolenic); 6-9-12-octadecatrienoic (γ-linolenic); 11-trans-eicosenoic; 8-eicosenoic; 11-eicosenoic; 5-eicosenoic; 11-14-eicosadienoic; 8-11-14-eicosatrienoic (homo-γ-linolenic); 11-14-17-eicosatrienoic; 5-8-11-14-eicosatetraenoic (arachidonic); 5-8-11-14-17-eicosapentaenoic; 7-10-13-16-19-docosapentaenoic; 13-docosenoic (erucic); 13-transdocosenoic (brassidic); 13-16-docosadienoic; 13-16-19-docosatrienoic; 7-10-13-16-docosatetraenoic; 4-7-10-13-16-19-docosahexaenoic (docosahexaenoic; DHA); 12-heneicosenoic; 12-15-heneicosadienoic; 14-tricosenoic; and 15-tetracosenoic (nervonic).

Conjugates to elastin-like peptides are described in U.S. Pat. No. 8,252,740 to Raucher et al., incorporated herein by this reference. Delivery by these conjugates is thermally activated. In one alternative, the conjugate comprises: (i) the cell-penetrating peptide Tat; (ii) an elastin-like peptide for thermal targeting; (iii) a GFLG (SEQ ID NO: 12) peptide as a cleavable linker; (iv) a cysteine residue; and (v) bisantrene or a derivative of bisantrene.

Conjugates with polyclonal or monoclonal antibodies, proteins, or peptides are disclosed in U.S. Pat. No. 8,389,697 to Beria et al., incorporated herein by this reference. These compounds incorporating bisantrene or a derivative or analog of bisantrene are characterized by the general formula:

[Bis-L-Z]$_m$-T, wherein: (i) Bis is a residue of bisantrene or a derivative or analog thereof; (ii) L is a linker; (iii) Z is a spacer; (iv) m is an integer from 1 to 30; and (v) T is a carrier such as a protein, peptide, monoclonal or polyclonal antibody or a chemically modified moiety thereof suitable to be attached to the [Bis-L-Z] moiety or moieties, or a polymeric character. In these conjugates, the linker L is typically is —CH$_2$O—, —N(R)$_m$(C$_1$-C$_{12}$ alkylene)-X$^1$, —N(R)—, —N(R)$_m$(C$_1$-C$_{12}$ alkylene)-, —N(R)$_m$(C$_2$-C$_8$ alkenylene)-, N(R)$_m$(CH$_2$CH$_2$O)$_n$—, or the structures

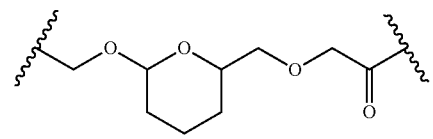

-continued

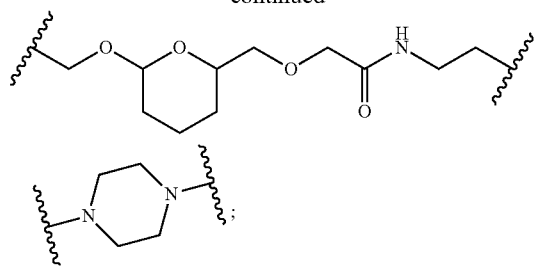

where the wavy lines indicate the attachments to Bis and Z; Z is an optional spacer selected from —$CH_2C(O)$—, —$CH_2C(O)NR(C_1$-$C_{12}$ alkylene)-, and the structures

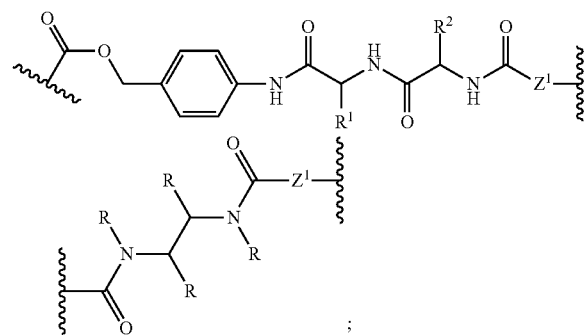

X is a reactive functional group selected from maleimide, thiol, amino, bromide, p-toluenesulfonate, iodide, hydroxyl, carboxyl, pyridyl disulfide, and N-hydroxysuccinimide; R is hydrogen, $C_1$-$C_{12}$ alkyl, or $C_6$-$C_{20}$ aryl; $R^1$ and $R^2$ are independently selected from an amino acid side chain; $Z^1$ is selected from —S—, —$CH_2C(O)$—, —$(CH_2CH_2O)_nCH_2C(O)$—, —$(CH_2CH_2O)_nCH_2$—, and —$(C_1$-$C_{12}$ alkylene)-; m is 0 or 1; n is 1; and T is a carrier moiety as described below. Carrier moieties may be derived from polyclonal antibodies raised against tumor associated antigens; or from monoclonal antibodies binding to antigens preferentially or selectively expressed on tumor cell populations; or from natural or recombinant peptides or proteins or growth factors preferentially or selectively binding to tumor cells; or from natural or synthetic polymeric carriers such as polylysine, polyglutamic acid, polyaspartic acid and their analogues and derivatives, or such as dextran or other polymeric carbohydrate analogues and their derivatives; or from synthetic copolymers such as those derived from N-(2-hydroxypropyl)methacrylamide (HPMA), or from poly(amino acid) copolymers such as poly(GluNa, Ala, Tyr) which are useful as targetable drug-carriers for lung tissue. The carrier portion may be also derived from portions of the above mentioned peptides or proteins obtained through recombinant DNA techniques.

Conjugates with cell-binding agents through a charged or pro-charged cross-linker are disclosed in United States Patent Application Publication No. 2009/0274713 by Chari et al., incorporated herein by this reference. In general, the cross-linkers possess three elements: (i) a substituent that is either charged or that will become charged when a conjugate employing the cross-linker is metabolized in vivo; the charge can be either anionic, which can be, but is not limited to, carboxylate, sulfonate, or phosphate, or cationic, which can be, but is not limited to, a tertiary, quaternary, or primary amine or a nitrogen-containing heterocycle; (ii) a group, such as, but not limited to, a N-hydroxysuccinimide ester, maleimido group, haloacetyl group, or hydrazide group, capable of reaction with a cell-binding agent; and (iii) a group, such as, but not limited to, disulfide, maleimide, haloacetyl, or hydrazide, capable of reaction with a drug. Other groups can, alternatively, be used as the groups capable of reaction with the cell-binding agent and the drug. The cross-linker may include a phenyl or substituted phenyl moiety or an optional polyethyleneoxy group. The cell-binding agent can be, for example, antibodies (including monoclonal antibodies or antibody fragments), adnectins, interferons, lymphokines, hormones, growth factors, vitamins, nutrient-transport molecules such as transferrin, or any other cell-binding agent.

Conjugates to antibodies targeted to tumor markers, in some cases with an amino-dextran intermediate carrier, are described in L. B. Shih et al., "Anthracycline Immunoconjugates Prepared by a Site-Specific Linkage via an Amino-Dextran Intermediate Carrier," Cancer Res. 51: 4192-4198 (1991), incorporated herein by this reference. In the procedure described in this reference, the drug is first conjugated to amino-dextran and the conjugate to the drug with amino-dextran is then attached using site-specific attachment to the antibody. Other conjugation procedures for linking therapeutic agents such as bisantrene or a derivative or analog thereof are known in the art.

Biodegradable polymer-bioactive moiety conjugates are disclosed in U.S. Pat. No. 8,535,655 to O'Shea et al., incorporated herein by this reference. The releasable bioactive moieties being pendant from and covalently bonded to the biodegradable polymer backbone; the biodegradable polymer backbone is formed from monomeric units that are each coupled via a biodegradable moiety, and the bioactive moieties are capable of being released at a rate equal to or faster than the rate of biodegradation of the polymer backbone. Typically, the copolymer is formed with at least one polyisocyanate, and the polyisocyanate is selected from the group consisting of m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexylmethane diisocyanates, 1,5-napthylene diisocyanate, 4,4'-diphenylmethane diisocyanate, 2,4'-diphenylmethane diisocyanate, 4,4'-biphenylene diisocyanate, 3,3'-dimethoxy-4,4'-biphenylene diisocyanate, 3,3'-dimethyl-diphenylpropane-4,4'-diisocyanate, 2,4,6-toluene triisocyanate, 4,4'-dimethyl-diphenylmethane-2,2',5,5'-tetraisocyanate, and alkyl esters of lysine diisocyanate.

Conjugates with 2-nitroimidazole compounds with a secondary basic nitrogen atom and a linker are disclosed in U.S. Pat. No. 8,518,371 to Lee et al., incorporated herein by this reference.

Conjugates with ladder frame polyether compounds are disclosed in United States Patent Application Publication No. 2014/0073604 by Bourdelais et al., incorporated herein by this reference. The polyether compounds can be derived from breveval, brevisin, tamulamide, brevetoxins, hemibrevetoxins, gambierols, and gambieric acids.

Conjugates to antibodies having one or more non-natural amino acid residues at specific positions in the heavy or light chains are disclosed in United States Patent Application Publication No. 2014/0046030 by Thanos et al., incorporated herein by this reference Conjugates to a sialoadhesin binding moiety are disclosed in United States Patent Application Publication No. 2013/0273080 by Elewaut et al., incorporated herein by this reference. The sialoadhesin binding moiety can be an antibody, or a fragment thereof, a sialoadhesin ligand or a small molecule. The antibody can be a monoclonal antibody. Sialoadhesin ligands can be natural sialylated ligands for sialoadhesin, including CD43, galactose-type C-type lectin 1, and MUC1 antigen.

Pheophorbide-α conjugates are disclosed in United States Patent Application Publication No. 2013/0210756 by Kim et al., incorporated herein by this reference. The conjugates typically include a chemical linker, including, but not limited to, a hydroxycinnamoyl moiety or an aminobenzyloxycarbonyl moiety.

Conjugates to multi-component nanochains are disclosed in PCT Patent Application Publication No. WO 2013/056092 by Karathanasis et al., incorporated herein by this reference. The multicomponent nanochains can include at least three nanoparticles linked together to form the nanochain. The nanochain can be linked to the bisantrene or analog or derivative thereof.

Conjugates including activatable antibodies that include a masking moiety, a cleavable moiety, and an antibody binding specifically to interleukin-6 are disclosed in PCT Patent Application Publication No. WO 2014/052462 by West et al., incorporated herein by this reference. The activatable antibody can include one or two linking peptides.

The use of conjugates including hydrophilic linkers is disclosed in PCT Patent Application Publication No. WO 2014/080251 by Zhao, incorporated herein by this reference.

The use of conjugates including antibodies specific for p97 is disclosed in PCT Patent Application Publication No. WO 2013/006706 by Hutchison et al., incorporated herein by this reference.

The use of conjugates including a modified amino acid incorporating an azido group is disclosed in PCT Patent Application Publication No. WO 2014/036492 by Stafford et al., incorporated herein by this reference. The conjugates can include an antibody. The use of conjugates to albumin is disclosed in F. Kratz, "DOXO-EMCH (INNO-206): The First Albumin-Binding Prodrug of Doxorubicin to Enter Clinical Trials," *Expert Opin. Invest. Drugs* 16: 855-866 (2007), incorporated herein by this reference. Such conjugates can include 6-maleimidocaproyl hydrazone derivatives of bisantrene or derivatives or analogs thereof; the 6-maleimidocaproyl hydrazone moiety binds selectively to the cysteine-34 amino acid residue of albumin via the maleimide moiety. The bisantrene or derivative or analog thereof is then released from the albumin carrier after cleavage of the acid-sensitive hydrazone linker in the acidic environment of tumors. The use of conjugates linked to folate is disclosed in J. Clarhaut et al., "A Galactosidase-Responsive Doxorubicin-Folate Conjugate for Selective Targeting of Acute Myelogenous Leukemia Blasts, *Leukemia Res.* 37: 948-955 (2013), incorporated herein by this reference.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonydiimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques," (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

When the improvement is made by use of a compound analog, the compound analog can be, but is not limited to, a compound analog selected from the group consisting of:
 (a) alteration of side chains to increase or decrease lipophilicity;
 (b) addition of an additional chemical functionality to alter a property selected from the group consisting of reactivity, electron affinity, and binding capacity; and
 (c) alteration of salt form.

When the improvement is made by use of a prodrug system, the prodrug system can be, but is not limited to, a prodrug system selected from the group consisting of:
 (a) the use of enzyme sensitive esters;
 (b) the use of dimers;
 (c) the use of Schiff bases;
 (d) the use of pyridoxal complexes;
 (e) the use of caffeine complexes;
 (f) the use of plasmin-activated prodrugs;
 (g) the use of a drug targeting complex comprising a targeting carrier molecule that is selectively distributed to a specific cell type or tissue containing the specific cell type; a linker which is acted upon by a molecule that is present at an effective concentration in the environs of the specific cell type; and a therapeutically active agent to be delivered to the specific cell type; and
 (h) the use of a prodrug molecule comprising a conjugate of bisantrene or a derivative or analog of bisantrene, a protease-specific cleavable peptide, and optionally, a targeting peptide, with the prodrug molecule being substantially inactive prior to degradation of the protease-specific cleavable peptide by a proteolytic enzyme within or in close proximity to the cancer cell.

The use of prodrug systems is described in T. Jarvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference.

Another potential prodrug system for bisantrene or analogs or derivatives of bisantrene is the use of a plasmin-activated prodrug as described in U.S. Pat. No. 7,402,556 to Trouet et al., incorporated herein by this reference. In general, these prodrugs comprise: (1) the therapeutically active agent capable of entering a target cell, in this case, bisantrene or a derivative or analog of bisantrene as described above; (2) an oligopeptide having the formula X-Y, wherein X is a plasmin peptide substrate of 2-4 amino acids and Y is a peptide fragment comprising 1-2 amino acids having large side chains; (3) a stabilizing group; and (4) optionally, a linker group not cleavable by plasmin. In this prodrug arrangement, the oligopeptide is directly linked to the stabilizing group at a first attachment site of the oligopeptide and the oligopeptide is directly linked to the therapeutically active agent (i.e., amonafide or a derivative or analog of amonafide) or indirectly linked through the linker group to the therapeutically active agent at a second attachment site of the oligopeptide. The stabilizing group hinders cleavage of the oligopeptide by enzymes present in whole blood. The prodrug incorporating the therapeutically active agent is cleavable by plasmin.

Yet another potential prodrug system for bisantrene and derivatives or analogs of bisantrene is the use of the drug complex of U.S. Pat. No. 6,368,598 to D'Amico et al., incorporated herein by this reference. In general, such a drug complex comprises a targeting carrier molecule that is selectively distributed to a specific cell type or tissue containing the specific cell type; a linker which is acted upon by a molecule that is present at an effective concentration in the environs of the specific cell type; and a therapeutically active agent to be delivered to the specific cell type, such as, in this application, bisantrene or a derivative or analog of bisantrene. In one application, the cell type is cells of the prostate and the drug complex is cleaved by the activity of prostate specific antigen (PSA).

The use of a prodrug molecule comprising a conjugate of bisantrene or a derivative or analog of bisantrene, a protease-specific cleavable peptide, and optionally, a targeting peptide, with the prodrug molecule being substantially inactive prior to degradation of the protease-specific cleavable peptide by a proteolytic enzyme within or in close proximity to the cancer cell is described in U.S. Pat. No. 8,314,060 to Gengrinovitch, incorporated herein by this reference.

When the improvement is made by use of a multiple drug system, the multiple drug system can be, but is not limited to, a multiple drug system selected from the group consisting of the use of bisantrene or a derivative or analog of amonafide with:
 (a) inhibitors of multi-drug resistance;
 (b) specific drug resistance inhibitors;
 (c) specific inhibitors of selective enzymes;
 (d) signal transduction inhibitors;
 (e) meisoindigo;
 (f) imatinib;
 (g) hydroxyurea;
 (h) dasatinib;
 (i) capecitabine;
 (j) nilotinib;
 (k) repair inhibition agents;
 (l) topoisomerase inhibitors with non-overlapping side effects;
 (m) PARP inhibitors;
 (n) EGFR inhibitors; and
 (o) HDAC inhibitors.

Multi-drug resistance inhibitors are described in U.S. Pat. No. 6,011,069 to Inomata et al., incorporated herein by this reference. Verapamil and calcium influx blocking agents have this property and have been used for this purpose. Additional multi-drug resistance inhibitors of particular utility for increasing the activity of antineoplastic drugs are described in U.S. Pat. No. 5,436,243 to Sachs et al., incorporated herein by this reference, including aminoanthraquinones, preferably 1,4bis(N-substituted anthraquinones). Additional multi-drug resistance inhibitors of particular utility for increasing the activity of antineoplastic drugs are also described in U.S. Pat. No. 5,639,887 to Powell et al., incorporated herein by this reference, including the following compounds: α-(4-chlorobutyl)-3,4-dimethoxy-α-[(4-methylphenyl)-thio]benzeneacetonitrile; α-(3-chloro-2-methylpropyl)-3,4-dimethoxy-α-[(4-methyl-phenyl)thio]

benzeneacetonitrile; α-(11-bromoundecyl)-3,4-dimethoxy-α-[(4-methylphenyl)-thio]benzeneacetonitrile; α-(5-chloropentyl)-3,4-dimethoxy-α-[(4-methylphenyl)-thio]benzeneacetonitrile; α-(5-bromooctyl)-3,4-dimethoxy-α-[(4-methylphenyl)-thio]benzeneacetonitrile; α-(5-iodopentyl)-3,4-dimethoxy-α-[(4-methylphenyl)-thio]benzeneacetonitrile; α-(5-aminopentyl)-3,4-dimethoxy-α-[(4-methylphenyl)-thio]benzeneacetonitrile; α-(5-chlorohexyl)-3,4-dimethoxy-α-[(4-methylphenyl)-thio]benzeneacetonitrile; 4-[4-chloro-1-[(4-methylphenyl)thio]butyl]-1,2-dimethoxybenzene; 4-[6-bromo-1-[(4-methylphenyl)thio]hexyl]-1,2-dimethoxybenzene; α-3,4-dimethoxyphenyl)-3-(hydroxymethyl)-α-[(4-methylphenyl)thio]benzenepropanenitrile; 1,3-(chloromethyl)-α-(dimethoxyphenyl)-α-[(4-methylphenyl)thio]benzenepropanenitrile; 4-[6-bromo-1-[(4-methylphenyl)thio]heptyl]-1,2-dimethoxybenzene; 5-[7-bromo-1-[(4-methylphenyl)thio]heptyl]-2-methoxy-phenoxy](1,2-dimethyl ethyl)dimethylsilane; α-(5-chloropentyl)-α-(cyclohexylthio)-3,4-dimethoxybenzeneacetonitrile; α-(5-aminopentyl)-α-(cyclohexylthio)-3,4-dimethoxybenzeneacetonitrile; 5-[6-bromo-1-[(4-methylphenyl)thio]hexyl-1,3-benzodioxole; 1-[6-bromo-1-[(methylphenyl)thio]hexyl]-4-(trifluoromethoxy)benzene; 1-[[6-bromo-1-(4-fluorophenyl)hexyl]thio]-4-methylbenzene; α-(5-bromopentyl)-3,4-dimethoxy-α-[(4-methylphenyl)-thio]benzeneacetonitrile; [(7-bromo-1-phenylheptyl)thio]benzene; α-(5-bromopentyl)-α-(cyclohexylthio)-3,4-dimethoxybenzeneacetonitrile; 7-bromo-2-(3,4-dimethoxyphenyl)-2-(2-pyridylthio)-heptanonitrile; and α-(5-hydroxypentyl)-3,4-dimethoxy-α-[(methylphenyl)-thio]benzeneacetic acid methyl ester. U.S. Pat. No. 5,994,130 to Shyjan, incorporated herein by this reference, discloses another multi-drug resistance protein, MRP-β and methods of inhibition thereof, including the use of antisense nucleotides. United States Patent Application Publication 2002/0156015 by Rabindran et al., incorporated herein by this reference, discloses agents that are capable of reversing multidrug resistance, including fumitremorgin A, fumitremorgin B, fumitremorgin C, and diketopiperazines. United States Patent Application Publication No. 2007/0009535 by Sikic et al., incorporated herein by this reference, discloses P-glycoprotein efflux pump inhibitors such as zosuquidar, tariquidar, and tesmilifene. Still additional multidrug resistance inhibitors are disclosed in United States Patent Application 2008/0207738 by Kiss, incorporated herein by this reference, including 9H-xanthene-9-carboxylic acid-3-{4-[2-(4-trimethylsilanyl-methoxy-benzoyloxy)-ethyl]-piperazin-1-yl}propyl ester dihydrochloride.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference.

Signal transduction inhibitors are described in A.V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference. Signal transduction inhibitors can include, but are not limited to, BCL/ABL kinase inhibitors, epidermal growth factor (EGF) receptor inhibitors, her-2/neu receptor inhibitors, and farnesyl transferase inhibitors, as described in U.S. Pat. No. 8,008,281 to Prendergast et al., incorporated herein by this reference.

Repair inhibition agents are described in N. M. Martin, "DNA Repair Inhibition and Cancer Therapy," *J. Photochem. Photobiol. B* 63: 162-170 (2001), incorporated herein by this reference.

HDAC inhibitors are described in further detail below with respect to the use of bisantrene and derivatives or analogs thereof to inhibit DNA methylation.

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:

(a) biological response modifiers;
(b) cytokines;
(c) lymphokines;
(d) therapeutic antibodies;
(e) antisense therapies;
(f) gene therapies;
(g) ribozymes;
(h) RNA interference;
(i) vaccines (cellular and non-cellular);
(j) stem cells; and
(k) autologous cell transplants.

Biological response modifiers are described in T. E. G. K. Murthy et al., "Biological Response Modifiers,' *Int. J. Pharmtech Res.* 2: 2152-2160 (2010), incorporated herein by this reference.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" in *Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" in *Drug Discovery Handbook* (S. C. Gad, ed., Wiley-Interscience, Hoboken, N.J., 2005), ch. 27, pp. 1278-1283, incorporated herein by this reference.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

Cancer vaccines are being developed. Typically, cancer vaccines are based on an immune response to a protein or proteins occurring in cancer cells that does not occur in normal cells such as, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, "Cancer Vaccines: Accomplishments and Challenges," *Crit. Rev. Oncol. Hematol.* 67: 93-102 (2008), incorporated herein by this reference, by activating cells via autologous transplant such as Provenge, or via checkpoint blockade, such as ipilimumab.

Therapeutic applications of the use of stem cells for the treatment of malignancies are also being developed. One avenue for the use of stem cells in the treatment of malignancies involves the administration of stem cells to initiate immune-reconstruction following high dose chemotherapy or radiation. Typically, in this alternative, the stem cells used are hemopoietic stem cells (HSCs). This use of stem cells is described in J. Sagar et al., "Role of Stem Cells in Cancer Therapy and Cancer Stem Cells: A Review," *Cancer Cell Internat.* 7:9 (2007), incorporated herein by this reference. This may be particularly useful for malignancies affecting the immune system, such as lymphomas. Another use of stem cells in cancer therapy is by targeting malignant cells directly with stem cells. Stem cells have tumoritropic migratory properties, and can be modified by the insertion of transgenes with antitumor effects. Transgene effects can include direct tumor-cell killing, promotion of local immune responses, oncolytic virus production, and prodrug activation schemes. This use of stem cells in cancer therapy is described in M. F. Corsten & K. Shah, "Therapeutic Stem-Cells for Cancer Treatment: Hopes and Hurdles in Tactical Warfare," *Lancet Oncol.* 9: 376-384 (2008), incorporated herein by this reference.

When the improvement is made by use of biotherapeutic resistance modulation, the biotherapeutic resistance modulation can be, but is not limited to, use against tumors resistant to a therapeutic agent or technique selected from the group consisting of:
(a) biological response modifiers;
(b) cytokines;
(c) lymphokines;
(d) therapeutic antibodies;
(e) antisense therapies;
(f) gene therapies;
(g) ribozymes; and
(h) RNA interference.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:
(a) use with hypoxic cell sensitizers;
(b) use with radiation sensitizers/protectors;
(c) use with photosensitizers;
(d) use with radiation repair inhibitors;
(e) use with thiol depletion;
(f) use with vaso-targeted agents;
(g) use with radioactive seeds;
(h) use with radionuclides;
(i) use with radiolabeled antibodies; and
(j) use with brachytherapy; and
(k) use with bioreductive alkylating agents.

Hypoxic cell sensitizers are described in C. C. Ling et al., "The Effect of Hypoxic Cell Sensitizers at Different Irradiation Dose Rates," *Radiation Res.* 109: 396-406 (1987), incorporated herein by this reference. Radiation sensitizers are described in T. S. Lawrence, "Radiation Sensitizers and Targeted Therapies," *Oncology* 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008), incorporated herein by this reference. Photosensitizers are described in R. R. Allison & C. H. Sibata, "Oncologic Photodynamic Therapy Photosensitizers: A Clinical Review," *Photodiagnosis Photodynamic Ther.* 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," *Radiation Res.* 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," *Cancer Res.* 67: 9455-9462 (2007), incorporated herein by this reference. Bioreductive alkylating agents include tirapazamine, described in W. A. Denny, "Prospects for Hypoxia-Activated Anticancer Drugs," *Curr. Med. Chem.* 4: 395-399 (2004), incorporated herein by this reference. Bioreductive alkylating agents also include nitroimidazoles, such as metronidazole, tinidazole, and nimorazole, and other substituted nitroheterocycles, described in A. Mital, "Synthetic Nitroimidazoles: Biological Activities and Mutagenicity Relationships," *Sci. Pharm.* 77: 497-520 (2009) and in M. R. Juchau, "Bioactivation in Chemical Teratogenesis," *Annu. Rev. Pharmacol. Toxicol.* 29: 165-187 (1989).

When the improvement is made by use of a novel mechanism of action, the novel mechanism of action can be, but is not limited to, a novel mechanism of action that is a therapeutic interaction with a target or mechanism selected from the group consisting of:
(a) inhibitors of poly-ADP ribose polymerase;
(b) agents that affect vasculature;
(c) agents that promote vasodilation;
(d) oncogenic targeted agents;
(e) signal transduction inhibitors;
(f) agents inducing EGFR inhibition;
(g) agents inducing Protein Kinase C inhibition;
(h) agents inducing Phospholipase C down regulation;
(i) agents including jun downregulation;
(j) agents modulating expression of histone genes;
(k) agents modulating expression of VEGF;
(l) agents modulating expression of ornithine decarboxylase;
(m) agents modulating expression of jun D;
(n) agents modulating expression of v-jun;
(o) agents modulating expression of GPCRs;
(p) agents modulating expression of protein kinase A;
(q) agents modulating expression of protein kinases other than protein kinase A;
(r) agents modulating expression of telomerase;
(s) agents modulating expression of prostate specific genes;
(t) agents modulating expression of histone deacetylase; and
(u) agents modulating expression of checkpoint regulators such as CTLA-4, PD-1, PD-2, and OX-40; and
(v) agents modulating expression of mTOR and related molecules such as Akt3 and PI3K.

Inhibitors of poly ADP-ribose polymerase include veliparib (ABT-888), AGO14699, iniparib (BSI-201), carboplatin, gemcitabine, INO-1001, MK4827, nicotinamide, olaparib, paclitaxel, temozolomide, and topotecan, and are described in E. A. Comen & M. Robson, "Inhibition of Poly(ADP)-Ribose Polymerase as a Therapeutic Strategy for Breast Cancer," *Oncology* 24: 55-62 (2010), incorporated herein by this reference. Agents promoting vasodilation include levosimendan, described in W. G. Toiler et al., "Levosimendan, a New Inotropic and Vasodilator Agent," *Anesthesiology* 104: 556-569 (2006), incorporated herein by this reference. EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005), incorporated herein by this reference. Protein kinase C inhibition is described in H. C. Swannie & S. B. Kaye, "Protein Kinase C Inhibitors," *Curr. Oncol. Rep.* 4: 37-46 (2002), incorporated herein by this reference. Phospholipase C downregulation is described in A. M. Martelli et al., "Phosphoinositide Signaling in Nuclei of Friend Cells: Phospholipase C β Downregulation Is Related to Cell Differentiation," *Cancer Res.* 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," *Oncogene* 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," *Proc. Natl. Acad. Sci. USA* 83: 1495-1498 (1986), incorporated herein by this reference. The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," *Surqery* 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," *Cancer Cell* 7: 433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," *Clin. Cancer Res.* 8: 2505-2511 (2002), incorporated herein by this reference. The role of Jun D as a target for therapeutic intervention is described in M. M. Caffarel et al., "JunD Is Involved in the Antiproliferative Effect of $\Delta^9$-Tetrahydrocannibinol on Human Breast Cancer Cells," *Oncogene* 27: 5033-5044 (2008), incorporated herein by this reference. The role of v-Jun as a target for therapeutic intervention is described in M. Gao et al., "Differential and Antagonistic Effects of v-Jun and c-Jun," *Cancer Res.* 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," *Eur. J. Cancer* 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," *Ann. Med.* 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," *Curr. Opin. Hematol.* 9: 322-332 (2002), incorporated herein by this reference.

CHK2 checkpoint kinase is a serine/threonine protein kinase which is required for checkpoint-mediated cell cycle arrest, activation of DNA repair and apoptosis in response to the presence of DNA double-strand breaks. CHK2 checkpoint kinase may also negatively regulate cell cycle progression during unperturbed cell cycles. Following activation, CHK2 checkpoint kinase phosphorylates numerous effectors preferentially at the consensus sequence L-X-R-X-S/T (SEQ ID NO: 13). CHK2 checkpoint kinase regulates cell cycle checkpoint arrest through phosphorylation of CDC25A, CDC25B and CDC25C, inhibiting their activity. The inhibition of CDC25 phosphatase activity leads to increased inhibitory tyrosine phosphorylation of CDK-cyclin complexes and blocks cell cycle progression. CHK2 checkpoint kinase may also phosphorylate NEK6 which is involved in G2/M cell cycle arrest. CHK2 checkpoint kinase also regulates also phosphorylate NEK6 which is involved in G2/M cell cycle arrest. CHK2 checkpoint kinase also phosphorylates NEK6 which is involved in G2/M cell cycle arrest. Additionally, CHK2 checkpoint kinase stimulates the transcription of genes involved in DNA repair (including BRCA2) through the phosphorylation and activation of the transcription factor FOXM1. CHK2 checkpoint kinase also regulates apoptosis through the phosphorylation of p53/TP53, MDM4 and PML; phosphorylation of p53/TP53 at Ser20 by CHK2 may alleviate inhibition by MDM2, leading to accumulation of active p53/TP53. Phosphorylation of MDM4 may also reduce degradation of p53/TP53. CHK2 checkpoint kinase also controls the transcription of pro-apoptotic genes through phosphorylation of the transcription factor. It is also believed to act as a tumor suppressor. It may also have a DNA damage-independent function in mitotic spindle assembly by phosphorylating BRCA1. Its absence may be a cause of the chromosomal instability observed in some cancer cells. A deletion mutation at position 1100 of CHEK2, which encodes the CHK2 checkpoint kinase, is associated with an increased risk of breast cancer, particularly in the European population (H. Meijers-Heijboer et al., "Low-Penetrance Susceptibility to Breast Cancer Due to CHEK2(*)1100delC in Noncarriers of BRCA1 or BRCA2 Mutations," *Nat. Genet.* 31: 55-59 (2002), incorporated herein by this reference). The activity of CHK2 checkpoint kinase is further described in J. Li et al., "Structural and Functional Versatility of the FHA Domain in DNA-Damage Signaling by the Tumor Suppressor Chk2," *Mol. Cell* 9: 1045-1054 (2002), incorporated herein by this reference. Inhibitors and modulators of the activity of CHK2 checkpoint kinases are known in the art, and are described, for example, in U.S. Pat. No. 8,334,309 to Klein et al., U.S. Pat. No. 8,329,709 to Banka et al., U.S. Pat. No. 8,329,701 to Mitchell et al., U.S. Pat. No. 8,318,740 to Wu, U.S. Pat. No. 8,318,735 to Shipps, Jr. et al., U.S. Pat. No. 8,252,795 to Fink et al., U.S. Pat. No. 8,227,605 to Shipps, Jr., et al., U.S. Pat. No. 8,211,054 to Guzi et al., U.S. Pat. No. 8,202,876 to Albaugh et al., and U.S. Pat. No. 8,168,651 to Chua et al., all of which are incorporated herein by this reference.

When the improvement is made by use of selective target cell population therapeutics, the use of selective target cell population therapeutics can be, but is not limited to, a use selected from the group consisting of:

(a) use against radiation sensitive cells;
    (b) use against radiation resistant cells;
    (c) use against energy depleted cells; and
    (d) use against endothelial cells.

When the improvement is made by use with an agent to enhance the activity of bisantrene and analogs and derivatives thereof, the agent to enhance the activity of bisantrene and analogs and derivatives thereof can be, but is not limited to, an agent selected from the group consisting of:

(a) nicotinamide;
    (b) caffeine;
    (c) tetandrine; and
    (d) berberine.

When the improvement is made by use of bisantrene or a derivative or analog thereof to modulate DNA methylation, the use of bisantrene or a derivative or analog thereof to modulate DNA methylation can be, but is not limited to, a use selected from the group consisting of:
(a) use to promote gene silencing; and
(b) use with a drug that inhibits DNA methylation.

The use of bisantrene or a derivative or analog thereof to promote gene silencing is described in L. Suarez & S. D. Gore, "Demethylation Demystification," *Blood* 121: 1488-1489 (2011), incorporated herein by this reference.

Drugs that inhibit DNA methylation include, but are not limited to, 5'-azacytidine, 5-aza-2'-deoxycytidine, zebularine, L-methionine, apicidine, hydralazine, procainamide, antisense oligonucleotides directed against mRNA for DNA methyltransferase, and histone deacetylase (HDAC) inhibitors.

When the improvement is made by use of bisantrene or a derivative or analog thereof to inhibit telomerase or induce telomere dysfunction, the use of bisantrene or a derivative or analog of bisantrene can be, but is not limited to, a use selected from the group consisting of:
(a) use to inhibit telomerase; and
(b) use to induce telomere dysfunction.

Bisantrene and derivatives or analogs thereof can be used with telomerase inhibitors such as, but not limited to, BPPA (2,6-bis(3-piperidinopropionamido)anthraquinone), (−)-epigallocatechin gallate, H-7 (2,6-bis(3-piperidinopropionamido)anthraquinone), β-rubromycin, and BIBR1532 (2-[[(2E)-3-(2-naphthalenyl)-1-oxo-2-butenyl1-yl]amino] benzoic acid).

When the improvement is made by use of bisantrene or a derivative or analog thereof to activate macrophages or induce innate and/or adaptive immunity, the use of bisantrene or a derivative or analog of bisantrene can be, but is not limited to, a use selected from the group consisting of:
(a) use to activate macrophages;
(b) use to induce innate immunity; and
(c) use to induce adaptive immunity.

When the improvement is made by use of bisantrene or a derivative or analog thereof to inhibit expression of survivin or by use of bisantrene or a derivative or analog thereof with an inhibitor of survivin, the use of bisantrene or a derivative or analog of bisantrene can be, but is not limited to, a use selected from the group consisting of:
(a) use to inhibit expression of survivin; and
(b) use with an inhibitor of survivin.

Inhibitors of survivin are described above.

When the improvement is made by use of bisantrene or a derivative or analog thereof with a multidrug resistance reversal agent, the use of bisantrene or a derivative or analog of bisantrene can be, but is not limited to, use with a multidrug resistance reversal agent to reduce multidrug resistance. Multidrug resistance reversal agents are described above; a particularly useful multidrug resistance reversal agent is verapamil.

When the improvement is made by use in combinatorial regimes, bisantrene and derivatives or analogs thereof can be employed in such combinatorial regimes, typically by combining newer immunotherapies with older cytotoxic modalities. Combinatorial therapy is described in L. S. Liebovitch et al., "Developing Combinatorial Multi-Component Therapies (CMCT) of Drugs That Are More Specific and Have Fewer Side Effects Than Traditional One Drug Therapies," *Nonlinear Biomed. Phys.* 1: 11 (2007), and in B. Al-Lazikani et al., "Combinatorial Drug Therapy for Cancer in the Post-Genomic Era," *Nat. Biotechnol.* 10: 679-692 (2012), both incorporated herein by this reference. Combinations for combinatorial therapeutics can be selected based on genomics or proteomics; for example, therapeutic agents can be chosen based on interactions with receptors or kinases in a single pathway or in pathways that interact. The use of bisantrene or a derivative or analog thereof in a combinatorial regime can be, but is not limited to:
(a) use in a combinatorial regime as a chemotherapeutic agent with at least one agent inducing immunoactivity;
(b) use in a combinatorial regime as a chemotherapeutic agent with at least one agent inducing macrophage activation;
(c) use in a combinatorial regime as a chemotherapeutic agent with at least one cytokine;
(d) use in a combinatorial regime as a chemotherapeutic agent with at least one agent inhibiting telomerase;
(e) use in a combinatorial regime as a chemotherapeutic agent with at least one agent inhibiting survivin;
(f) use in a combinatorial regime as a chemotherapeutic agent with at least one agent inducing demethylation;
(g) use in a combinatorial regime as a chemotherapeutic agent with at least one adjuvant;
(h) use in a combinatorial regime as a chemotherapeutic agent with at least one antibody;
(i) use in a combinatorial regime as a chemotherapeutic agent with at least one innate or adaptive immune stimulator;
(j) use in a combinatorial regime as a chemotherapeutic agent with at least one checkpoint inhibitor;
(k) use in a combinatorial regime as a chemotherapeutic agent with at least one mTOR antagonist;
(l) use in a combinatorial regime as a chemotherapeutic agent with at least one Akt inhibitor;
(m) use in a combinatorial regime as a chemotherapeutic agent with at least one notch inhibitor;
(n) use in a combinatorial regime as a chemotherapeutic agent with at least one HSP inhibitor;
(o) use in a combinatorial regime as a chemotherapeutic agent with at least one phosphatidylinositide 3-kinase inhibitor;
(p) use in a combinatorial regime as a chemotherapeutic agent with at least one kinase inhibitor;
(q) use in a combinatorial regime as a chemotherapeutic agent with cytarabine;
(r) use in a combinatorial regime as a chemotherapeutic agent with taxane;
(s) use in a combinatorial regime as a chemotherapeutic agent with taxol;
(t) use in a combinatorial regime as an agent inducing macrophage activation with at least one agent inducing telomerase inhibition;
(u) use in a combinatorial regime as an agent inducing macrophage activation with at least one cytokine;
(v) use in a combinatorial regime as an agent inducing macrophage activation with at least one agent inhibiting survivin;
(w) use in a combinatorial regime as an agent inducing macrophage activation with at least one agent inducing demethylation;
(x) use in a combinatorial regime as an agent inducing macrophage activation with at least one adjuvant;
(y) use in a combinatorial regime as an agent inducing macrophage activation with at least one antibody;
(z) use in a combinatorial regime as an agent inducing macrophage activation with at least one innate or adaptive immune stimulator;
(aa) use in a combinatorial regime as an agent inducing macrophage activation with at least one checkpoint inhibitor;

(ab) use in a combinatorial regime as an agent inducing macrophage activation with at least one mTOR antagonist;

(ac) use in a combinatorial regime as an agent inducing macrophage activation with at least one Akt inhibitor;

(ad) use in a combinatorial regime as an agent inducing macrophage activation with at least one notch inhibitor;

(ae) use in a combinatorial regime as an agent inducing macrophage activation with at least one HSP inhibitor;

(af) use in a combinatorial regime as an agent inducing macrophage activation with at least one phosphatidylinositide 3-kinase inhibitor;

(ag) use in a combinatorial regime as an agent inducing macrophage activation with at least one kinase inhibitor;

(ah) use in a combinatorial regime as an agent inducing macrophage activation with cytarabine;

(aj) use in a combinatorial regime as an agent inducing macrophage activation with taxane; and (ak) use in a combinatorial regime as an agent inducing macrophage activation with taxol.

Agents inducing demethylation include, but are not limited to, 5-azacytidine, 5-aza-2'-deoxycytidine, zebularine, L-methionine, apicidine, hydralazine, procainamide, and antisense oligonucleotides directed against mRNA for DNA methyltransferase. Additional drugs that inhibit DNA methylation include inhibitors of histone deacetylase (HDAC). These compounds include, but are not limited to, compounds disclosed in PCT Patent Application Publication No. WO 02/22577 by Bair et al., incorporated herein by this reference, including, but not limited to, N-hydroxy-3-[4-[[(2-hydroxyethyl)[2-(1H-indol-3-yl)ethyl]-amino]methyl]phenyl]-2E-2-propenamide, suberoylanilide hydroxamic acid, 4-(2-amino-phenylcarbamoyl)-benzyl]-carbamic acid pyridine-3-ylmethyl ester and derivatives thereof, butyric acid, pyroxamide, trichostatin A, oxamflatin, apicidin, depsipeptide, depudecin, trapoxin, HC toxin, and sodium phenylbutyrate.

Survivin is a regulator of apoptosis and acts to counter apoptosis as described above. Inhibitors or modulators of survivin activity or expression are described above.

Macrophage activators include, but are not limited to: *Bacillus* Calmette-Guérin; *Corynebacterium parvum*; endotoxins; muramyl dipeptide; pI:pC copolymer; pyran copolymer; lymphokines; Adriamycin; cyclophosphamide; mitomycin C; mycoplasmal lipoproteins; bisacyloxypropylcysteine conjugates, as described in U.S. Pat. No. 8,119,689 to Ebenstein et al. incorporated herein by this reference; glycolipopeptides as described in U.S. Pat. No. 7,820,797 to Boons, incorporated herein by this reference; mineral oil; starch; polycarbophil; and bisantrene, as well as various chemokines, lymphokines, and cancer vaccines described previously herein.

Checkpoint kinases are involved in the regulation of a number of cellular processes, including the cell cycle. Eukaryotes have evolved elaborate sensory networks to detect and repair DNA damage and prevent alterations in their genetic material. In response to DNA damage, eukaryotic cells arrest either in G1 or S phase, to prevent replication of damaged genes, or in G2 phase to avoid segregation of defective chromosomes. Checkpoint kinases, CHK1 and CHK2, participate in various DNA-damage responses, including cell-cycle checkpoints, genome maintenance, DNA repair, and apoptosis. They phosphorylate several key proteins involved in the cell cycle and block their activity. CHK1, an evolutionarily conserved protein kinase, is expressed in the S and G2 phases of cell cycle of proliferating cells. It is activated by phosphorylation on $Ser^{317}$ and $Ser^{345}$ in response to DNA damage. Once activated, CHK1 phosphorylates $Ser^{123}$ of Cdc25A, which targets it for ubiquitin-mediated degradation. The phosphorylated Cdc25A cannot dephosphorylate and activate Cdk1 and Cdk2, resulting in an arrest of cell cycle in the G1, S, and G2 phases. CHK1 also phosphorylates $Ser^{216}$ (14-3-3 binding site) on Cdc25C and prevents its activation in the G2 phase. Phosphorylated Cdc25C cannot dephosphorylate and activate Cdk1. Recent research indicates that CHK1 is an ideal chemosensitization target and its inhibition can sensitize tumors, particularly those with p53-deficiency, to various chemotherapeutic agents. CHK2 is structurally different from CHK1, but they share overlapping substrate specificities. CHK2 is activated following exposure to infrared light or topotecan, whereas CHK1 is activated by agents that interfere with DNA replication. This observation has led to the belief that CHK1 blocks cell-cycle progression when replication is inhibited, whereas CHK2 acts when there are double-strand breaks induced in DNA. CHK2 is activated by DNA-strand-breaking agents such as ionizing radiation and topoisomerase inhibitors through the ATM-dependent pathway. The role of CHK2 in checkpoints is not clearly understood. However, it is reported to phosphorylate Cdc25A and inhibit its activity. CHK2 also phosphorylates $Ser^{20}$ at the amino-terminal activation domain of p53 and regulates levels of p53 in response to DNA double strand breaks. Phosphorylation of $Ser^{20}$ is not the only important event for p53 response induced by UV light. CHK2 can also regulate p53 through targeting several other phosphorylation sites. Many current cancer treatments, including certain classes of chemotherapeutic agents, induce cytotoxicity by damaging DNA. However, many cancers become resistant to these therapies. Thus, modulating DNA-damage responses to selectively enhance the sensitivity of cancer cells to these therapies is highly desirable. Inhibitors of CHK1 and CHK2 have shown potential to enhance the efficacy of DNA-damaging cancer therapeutic agents by selectively increasing the sensitivity of tumor cells.

Checkpoint kinase inhibitors include, but are not limited to, AZD7762 (1-(2-((S)-piperidin-3-ylcarbamoyl)-5-(3-fluorophenyl)thiophen-3-yl)urea), LY2603618 ((S)-1-(5-bromo-4-methyl-2-(morpholin-2-ylmethoxy)phenyl)-3-(5-methylpyrazin-2-yl)urea), CHIR-124 ((S)-3-(1H-benzo[d]imidazol-2-yl)-6-chloro-4-(quinuclidin-3-ylamino)quinolin-2(1H)-one), SCH 900776 (6-bromo-3-(1-methyl-1H-pyrazol-4-yl)-5-((R)-piperidin-3-yl)pyrazolo[1,5-a]pyrimidin-7-amine), and PF 477736.

Additional inhibitors of checkpoint kinases are described in the following United States patents and patent applications, all of which are incorporated herein by this reference: U.S. Pat. No. 8,455,471 to Wisdom et al.; U.S. Pat. No. 8,435,970 to Curry et al.; U.S. Pat. No. 8,410,279 to Gazzard et al.; U.S. Pat. No. 8,372,842 to Blake et al.; U.S. Pat. No. 8,324,226 to Collins et al.; U.S. Pat. No. 8,314,108 to Farouz et al.; U.S. Pat. No. 8,277,807 to Gallagher et al.; U.S. Pat. No. 8,178,131 to Le Huerou et al.; U.S. Pat. No. 8,093,244 to Diaz et al.; U.S. Pat. No. 7,825,132 to Cai et al.; U.S. Pat. No. 7,781,580 to Lee et al.; U.S. Pat. No. 7,608,618 to Kesicki et al.; U.S. Pat. No. 7,560,462 to Gaudino et al.; U.S. Pat. No. 7,550,477 to Brnardic et al.; U.S. Pat. No. 7,501,435 to Arrington et al.; U.S. Pat. No. 7,485,649 to Brnardic et al.; U.S. Pat. No. 7,470,709 to Barsanti et al.; U.S. Pat. No. 7,462,713 to Benedict et al.; U.S. Pat. No. 7,202,244 to Boyle et al.; U.S. Pat. No. 7,132,533 to Benedict et al.; U.S. Pat. No. 7,094,798 to Booth et al.; U.S. Pat. No. 7,067,506 to Keegan et al.; U.S. Pat. No. 6,967,198 to Benedict et al.;

U.S. Pat. No. 6,670,167 to Chen et al.; United States Patent Application Publication No. 2013/0045286 by Le Huerou et al.; United States Patent Application Publication No. 2012/0232082 by Wu; United States Patent Application Publication No. 2012/0184505 by Popovici-Muller et al.; United States Patent Application Publication No. 2012/0114765 by Cao et al.; United States Patent Application Publication No. 2011/0201592 by Collins et al.; United States Patent Application Publication No. 2011/0183938 by Dyke et al.; United States Patent Application Publication No. 2011/0183933 by Guzi et al.; United States Patent Application Publication No. 2011/0124654 by Chen et al.; United States Patent Application Publication No. 2011/0118230 by Chen et al.; United States Patent Application Publication No. 2011/0021498 by Stokes et al.; United States Patent Application Publication No. 2011/0009415 by Wu; United States Patent Application Publication No. 2010/0260868 by Humphries et al.; United States Patent Application Publication No. 2010/0226917 by Brown et al.; United States Patent Application Publication No. 2010/0143332 by Parry et al. (including pyrazolopyrimidines, imidazopyrazines, UCN-01, indolcarbazole compounds, Go6976, SB-218078, staurosporine, ICP-1, CEP-3891, isogranulatimide, debromohymenialdisine (DBH), pyridopyrimidine derivatives, PD0166285, scytonemin, diaryl ureas, benzimidazole quinolones, CHR 124, CHR 600, tricyclic diazopinoindolones, PF-00394691, furanopyrimidines, pyrrolopyrimidines, indolinones, substituted pyrazines, compound XL844, pyrimidinylindazolyamines, aminopyrazoles, 2-ureidothiophenes, pyrimidines, pyrrolopyrimidines, 3-ureidothiophenes, indenopyrazoles, triazlones, dibenzodiazepinones, macrocyclic ureas, pyrazoloquinoloines, and the peptidomimetic CBP501 as CHK1 inhibitors); United States Patent Application Publication No. 2010/0105683 by Keegan et al.; United States Patent Application Publication No. 2010/0069423 by Pommier et al.; United States Patent Application Publication No. 2009/0312280 by Anderes et al. (including (2R,Z)-2-amino-2-cyclohexyl-N-(5-(1-methyl-1H-pyrazol-4-yl)-1-oxo-2,6-dihydro-1H-[1,2]diazepino[4,5,6-cd]indol-8-yl)acetamide); United States Patent Application Publication No. 2009/0143357 by Diaz et al. (including 1-[5-chloro-2-S-([1,4]oxazepan-2-ylmethoxy)-phenyl]-3-(5-methyl-pyrazin-2-yl)-urea, 1-[5-chloro-2-([1,4]oxazepan-2-ylmethoxy)-phenyl]-3-(5-methyl-pyrazin-2-yl)-urea, 1-[5-chloro-2-R-([1,4]oxazepan-2-ylmethoxy)-phenyl]-3-(5-methyl-pyrazin-2-yl)-urea, 1-[5-chloro-4-methyl-2-S-([1,4]-oxazepan-2-ylmethoxy)-phenyl]-3-(5-methyl-pyrazin-2-yl)-urea, 1-[5-bromo-2-([1,4]oxazepan-2-ylmethoxy)-phenyl]-3-(5-methyl-pyrazin-2-yl-)-urea, 1-[5-bromo-2-(4-methyl-[1,4]oxazepan-2-ylmethoxy)-phenyl]-3-(5-methyl-pyrazin-2-yl)-urea, 1-[2-(1,4-dimethyl-piperazin-2-ylmethoxy)-5-methyl-phenyl]-3-(5-methyl-pyrazin-2-yl)-urea, 1-[5-methyl-2-(1-methyl-piperazin-2-ylmethoxy)-phenyl]-3-(5-methyl-pyrazin-2-yl)-urea, 1-[5-chloro-2-(1-methyl-piperazin-2-ylmethoxy)-phenyl]-3-(5-methyl-pyrazin-2-yl)-urea, 1-[5-chloro-2-S-(1-methyl-piperazin-2-ylmethoxy)-phenyl]-3-(5-methyl-pyrazin-2-yl)-urea, 1-(5-cyano-pyrazin-2-yl)-3-[5-methyl-2-(4-methyl-morpholin-2-ylmethoxy)-phenyl]-urea, 1-[5-bromo-2-S-(4-methyl-morpholin-2-ylmethoxy)-phenyl]-3-(5-methyl-pyrazin-2-yl)-urea, 1-[5-chloro-2-S-(4-cyanomethyl-morpholin-2-ylmethoxy)-phenyl]-3-(5-methyl-pyrazin-2-yl)-urea, 1-[5-chloro-2-S-(4-methyl-morpholin-2-ylmethoxy)-phenyl]-3-(5-cyano-pyrazin-2-yl)-urea, 1-[5-chloro-2-(S-4-methyl-morpholin-2-ylmethoxy)-phenyl]-3-(5-methyl-pyrazin-2-yl)-urea, 1-[5-chloro-2-(R-morpholin-3-ylmethoxy)-phenyl]-3-(5-methyl-pyrazin-2-yl)-urea, 1-[4,5-dichloro-2-(S-morpholin-2-ylmethoxy)-phenyl]-3-(5-methyl-pyrazin-2-yl)-urea, 1-(5-cyano-pyrazin-2-yl)-3-[5-methyl-2-(morpholin-2-ylmethoxy)-phenyl]-urea, 1-[5-chloro-4-methyl-2-(S-morpholin-2-ylmethoxy)-phenyl]-3-(5-methyl-pyrazin-2-yl)-urea, 1-[5-chloro-4-methyl-2-(R-morpholin-2-ylmethoxy)-phenyl]-3-(5-methyl-pyrazin-2-yl)-urea, 1-[4,5-dichloro-2-(R-morpholin-2-ylmethoxy)-phenyl]-3-(5-methyl-pyrazin-2-yl)-urea, 1-[4,5-dimethyl-2-(morpholin-2-ylmethoxy)-phenyl]-3-(5-methyl-pyrazin-2-yl)-urea, 1-[4-chloro-5-methyl-2-(S-morpholin-2-ylmethoxy)-phenyl]-3-(5-methyl-pyrazin-2-yl)-urea, 1-[5-cyano-2-(S-morpholin-2-ylmethoxy)-phenyl]-3-(5-methyl-pyrazin-2-yl)-urea, 1-[5-chloro-4-ethyl-2-(S-morpholin-2-ylmethoxy)-phenyl]-3-(5-methyl-pyrazin-2-yl)-urea, 1-[5-chloro-4-methoxy-2-(S-morpholin-2-ylmethoxy)-phenyl]-3-(5-methyl-pyrazin-2-yl)-urea, 1-[5-dimethylamino-2-(S-morpholin-2-ylmethoxy)-phenyl]-3-(5-methyl-pyrazin-2-yl)-urea, 1-[5-methyl-2-(morpholin-2-ylmethoxy)-phenyl]-3-(5-methyl-pyrazin-2-yl)-urea, 1-[5-chloro-2-(morpholin-2-ylmethoxy)-phenyl]-3-(5-methyl-pyrazin-2-yl)-urea, 1-[5-chloro-2-(S-morpholin-2-ylmethoxy)-phenyl]-3-(5-methyl-pyrazin-2-yl)-urea, 1-[5-methyl-2-(S-morpholin-2-ylmethoxy)-phenyl]-3-(5-methyl-pyrazin-2-yl)-urea, 1-[5-chloro-2-(R-morpholin-2-ylmethoxy)-phenyl]-3-(5-methyl-pyrazin-2-yl)-urea, 1-[5-bromo-2-(S-morpholin-2-ylmethoxy)-phenyl]-3-(5-methyl-pyrazin-2-yl)-urea, 1-[5-bromo-2-R—(R-morpholin-2-ylmethoxy)-phenyl]-3-(5-methyl-pyrazin-2-yl)-urea, 1-(5-methyl-pyrazin-2-yl)-3-[3-S-(morpholin-2-ylmethoxy)-5,6,7,8-tetrahydro-naphthalen-2-yl]-urea, 1-[5-chloro-2-S-(morpholin-3-ylmethoxy)-phenyl]-3-(5-methyl-pyrazin-2-yl)-urea, 1-[5-methyl-2-R-(morpholin-3-ylmethoxy)-phenyl]-3-(5-methyl-pyrazin-2-yl)-urea, 1-[5-chloro-2-S-(morpholin-2-ylmethoxy)-phenyl]-3-(5-trifluoromethyl-pyrazin-2-yl)-urea, 1-[4-chloro-5-methyl-2-S-(morpholin-2-ylmethoxy)-phenyl]-3-(5-cyano-pyrazin-2-yl)-urea, 1-[5-chloro-4-methoxy-2-(S-morpholin-2-ylmethoxy)-phenyl]-3-(5-cyano-pyrazin-2-yl)-urea, 1-[5-chloro-2-S-(morpholin-2-ylmethoxy)-phenyl]-3-(5-cyano-pyrazin-2-yl)-urea, 1-[5-chloro-2-(thiomorpholin-2-ylmethoxy)-phenyl]-3-(5-methyl-pyrazin-2-yl)-urea); United States Patent Application Publication No. 2009/0131470 by Walmsley et al.; United States Patent Application Publication No. 2007/0179161 by Parratt et al.; United States Patent Application Publication No. 2005/0256157 by Gesner et al.; United States Patent Application Publication No. 2005/0245525 by Keegan et al. (including N-(2-dimethylamino-1-phenylethyl)-3-methoxy-4-[3-(5-methyl-pyrazin-2-yl)-ureido]-benzamine; N-(1-aza-bicyclo[2.2.2]oct-3-yl)-3-methoxy-4-[3-(5-methyl-pyrazin-2-yl)-ureido]-benzamide; N-(3-R-1-cyclohexylmethyl-pyrrolidin-3-yl)-3-methoxy-4-[3-(5-methyl-pyrazin-2-yl)ureido]-benzamide; 1-[2-(2-dimethylamino-ethoxy)-5-methyl-phenyl]-3-pyrazin-2-yl-urea; 1-[2-(3-dimethylamino-propoxy)-5-methyl-phenyl]-3-(5-methyl-pyrazin-2-yl)-urea; 1-(5-methyl-pyrazin-2-yl)-3-[5-methyl-2-(pyridin-3-ylmethoxy)-phenyl]-urea; 1-[2-(2-dimethylamino-1-dimethylaminomethyl-ethoxy)-5-methyl-phenyl]-3-(5-methyl-pyrazin-2-yl)-urea; 1-[5-methyl-2-(2-S-1-methyl-pyrrolidin-2-ylmethoxy)-phenyl]-3-(5-methyl-pyrazin-2-yl)-urea; 1-{5-methyl-2-[2-(1-methyl-pyrrolidin-2-yl)-ethoxy]-phenyl}-3-(5-methyl-pyrazin-2-yl)-urea; 1-{5-methyl-2-(1-methyl-piperidin-4-yloxy)-phenyl]-3-(5-methyl-pyrazin-2-yl)-urea; 1-[5-methyl-2-(3-(S)-1-methyl-piperidin-3-ylmethoxy)-phenyl]-3-(5-methyl-pyrazin-2-yl)-urea; 1-[5-methyl-2-(3-(R)-1-methyl-piperidin-3-ylmethoxy)-phenyl]-3-(5-methyl-pyrazin-2-yl)-urea; 1-[5-methyl-2-(1-methyl-piperidin-2-ylmethoxy)-phenyl]-3-(5-methyl-pyrazi-n-2-yl)-urea; 1-[5-methyl-2-(1-methyl-piperidin-3- yloxy)-phenyl]-3-(5-methyl-pyrazin-2-yl)-urea; 1-[5-methyl-2-(1-methyl-piperidin-3-ylmethoxy)-phenyl]-3-quinoxalin-2-yl-urea; 1-[5-methyl-2-(piperidin-3-ylmethoxy)-phenyl]-3-(5-methyl-pyrazin-2-yl)-urea; 1-[5-fluoro-2-(1-methyl-piperidin-3-ylmethoxy)-phenyl]-3-(5-methyl-pyrazin-2-yl)-urea; 1-[5-fluoro-2-(1-methyl-piperidin-4-yloxy)-phenyl]-3-(5-methyl-piperidin-2-yl)-urea; 1-[4-fluoro-2-(1-methyl-piperidin-4-yloxy)-phenyl]-3-(5-methyl-pyrazin-2-yl)-urea; 1-(2-methoxy-4-methylaminomethyl-phenyl)-3-(5-methyl-pyrazin-2-yl)-urea; 1-(4-{[(furan-3-ylmethyl)-amino]-methyl}-2-methoxy-phenyl)-3(5-methyl-pyrazin-2-yl)-urea; and 1-{2-methoxy-4-[(4-methoxy-benzylamino)-methyl]-phenyl}-3-(5-methyl-pyrazin-2-yl)-urea); United States Patent Application Publication No. 2005/0148643 by Rui et al.; and United States Patent Application Publication No. 2005/0043381 by Johnson et al., all of which are incorporated herein by this reference.

The kinase mammalian target of rapamycin (mTOR) is a serine-threonine kinase related to the lipid kinases of the PI3K family. The mTOR molecule has been implicated in a wide range of biological processes including cell growth, cell proliferation, cell motility and survival. Dysregulation of the mTOR pathway has been reported in various types of cancer. The kinase mTOR is a multifunctional kinase that integrates growth factor and nutrient signals to regulate protein translation, nutrient uptake, autophagy, and mitochondrial function. mTOR exists in two complexes, mTORC1 and mTORC2. mTORC1 contains the raptor subunit and mTORC2 contains rictor. These complexes are differentially regulated, and have distinct substrate specificities and rapamycin sensitivity. For example, mTORC1 phosphorylates S6 kinase (S6K) and 4EBP1, promoting increased translation and ribosome biogenesis to facilitate cell growth and cell cycle progression. S6K also acts in a feedback pathway to attenuate PI3K/Akt activation. mTORC2 is generally insensitive to rapamycin. mTORC2 is thought to modulate growth factor signaling by phosphorylating the C-terminal hydrophobic motif of some AGC kinases such as Akt. In many cellular contexts, mTORC2 is required for phosphorylation of the S473 site of Akt.

Inhibitors of mTOR include, but are not limited to: sirolimus: temsirolimus, everolimus; rapamune; ridaforolimus; AP23573 (deforolimus); CCI-779 (rapamycin 42-ester with 3-hydroxy-2-(hydroxymethyl)-2-methylpropionic acid); AZD8055 ((5-(2,4-bis((S)-3-methylmorpholino)pyrido[2,3-d]pyrimidin-7-yl)-2-methoxyphenyl)methanol); PKI-587 (1-(4-(4-(dimethylamino)piperidine-1-carbonyl)phenyl)-3-(4-(4,6-dimorpholino-1,3,5-triazin-2-yl)phenyl)urea); NVP-BEZ235 (2-methyl-2-{4-[3-methyl-2-oxo-8-(quinolin-3-yl)-2,3-dihydro-1H-imidazo[4,5-c]quinolin-1-yl]phenyl}propanenitrile); LY294002 ((2-(4-morpholinyl)-8-phenyl-4H-1-benzopyran-4-one); 40-O-(2-hydroxyethyl)-rapamycin; ABT578 (zotarolimus); biolimus-7; biolimus-9; AP23675; AP23841; TAFA-93; 42-O-(methyl-D-glucosylcarbonyl)rapamycin; 42-O-[2-(methyl-D-glucosylcarbonyloxy)ethyl]rapamycin; 31-O-(methyl-D-glucosylcarbonyl)rapamycin; 42-O-(2-hydroxyethyl)-31-O-(methyl-D-glucosylcarbonyl)rapamycin; 42-O-(2-O-methyl-D-fructosylcarbonyl)rapamycin; 42-O-[2-(2-O-methyl-D-fructosylcarbonyloxy)ethyl]rapamycin; 42-O-(2-O-methyl-L-fructosylcarbonyl)rapamycin; 42-O-[2-(2-O-methyl-L-fructosylcarbonyloxy)ethyl]rapamycin; 31-O-(2-O-methyl-D-fructosylcarbonyl)rapamycin; 42-O-(2-hydroxyethyl)-31-O-(2-O-methyl-D-fructosylcarbonyl)rapamycin; 31-O-(2-O-methyl-L-fructosylcarbonyl)rapamycin; 42-O-(2-hydroxyethyl)-31-O-(2-O-methyl-L-fructosylcarbonyl)rapamycin; 42-O-(D-allosylcarbonyl)rapamycin; 42-O-[2-(D-allosylcarbonyloxy)ethyl]rapamycin; 42-O-(L-allosylcarbonyl)rapamycin; 42-O-[2-(L-allosylcarbonyloxy)ethyl]rapamycin; 31-O-(D-allosylcarbonyl)rapamycin; 42-O-(2-hydroxyethyl)-31-O-(D-allosylcarbonyl)rapamycin; 31-O-(L-allosylcarbonyl)rapamycin; 42-O-(2-hydroxyethyl)-31-O-(L-allosylcarbonyl)rapamycin; 42-O-(D-fructosylcarbonyl)rapamycin; 42-O-[2-(D-fructosylcarbonyloxy)ethyl]rapamycin; 42-O-(L-fructosylcarbonyl)rapamycin; 42-O-[2-(L-fructosylcarbonyloxy)ethyl]rapamycin; 31-O-(D-fructosylcarbonyl)rapamycin; 42-O-(2-hydroxyethyl)-31-O-(D-fructosylcarbonyl)rapamycin; 31-O-(L-fructosylcarbonyl)rapamycin; 42-O-(2-hydroxyethyl)-31-O-(L-fructosylcarbonyl)rapamycin; 42-O-(D-fucitolylcarbonyl)rapamycin; 42-O-[2-(D-fucitolylcarbonyloxy)ethyl]rapamycin; 42-O-(L-fucitolylcarbonyl)rapamycin; 42-O-[2-(L-fucitolylcarbonyloxy)ethyl]rapamycin; 31-O-(D-fucitolylcarbonyl)rapamycin; 42-O-(2-hydroxyethyl)-31-O-(D-fucitolylcarbonyl)rapamycin; 31-O-(L-fucitolylcarbonyl)rapamycin; 42-O-(2-hydroxyethyl)-31-O-(L-fucitolylcarbonyl)rapamycin; 42-O-(D-glucalylcarbonyl)rapamycin; 42-O-[2-(D-glucalylcarbonyloxy)ethyl]rapamycin; 42-O-(D-glucosylcarbonyl)rapamycin; 42-O-[2-(D-glucosylcarbonyloxy)ethyl]rapamycin; 42-O-(L-glucosylcarbonyl)rapamycin; 42-O-[2-(L-glucosylcarbonyloxy)ethyl]rapamycin; 31-O-(D-glucalylcarbonyl)rapamycin; 42-O-(2-hydroxyethyl)-31-O-(D-glucalylcarbonyl)rapamycin; 31-O-(D-glucosylcarbonyl)rapamycin; 42-O-(2-hydroxyethyl)-31-O-(D-glucosylcarbonyl)rapamycin; 31-O-(L-glucosylcarbonyl)rapamycin; 42-O-(2-hydroxyethyl)-31-O-(L-glucosylcarbonyl)rapamycin; 42-O-(L-sorbosylcarbonyl)rapamycin; 42-O-(D-sorbosylcarbonyl)rapamycin; 31-O-(L-sorbosylcarbonyl)rapamycin; 31-O-(D-sorbosylcarbonyl)rapamycin; 42-O-[2-(L-sorbosylcarbonyloxy)ethyl]rapamycin; 42-O-[2-(D-sorbosylcarbonyloxy)ethyl]rapamycin; 42-O-(2-hydroxyethyl)-31-O-(D-sorbosylcarbonyl)rapamycin; 42-O-(2-hydroxyethyl)-31-O-(L-sorbosylcarbonyl)rapamycin; 42-O-(D-lactalylcarbonyl)rapamycin; 42-O-[2-(D-lactalylcarbonyloxy)ethyl]rapamycin; 31-O-(D-lactalylcarbonyl)rapamycin; 42-O-(2-hydroxyethyl)-31-O-(D-lactalylcarbonyl)rapamycin; 42-O-(D-sucrosylcarbonyl)rapamycin; 42-O-[2-(D-sucrosylcarbonyloxy)ethyl]rapamycin; 31-O-(D-sucrosylcarbonyl)rapamycin; 42-O-(2-hydroxyethyl)-31-O-(D-sucrosylcarbonyl)rapamycin; 42-O-(D-gentobiosylcarbonyl)rapamycin 42-O-[2-(D-gentobiosylcarbonyloxy)ethyl]rapamycin; 31-O-(D-gentobiosylcarbonyl)rapamycin 42-O-(2-hydroxyethyl)-31-O-(D-gentobiosylcarbonyl)rapamycin 42-O-(D-cellobiosylcarbonyl)rapamycin; 42-O-[2-(D-cellobiosylcarbonyloxy)ethyl]rapamycin; 31-O-(D-cellobiosylcarbonyl)rapamycin; 42-O-(2-hydroxyethyl)-31-O-(D-cellobiosylcarbonyl)rapamycin; 42-O-(D-turanosylcarbonyl)rapamycin; 42-O-[2-(D-turanosylcarbonyloxy)ethyl]rapamycin; 31-O-(D-turanosylcarbonyl)rapamycin; 42-O-(2-hydroxyethyl)-31-O-(D-turanosylcarbonyl)rapamycin; 42-O-(D-palatinosylcarbonyl)rapamycin; 42-O-[2-(D-palatinosylcarbonyloxy)ethyl]rapamycin; 31-O-(D-palatinosylcarbonyl)rapamycin; 42-O-(2-hydroxyethyl)-31-O-(D-palatinosylcarbonyl)rapamycin; 42-O-(D-isomaltosylcarbonyl)rapamycin; 42-O-[2-(D-isomaltosylcarbonyloxy)ethyl]rapamycin; 31-O-(D-isomaltosylcarbonyl)rapamycin; 42-O-(2-hydroxyethyl)-31-O-(D-isomaltosylcarbonyl)rapamycin; 42-O-(D-maltulosylcarbonyl)rapamycin; 42-O-[2-(D-maltulosylcarbonyloxy)ethyl]rapamycin; 42-O-(D-maltosylcarbonyl)rapamycin; 42-O-[2-(D-maltosylcarbonyloxy)ethyl]rapamycin; 31-O-(D-maltosylcarbonyl)rapamycin; 42-O-(2-hydroxyethyl)-31-O-(D-maltulosylcarbonyl)rapamycin; 31-O-(D-maltosylcarbonyl)rapamycin; 42-O-(2-hydroxyethyl)-31-O-(D-maltosylcarbonyl)rapamycin;

42-O-(D-lactosylcarbonyl)rapamycin; 42-O-[2-(D-lactosylcarbonyloxy)ethyl]rapamycin; 31-O-(methyl-D-lactosylcarbonyl)rapamycin; 42-O-(2-hydroxyethyl)-31-O-(methyl-D-lactosylcarbonyl)rapamycin; 42-O-(D-melibiosylcarbonyl)rapamycin; 31-O-(D-melibiosylcarbonyl)rapamycin; 42-O-(2-hydroxyethyl)-31-O-(D-melibiosylcarbonyl)rapamycin; 42-O-(D-leucrosylcarbonyl)rapamycin; 42-O-[2-(D-leucrosylcarbonyloxy)ethyl]rapamycin; 31-O-(D-leucrosylcarbonyl)rapamycin; 42-O-(2-hydroxyethyl)-31-O-(D-leucrosylcarbonyl)rapamycin; 42-O-(D-raffi nosylcarbonyl)rapamycin; 42-O-[2-(D-raffinosylcarbonyloxy)ethyl]rapamycin; 31-O-(D-raffinosylcarbonyl)rapamycin; 42-O-(2-hydroxyethyl)-31-O-(D-raffinosylcarbonyl)rapamycin; 42-O-(D-isomaltotriosylcarbonyl)rapamycin; 42-O-[2-(D-isomaltosylcarbonyloxy)ethyl]rapamycin; 31-O-(D-isomaltotriosylcarbonyl)rapamycin; 42-O-(2-hydroxyethyl)-31-O-(D-isomaltotriosylcarbonyl)rapamycin; 42-O-(D-cellotetraosylcarbonyl)rapamycin; 42-O-[2-(D-cellotetraosylcarbonyloxy)ethyl]rapamycin; 31-O-(D-cellotetraosylcarbonyl)rapamycin; 42-O-(2-hydroxyethyl)-31-O-(D-cellotetraosylcarbonyl)rapamycin; 42-O-(valiolylcarbonyl)rapamycin; 42-O-[2-(D-valiolylcarbonyloxy)ethyl]rapamycin; 31-O-(valiolylcarbonyl)rapamycin; 42-O-(2-hydroxyethyl)-31-O-(valiolylcarbonyl)rapamycin; 42-O-(valiolonylcarbonyl)rapamycin; 42-O-[2-(D-valiolonylcarbonyloxy)ethyl] rapamycin; 31-O-(valiolonylcarbonyl)rapamycin; 42-O-(2-hydroxyethyl)-31-O-(valiolonylcarbonyl)rapamycin; 42-O-(valienolylcarbonyl)rapamycin 42-O-[2-(D-valienolylcarbonyloxy)ethyl]rapamycin; 31-O-(valienolylcarbonyl)rapamycin; 42-O-(2-hydroxyethyl)-31-O-(valienolylcarbonyl)rapamycin; 42-O-(valienoneylcarbonyl)rapamycin; 42-O-[2-(D-valienoneylcarbonyloxy)ethyl]rapamycin; 31-O-(valienoneylcarbonyl)rapamycin; 42-O-(2-hydroxyethyl)-31-O-(valienoneylcarbonyl)rapamycin; PI-103 (3-[4-(4-morpholinyl)pyrido[3',2':4,5]furo[3,2-d]pyrimidin-2-yl]-phenol); KU-0063794 ((5-(2-((2R,6S)-2,6-dimethylmorpholino)-4-morpholinopyrido[2,3-d]pyrimidin-7-yl)-2-methoxyphenyl)methanol); PF-04691502 (2-amino-8-((1r,4r)-4-(2-hydroxyethoxy)cyclohexyl)-6-(6-methoxypyridin-3-yl)-4-methylpyrido[2,3-d]pyrimidin-7(8H)-one); CH132-799; RG7422 ((S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one); Palomid 529 (3-(4-methoxybenzyloxy)-8-(1-hydroxyethyl)-2-methoxy-6H-benzo[c]chromen-6-one); PP242 (2-(4-amino-1-isopropyl-1H-pyrazolo[3,4-d]pyrimidin-3-yl)-1H-indol-5-ol); XL765 (N-[4-[[[3-[(3,5-dimethoxyphenyl)amino]-2-quinoxalinyl] amino]sulfonyl]phenyl]-3-methoxy-4-methyl-benzamide); GSK1059615 ((Z)-5-((4-(pyridin-4-yl)quinolin-6-yl)methylene)thiazolidine-2,4-dione); PKI-587 (1-(4-(4-(dimethylamino)piperidine-1-carbonyl)phenyl)-3-(4-(4,6-dimorpholino-1,3,5-triazin-2-yl)phenyl)urea); WAY-600 (6-(1H-indol-5-yl)-4-morpholino-1-(1-(pyridin-3-ylmethyl)piperidin-4-yl)-1H-pyrazolo[3,4-d]pyrimidine); WYE-687 (methyl 4-(4-morpholino-1-(1-(pyridin-3-ylmethyl)piperidin-4-yl)-1H-pyrazolo[3,4-d]pyrimidin-6-yl)phenylcarbamate); WYE-125132 (N-[4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl]-N'-methyl-urea); and WYE-354.

Additional inhibitors of mTOR are described in the following United States patents and patent applications, all of which are incorporated herein by this reference: U.S. Pat. No. 8,461,157 to Cai et al.; U.S. Pat. No. 8,440,662 to Smith et al.; U.S. Pat. No. 8,436,012 to Ohtsuka et al.; U.S. Pat. No. 8,394,818 to Gray et al.; U.S. Pat. No. 8,362,241 to D'Angelo et al.; U.S. Pat. No. 8,314,111 to Chen et al.; U.S. Pat. No. 8,309,546 to Nakayama et al. (including 6-morpholinopurine derivatives); U.S. Pat. No. 8,268,819 to Jin et al.; U.S. Pat. No. 8,211,669 to Reed et al.; U.S. Pat. No. 8,163,755 Jin et al.; U.S. Pat. No. 8,129,371 Zask et al.; U.S. Pat. No. 8,097,622 to Nakayama et al.; U.S. Pat. No. 8,093,050 to Cho et al.; U.S. Pat. No. 8,008,318 to Beckmann et al.; U.S. Pat. No. 7,943,767 to Chen et al.; U.S. Pat. No. 7,923,555 to Chen et al.; U.S. Pat. No. 7,897,608 to Wilkinson et al.; U.S. Pat. No. 7,700,594 to Chen et al.; U.S. Pat. No. 7,659,274 to Crew et al.; U.S. Pat. No. 7,655,673 to Zhang et al. (39-desmethoxyrapamycin); U.S. Pat. No. 7,648,996 to Beckman et al.; U.S. Pat. No. 7,504,397 to Hummersone et al.; U.S. Pat. No. 7,169,817 to Pan et al.; U.S. Pat. No. 7,160,867 to Abel et al. (carbohydrate derivatives of rapamycin); U.S. Pat. No. 7,091,213 to Metcalf III et al. ("rapalogs"); United States Patent Application Publication No. 2013/0079303 by Andrews et al.; and United States Patent Application Publication No. 2013/0040973 by Vannuchi et al.

Akt, also known as Protein Kinase B, is a serine/threonine-specific protein kinase that plays a key role in many cellular processes such as glucose metabolism, apoptosis, cellular proliferation, transcription, and cell migration. It is associated with tumor cell survival, proliferation, and invasiveness. The activation of Akt is frequently observed in tumor cells. Akt comprises an N-terminal pleckstrin homology (PH) domain, a kinase domain and a C-terminal "tail" region. Three isoforms of human Akt kinase (Akt-1, -2 and -3) have been reported so far. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1). Lipid binding to the PH domain promotes translocation of Akt to the plasma membrane and facilitates phosphorylation by another PH-domain-containing protein kinases, PDK1 at Thr308, Thr309, and Thr305 for the Akt isoforms 1, 2 and 3, respectively. A second, as of yet unknown, kinase is required for the phosphorylation of Ser473, Ser474 or Ser472 in the C-terminal tails of Akt-1, -2 and -3 respectively, in order to yield a fully activated Akt enzyme. Once localized to the membrane, Akt mediates several functions within the cell including the metabolic effects of insulin, induction of differentiation and/or proliferation, protein synthesis, and stress responses.

Akt inhibitors include, but are not limited to: triciribine: RX-0201 (a 20-mer oligonucleotide); perifosine; PX-316 ((R)-2-methoxy-3-(octadecyloxy)propyl ((1R,2R,3S,4R,6R)-2,3,4,6-tetrahydroxycyclohexyl) hydrogen phosphate); API-1 (4-amino-5,8-dihydro-5-oxo-8-3-D-ribofuranosylpyrido[2,3-d]pyrimidine-6-carboxamide); SR13668 (diethyl 6-methoxy-5,7-dihydroindolo[2,3-b]carbazole-2,10-dicarboxylate); AZD5363 (4-amino-N-[(1S)-1-(4-chlorophenyl)-3-hydroxypropyl]-1-(7H-pyrrolo[2,3-d]pyrimidin-4-yl)-4-piperidinecarboxamide); miltefosine; miltefosine; GSK-690693 (4-(2-(4-amino-1,2,5-oxadiazol-3-yl)-1-ethyl-7-((S)-piperidin-3-ylmethoxy)-1H-imidazo[4,5-c]pyridin-4-yl)-2-methylbut-3-yn-2-ol); A-443654 ((2S)-1-(1H-indol-3-yl)-3-[5-(3-methyl-2H-indazol-5-yl)pyridin-3-yl] oxypropan-2-amine); and SR13668 (diethyl 6-methoxy-5,7-dihydroindolo[2,3-b]carbazole-2,10-dicarboxylate).

Additional inhibitors of Akt are described in the following United States patents and patent applications, all of which are incorporated herein by this reference: U.S. Pat. No. 8,450,305 to Winssinger et al.; U.S. Pat. No. 8,445,509 to Miyamoto et al. (N-[4-({2-[(cyclopropylcarbonyl)amino]imidazo[1,2-a]pyridin-6-yl}oxy)-3-fluorophenyl]-N'-phenylcyclopropane-1,1-dicarboxamide, N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide, N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide, and N-[5-({2-[(cyclopropylcarbonyl)amino]imidazo[1,2-a]pyridin-6-yl}oxy)pyridin-2-yl]-6-(4-fluorophenyl)-5-methylpyridine-2-carboxamide 1-oxide); U.S. Pat. No. 8,436,002 to Beight et al. ((R)-5-methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one; (R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one; and (R)-4-(4-(1-(2-(azetidin-1-yl)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one); U.S. Pat. No. 8,420,690 to Seefeld et al. (N-(2-amino-1-phenylethyl)-5-(1-methyl-1H-pyrazol-5-yl)-3-thiophenecarboxamide; N-[2-amino-1-(phenylmethyl)ethyl]-5-(1-methyl-1H-pyrazol-5-yl)-3-thiophenecarboxamide; N-((1S)-2-amino-1-{[2-(trifluoromethyl)phenyl]methyl}ethyl)-5-(1-methyl-1H-pyrazol-5-yl)-3-thiophenecarboxamide; N-{(1S)-2-amino-1-[(2-fluorophenyl)methyl]ethyl}-5-(1-methyl-1H-pyrazol-5-yl)-3-thiophenecarboxamide; N-{(1S)-2-amino-1-[(2-chlorophenyl)methyl]ethyl}-5-(1-methyl-1H-pyrazol-5-yl)-3-thiophenecarboxamide; N[1-(aminomethyl)-2-methyl-2-phenylpropyl]-5-(1-methyl-1H-pyrazol-5-yl)-3-thiophenecarboxamide; N[2-amino-1-(1-naphthalenyl)ethyl]-5-(1-methyl-1H-pyrazol-5-yl)-3-thiophenecarboxamide; N[2-amino-1-(phenylmethyl)ethyl]-2-(3-furanyl)-5-(1-methyl-1H-pyrazol-5-yl)-3-thiophenecarboxamide; N-((1S)-2-amino-1-{[2-(trifluoromethyl)phenyl]methyl}ethyl)-5-(1-methyl-1H-pyrazol-5-yl)-3-furancarboxamide; N-((1S)-2-amino-1-{[2-(trifluoromethyl)phenyl]methyl}ethyl)-1-methyl-5-(1-methyl-1H-pyrazol-5-yl)-1H-pyrrole-3-carboxamide; N-((1S)-2-amino-1-{[2-(trifluoromethyl)phenyl]methyl}ethyl)-2-chloro-1-methyl-5-(1-methyl-1H-pyrazol-5-yl)-1H-pyrrole-3-carboxamide; and N-((1S)-2-amino-1-{[2-(trifluoromethyl)phenyl]methyl}ethyl)-2-chloro-5-(4-chloro-1-methyl-1H-pyrazol-5-yl)-1-methyl-1H-pyrrole-3-carboxamide); U.S. Pat. No. 8,420,678 to Mahadevan et al.; U.S. Pat. No. 8,410,158 to Seefeld et al. (N-{(1S)-2-amino-1-[(3,4-difluorophenyl)methyl]ethyl}-5-chloro-4-(4-chloro-1-methyl-1H-pyrazol-5-yl)-2-furancarboxamide); U.S. Pat. No. 8,338,434 to Seefeld et al. (N-[2-amino-1-(phenylmethyl)ethyl]-4-(1-methyl-1H-pyrazol-5-yl)benzamide; N-[2-amino-1-(phenylmethyl)ethyl]-2-chloro-4-(1-methyl-1H-pyrazol-5-yl)benzamide; N-[2-amino-1-(phenylmethyl)ethyl]-3-chloro-4-(1-methyl-1H-pyrazol-5-yl)benzamide; N-[2-amino-1-(phenylmethyl)ethyl]-4-(1-methyl-1H-pyrazol-5-yl)-3-(trifluoromethyl)benzamide; N-((1S)-2-amino-1-{[2-(trifluoromethyl)phenyl]methyl}ethyl)-3-chloro-4-(1-methyl-1H-pyrazol-5-yl)benzamide; N-[2-amino-1-(phenylmethyl)ethyl]-3-methyl-4-(1-methyl-1H-pyrazol-5-yl)benzamide; N-((1S)-2-amino-1-{[2-(trifluoromethyl)phenyl]methyl}ethyl)-3-fluoro-4-(1-methyl-1H-pyrazol-5-yl)benzamide; N-((1S)-2-amino-1-{[2-(trifluoromethyl)phenyl]methyl}ethyl)-3-methyl-4-(1-methyl-1H-pyrazol-5-yl)benzamide; N-[2-amino-1-(phenylmethyl)ethyl]-3-hydroxy-4-(1-methyl-1H-pyrazol-5-yl)benzamide; N-[2-amino-1-(phenylmethyl)ethyl]-3-fluoro-4-(1-methyl-1H-pyrazol-5-yl)benzamide; N-((1S)-2-amino-1-{[2-(trifluoromethyl)phenyl]methyl}ethyl)-4-chloro-5-(1-methyl-1H-pyrazol-5-yl)-2-pyridinecarboxamide; N-[2-amino-1-(phenylmethyl)ethyl]-4-(4-chloro-1-methyl-1H-pyrazol-5-yl)-3-fluorobenzamide; N-[2-amino-1-(phenylmethyl)ethyl]-3-chloro-4-(4-chloro-1-methyl-1H-pyrazol-5-yl)benzamide; N-((1S)-2-amino-1-{[2-(trifluoromethyl)phenyl]methyl}ethyl)-3-fluoro-4-(4-chloro-1-methyl-1H-pyrazol-5-yl)benzamide; N-((1S)-2-amino-1-{[2-(trifluoromethyl)phenyl]methyl}ethyl)-3-chloro-4-(4-chloro-1-methyl-1H-pyrazol-5-yl)benzamide; N-[2-amino-1-(phenylmethyl)ethyl]-3-bromo-4-(1-methyl-1H-pyrazol-5-yl)benzamide; N-((1S)-2-amino-1-{[2-(trifluoromethyl)phenyl]methyl}ethyl)-3-bromo-4-(1-methyl-1H-pyrazol-5-yl)benzamide; 3-amino-N-[3-chloro-4-(1-methyl-1H-pyrazol-5-yl)phenyl]-2-phenylpropanamide; and 3-amino-N-[3-chloro-4-(1-methyl-1H-pyrazol-5-yl)phenyl]-2-(phenylmethyl)propanamide); U.S. Pat. No. 8,273,782 to Seefeld et al. (N-{(1S)-2-amino-1-[(3-fluorophenyl)methyl]ethyl}-5-chloro-4-(4-chloro-1-methyl-1H-pyrazol-5-yl)-2-thiophenecarboxamide); U.S. Pat. No. 8,263,357 to Reed; U.S. Pat. No. 8,242,147 to Dumas et al.; U.S. Pat. No. 8,183,249 to Cheng et al.; U.S. Pat. No. 8,124,630 to Riedl et al.; U.S. Pat. No. 8,114,870 to Xiao et al.; U.S. Pat. No. 8,101,623 to Luke et al. ((S)-4-amino-N-(1-(4-chlorophenyl)-3-hydroxypropyl)-1-(7H-pyrrolo[2,3-d]pyrimidin-4-yl)piperidine-4-carboxamide); U.S. Pat. No. 8,067,412 to Winssinger et al.; U.S. Pat. No. 7,998,977 to Joseph et al. (4-[5-(2-amino-ethanesulfonyl)-isoquinolin-7-yl]-phenol); U.S. Pat. No. 7,982,037 to Bebbington et al.; U.S. Pat. No. 7,951,820 to Bebbington et al.; U.S. Pat. No. 7,987,623 to Riedl et al. (N-(4-chloro-3-(trifluoromethyl)phenyl)-N'-(4-(2-(N-methylcarbamoyl)-4-pyridyloxy)phenyl)urea); U.S. Pat. No. 7,879,853 to Stadlwieser et al. (N-[4-(6-dibenzofuran-4-yl-pyrimidin-4-ylamino)-phenyl]-4-morpholin-4-yl-benzamide, N-[4-(6-dibenzofuran-4-yl-pyrimidin-4-ylamino)-phenyl]-4-dimethylamino-benzamide, N-[4-(6-dibenzofuran-4-yl-pyrimidin-4-ylamino)-phenyl]-4-(4-methyl-piperazin-1-ylmethyl)-benzamide, N-[4-(6-dibenzofuran-4-yl-pyrimidin-4-ylamino)-phenyl]-2-(4-dimethyl-amino-phenyl)-acetamide, N-[4-(6-dibenzofuran-4-yl-pyrimidin-4-ylamino)-phenyl]-2-dimethylamino-benzamide, N-[4-(6-dibenzofuran-4-yl-pyrimidin-4-ylamino)-phenyl]-3-pyrrolidin-1-ylbenzamide, N-[4-(6-dibenzofuran-4-yl-pyrimidin-4-ylamino)-phenyl]-benzamide, 4-tert-butyl-N-[4-(6-dibenzofuran-4-yl-pyrimidin-4-ylamino)-phenyl]-benzamide, 3,4-dichloro-N-[4-(6-dibenzofuran-4-yl-pyrimidin-4-ylamino)-phenyl]-benzamide, N-[4-(6-dibenzofuran-4-yl-pyrimidin-4-ylamino)-phenyl]-3-dimethylamino-benzamide, N-[4-(6-dibenzofuran-4-yl-pyrimidin-4-ylamino)-phenyl]-isonicotinamide, N-[4-(6-dibenzofuran-4-yl-pyrimidin-4-ylamino)-phenyl]-4-dimethylaminomethyl-benzamide, N-[4-(6-dibenzofuran-4-yl-pyrimidin-4-ylamino)-phenyl]-4-morpholin-4-ylmethyl-benzamide, N-[4-(6-dibenzofuran-4-yl-pyrimidin-4-ylamino)-phenyl]-4-(4-methylpiperazin-1-yl)-benzamide, N-[4-(6-dibenzofuran-4-yl-pyrimidin-4-ylamino)-phenyl]-6-morpholin-4-yl-nicotinamide, N-[4-(6-dibenzofuran-4-yl-pyrimidin-4-ylamino)-phenyl]-3-[3-methoxy-1-(2-methoxyethyl)-propyl]-benzamide, tert-butyl N-{4-[4-(6-dibenzofuran-4-yl-pyrimidin-4-ylamino)-phenylcarbamoyl]-benzyl}-carbamate, tert-butyl N-{2-[4-(6-dibenzofuran-4-yl-pyrimidin-4-ylamino)-phenylcarbamoyl-phenyl]-carbamate, tert-butyl N-{3-[4-(6-dibenzofuran-4-yl-pyrimidin-4-ylamino)-phenylcarbamoyl-phenyl}-carbamate, tert-butyl 3-{4-[4-(6-dibenzofuran-4-yl-pyrimidin-4-ylamino)-phenylcarbamoyl]-phenyl}-piperidin-1-carboxylate, tert-butyl N-(4-{[4-(6-dibenzofuran-4-yl-pyrimidin-4-ylamino)-phenylcarbamoyl]-methyl}-phenyl)-carbamate, tert-butyl N-{3-[4-(6-dibenzofuran-4-yl-pyrimidin-4-ylamino)-phenylcarbamoyl]-benzyl}-carbamate, tert-butyl N-(2-{4-[4-(6-dibenzofuran-4-yl-pyrimidin-4-ylamino)-phenylcarbamoyl]phenyl}-ethyl)-carbamate, tert-butyl N-{2-[4-(6-dibenzofuran-4-yl-pyrimidin-4-ylamino)-phenylcarbamoyl]-pyridin-4-ylmethyl}-carbamate, tert-butyl N-{4-[4-(6-dibenzofuran-4-yl-pyrimidin-4-ylamino)-phenylcarbamoyl]-benzyl}-methyl-carbamate, tert-butyl {5-[4-(6-dibenzofuran-4-yl-pyrimidin-4-ylamino)-phenylcarbamoyl]-pyridin-2-ylmethyl}-carbamate, tert-butyl {4-[4-(6-dibenzofuran-4-yl-pyrimidin-4-ylamino)-phenylcarbamoyl]-pyridin-2-ylmethyl}-carbamate, tert-butyl (4-{[4-(6-dibenzofuran-4-yl-pyrimidin-4-ylamino)-phenylcarbamoyl]-methyl}-benzyl)-carbamate, tert-butyl N-(1-{4-[4-(6-dibenzofuran-4-yl-pyrimidin-4-ylamino)-phenylcarbamoyl]-phenyl}-1-methyl-ethyl)-carbamate, tert-butyl N-(2-{3-[4-(6-dibenzofuran-4-yl-pyrimidin-4-ylamino)-phenylcarbamoyl]-phenyl}-ethyl)-carbamate, tert-butyl {4-[4-(6-dibenzofuran-4-yl-pyrimidin-4-ylamino)-phenylcarbamoyl]-phenyl}-(2-methoxyethyl)-carbamate, tert-butyl N-{4-[4-(6-dibenzofuran-4-yl-pyrimidin-4-ylamino)-phenylcarbamoyl]-3-fluorobenzyl}carbamate, tert-butyl {6-[4-(6-dibenzofuran-4-yl-pyrimidin-4-ylamino)-phenylcarbamoyl]-pyridin-2-ylmethyl}-carbamate, tert-butyl N-{5-[4-(6-dibenzofuran-4-yl-pyrimidin-4-ylamino)-phenylcarbamoyl]-pyridin-3-ylmethyl}-carbamate, 3-cyano-N-[4-(6-dibenzofuran-4-yl-pyrimidin-4-ylamino)-phenyl]-benzamide, 3-carbamimidoyl-N-[4-(6-dibenzofuran-4-yl-pyrimidin-4-ylamino)-phenyl]-benzamide, 4-cyano-N-[4-(6-dibenzofuran-4-yl-pyrimidin-4-ylamino)-phenyl]-benzamide, 4-carbamimidoyl-N-[4-(6-dibenzofuran-4-yl-pyrimidin-4-ylamino)-phenyl]-benzamide, 4-aminomethyl-N-[4-(6-dibenzofuran-4-yl-pyrimidin-4-ylamino)-phenyl]-benzamide, 2-amino-N-[4-(6-dibenzofuran-4-yl-pyrimidin-4-ylamino)-phenyl]-benzamide, 3-amino-N-[4-(6-dibenzofuran-4-yl-pyrimidin-4-ylamino)-phenyl]-benzamide, N-[4-(6-dibenzofuran-4-yl-pyrimidin-4-ylamino)-phenyl]-4-piperidin-3-yl-benzamide, 2-(4-amino-phenyl)-N-[4-(6-dibenzofuran-4-yl-pyrimidin-4-ylamino)-phenyl]-acetamide, 3-aminomethyl-N-[4-(6-dibenzofuran-4-yl-pyrimidin-4-ylamino)-phenyl]-benzamide, 4-(2-amino-ethyl)-N-[4-(6-dibenzofuran-4-yl-pyrimidin-4-ylamino)-phenyl]-benzamide, N-[4-(6-dibenzofuran-4-yl-pyrimidin-4-ylamino)-phenyl]-4-methylaminomethyl-benzamide, 6-aminomethyl-N-[4-(6-dibenzofuran-4-yl-pyrimidin-4-ylamino)-phenyl]-nicotinamide, 2-aminomethyl-N-[4-(6-dibenzofuran-4-yl-pyrimidin-4-ylamino)-phenyl]-isonicotinamide, 2-(4-aminomethyl-phenyl)-N-[4-(6-dibenzofuran-4-yl-pyrimidin-4-ylamino)-phenyl]-acetamide, 4-(1-amino-1-methyl-ethyl)-N-[4-(6-dibenzofuran-4-yl-pyrimidin-4-ylamino)-phenyl]-benzamide, 3-(2-amino-ethyl)-N-[4-(6-dibenzofuran-4-yl-pyrimidin-4-ylamino)-phenyl]-benzamide, N-[4-(6-dibenzofuran-4-yl-pyrimidin-4-ylamino)-phenyl]-4-(2-methoxyethylamino)benzamide, 4-aminomethyl-N-[4-(6-dibenzofuran-4-yl-pyrimidin-4-ylamino)-phenyl]-2-fluorobenzamide, 5-aminomethyl-N-[4-(6-dibenzofuran-4-yl-pyrimidin-4-ylamino)-phenyl]-nicotinamide, 3-amino-N-[4-(6-dibenzofuran-4-yl-pyrimidin-4-ylamino)-phenyl]-2-(3,4-dichloro-phenyl)-propionamide, 5-aminomethyl-pyridine-2-carboxylic acid [4-(6-dibenzofuran-4-yl-pyrimidin-4-ylamino)-phenyl]-amide, 1,2,3,4-tetrahydro-isoquinoline-6-carboxylic acid [4-(6-dibenzofuran-4-yl-pyrimidin-4-ylamino)-phenyl]-amide, tert-butyl {4-[3-(6-dibenzofuran-4-yl-pyrimidin-4-ylamino)-phenylcarbamoyl]-benzyl}-carbamate, tert-butyl N-(2-{4-[3-(6-dibenzofuran-4-yl-pyrimidin-4-ylamino)-phenylcarbamoyl]-phenyl}-ethyl)-carbamate, tert-butyl N-{2-[3-(6-dibenzofuran-4-yl-pyrimidin-4-ylamino)-phenylcarbamoyl]-phenyl}-carbamate, tert-butyl {3-[3-(6-dibenzofuran-4-yl-pyrimidin-4-ylamino)-phenylcarbamoyl]-phenyl}-carbamate, tert-butyl N-{3-[3-(6-dibenzofuran-4-yl-pyrimidin-4-ylamino)-phenylcarbamoyl]-benzyl}-carbamate, tert-butyl N-{4-[3-(6-dibenzofuran-4-yl-pyrimidin-4-ylamino)-phenylcarbamoyl]-phenyl}-carbamate, tert-butyl N-{4-[3-(6-dibenzofuran-4-yl-pyrimidin-4-ylamino)-4-methyl-phenylcarbamoyl]-benzyl}-carbamate, N-[3-(6-dibenzofuran-4-yl-pyrimidin-4-ylamino)-phenyl]-4-dimethylamino-benzamide, N-[3-(6-dibenzofuran-4-yl-pyrimidin-4-ylamino)-phenyl]-4-dimethylaminomethyl-benzamide, N-[3-(6-dibenzofuran-4-yl-pyrimidin-4-ylamino)-phenyl]-3-dimethylamino-benzamide, 4-aminomethyl-N-[3-(6-dibenzofuran-4-yl-pyrimidin-4-ylamino)-phenyl]-benzamide, 4-(2-amino-ethyl)-N-[3-(6-dibenzofuran-4-yl-pyrimidin-4-ylamino)-phenyl]-benzamide, 2-amino-N-[3-(6-dibenzofuran-4-yl-pyrimidin-4-ylamino)-phenyl]-benzamide, 3-amino-N-[3-(6-dibenzofuran-4-yl-pyrimidin-4-ylamino)-phenyl]-benzamide, 3-aminomethyl-N-[3-(6-dibenzofuran-4-yl-pyrimidin-4-ylamino)-phenyl]-benzamide, 4-amino-N-[3-(6-dibenzofuran-4-yl-pyrimidin-4-ylamino)-phenyl]-benzamide, 4-aminoethyl-N-[3-(6-dibenzofuran-4-yl-pyrimidin-4-ylamino)-4-methyl-phenyl]-benzamide, 3-amino-N-[3-(6-dibenzofuran-4-yl-pyrimidin-4-ylamino)-phenyl]-2-(3,4-dichlorophenyl)-propionamide); U.S. Pat. No. 7,807,705 to Chen et al.; U.S. Pat. No. 7,795,290 to Dickson, Jr. et al.; U.S. Pat. No. 7,745,446 to Maier et al.; U.S. Pat. No. 7,691,853 to Bebbington et al.; U.S. Pat. No. 7,652,135 to Binch et al.; U.S. Pat. No. 7,652,027 to Lee et al.; U.S. Pat. No. 7,625,913 to Bebbington et al.; U.S. Pat. No. 7,625,890 to Heerding et al. (4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol; 4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol; 4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol; and 4-[2-(4-amino-1,2,5-oxadiazol-3-yl)-1-ethyl-7-({[(2R)-6-methyl-2-morpholinyl]methyl}oxy)-1H-imidazo[4,5-c]pyridin-4-yl]-2-methyl-3-butyn-2-ol); U.S. Pat. No. 7,531,556 to Green; U.S. Pat. No. 7,449,477 to Barda et al.; U.S. Pat. No. 7,414,063 to Al-Awar et al.; U.S. Pat. No. 7,410,988 to Dickson, Jr. et al. (2-amidothiazole-based compounds); U.S. Pat. No. 7,390,815 to Davies et al. (pyrazole compounds); U.S. Pat. No. 7,354,919 to Hale et al. (isoxazole compounds); U.S. Pat. No. 7,345,054 to Hale et al.; U.S. Pat. No. 7,304,061 to Hale et al.; U.S. Pat. No. 7,253,187 to Cao et al.; U.S. Pat. No. 7,115,739 to Bebbington et al.; U.S. Pat. No. 7,098,330 to Bebbington et al. (pyrazolylamine-substituted quinazoline compounds); U.S. Pat. No. 7,087,603 to Bebbington et al. (pyrazole compounds); U.S. Pat. No. 7,041,687 to Binch et al. (indazole compounds); U.S. Pat. No. 7,008,948 to Bebbington et al. (fused pyrimidyl pyrazole compounds); U.S. Pat. No. 6,989,385 to Bebbington et al. (pyrazole compounds); U.S. Pat. No. 6,743,791 to Cao et al.; U.S. Pat. No. 6,696,452 to Bebbington et al. (pyrazole compounds); U.S. Pat. No. 6,664,247 to Bebbington et al. ((5-cyclopropyl-2H-pyrazol-3-yl)-[2-(naphthalen-2-ylsulfanyl)-6-phenylpyrimidin-4-yl]-amine; (5-cyclopropyl-2H-pyrazol-3-yl)-[2-(3-methoxycarbonyl-phenylsulfanyl)-6-phenylpyrimidin-4-yl]-amine; (5-cyclopropyl-2H-pyrazol-3-yl)-[2-(naphthalen-2-ylsulfan- yl)-pyrimidin-4-yl]-amine; (5-cyclopropyl-2H-pyrazol-3-yl)-[5,6-dimethyl-2-(naphthalen-2-ylsulfanyl)-pyrimidin-4-yl]-amine; (5-cyclopropyl-2H-pyrazol-3-yl)-[5-methyl-2-(naphthalen-2-ylsulfanyl)-pyrimidin-4-yl]-amine; (5-cyclopropyl-2H-pyrazol-3-yl)-[6-methyl-2-(naphthalen-2-ylsulfanyl)-pyrimidin-4-yl]-amine; (5-cyclopropyl-2H-pyrazol-3-yl)-[6-(morpholin-4-yl)-2-(naphthalen-2-ylsulfanyl)-pyrimidin-4-yl]-amine; (5-cyclopropyl-2H-pyrazol-3-yl)-[6-(1-methylpiperazin-4-yl)-2-(naphthalen-2-ylsulfanyl)-pyrimidin-4-yl]-amine; [6-(2,6-dimethylphenyl)-2-(naphthalen-2-ylsulfanyl)-pyrimidin-4-yl]-(5-methyl-2H-pyrazol-3-yl)-amine; [6-(2-methylphenyl)-2-(naphthalen-2-ylsulfanyl)-pyrimidin-4-yl]-(5-methyl-2H-pyrazol-3-yl)-amine; [2-(4-acetamido-phenylsulfanyl)-6-phenyl-pyrimidin-4-yl]-(5-methyl-2H-pyrazol-3-yl)-amine; (5-methyl-2H-pyrazol-3-yl)-[2-(naphthalen-2-ylsulfanyl)-6-phenyl-pyrimidin-4-yl]-amine; [2-(4-isobutyrylylamino-phenylsulfanyl)-6-phenylpyrimidin-4-yl]-(5-methyl-2H-pyrazol-3-yl)-amine; [6-(4-methylpiperazin-1-yl)-2-methylsulfanyl-pyrimidin-4-yl]-(5-methyl-2H-pyrazol-3-yl)-amine; (5-methyl-2H-pyrazol-3-yl)-[6-phenyl-2-(4-propionylamino-phenylsulfanyl)-pyrimidin-4-yl]-amine; [2-(4-cyclopropanecarbonylamino-phenylsulfanyl)-6-phenylpyrimidin-4-yl]-(5-methyl-2H-pyrazol-3-yl)-amine; (5-methyl-2H-pyrazol-3-yl)-{6-phenyl-2-[4-(propane-1-sulfonylamino)-phenylsulfanyl]-pyrimidin-4-yl}-amine; [2-(4-ethanesulfonylamino-phenylsulfanyl)-6-phenyl-pyrimidin-4-yl]-(5-methyl-2H-pyrazol-3-yl)-amine; [2-(4-acetamidophenyl-sulfanyl)-6-(2-methylphenyl)-pyrimidin-4-yl]-(5-methyl-2H-pyrazol-3-yl)-amine; [2-(4-isobutanecarbonylamino-phenyl-sulfanyl)-6-phenyl-pyrimidin-4-yl]-(5-methyl-2H-pyrazol-3-yl)-amine; [2-(4-acetamido-phenyl-sulfanyl)-5-methyl-6-phenyl-pyrimidin-4-yl]-(5-methyl-2H-pyrazol-3-yl)-amine; [2-(4-acetamido-phenyl-sulfanyl)-6-(4-methoxyphenyl)-pyrimidin-4-yl]-(5-methyl-2H-pyrazol-3-yl)-amine; [6-(3-acetamidophenyl)-2-(4-acetamido-phenyl-sulfanyl)-pyrimidin-4-yl]-(5-methyl-2H-pyrazol-3-yl)-amine; [2-(4-isopropanesulfonylamino-phenyl-sulfanyl)-6-phenyl-pyrimidin-4-yl]-(5-methyl-2H-pyrazol-3-yl)-amine; {2-[4-(2-dimethylamino-acetylamino)-phenylsulfanyl]-6-phenyl-pyrimidin-4-yl}-(5-methyl-2H-pyrazol-3-yl)-amine; [2-(3-chloro-benzylsulfanyl)-6-morpholin-4-yl-pyrimidin-4-yl]-(5-methyl-2H-pyrazol-3-yl)-amine; [2-(3-chloro-benzylsulfanyl)-6-(2-methoxy-ethylamino)-pyrimidin-4-yl]-(5-methyl-2H-pyrazol-3-yl)-amine; [2-benzylsulfanyl-6-(4-methylpiperazin-1-yl)-pyrimidin-4-yl]-(5-methyl-2H-pyrazol-3-yl)-amine; [2-benzylsulfanyl-6-morpholin-4-yl-pyrimidin-4-yl]-(5-methyl-2H-pyrazol-3-yl)-amine; [2-(3-chloro-benzylsulfanyl)-6-(4-methylpiperazin-1-yl)-pyrimidin-4-yl]-(5-methyl-2H-pyrazol-3-yl)-amine; [2-(4-methoxy-benzylsulfanyl)-6-(4-methylpiperazin-1-yl)-pyrimidin-4-yl]-(5-methyl-2H-pyrazol-3-yl)-amine; [2-(4-acetamido-phenyl-sulfanyl)-6-tert-butyl-pyrimidin-4-yl]-(5-methyl-2H-pyrazol-3-yl)-amine; (5-cyclopropyl-2H-pyrazol-3-yl)-[6-phenyl-2-(4-propionylamino-phenyl-sulfanyl)-pyrimidin-4-yl]-amine; [2-(3-chloro-benzylsulfanyl)-6-(piperidin-1-yl)-pyrimidin-4-yl]-(5-methyl-2H-pyrazol-3-yl)-amine; (5-methyl-2H-pyrazol-3-yl)-{2-[4-(morpholinesulfonyl)-benzylsulfanyl]-6-morpholin-4-yl-pyrimidin-4-yl}-amine; {6-(2-methoxy-ethylamino)-2-[4-(morpholinesulfonyl)-benzylsulfanyl]-pyrimidin-4-yl}-(5-methyl-2H-pyrazol-3-yl)-amine; {6-(4-methylpiperazin-1-yl)-2-[4-(morpholinesulfonyl)-benzylsulfanyl]-pyrimidin-4-yl}-(5-methyl-2H-pyrazol-3-yl)-amine; [6-methoxymethyl-2-(4-propionylamino-phenyl-sulfanyl)-pyrimidin-4-yl]-(5-methyl-2H-pyrazol-3-yl)-amine; [2-(4-methoxycarbonyl-phenyl-sulfanyl)-6-methoxymethyl-pyrimidin-4-yl]-(5-methyl-2H-pyrazol-3-yl)-amine; [2-(3,5-dimethoxy-benzylsulfanyl)-6-morpholin-4-yl-pyrimidin-4-yl]-(5-methyl-2H-pyrazol-3-yl)-amine; [2-(3,5-dimethoxy-benzylsulfanyl)-6-pyrrolidin-4-yl-pyrimidin-4-yl]-(5-methyl-2H-pyrazol-3-yl)-amine; (5-methyl-2H-pyrazol-3-yl)-[6-morpholin-4-yl-2-(naphthalene-2-yl-methylsulfanyl)-pyrimidin-4-yl]-amine; {2-(4-acetamido-phenyl-sulfanyl)-6-[4-(3-dimethylamino-propoxy)phenyl]-pyrimidin-4-yl}-(5-methyl-2H-pyrazol-3-yl)-amine; [2-(4-acetamidophenylsulfanyl)-6-(morpholin-4-yl)-pyrimidin-4-yl]-(5-methyl-2H-pyrazol-3-yl)-amine; [6-hydroxymethyl-2-(4-propionylamino-phenyl-sulfanyl)-pyrimidin-4-yl]-(5-methyl-2H-pyrazol-3-yl)-amine; [2-(4-acetamido-phenyl-sulfanyl)-pyrimidin-4-yl]-(5-methyl-2H-pyrazol-3-yl)-amine; [6-(1-butoxycarbonyl)-2-(4-propionylamino-phenyl-sulfanyl)pyrimidin-4-yl]-(5-methyl-2H-pyrazol-3-yl)-amine; and [6-methoxycarbonyl-2-(4-propionylamino-phenyl-sulfanyl)-pyrimidin-4-yl]-(5-methyl-2H-pyrazol-3-yl)-amine); U.S. Pat. No. 6,660,731 to Bebbington et al.; U.S. Pat. No. 6,653,301 to Bebbington et al. (pyrazole compounds); U.S. Pat. No. 6,649,640 to Hale et al. (isoxazole compounds); U.S. Pat. No. 6,638,926 to Davies et al. (pyrazole compounds); U.S. Pat. No. 6,613,716 to Knegtel et al. (pyrazole compounds); United States patent No. to U.S. Pat. No. 6,610,677 Davies et al. (pyrazole compounds); U.S. Pat. No. 6,495,582 to Hale et al. (isoxazole compounds, including 4-(4-{3-chloro-4-[(2-dimethylamino-acetylamino)-methyl]-phenyl}-isoxazol-5-yl)-1H-pyrrole-2-carboxylic acid [1-(3,5-dichloro-phenyl)-2-hydroxy-ethyl]-amide); United States Patent Application Publication No. 2013/0034598 by Cheng et al.; United States Patent Application Publication No. 2012/0329793 by Ashwell et al. (substituted imidazopyridinyl compounds); United States Patent Application Publication No. 2012/0329791 by Ashwell et al. (substituted imidazopyridinyl-aminopyridine compounds); United States Patent Application Publication No. 2012/0190707 by Ronai et al.; United States Patent Application Publication No. 2012/0149684 by Beight et al. ((R)-5-methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one; (R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one; and (R)-4-(4-(1-(2-(azetidin-1-yl)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one); United States Patent Application Publication No. 2012/0108574 by Ashwell et al.; United States Patent Application Publication No. 2012/0071657 by Bebbington et al.; United States Patent Application Publication No. 2011/0318393 by Ladouceur et al.; United States Patent Application Publication No. 2011/0228142 by Chen et al. (N-{(1S)-2-amino-1-[(3-fluorophenyl)methyl]ethyl}-5-chloro-4-(4-chloro-1-methyl-1H-pyrazol-5-yl)-2-thiophenecarboxamide); United States Patent Application Publication No. 2011/0196009 by Rouse et al. (3-amino-N-[5-chloro-4-(4-chloro-1-methyl-1H-pyrazol-5-yl)-2-thienyl]-2-phenylpropanamide; 3-amino-N-[5-chloro-4-(4-chloro-1-methyl-1H-pyrazol-5-yl)-2-thienyl]-2-(phenylmethyl)propanamide; (2S)-3-amino-N-[5-chloro-4-(4-chloro-1-methyl-1H-pyrazol-5-yl)-2-thienyl]-2-(phenylmethyl)propanamide; (2R)-3-amino-N-[5-chloro-4-(4-chloro-1-methyl-1H-pyrazol-5-yl)-2-thienyl]-2-(phenylmethyl)propanamide; 3-amino-N-[3,5-dichloro-4-(1-methyl-1H-pyrazol-5-yl)-2-thienyl]-2-phenylpropanamide; 3-amino-N-[3,5-dichloro-4-(1-methyl-1H-pyrazol-5-yl)-2-thienyl]-2-(phenylmethyl)propanamide; (2S)-3-amino-N-[5-chloro-4-(4-chloro-1-methyl-1H-pyrazol-5-yl)-2-thienyl]-2-[(3,4-difluorophenyl)methyl]propanamide; (2R)-3-amino-N-[5-chloro-4-(4-chloro-1-methyl-1H-pyrazol-5-yl)-2-thienyl]-2-[(3,4-difluorophenyl)methyl]propanamide; (2S)-3-amino-N-[5-chloro-4-(4-chloro-1-methyl-1H-pyrazol-5-yl)-2-thienyl]-2-[(2-fluorophenyl)methyl]propanamide; (2R)-3-amino-N-[5- chloro-4-(4-chloro-1-methyl-1H-pyrazol-5-yl)-2-thienyl]-2-[(2-fluorophenyl)methyl]propanamide; (2S)-3-amino-N-[5-chloro-4-(4-chloro-1-methyl-1H-pyrazol-5-yl)-2-thienyl]-2-[(4-fluorophenyl)methyl]propanamide; (2R)-3-amino-N-[5-chloro-4-(4-chloro-1-methyl-1H-pyrazol-5-yl)-2-thienyl]-2-[(4-fluorophenyl)methyl]propanamide; (2S)-3-amino-N-[5-chloro-4-(4-chloro-1-methyl-1H-pyrazol-5-yl)-2-thienyl]-2-[(3-fluorophenyl)methyl]propanamide; and (2R)-3-amino-N-[5-chloro-4-(4-chloro-1-methyl-1H-pyrazol-5-yl)-2-thienyl]-2-[(3-fluorophenyl)methyl]propanamide); United States Patent Application Publication No. 2011/0160256 by Rouse et al. (heteropyrrole compounds); United States Patent Application Publication No. 2011/0160255 by Rouse et al. (heteropyrrole compounds); United States Patent Application Publication No. 2011/0129455 by Lin et al. (pyrrole compounds); United States Patent Application Publication No. 2011/0098221 by Lin et al. (heteropyrrole compounds, including N-{(1S)-2-amino-1-[(3-fluorophenyl)methyl]ethyl}-5-(1-methyl-1H-pyrazol-5-yl)-1,3-thiazole-2-carboxamide and N-{(1S)-2-amino-1-[(3,4-difluorophenyl)methyl]ethyl}-4-chloro-5-(1-methyl-1H-pyrazol-5-yl)-1H-imidazole-2-carboxamide); United States Patent Application Publication No. 2011/092423 by Rouse et al. (heteropyrrole compounds, including N-{(1S)-2-amino-1-[(3-fluorophenyl)methyl]ethyl}-2-(1-methyl-1H-pyrazol-5-yl)-1,3-thiazole-5-carboxamide; N-{(1S)-2-amino-1-[(3-fluorophenyl)methyl]ethyl}-2-(4-chloro-1-methyl-1H-pyrazol-5-yl)-1,3-thiazole-5-carboxamide; N-{(1S)-2-amino-1-[(3-fluorophenyl)methyl]ethyl}-2-(1-methyl-1H-pyrazol-5-yl)-1,3-oxazole-5-carboxamide; and N-{(1S)-2-amino-1-[(3-fluorophenyl)methyl]ethyl}-2-(4-chloro-1-methyl-1H-pyrazol-5-yl)-1,3-oxazole-5-carboxamide); United States Patent Application Publication No. 2011/0071182 by Seefeld et al. (heterocyclic carboxamide compounds, including N-{(1S)-2-amino-1-[(3,4-difluorophenyl)methyl]ethyl}-5-chloro-4-(4-chloro-1-methyl-1H-pyrazol-5-yl)-2-furancarboxamide); United States Patent Application Publication No. 2011/0053972 by Seefeld et al. (heterocyclic carboxamide compounds, including N-(2-amino-1-phenylethyl)-5-(1-methyl-1H-pyrazol-5-yl)-3-thiophenecarboxamide; N-[2-amino-1-(phenylmethyl)ethyl]-5-(1-methyl-1H-pyrazol-5-yl)-3-thiophenecarboxamide; N-((1S)-2-amino-1-{[2-(trifluoromethyl)phenyl]methyl}ethyl)-5-(1-methyl-1H-pyrazol-5-yl)-3-thiophenecarboxamide; N-{(1S)-2-amino-1-[(2-fluorophenyl)methyl]ethyl}-5-(1-methyl-1H-pyrazol-5-yl)-3-thiophenecarboxamide; N-{(1S)-2-amino-1-[(2-chlorophenyl)methyl]ethyl}-5-(1-methyl-1H-pyrazol-5-yl)-3-thiophenecarboxamide; N-[1-(aminomethyl)-2-methyl-2-phenylpropyl]-5-(1-methyl-1H-pyrazol-5-yl)-3-thiophenecarboxamide; N-[2-amino-1-(1-naphthalenyl)ethyl]-5-(1-methyl-1H-pyrazol-5-yl)-3-thiophenecarboxamide; N-[2-amino-1-(phenylmethyl)ethyl]-2-(3-furanyl)-5-(1-methyl-1H-pyrazol-5-yl)-3-thiophenecarboxamide; N-((1S)-2-amino-1-{[2-(trifluoromethyl)phenyl]methyl}ethyl)-5-(1-methyl-1H-pyrazol-5-yl)-3-furancarboxamide; N-((1S)-2-amino-1-{[2-(trifluoromethyl)phenyl]methyl}ethyl)-1-methyl-5-(1-methyl-1H-pyrazol-5-yl)-1H-pyrrole-3-carboxamide; N-((1S)-2-amino-1-{[2-(trifluoromethyl)phenyl]methyl}ethyl)-2-chloro-1-methyl-5-(1-methyl-1H-pyrazol-5-yl)-1H-pyrrole-3-carboxamide; and N-((1S)-2-amino-1-{[2-(trifluoromethyl)phenyl]methyl}ethyl)-2-chloro-5-(4-chloro-1-methyl-1H-pyrazol-5-yl)-1-methyl-1H-pyrrole-3-carboxamide); United States Patent Application Publication No. 2010/0267759 by Seefeld et al. (heterocyclic carboxamide compounds); United States Patent Application Publication No. 2010/0137338 by Seefeld et al. (pyrazole compounds, including N-[2-amino-1-(phenylmethyl)ethyl]-5-(1-methyl-1H-pyrazol-5-yl)-2-pyridine-carboxamide; N-[2-amino-1-(phenylmethyl)ethyl]-6-(1-methyl-1H-pyrazol-5-yl)-3-pyridine-carboxamide; N-(2-amino-1-benzylethyl)-5-(1-methyl-1H-pyrazol-5-yl)pyrimidine-2-carboxamide; N-[2-amino-1-(phenylmethyl)ethyl]-4-(1-methyl-1H-pyrazol-5-yl)benzamide; N-[2-amino-1-(phenylmethyl)ethyl]-2-chloro-4-(1-methyl-1H-pyrazol-5-yl)benzamide; N-[2-amino-1-(phenylmethyl)ethyl]-3-chloro-4-(1-methyl-1H-pyrazol-5-yl)benzamide; N-[2-amino-1-(phenylmethyl)ethyl]-4-(1-methyl-1H-pyrazol-5-yl)-3-(trifluoromethyl)benzamide; N-((1S)-2-amino-1-{[2-(trifluoromethyl)phenyl]methyl}ethyl)-5-(1-methyl-1H-pyrazol-5-yl)-2-pyridinecarboxamide; N-((1S)-2-amino-1-{[2-(trifluoromethyl)phenyl]methyl}ethyl)-3-chloro-4-(1-methyl-1H-pyrazol-5-yl)benzamide; N-[2-amino-1-(phenylmethyl)ethyl]-4-chloro-5-(1-methyl-1H-pyrazol-5-yl)-2-pyridinecarboxamide; N-[2-amino-1-(phenylmethyl)ethyl]-6-chloro-5-(1-methyl-1H-pyrazol-5-yl)-2-pyridinecarboxamide; N-[2-amino-1-(phenylmethyl)ethyl]-3-methyl-4-(1-methyl-1H-pyrazol-5-yl)benzamide; N-((1S)-2-amino-1-{[2-(trifluoromethyl)phenyl]methyl}ethyl)-3-fluoro-4-(1-methyl-1H-pyrazol-5-yl)benzamide; N-((1S)-2-amino-1-{[2-(trifluoromethyl)phenyl]methyl}ethyl)-3-methyl-4-(1-methyl-1H-pyrazol-5-yl)benzamide; N-[2-amino-1-(phenylmethyl)ethyl]-3-hydroxy-4-(1-methyl-1H-pyrazol-5-yl)benzamide; N-[2-amino-1-(phenylmethyl)ethyl]-3-fluoro-4-(1-methyl-1H-pyrazol-5-yl)benzamide; N-((1S)-2-amino-1-{[2-(trifluoromethyl)phenyl]methyl}ethyl)-4-chloro-5-(1-methyl-1H-pyrazol-5-yl)-2-pyridinecarboxamide; N-[2-amino-1-(phenylmethyl)ethyl]-4-(4-chloro-1-methyl-1H-pyrazol-5-yl)-3-fluorobenzamide; N-[2-amino-1-(phenylmethyl)ethyl]-3-chloro-4-(4-chloro-1-methyl-1H-pyrazol-5-yl)benzamide; N-((1S)-2-amino-1-{[2-(trifluoromethyl)phenyl]methyl}ethyl)-3-fluoro-4-(4-chloro-1-methyl-1H-pyrazol-5-yl)benzamide; N-((1S)-2-amino-1-{[2-(trifluoromethyl)phenyl]methyl}ethyl)-3-chloro-4-(4-chloro-1-methyl-1H-pyrazol-5-yl)benzamide; N-[2-amino-1-(phenylmethyl)ethyl]-3-bromo-4-(1-methyl-1H-pyrazol-5-yl)benzamide; N-((1S)-2-amino-1-{[2-(trifluoromethyl)phenyl]methyl}ethyl)-3-bromo-4-(1-methyl-1H-pyrazol-5-yl)benzamide; 3-amino-N-[3-chloro-4-(1-methyl-1H-pyrazol-5-yl)phenyl]-2-phenylpropanamide; 3-amino-N-[3-chloro-4-(1-methyl-1H-pyrazol-5-yl)phenyl]-2-(phenylmethyl)propanamide; N-((1S)-2-amino-1-{[2-(trifluoromethyl)phenyl]methyl}ethyl)-4-(1-methyl-1H-1,2,4-triazol-5-yl)benzamide; N-[(1S)-2-amino-1-(phenylmethyl)ethyl]-4-(1-methyl-1H-1,2,4-triazol-5-yl)benzamide; N-{(1S)-2-amino-1-[(3-fluorophenyl)methyl]ethyl}-4-(1-methyl-1H-1,2,4-triazol-5-yl)benzamide; N-((1S)-2-amino-1-{[2-(trifluoromethyl)phenyl]methyl}ethyl)-3-chloro-4-(1-methyl-1H-1,2,4-triazol-5-yl)benzamide; N-{(1S)-2-amino-1-[(3-fluorophenyl)methyl]ethyl}-3-chloro-4-(1-methyl-1H-1,2,4-triazol-5-yl)benzamide; N-[(1S)-2-amino-1-(phenylmethyl)ethyl]-3-chloro-4-(1-methyl-1H-1,2,4-triazol-5-yl)benzamide; N-((1S)-2-amino-1-{[2-(trifluoromethyl)phenyl]methyl}ethyl)-4-(1-methyl-1H-1,2,3-triazol-5-yl)benzamide; N-((1S)-2-amino-1-{[2-(trifluoromethyl)phenyl]methyl}ethyl)-4-(4-chloro-1-methyl-1H-1,2,3-triazol-5-yl)benzamide; N-[(1S)-2-amino-1-(phenylmethyl)ethyl]-4-(4-chloro-1-methyl-1H-1,2,3-tria-zol-5-yl)benzamide; N-{(1S)-2-amino-1-[(3-fluorophenyl)methyl]ethyl}-4-(4-chloro-1-methyl-1H-1,2,3-triazol-5-yl)benzamide; N-[(1S)-2-amino-1-(phenylmethyl)ethyl]-4-(1-methyl-1H-1,2,3-triazol-5-yl)benzamide; and N-{(1S)-2-amino-1-[(3-fluorophenyl)methyl]ethyl}-4-(1-methyl-1H-1,2,3-triazol-5-yl)benzamide); United States Patent Application Publication No. 2010/0056523 by Heerding et al. (1H-imidazo[4,5-c]pyridin-2-yl compounds including 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol; 4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol; 4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol; and 4-[2-(4-amino-1,2,5-oxadiazol-3-yl)-1-ethyl-7-({[(2R)-6-methyl-2-morpholinyl]methyl}oxy)-1H-imidazo[4,5-c]pyridin-4-yl]-2-methyl-3-butyn-2-ol); PCT Patent Application Publication No. WO 2008/70016 by Kelly et al. (substituted naphthyridine compounds, including (8-[4-(1-aminocyclobutyl)phenyl]-9-phenyl[1,2,4]triazolo[3,4-f]-1,6-naphthyridin-3(2H)-one); and PCT Patent Application Publication No. WO 2007/58850 by Heerding et al. (1H-imidazo[4,5-c]pyridin-2-yl compounds).

The Notch signaling pathway has been identified as playing an important role in many diverse biological functions, including differentiation, and cellular proliferation. Mutations that increase Notch signaling have been associated with the development of leukemia and inhibitors of Notch are being studied for their potential use in the treatment of neurological diseases and cancer. The Notch pathway is activated by four different transmembrane receptor subtypes (designated as Notch-1-Notch-4) that rely upon regulated proteolysis. Expression patterns of Notch depend on cell type. Following ligand binding, the receptor undergoes sequential cleavage by metalloproteases of the ADAM family and the presenilin-dependent gamma-secretase. The final proteolytic cleavage step permits the intracellular domain of the Notch receptor to translocate to the cell nucleus where it interacts with transcription factors to induce target gene expression. In the cell nucleus, the Notch intracellular domain undergoes ubiquitilation. Proteolytic processing of the Notch precursor protein by furin-protease and its trafficking to the cell membrane also determine turnover and availability of receptors, and, in turn, activation of this signaling pathway. Altered glycosylation of the Notch extracellular domain by Fringe protein family members may also modify efficiency of ligand binding.

Notch inhibitors include, but are not limited to, semagacestat, 7-(S)—[N'(3,5-difluorophenylacetyl)-L-alaninyl]amino-5-methyl-5,7-dihydro-6H-dibenz[b,d]azepen-6-one (YO-01027), and (2R,3S)—N-[(3S)-1-methyl-2-oxo-5-phenyl-2,3-dihydro-1H-1,4-benzodiazepin-3-yl]-2,3-bis(3,3,3-trifluoropropyl)succinamide (BMS-906024).

Additional inhibitors of Notch are described in the following United States patents and patent applications, all of which are incorporated herein by this reference: U.S. Pat. No. 8,377,886 to Susztak et al.; U.S. Pat. No. 8,362,075 to Lewis et al.; U.S. Pat. No. 8,343,923 to Long et al. (DAPT (N—[N-(3,5-difluorophenacetyl-L-alanyl)]-S-phenylglycine tert-butyl ester), 1-(S)-endo-N-(1,3,3)-trimethylbicyclo [2.2.1]hept-2-yl)-4-fluorophenyl sulfonamide, WPE-III31C, S-3-[N'-(3,5-difluorophenyl-alpha-hydroxyacetyl)-L-alaninyl]amino-2,3-dihydro-1-methyl-5-phenyl-1H-1,4-benzodiazepin-2-one, (N)—[(S)-2-hydroxy-3-methyl-butyryl]-1-(L-alaninyl)-(S)-1-amino-3-methyl-4,5,6,7-tetrahydro-2H-3-benzazepin-2-one); U.S. Pat. No. 8,242,103 to Lewis et al.; U.S. Pat. No. 8,133,857 to Aikawa; U.S. Pat. No. 8,119,366 to Stylianou; U.S. Pat. No. 7,901,876 to Di Fiore et al.; U.S. Pat. No. 7,837,993 to Conboy et al.; U.S. Pat. No. 7,807,630 to Dang et al.; United States Patent Application Publication No. 2013/0064832 by Aikawa et al.; United States Patent Application Publication No. 2013/0039930 by Alitalo et al.; United States Patent Application Publication No. 2013/0029972 by Hipskind et al. (4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide); United States Patent Application Publication No. 2012/0328608 by Siebel (antagonist antibodies and anti-Notch3 NRR (negative regulatory region) antibodies); United States Patent Application Publication No. 2011/0223183 by Kitajewski et al. (fusion proteins as decoy inhibitors); United States Patent Application Publication No. 2011/0178046 by Ross et al. (gamma secretase inhibitors, including semagacestat ((2S)-2-Hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]butanamide, also known as LY450139; Eli Lilly and Co.), Compound E ([(2S)-2-{[(3,5-difluorophenyl)acetyl]amino}-N-[(3S)-1-methyl-2-oxo-5-phe-nyl-2,3-dihydro-1H-1,4-benzodiazepin-3-yl]propanamide], available from Alexis Biochemicals), LY411575 (Eli Lilly and Co.), L-685,458 (Sigma-Aldrich), BMS-289948 (4-chloro-N-(2,5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl)sulfonyl]-2,5-difluoroanilino}ethyl)-5-fluorophenyl]butanoic acid) (Bristol Myers Squibb), MK0752 (Merck), and MRK-003 (Merck); United States Patent Application Publication No. 2011/0059096 by Dang et al. (antibodies that bind to epitopes selected from the group consisting of CFNTLGGHS (SEQ ID NO: 14), CVCVNGWTGES (SEQ ID NO: 15), CATAV (SEQ ID NO: 16), CFHGAT (SEQ ID NO: 17), CVSNP (SEQ ID NO: 18) and CLNGGS (SEQ ID NO: 19)); United States Patent Application Publication No. 2010/0292165 by Clevers et al. (gamma secretase inhibitors including DAPT ((N—[N-(3,5-difluorophenylacetyl)-L-alanyl]-S-phenylglycine tert-butyl ester), dibenzazepine, and a benzodiazepine); United States Patent Application Publication No. 2010/0267801 by Lewis et al.; United States Patent Application Publication No. 2010/0222283 by Susztak et al. (gamma secretase inhibitors including gamma secretase inhibitor I, gamma secretase inhibitor II, gamma secretase inhibitor III, gamma secretase inhibitor IV, gamma secretase inhibitor V, gamma secretase inhibitor VI, gamma secretase inhibitor VII, gamma secretase inhibitor IX, gamma secretase inhibitor X, gamma secretase inhibitor XI, gamma secretase inhibitor XII, gamma secretase inhibitor XIII, gamma secretase inhibitor XIV, gamma secretase inhibitor XVI, gamma secretase inhibitor XVII, gamma secretase inhibitor XIX, gamma secretase inhibitor XX, gamma secretase inhibitor XXI, gamma40 secretase inhibitor I, gamma40 secretase inhibitor II, and isovaleryl-V-V-Sta-A-Sta-OCH$_3$); and PCT Patent Application Publication No. WO 2012/129353 by Quesnelle et al.

The 90 kDa heat shock proteins ("Hsp90") belong to a family of chaperones that regulate intracellular functions and are required for the refolding of denatured proteins following heat shock, as well as the conformational maturation of a large number of key proteins involved in cellular processes. The Hsp90 family of chaperones is comprised of four different isoforms. Hsp90-alpha and Hsp90-beta are found predominately in the cytosol, the 94-kDa glucose-regulated protein ("GRP94') is localized to the endoplasmic reticulum, and Hsp75/tumor necrosis factor receptor associated protein 1 ("TRAP-1") resides mainly in the mitochondrial matrix. These Hsp90s bind to client proteins in the presence of cochaperones, immunophilins, and partner proteins to make the multiprotein complex responsible for conformational maturation of newly formed nascent peptides into biologically active three-dimensional structures.

Hsp90 is an ATP-dependent protein with an ATP binding site in the N-terminal region of the active homodimer. Disruption of the ATPase activity of Hsp90 results in the destabilization of multiprotein complexes and subsequent ubiquitination of the client protein, which undergoes proteasome-mediated hydrolysis. More specifically, in an ATP-dependent fashion, Hsp70 binds to newly synthesized proteins cotranslationally and/or posttranslationally to stabilize the nascent peptide by preventing aggregation. Stabilization of the Hsp70/polypeptide binary complex is dependent upon the binding of Hsp70 interacting protein ("HIP"), which occurs after Hsp70 binds to the newly formed peptide. Hsp70-Hsp90 organizing protein ("HOP") contains highly conserved tetratricopeptide repeats ("TPRs") that are recognized by both Hsp70 and Hsp90, promoting the union of Hsp70/HIP and Hsp90, which results in a heteroprotein complex. In the case of telomerase and steroid hormone receptors, the client protein is transferred from the Hsp70 system to the Hsp90 homodimer with concomitant release of Hsp70, HIP, and HOP. Upon binding of ATP and an immunophilin with cis/trans peptidyl prolyl-isomerase activity (FKBP51, FKBP52, or CyPA), the ensemble folds the client protein into its three-dimensional structure. In a subsequent event, p23 binds Hsp90 near the N-terminal region promoting the hydrolysis of ATP and release of the folded protein, Hsp90 partner proteins, and ADP. Hsp90 (heat shock protein 90) is a chaperone protein that has a number of functions, including assisting proteins to fold properly, stabilizing proteins against heat stress, and aiding in protein degradation. It also has the effect of stabilizing a number of proteins required for tumor growth. Hsp90 has four structural domains: (i) a highly conserved amino-terminal domain of about 25 kDa; (ii) a charged linker region that connects the amino-terminal domain with the middle domain; (iii) a middle domain of about 40 kDa; and (iv) a carboxy-terminal domain of about 12 kDa. Hsp90 typically forms homodimers. Functionally, Hsp90 contains three domains, the ATP-binding, protein-binding, and dimerizing domains. Hsp90 also interacts with the glucocorticoid receptor (GR) and the functioning of GR in binding cortisol is dependent on Hsp90. Hsp90 also binds immunophilins and other steroid receptors. In cancer cells, Hsp90 stabilizes EGFR and signal transduction proteins such as PI3K and Akt; inhibition of Hsp90 can therefore trigger apoptosis through the inhibition of the PI3K/Akt pathway and various pathways of growth factor signaling. Hsp90 may also stabilize mutant proteins such as v-Src, the fusion oncogene Bcr/Abl, and mutant forms of p53 that appear during cell transformation. Hsp90 also is important for the functioning of vascular endothelial growth factor (VEGF) and nitric oxide synthase (NOS) in malignant cells; the activities of these proteins are required to promote angiogenesis in tumor cells. Hsp90 also promotes the spread of tumors by assisting matrix metalloproteinase MMP2. Another heat shock protein that acts as a chaperone is Hsp60. Hsp60 is implicated in mitochondrial protein import and macromolecular assembly. Under normal physiological conditions, Hsp60 is a 60-kilodalton oligomer comprised of monomers that form a complex arranged as two stacked heptameric rings. This double ring structure forms a large central cavity in which the unfolded protein binds via hydrophobic interactions. Hsp60 may also be found in the cytoplasm. Each subunit of Hsp60 has three domains: the apical domain, the equatorial domain, and the intermediate domain. Hsp60 also functions in the replication of mitochondrial DNA.

Hsp90 inhibitors include, but are not limited to, IPI-493 (17-amino-17-demethoxygeldanamycin); IPI-504 (retaspimycin hydrochloride); 17-demethoxy-17-(2-propylamino)-geldanamycin; AUY-922 (5-(2,4-dihydroxy-5-isopropylphenyl)-N-ethyl-4-(4-(morpholinomethyl)phenyl) isoxazole-3-carboxamide); elesclomol; ganetispib; alvespimycin (17-demethoxy-17-[[2-(dimethylamino)ethyl] amino]-geldanamycin hydrochloride); 5'-O-[(4-cyanophenyl)methyl]-8-[[(3,4-dichlorophenyl)methyl]amino]-adenosine; N1-[(3-endo)-8-[5-(cyclopropylcarbonyl)-2-pyridinyl]-8-azabicyclo[3.2.1]oct-3-yl]-2-methyl-5-[[(1R)-1-methylpropyl]amino]-1,4-benzenedicarboxamide; (2,4-dihydroxy-5-isopropylphenyl)(5-((4-methylpiperazin-1-yl) methyl)isoindolin-2-yl)methanone; 4-(6,6-dimethyl-4-oxo-3-(trifluoromethyl)-4,5,6,7-tetrahydroindazol-1-yl)-2-((1r, 4r)-4-hydroxycyclohexylamino)benzamide; (1r,4r)-4-(2-carbamoyl-5-(6,6-dimethyl-4-oxo-3-(trifluoromethyl)-4,5, 6,7-tetrahydroindazol-1-yl)phenylamino)cyclohexyl 2-aminoacetate; 2-amino-4-(2,4-dichloro-5-(2-(pyrrolidin-1-yl) ethoxy)phenyl)-N-ethylthieno[2,3-d]pyrimidine-6-carboxamide; 6-chloro-9-((4-methoxy-3,5-dimethylpyridin-2-yl) methyl)-9H-purin-2-amine; MPC-3100 ((S)-1-(4-(2-(6-amino-8-((6-bromobenzo[d][1,3]dioxol-5-yl)thio)-9H-purin-9-yl)ethyl)piperidin-1-yl)-2-hydroxypropan-1-one); CCT-018159 (4-[4-(2,3-dihydro-1,4-benzodioxin-6-yl)-5-methyl-1H-pyrazol-3-yl]-6-ethyl-1,3-benzenediol); CCT-129397 (3-(5-chloro-2,4-dihydroxyphenyl)-N-ethyl-4-(4-methoxyphenyl)-1H-pyrazole-5-carboxamide); PU-H71 (6-amino-8-[(6-iodo-1,3-benzodioxol-5-yl)thio]-N-(1-methylethyl)-9H-purine-9-propanamine); SNX-2112 (4-(6, 6-dimethyl-4-oxo-3-(trifluoromethyl)-4,5,6,7-tetrahydroindazol-1-yl)-2-((1r,4r)-4-hydroxycyclohexylamino)benzamide; STA-9090; AT-13387; XL-888; CU-0305; CNF-1010; macbecin I; macbecin II; 11-O-methyl derivatives of geldanamycin; 17-allylamino-17-demethoxygeldanamycin, 17-(dimethylaminoethylamino)-17-demethoxygeldanamycin; 17-[2-(pyrrolidin-1-yl)ethyl]amino-17-demethoxygeldanamycin; 17-(dimethylaminopropylamino)-17-demethoxygeldanamycin; KF58333 (E isomer); cyclopropardicicol; pochonin D; B-zearalenol; celastrol; gedunin; LAQ824; or FK228. Other inhibitors of Hsp90 are known, including: (i) agents that affect post-translational modification, such as acetylation or phosphorylation, of Hsp90; or (ii) recombinant antibodies such as efungumab.

Additional inhibitors of Hsp90 are described in the following United States patents and patent applications, all of which are incorporated herein by this reference: U.S. Pat. No. 8,399,426 to Kim et al.; U.S. Pat. No. 8,343,913 to Cowen et al. (geldanamycin, 17-allylamino-17-demethoxygeldanamycin (17-AAG), 17-(desmethoxy)-17-dimethylaminoethylamino-geldanamycin (17-DMAG), radicicol); U.S. Pat. No. 8,329,179 to Ni et al. (17-aminogeldanamycin); U.S. Pat. No. 8,158,638 to Ohsuki et al. (pyrazolopyrimidine derivatives); U.S. Pat. No. 7,129,244 to Kasibhatla et al.; U.S. Pat. No. 6,903,116 to Yokota et al. (benzo-1,3-dioxole); U.S. Pat. No. 6,887,993 to Tian et al. (11-O-methylgeldanamycin compounds); U.S. Pat. No. 6,875,863 to Tian et al.; U.S. Pat. No. 6,872,715 to Santi et al. (benzoquinone amsacrin analogs); U.S. Pat. No. 5,392,566 to Schnur et al. (geldanamycin derivatives); U.S. Pat. No. 5,387,584 to Schnur et al.; U.S. Pat. No. 4,261,989 to Sasaki et al. (geldanamycin derivatives); United States Patent Application Publication No. 2012/0245186 by Blackman et al. (3-(2,4-dihydroxyphenyl)-4-(1-ethyl-indol-4-yl)-5-mercapto-[1,2,4]triazole; 3-(2,4-dihydroxyphenyl)-4-(1-isopropyl-indol-4-yl)-5-mercapto-[1,2,4]triazole; 3-(2,4-dihydroxyphenyl)-4-(indol-4-yl)-5-mercapto-[1,2,4]triazole; 3-(2, 4-dihydroxyphenyl)-4-(1-methoxyethyl-indol-4-yl)-5-mercapto-[1,2,4]triazole; 3-(2,4-dihydroxy-5-ethyl-phenyl)-4-

(1-isopropyl-indol-4-yl)-5-mercapto-[1,2,4]triazole; 3-(2,4-dihydroxyphenyl)-4-(1-dimethylcarbamoyl-indol-4-yl)-5-mercapto-[1,2,4]triazole; 3-(2,4-dihydroxy-5-ethyl-phenyl)-4-(1-propyl-indol-4-yl)-5-mercapto-[1,2,4]triazole; 3-(2,4-dihydroxy-5-ethyl-phenyl)-4-(1,2,3-trimethyl-indol-5-yl)-5-mercapto-[1,2,4]triazole; 3-(2,4-dihydroxy-5-ethyl-phenyl)-4-(2,3-dimethyl-indol-5-yl)-5-mercapto-[1,2,4]triazole; 3-(2,4-dihydroxy-5-ethyl-phenyl)-4-(1-acetyl-2,3-dimethyl-indol-5-yl)-5-mercapto-[1,2,4]triazole; 3-(2,4-dihydroxy-5-ethyl-phenyl)-4-(1-isopropyl-7-methoxy-indol-4-yl)-5-mercapto-[1,2,4]triazole; 3-(2,4-dihydroxy-5-ethyl-phenyl)-4-(1-propyl-2,3-dimethyl-indol-5-yl)-5-mercapto-[1,2,4]triazole; 3-(2,4-dihydroxy-5-ethyl-phenyl)-4-(N-methyl-tetrahydrocarbozol-7-yl)-5-mercapto-[1,2,4]triazole; 3-(2,4-dihydroxy-5-ethyl-phenyl)-4-(N-methyl-cyclononan[a]indol-5-yl)-5-mercapto-[1,2,4]triazole; 3-(2,4-dihydroxy-5-ethyl-phenyl)-4-(1-n-butyl-indol-4-yl)-5-mercapto-[1,2,4]triazole; 3-(2,4-dihydroxy-5-ethyl-phenyl)-4-(1-n-pentyl-indol-4-yl)-5-mercapto-[1,2,4]triazole; 3-(2,4-dihydroxy-5-ethyl-phenyl)-4-(1-n-hexyl-indol-4-yl)-5-mercapto-[1,2,4]triazole; 3-(2,4-dihydroxy-5-cyclopropyl-phenyl)-4-(1-(1-methylcyclopropyl)-indol-4-yl)-5-mercapto-[1,2,4]triazole; 3-(2,4-dihydroxy-5-cyclopropyl-phenyl)-4-(1-isopropyl-7-methoxy-indol-4-yl)-5-mercapto-[1,2,4]triazole; 3-(2,4-dihydroxy-5-cyclopropyl-phenyl)-4-(1,2,3-trimethyl-indol-5-yl)-5-mercapto-[1,2,4]triazole; 3-(2,4-dihydroxy-5-ethyl-phenyl)-4-(1-isopropyl-7-methoxy-indol-4-yl)-5-mercapto-[1,2,4]triazole disodium salt; 3-(2,4-dihydroxy-5-tert-butyl-phenyl)-4-(1-isopropyl-7-methoxy-indol-4-yl)-5-mercapto-[1,2,4]triazole; 3-(2,4-dihydroxy-5-cyclopropyl-phenyl)-4-(1-propyl-7-methoxy-indol-4-yl)-5-mercapto-[1,2,4]triazole; 3-(2,4-dihydroxy-5-ethyl-phenyl)-4-(1-methyl-3-ethyl-indol-5-yl)-5-mercapto-[1,2,4]triazole; 3-(2,4-dihydroxy-5-ethyl-phenyl)-4-(1,3-dimethyl-indol-5-yl)-5-mercapto-[1,2,4]triazole; 3-(2,4-dihydroxy-5-isopropyl-phenyl)-4-(1-isopropyl-7-methoxy-indol-4-yl)-5-mercapto-[1,2,4]triazole; 3-(2,4-dihydroxy-5-ethyl-phenyl)-4-(1-methyl-3-isopropyl-indol-5-yl)-5-mercapto-[1,2,4]triazole, 3-(2,4-dihydroxy-5-ethyl-phenyl)-4-(N-ethyl-carbozol-7-yl)-5-mercapto-[1,2,4]triazole; 3-(2,4-dihydroxy-5-ethyl-phenyl)-4-(1-isopropyl-7-hydroxy-indol-4-yl)-5-mercapto-[1,2,4]triazole; 3-(2,4-dihydroxy-5-ethyl-phenyl)-4-(1-isopropyl-7-ethoxy-indol-4-yl)-5-mercapto-[1,2,4]triazole; 3-(2,4-dihydroxy-5-ethyl-phenyl)-4-(1,2-dimethyl-indol-5-yl)-5-mercapto-[1,2,4]triazole; 3-(2,4-dihydroxy-5-ethyl-phenyl)-4-(N-methyl-indol-5-yl)-5-mercapto-[1,2,4]triazole; 3-(2,4-dihydroxy-5-isopropyl-phenyl)-4-(1,3-dimethyl-indol-5-yl)-5-mercapto-[1,2,4]triazole; 3-(2,4-dihydroxy-5-cyclopropyl-phenyl)-4-(1,3-dimethyl-indol-5-yl)-5-mercapto-[1,2,4]triazole; 3-(2,4-dihydroxy-5-cyclopropyl-phenyl)-4-(1-methyl-indol-5-yl)-5-mercapto-[1,2,4]triazole; 3-(2,4-dihydroxy-5-isopropyl-phenyl)-4-(1H-indol-5-yl)-5-mercapto-[1,2,4]triazole; 3-(2,4-dihydroxy-5-ethyl-phenyl)-4-(1,2-dimethyl-indol-5-yl)-5-mercapto-[1,2,4]triazole; 3-(2,4-dihydroxy-5-isopropyl-phenyl)-4-(1-ethyl-indol-5-yl)-5-mercapto-[1,2,4]triazole; and 3-(2,4-dihydroxy-5-isopropyl-phenyl)-4-(1-propyl-indol-5-yl)-5-mercapto-[1,2,4]triazole); United States Patent Application Publication No. 2012/0022026 by Krawczyk et al. (17-allylamino-17-demethoxygeldanamycin hydroquinone hydrochloride, pochonin, radester, 8-arylsulfanyladenine derivatives, 3,4-diarylpyrazoleresorcinol derivatives, sheperdin and derivatives thereof, retaspimycin hydrochloride, (−) epigallocatechin-3-gallate, and 4,5-diarylisoxazole derivatives); United States Patent Application Publication No. 2011/0118298 by Fritz et al.; United States Patent Application Publication No. 2010/0093824 by Frydman et al.; United States Patent Application Publication No. 2010/0022635 by Rajewski (N-(7-((2R,3R,4S,5R)-3,4-dihydroxy-5-methoxy-6,6-dimethyl-tetrahydro-2H-pyran-2-yloxy)-2-oxo-2H-chromen-3-yl)acetamide; N-(7-((2R,3R,4S,5R)-3,4-dihydroxy-5-methoxy-6,6-dimethyltetrahydro-2H-pyran-2-yloxy)-8-methyl-2-oxo-2H-chromen-3-yl)acetamide; N-(7-((2R,3R,4S,5R)-3,4-dihydroxy-5-methoxy-6,6-dimethyltetrahydro-2H-pyran-2-yloxy)-8-methyl-2-oxo-2H-chromen-3-yl)-1H-indole-2-carboxamide; N-(7-((2R,3R,4S,5R)-3,4-dihydroxy-5-methoxy-6,6-dimethyl-tetrahydro-2H-pyran-2-yloxy)quinolin-3-yl)-4-methoxy-3-(3-methoxyphenyl)-benzamide; 3-(3',6-dimethoxybiphenyl-3-ylcarboxamido)-8-methyl-2-oxo-2H-chromen-7-yl propionate; 3-(3',6-dimethoxybiphenyl-3-ylcarboxamido)-8-methyl-2-oxo-2H-chromen-7-yl cyclopropane carboxylate; and 3-(3',6-dimethoxybiphenyl-3-ylcarboxamido)-6-methoxy-8-methyl-2-oxo-2H-chromen-7-yl acetate).

The antibody used in a combinatorial regime can be, but is not limited to, an antibody that specifically binds a surface marker expressed on a tumor cell such that the surface marker is immunologically distinct from a surface marker expressed on a non-tumor cell. Examples include, but are not limited to, Her2 (Herceptin). Additionally, many tumors respond to anti-angiogenic antibodies such as antibodies to VEGF-2, antibodies to high molecular weight melanoma-associated antigen (HMW-MAA), antibodies to CD105 (endoglin), and other antibodies, and such antibodies can be employed in a combinatorial regime according to the present invention.

When an adjuvant is used in a combinatorial regime, the adjuvant can be, but is not limited to, GM-CSF, poly-ICLC (carboxymethylcellulose, polyinosinic-polycytidylic acid, and poly L-lysine), nanoparticles, microparticles, aluminum salts, squalene, QS-21 (a plant extract from *Quillaja saponaria* containing water-soluble triterpene glycosides), virosomes, IL-2, IL-7, IL-21, and type 1 interferons.

Phosphatidylinositide 3-kinases (PI3K) are a family of enzymes involved in a large number of cellular functions including cell growth, proliferation, cellular differentiation, motility, survival, and intracellular trafficking. These functions are also implicated in cancer, and PI3K has become an increasingly important target for the treatment of malignancies. PI3Ks are a family of related intracellular signal transducer enzymes capable of phosphorylating the 3-position hydroxyl group of the inositol ring of phosphatidylinositol. In vivo, the PI3Ks interact with the insulin receptor substrate (IRS) to regulate glucose uptake through a series of phosphorylation events. The PI3K family is divided into three classes, Class I, Class II, and Class III, based on primary structure, regulation, and in vitro lipid substrate specificity. Class I PI3Ks are responsible for the production of phosphatidylinositol 3-phosphate (PI(3)P), phosphatidylinositol 3,4-bisphosphate (PI(3,4)$P_2$), and phosphatidylinositol 3,4,5-trisphosphate (PI(3,4)$P_3$). These PI3Ks are activated by G protein-coupled receptors and tyrosine kinase receptors. They are heterodimeric molecules composed of a regulatory and a catalytic subunit; they are further divided between IA and IB subsets on sequence similarity. Class IA PI3K is composed of a heterodimer between a p110 catalytic subunit and a p85 regulatory subunit. There are five variants of the p85 regulatory subunit, designated p85α, p55α, p50α, p85β, and p85γ. There are also three variants of the p110 catalytic subunit designated p110α, β, or δ catalytic subunit. The first three regulatory subunits are all splice variants of the same gene (Pik3r1), the other two being expressed by other genes (Pik3r2 and Pik3r3, p85β, and p55γ, respectively). The most highly expressed regulatory subunit is p85α; all three catalytic subunits are expressed by separate genes. Class II and III PI3K are differentiated from the Class I by their structure and function. Class II comprises three catalytic isoforms (C2α, C2β, and C2γ), but, unlike Classes I and III, no regulatory proteins. Class II PI3Ks catalyze the production of PI(3)P and PI(3,4)P$_2$ from PI; however, little is known about their role in immune cells. The distinct feature of Class II PI3Ks is the C-terminal C2 domain. This domain lacks critical Asp residues to coordinate binding of Ca$^{2+}$, which suggests class II PI3Ks bind lipids in a Ca$^{2+}$-independent manner. Class III produces only PI(3)P from PI but are more similar to Class I in structure, as they exist as a heterodimers of a catalytic (Vps34) and a regulatory (Vps15/p150) subunit. Class III seems to be primarily involved in the trafficking of proteins and vesicles. There is, however, evidence to show that they are able to contribute to the effectiveness of several processes important to immune cells, not least phagocytosis. PI3Ks can activate Akt, as in the PI3K/Akt/mTOR pathway. The various 3-phosphorylated inositides produced by the catalytic activity of PI3Ks function in a mechanism by which various signaling proteins, containing the PX domain, pleckstrin homology domains (PH domains), FYVE domains, and other phosphoinositide-binding domains are recruited to cell membranes. In general, The pleckstrin homology domain of Akt binds directly to PI(3,4)P$_2$ and PI(3,4,5)P$_3$, which are produced by activated PI 3-kinase. Since PI(3,4)P$_2$ and PI(3,4,5)P$_3$ are restricted to the plasma membrane, this results in translocation of Akt to the plasma membrane. Likewise, the phosphoinositide-dependent kinase-1 also contains a pleckstrin homology domain that binds directly to PI(3,4)P$_2$ and PI(3,4,5)P$_3$, causing it to also translocate to the plasma membrane upon activation of PI3K. The colocalization of activated phosphoinositide-dependent kinase-1 and Akt allows Akt to become phosphorylated by phosphoinositide-dependent kinase-1 on threonine 308, leading to partial activation of Akt. Full activation of Akt occurs upon phosphorylation of serine 473 by the TORC2 complex of the mTOR protein kinase. This signaling pathway has been shown to be required for an extremely diverse array of cellular activities, most notably cellular proliferation and survival. The phosphatidylinositol 3-kinase/protein kinase B pathway is stimulated in protection of astrocytes from ceramide-induced apoptosis. Additionally, the Class IA PI3K p110a is mutated in many malignancies; many of these mutations cause the kinase to be more active. These mutations have been associated with a number of types of cancer, including ovarian cancer, cervical cancer, breast cancer, colorectal cancer, endometrial cancer, gastric carcinomas, hepatocellular carcinoma, small and non-small cell lung cancer, thyroid carcinoma, acute myelogenous leukemia (AML), chronic myelogenous leukemia (CML), and glioblastomas.

Inhibitors of phosphatidylinositide 3-kinase (PI3K) include, but are not limited to, wortmannin, LY294002, BEZ-205 (2-methyl-2-(4-(3-methyl-2-oxo-8-(quinolin-3-yl)-2,3-dihydroimidazo[4,5-c]quinolin-1-yl)phenyl)propanenitrile), GDC-0941 (2-(1H-indazol-4-yl)-6-((4-(methylsulfonyl)piperazin-1-yl)methyl)-4-morpholinothieno[3,2-d]pyrimidine), idelalisib, buparlisib, GDC-0032 (4-[5,6-dihydro-2-[3-methyl-1-(1-methylethyl)-1H-1,2,4-triazol-5-yl]imidazo[1,2-d][1,4]benzoxazepin-9-yl]-α,α-dimethyl-1H-pyrazole-1-acetamide), SF-1126 (N2-[1,4-dioxo-4-[[4-(4-oxo-8-phenyl-4H-1-benzopyran-2-yl)morpholinium-4-yl]methoxy]butyl]-L-arginylglycyl-L-α-aspartyl-L-serine inner salt), NU7441 (8-(4-dibenzothienyl)-2-(4-morpholinyl)-4H-1-benzopyran-4-one), BYL-719 ((2S)-N1-[4-methyl-5-[2-(2,2,2-trifluoro-1,1-dimethylethyl)-4-pyridinyl]-2-thiazolyl]-2-pyrrolidinedicarboxamide), IPI-145 (8-chloro-2-phenyl-3-[(1S)-1-(9H-purin-6-ylamino)ethyl]-1(2H)-isoquinolinone), GSK2636771 (2-methyl-1-[[2-methyl-3-(trifluoromethyl)phenyl]methyl]-6-(4-morpholinyl)-1H-Benzimidazole-4-carboxylic acid), TG-100713 (3-(2,4-diamino-6-pteridinyl)-phenol), PI3K/HDAC Inhibitor I (N-hydroxy-2-(((2-(6-methoxypyridin-3-yl)-4-morpholinothieno[3,2-d]pyrimidin-6-yl)methyl)(methyl)amino)pyrimidine-5-carboxamide), YM201636 (6-amino-N-[3-[4-(4-morpholinyl)pyrido[3',2':4,5]furo[3,2-d]pyrimidin-2-yl]phenyl]-3-pyridinecarboxamide), NVP-BGT226 (8-(6-methoxypyridin-3-yl)-3-methyl-1-(4-(piperazin-1-yl)-3-(trifluoromethyl)phenyl)-1H-imidazo[4,5-c]quinolin-2(3H)-one maleic acid), PF-04691502 (2-amino-8-((1r,4r)-4-(2-hydroxyethoxy)cyclohexyl)-6-(6-methoxypyridin-3-yl)-4-methylpyrido[2,3-d]pyrimidin-7(8H)-one), PKI-402 (1-(4-(3-ethyl-7-morpholino-3H-[1,2,3]triazolo[4,5-d]pyrimidin-5-yl)phenyl)-3-(4-(1-methylpiperazine-4-carbonyl)phenyl)urea), CH5132799 (5-(7-(methylsulfonyl)-2-morpholino-6,7-dihydro-5H-pyrrolo[2,3-d]pyrimidin-4-yl)pyrimidin-2-amine), AS-252424 ((Z)-5-((5-(4-fluoro-2-hydroxyphenyl)furan-2-yl)methylene)thiazolidine-2,4-dione), AS-604850 ((Z)-5-((2,2-difluorobenzo[d][1,3]dioxol-5-yl)methylene)thiazolidine-2,4-dione), CAY10505 ((E)-5-((5-(4-fluorophenyl)furan-2-yl)methylene)thiazolidine-2,4-dione), GSK2126458 (2,4-difluoro-N-(2-methoxy-5-(4-(pyridazin-4-yl)quinolin-6-yl)pyridin-3-yl)benzenesulfonamide), A66 ((2S)—N1-(5-(2-tert-butylthiazol-4-yl)-4-methylthiazol-2-yl)pyrrolidine-1,2-dicarboxamide), PF-05-212384 (1-(4-(4-(dimethylamino)piperidine-1-carbonyl)phenyl)-3-(4-(4,6-dimorpholino-1,3,5-triazin-2-yl)phenyl)urea), PIK-294 (2-((4-amino-3-(3-hydroxyphenyl)-1H-pyrazolo[3,4-d]pyrimidin-1-yl)methyl)-5-methyl-3-o-tolylquinazolin-4(3H)-one), PIK-293 (2-((4-amino-1H-pyrazolo[3,4-d]pyrimidin-1-yl)methyl)-5-methyl-3-o-tolylquinazolin-4(3H)-one), XL765 (N-[4-[[[3-[(3,5-dimethoxyphenyl)amino]-2-quinoxalinyl]amino]sulfonyl]phenyl]-3-methoxy-4-methyl-benzamide), PIK-93 (N-[5-[4-chloro-3-[(2-hydroxyethyl)sulfamoyl]phenyl]-4-methylthiazol-2-yl]acetamide), AZD6482 ((R)-2-(1-(7-methyl-2-morpholino-4-oxo-4H-pyrido[1,2-a]pyrimidin-9-yl)ethylamino)benzoic acid), AS-605240 ((Z)-5-(quinoxalin-6-ylmethylene)thiazolidine-2,4-dione), GSK1059615 ((Z)-5-((4-(pyridin-4-yl)quinolin-6-yl)methylene)thiazolidine-2,4-dione), TG100-115 (6,7-bis(3-hydroxyphenyl)pteridine-2,4-diamine), IC-87114 (2-((6-amino-9H-purin-9-yl)methyl)-5-methyl-3-o-tolylquinazolin-4(3H)-one), PIK-75 ((E)-N'-((6-bromoH-imidazo[1,2-a]pyridin-3-yl)methylene)-N,2-dimethyl-5-nitrobenzenesulfonohydrazide hydrochloride), PIK-90, XL147 (N-(3-(benzo[c][1,2,5]thiadiazol-5-ylamino)quinoxalin-2-yl)-4-methylbenzenesulfonamide), ZSTK474 (2-(difluoromethyl)-1-(4,6-dimorpholino-1,3,5-triazin-2-yl)-1H-benzo[d]imidazole), and PI-103 (3-[4-(4-morpholinyl)pyrido[3',2':4,5]furo[3,2-d]pyrimidin-2-yl]-phenol).

Additional inhibitors of PI3K are described in the following United States patents and patent applications, all of which are incorporated herein by this reference: U.S. Pat. No. 8,481,001 to Lamb et al. (quinoxalines); U.S. Pat. No. 8,476,431 to Ren et al. (benzoxazoles); U.S. Pat. No. 8,476,282 to Ren et al. (benzoxazoles); U.S. Pat. No. 8,476,268 to Fairhurst et al. (pyrrolidine-1,2-dicarboxamide derivatives, including (S)-pyrrolidine-1,2-dicarboxylic acid 2-amide 1-{[5-(2-cyclopropyl-pyridin-4-yl)-4-methyl-thiazol-2-yl]-amide}; (S)-pyrrolidine-1,2-dicarboxylic acid 2-amide 1-({5-[2-(2-fluoro-phenyl)-pyridin-4-yl]-4-methyl-thiazol- 2-yl}-amide); (S)-pyrrolidine-1,2-dicarboxylic acid 2-amide 1-{[5-(2-cyclobutyl-pyridin-4-yl)-4-methyl-thiazol-2-yl]-amide}; (S)-pyrrolidine-1,2-dicarboxylic acid 2-amide 1-({4-methyl-5-[2-(1-methyl-cyclopropyl)-pyridin-4-yl]-thiazol-2-yl}-amide); (S)-pyrrolidine-1,2-dicarboxylic acid 2-amide 1-({4-methyl-5-[2-(1-methyl-cyclobutyl)-pyridin-4-yl]-thiazol-2-yl}-amide); (S)-pyrrolidine-1,2-dicarboxylic acid 2-amide 1-{[5-(2-cyclobutyl-pyridin-4-yl)-thiazol-2-yl]-amide}; (S)-pyrrolidine-1,2-dicarboxylic acid 2-amide 1-({5-[2-(1-methyl-cyclopropyl)-pyridin-4-yl]-thiazol-2-yl}-amide); (S)-pyrrolidine-1,2-dicarboxylic acid 2-amide 1-({5-[2-(1-trifluoromethyl-cyclopropyl)-pyridin-4-yl]-thiazol-2-yl}-amide); (S)-pyrrolidine-1,2-dicarboxylic acid 2-amide 1-({5-[2-(2,2,2-trifluoro-1,1-dimethyl-ethyl)-pyridin-4-yl]-thiazol-2-yl}-amide); (S)-pyrrolidine-1,2-dicarboxylic acid 2-amide 1-({5-[2-(1-trifluoromethyl-cyclobutyl)-pyridin-4-yl]-thiazol-2-yl}-amide); (S)-pyrrolidine-1,2-dicarboxylic acid 2-amide 1-({4-methyl-5-[2-(1-trifluoromethyl-cyclopropyl)-pyridin-4-yl]-thiazol-2-yl}-amide); (S)-pyrrolidine-1,2-dicarboxylic acid 2-amide 1-({4-methyl-5-[2-(1-trifluoromethyl-cyclobutyl)-pyridin-4-yl]-thiazol-2-yl}-amide); (S)-pyrrolidine-1,2-dicarboxylic acid 2-amide 1-({5-[2-(1-methyl-cyclobutyl)-pyridin-4-yl]-thiazol-2-yl}-amide); (S)-pyrrolidine-1,2-dicarboxylic acid 2-amide 1-({5-[2-(1-cyano-cyclopropyl)-pyridin-4-yl]-4-methyl-thiazol-2-yl}-amide); (S)-pyrrolidine-1,2-dicarboxylic acid 2-amide 1-({5-[2-(1-cyano-cyclobutyl)-pyridin-4-yl]-4-methyl-thiazol-2-yl}-amide); (S)-pyrrolidine-1,2-dicarboxylic acid 2-amide 1-({5-[2-(1-carbamoyl-cyclobutyl)-pyridin-4-yl]-4-methyl-thiazol-2-yl}-amide); (S)-pyrrolidine-1,2-dicarboxylic acid 2-amide 1-({5-[2-(2-dimethylamino-1,1-dimethyl-ethyl)-pyridin-4-yl]-4-methyl-thiazol-2-yl}-amide); (S)-pyrrolidine-1,2-dicarboxylic acid 2-amide 1-{[5-(2-diethylamino-pyridin-4-yl)-4-methyl-thiazol-2-yl]-amide}; (S)-pyrrolidine-1,2-dicarboxylic acid 2-amide 1-{[5-(2-diethylamino-pyridin-4-yl)-thiazol-2-yl]-amide}; (S)-pyrrolidine-1,2-dicarboxylic acid 2-amide 1-[(5-{2-[1-(4-methoxy-phenyl)-1-methyl-ethyl]-pyridin-4-yl}-4-methyl-thiazol-2-yl)-amide]; (S)-pyrrolidine-1,2-dicarboxylic acid 2-amide 1-[(5-{2-[1-(4-methoxy-phenyl)-1-methyl-ethyl]-pyridin-4-yl}-thiazol-2-yl)-amide]; (S)-pyrrolidine-1,2-dicarboxylic acid 2-amide 1-[(5-{2-[1-(4-methoxy-phenyl)-cyclopropyl]-pyridin-4-yl}-4-methyl-thiazol-2-yl)-amide]; (S)-pyrrolidine-1,2-dicarboxylic acid 2-amide 1-[(5-{2-[1-(4-methoxy-phenyl)-cyclopropyl]-pyridin-4-yl}-thiazol-2-yl)-amide]; (S)-pyrrolidine-1,2-dicarboxylic acid 2-amide 1-{[5-(2-{1-[4-(3-dimethylamino-propoxy)-phenyl]-1-methyl-ethyl}-pyridin-4-yl)-4-methyl-thiazol-2-yl]-amide}; (S)-pyrrolidine-1,2-dicarboxylic acid 2-amide 1-({4-methyl-5-[2-(1-d$_3$-methyl-cyclobutyl)-pyridin-4-yl]-thiazol-2-yl}-amide); (S)-pyrrolidine-1,2-dicarboxylic acid 2-amide 1-({5-[2-(1-d$_3$-methyl-cyclobutyl)-pyridin-4-yl]-thiazol-2-yl}-amide); (S)-pyrrolidine-1,2-dicarboxylic acid 2-amide 1-({4-d$_3$-methyl-5-[2-(1-methyl-cyclopropyl)-pyridin-4-yl]-thiazol-2-yl}-amide); (S)-pyrrolidine-1,2-dicarboxylic acid 2-amide 1-({4-d$_3$-methyl-5-[2-(2,2,2-trifluoro-1,1-dimethyl-ethyl)-pyridin-4-yl]-thiazol-2-yl}-amide); (S)-pyrrolidine-1,2-dicarboxylic acid 2-amide 1-({4-dimethylaminomethyl-5-[2-(1-d$_3$-methyl-cyclobutyl)-pyridin-4-yl]-thiazol-2-yl}-amide); (S)-pyrrolidine-1,2-dicarboxylic acid 2-amide 1-({4-chloro-5-[2-(2,2,2-trifluoro-, 1-dimethyl-ethyl)-pyridin-4-yl]-thiazol-2-yl}-amide); (S)-pyrrolidine-1,2-dicarboxylic acid 2-amide 1-({4-fluoromethyl-5-[2-(2,2,2-trifluoro-1,1-dimethyl-ethyl)-pyridin-4-yl]-thiazol-2-yl}-amide); (S)-pyrrolidine-1,2-dicarboxylic acid 2-amide 1-({5-[2-(2-fluoro-1,1-dimethyl-ethyl)-pyridin-4-yl]-4-methyl-thiazol-2-yl}-amide); and (S)-pyrrolidine-1,2-dicarboxylic acid 2-amide 1-({5-[2-(2-fluoro-1-fluoromethyl-1-methyl-ethyl)-pyridin-4-yl]-4-methyl-thiazol-2-yl}-amide); U.S. Pat. No. 8,466,283 to Hentemann et al. (substituted 2,3-dihydroimidazo[1,2-c]quinazoline derivatives); U.S. Pat. No. 8,461,158 to Rewcastle et al. (pyrimidinyl and 1,3,5-triazinyl benzimidazole sulfonamides); U.S. Pat. No. 8,461,157 to Cai et al. (deazapurines, thienopyrimidines and furopyrimidines with zinc-binding moiety); U.S. Pat. No. 8,445,487 to Castanedo et al. (purines, including 2-(2-(2-amino-4-methylpyrimidin-5-yl)-9-(2-hydroxyethyl)-6-morpholino-9H-purin-8-yl)propan-2-ol; 2-(2-(2-aminopyrimidin-5-yl)-9-butyl-6-morpholino-9H-purin-8-yl)propan-2-ol; 2-(2-(2-aminopyrimidin-5-yl)-6-morpholino-9-propyl-9H-purin-8-yl)propan-2-ol; 3-(2-(2-aminopyrimidin-5-yl)-8-(2-hydroxypropan-2-yl)-6-morpholino-9H-purin-9-yl)propan-1-ol; 2-(2-(2-aminopyrimidin-5-yl)-9-(2-hydroxyethyl)-6-morpholino-9H-purin-8-yl)propan-2-ol; 1-(4-((2-(2-aminopyrimidin-5-yl)-6-morpholino-9H-purin-9-yl)methyl)piperidin-1-yl)ethanone; 1-(3-((2-(2-aminopyrimidin-5-yl)-6-morpholino-9H-purin-9-yl)methyl)pyrrolidin-1-yl)ethanone; (R)-3-(2-(2-aminopyrimidin-5-yl)-6-morpholino-9H-purin-9-yl)-1-(3-hydroxypyrrolidin-1-yl)propan-1-one; (S)-3-(2-(2-aminopyrimidin-5-yl)-6-morpholino-9H-purin-9-yl)-1-(3-hydroxypyrrolidin-1-yl)propan-1-one; 1-(3-(2-(2-aminopyrimidin-5-yl)-6-morpholino-9H-purin-9-yl)propanoyl)-N-methylpiperidine-4-carboxamide; 3-(2-(2-aminopyrimidin-5-yl)-6-morpholino-9H-purin-9-yl)-1-(4-(methylsulfonyl)piperazin-1-yl)propan-1-one; 3-(2-(2-aminopyrimidin-5-yl)-6-morpholino-9H-purin-9-yl)-1-morpholinopropan-1-one; 3-(2-(2-aminopyrimidin-5-yl)-6-morpholino-9H-purin-9-yl)propanoic acid; 5-(9-(4-(methylsulfonyl)benzyl)-6-morpholino-9H-purin-2-yl)pyrimidin-2-amine; methyl 4-((2-(2-aminopyrimidin-5-yl)-6-morpholino-9H-purin-9-yl)methyl)benzoate; 5-(6-morpholino-9-(2-morpholinoethyl)-9H-purin-2-yl)pyrimidin-2-amine; 5-(9-(3-methoxybenzyl)-6-morpholino-9H-purin-2-yl)pyrimidin-2-amine; methyl 3-((2-(2-aminopyrimidin-5-yl)-6-morpholino-9H-purin-9-yl)methyl)benzoate; 3-(2-(2-aminopyrimidin-5-yl)-6-morpholino-9H-purin-9-yl)propan-1-ol; 2-(2-(2-aminopyrimidin-5-yl)-6-morpholino-9H-purin-9-yl)ethanol; 1-(2-(2-(2-aminopyrimidin-5-yl)-6-morpholino-9H-purin-9-yl)acetyl)-N-methylpiperidine-4-carboxamide; 2-(2-(2-aminopyrimidin-5-yl)-6-morpholino-9H-purin-9-yl)-1-(4-(methylsulfonyl)piperazin-1-yl)ethanone; 2-(2-(2-aminopyrimidin-5-yl)-6-morpholino-9H-purin-9-yl)-1-morpholinoethanone; 2-(2-(2-aminopyrimidin-5-yl)-6-morpholino-9H-purin-9-yl)acetic acid; methyl 2-(2-(2-aminopyrimidin-5-yl)-6-morpholino-9H-purin-9-yl)acetate; 5-(9-methyl-6-morpholino-9H-purin-2-yl)pyrimidin-2-amine; 5-(9-methyl-6-morpholino-9H-purin-2-yl)pyridin-2-amine; 2-(2-(2-aminopyrimidin-5-yl)-9-methyl-6-morpholino-9H-purin-8-yl)propan-2-ol; 2-(2-(6-aminopyridin-3-yl)-9-methyl-6-morpholino-9H-purin-8-yl)propan-2-ol; 5-(9-methyl-8-((4-(methylsulfonyl)piperazin-1-yl)methyl)-6-morpholino-9H-purin-2-yl)pyridin-2-amine; 4-(2-(2-methoxypyrimidin-5-yl)-9-methyl-8-((4-(methylsulfonyl)piperazin-1-yl)methyl)-9H-purin-6-yl)morpholine; 4-(9-methyl-8-((4-(methylsulfonyl)piperazin-1-yl)methyl)-2-(pyridin-3-yl)-9H-purin-6-yl)morpholine; 5-(8-((4-(dimethylamino)piperidin-1-yl)methyl)-9-ethyl-6-morpholino-9H-purin-2-yl)pyrimidin-2-amine; 5-(8-((4-(azetidin-1-yl)piperidin-1-yl)methyl)-9-ethyl-6-morpholino-9H-purin-2-yl)pyrimidin-2-amine; 5-(8-((4-(azetidin-1-yl)piperidin-1-yl)methyl)-9-ethyl-6-morpholino-9H-purin-2-yl)-4-methylpyrimidin-2-amine; 2-(4-((2-(2-amino-4-methylpyrimidin-5-yl)-9-ethyl-6-morpholino-9H-purin-8-yl)methyl)piperazin-1-yl)-2-methylpropanamide; 5-(8-((4-(dimethylamino)piperidin-1-yl)methyl)-9-ethyl-6-morpholino-9H-purin-2-yl)-4-methylpyrimidin-2-amine; 5-(8-(1,4'-bipiperidin-1'-ylmethyl)-9-ethyl-6-morpholino-9H-purin-2-yl)-4-methylpyrimidin-2-amine; 5-(8-(1,4'-bipiperidin-1'-ylmethyl)-9-ethyl-6-morpholino-9H-purin-2-yl)pyrimidin-2-amine; 5-(9-ethyl-6-morpholino-8-((4-morpholinopiperidin-1-yl)methyl)-9H-purin-2-yl)-4-methylpyrimidin-2-amine; 5-(9-ethyl-6-morpholino-8-((4-morpholinopiperidin-1-yl)methyl)-9H-purin-2-yl)pyrimidin-2-amine; N-(1-((2-(2-amino-4-methylpyrimidin-5-yl)-9-ethyl-6-morpholino-9H-purin-8-yl)methyl)piperidin-4-yl)methylmethanesulfonamide; and N-(1-((2-(2-aminopyrimidin-5-yl)-9-ethyl-6-morpholino-9H-purin-8-yl)methyl)piperidin-4-yl)-N-methylmethanesulfonamide); U.S. Pat. No. 8,445,486 to Venkatesan et al (triazines, including 1-{4-[4-morpholin-4-yl-6-(3-oxa-8-azabicyclo[3.2.1]oct-8-yl)-1,3,5-triazin-2-yl]phenyl}-3-pyridin-4-ylurea); U.S. Pat. No. 8,440,677 to Evarts et al. (2-purinyl-3-tolyl-quinazolinone derivatives); U.S. Pat. No. 8,440,651 to Castanedo et al. (pyrido[3,2-d]pyrimidines); U.S. Pat. No. 8,436,177 to Stowasser et al. (2-methyl-2-[4-(3-methyl-2-oxo-8-quinolin-3-yl-2,3-dihydro-imidazo[4,5-c]quinolin-1-yl)-phenyl]-propionitrile); U.S. Pat. No. 8,436,001 to Wang (pyrazol-4-yl-heterocyclyl-carboxamides); U.S. Pat. No. 8,435,988 to Qu et al. (benzimidazoles); U.S. Pat. No. 8,435,976 to Wang et al. (4-substituted pyridin-3-yl-carboxamides, including (S)-5-amino-N-(4-(3-aminopiperidin-1-yl)pyridin-3-yl)-2-(2,6-difluorophenyl)thiazole-4-carboxamide); U.S. Pat. No. 8,431,592 to Garcia-Echeverria et al. (1,3-dihydro-imidazo[4,5-c]quinolin-2-ones, including 2-methyl-2-[4-(3-methyl-2-oxo-8-quinolin-3-yl-2,3-dihydro-imidazo[4,5-c]quinolin-1-yl)-phenyl]-propionitrile); U.S. Pat. No. 8,431,584 to Artman III et al. (heterobicyclic carboxamides); U.S. Pat. No. 8,426,402 to Li et al. (benzodiazepines); U.S. Pat. No. 8,415,376 to Bo et al. (N-(2-chloro-5-(4-chloro-6-quinolinyl)-3-pyridinyl)-4-fluorobenzenesulfonamide; tert-butyl (2-((6-(6-chloro-5-(((4-fluorophenyl)sulfonyl)amino)-3-pyridinyl)-4-quinolinyl)oxy)ethyl)carbamate; N-(2-chloro-5-(4-phenoxy-6-quinolinyl)-3-pyridinyl)methanesulfonamide; N-(2-chloro-5-(4-methoxy-6-quinolinyl)-3-pyridinyl)-4-fluorobenzenesulfonamide; N-(2-chloro-5-(4-chloro-6-quinolinyl)-3-pyridinyl)methanesulfonamide; N-(2-chloro-5-(4-hydroxy-6-quinolinyl)-3-pyridinyl)-4-fluorbenzenesulfonamide; N-(2-chloro-5-(4-(2-methoxyethoxy)-6-quinolinyl)-3-pyridinyl)-4-fluorobenzenesulfonamide; N-(2-chloro-5-(4-(dimethylamino)-6-quinolinyl)-3-pyridinyl)-4-methoxybenzenesulfonamide; 2-chloro-5-(4-chloro-6-quinolinyl)-N,N-dimethyl-3-pyridinamine; N-(2-chloro-5-(4-(((5-cyclopropyl-1,2,4-oxadiazol-3-yl)methyl)(ethyl)amino)-6-quinolinyl)-3-pyridinyl)methanesulfonamide; N-(2-chloro-5-(4-((2-cyanoethyl)(ethyl)amino)-6-quinolinyl)-3-pyridinyl)methanesulfonamide; N-(2-chloro-5-(4-((2-methoxy-2-methylpropyl)amino)-6-quinolinyl)-3-pyridinyl)methanesulfonamide; N-(2-chloro-5-(4-((3-fluorobenzyl)(methyl)amino)-6-quinolinyl)-3-pyridinyl)methanesulfonamide; N-(2-chloro-5-(4-((2,5-dimethoxybenzyl)amino)-6-quinolinyl)-3-pyridinyl)methanesulfonamide; N-(2-chloro-5-(4-(4-piperidinylamino)-6-quinolinyl)-3-pyridinyl)methanesulfonamide; N-(2-chloro-5-(4-(dimethylamino)-6-quinolinyl)-3-pyridinyl)-4-fluorobenzenesulfonamide; N-(2-chloro-5-(4-((2-methoxyethyl)amino)-6-quinolinyl)-3-pyridinyl)-4-fluorobenzenesulfonamide; N-(2-chloro-5-(4-((2-methoxy-1-methylethyl)amino)-6-quinolinyl)-3-pyridinyl)-4-fluorobenzenesulfonamide; N-(2-chloro-5-(4-(tetrahydro-2H-thiopyran-4-ylmethoxy)-6-quinolinyl)-3-pyridinyl)-4-fluorobenzenesulfonamide; N-(2-chloro-5-(4-(tetrahydro-3-thiophenyloxy)-6-quinolinyl)-3-pyridinyl)-4-fluorobenzenesulfonamide; N-(2-chloro-5-(4-((tetrahydro-2H-thiopyran-1,1-dioxide-4-yl)methoxy)quinolin-6-yl)pyridin-3-yl)-4-fluorobenzenesulfonamide; N-(2-chloro-5-(4-(tetrahydrothiophen-1,1-dioxide-3-yloxy)quinolin-6-yl)pyridin-3-yl)-4-fluorobenzenesulfonamide; N'-(2-chloro-5-(4-chloro-6-quinolinyl)-3-pyridinyl)-N,N-dimethylsulfamide; and N'-(2-chloro-5-(4((2-methoxyethyl)(methyl)amino)-6-quinolinyl)-3-pyridinyl)-N-(2-methoxyethyl)-N-methylsulfamide); U.S. Pat. No. 8,410,095 to Lin et al. (thiazolopyrimidinone derivatives, including 5-methyl-4-{[2-methyl-3-(trifluoromethyl)phenyl]methyl}-2-(4-morpholinyl)[1,3]thiazolo[4,5-d]pyrimidin-7(4H)-one and 4-[(3-chloro-2-methylphenyl)methyl]-5-ethyl-2-(4-morpholinyl)[1,3]thiazolo[4,5-d]pyrimidin-7(4H)-one); U.S. Pat. No. 8,404,837 to Adams et al. (quinoline derivatives); U.S. Pat. No. 8,399,690 to Do et al. (4,5-dihydro-6-oxa-3-thia-1-aza-benzo[e]azulenes, including 4,5-dihydro-6-oxa-3-thia-1-aza-benzo[e]azulene-2-carboxylic acid (2-chloro-4-methyl-carbamoyl-phenyl)-methyl-amide; 4,5-dihydro-6-oxa-3-thia-1-aza-benzo[e]azulene-2-carboxylic acid (2-chloro-phenyl)-methyl-amide; and 8-bromo-2-[4-(2-chloro-phenyl)-4H-[1,2,4]triazol-3-yl]-4,5-dihydro-6-oxa 3-thia-1-aza-benzo[e]azulene; U.S. Pat. No. 8,399,483 to Allen et al. (heteroaryl-substituted quinoxaline and quinoline derivatives); U.S. Pat. No. 8,394,796 to Castanedo et al. (bicyclic pyrimidine compounds); U.S. Pat. No. 8,362,241 to D'Angelo et al. (4-(2-(5-fluoro-6-methoxypyridin-3-ylamino)-5-(1-(4-(methylsulfonyl)piperazin-1-yl)ethyl)pyridin-3-yl)-6-methyl-1,3,5-triazin-2-amine); U.S. Pat. No. 8,357,707 to Fairhurst et al. (2-carboxamide cycloamino ureas); U.S. Pat. No. 8,343,955 to Blaquiere et al. (benzoxazepines, including 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)ethanol, 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, and 2-(4-(2-(1-isopropyl-1H-1,2,4-triazol-5-yl)-5,6-dihydrobenzo[f]imidazo[1,2-d][1,4]oxazepin-9-yl)-1H-imidazol-1-yl)ethanol); U.S. Pat. No. 8,309,546 to Nakayama et al. (morpholinopurine derivatives); U.S. Pat. No. 8,293,793 to Fairhurst et al. (substituted 2-carboxamide cycloamino ureas, including (2S,3R)-3-methyl-pyrrolidine-1,2-dicarboxylic acid 2-amide 1-({4-methyl-5-[2-(1-methyl-cyclopropyl)-pyridin-4-yl]-thiazol-2-yl}-amide); (2S,3R)-3-methyl-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide); (2S,3S)-3-(acetylamino-methyl)-pyrrolidine-1,2-dicarboxylic acid 2-amide 1-({4-methyl-5-[2-(1-methyl-cyclopropyl)-pyridin-4-yl]-thiazol-2-yl}-amide); (2S,3S)-3-(acetylamino-methyl)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide); (2S,3S)-3-morpholin-4-ylmethyl-pyrrolidine-1,2-dicarboxylic acid 2-amide 1-({4-methyl-5-[2-(1-methyl-cyclopropyl)-pyridin-4-yl]-thiazol-2-yl}-amide); (2S,3S)-3-morpholin-4-ylmethyl-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide); (2S,3R)-3-methyl-pyrrolidine-1,2-dicarboxylic acid 2-amide 1-({5-[2-(1-fluoro-1-methyl-ethyl)-pyrimidin-4-yl]-4-methyl-thiazol-2-yl}-amide); (2S,3R)-3-methyl-pyrrolidine-1,2-dicarboxylic acid 2-amide 1-{[5-(2-d$_9$-tert-butyl-pyrimidin-4-yl)-4-methyl-thiazol-2-yl]-amide}; (2S,3R)-3-methyl-pyrrolidine-1,2-dicarboxylic acid 2-amide 1-{[5-(6-dio-diethylamino-pyrazin-2-yl)-4-methyl-thiazol-2-yl]-amide}; (2S,3R)-3-methoxymethyl-pyrrolidine-1,2- dicarboxylic acid 2-amide 1-({4-methyl-5-[2-(2,2,2-trifluoro-, 1-dimethyl-ethyl)-pyridin-4-yl]-thiazol-2-yl}-amide); (2S,3S)-3-dimethylaminomethyl-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide; (2S,3R)-3-methyl-pyrrolidine-1,2-dicarboxylic acid 2-amide 1-{[5-(2-tert-butyl-pyridin-4-yl)-4-methyl-thiazol-2-yl]-amide}); U.S. Pat. No. 8,263,633 to Blaquiere et al. (benzoxazepines, including 2-(3-amino-1-(2,4-difluorophenyl)-1H-1,2,4-triazol-5-yl)-N-methyl-4,5-dihydrobenzo[b]thieno[2,3-d]oxepine-8-carboxamide); U.S. Pat. No. 8,247,408 to Baik et al. (pyridopyrimidinones); U.S. Pat. No. 8,242,104 to Blaquiere et al. (benzoxazepines, including 1-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol; 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)ethanol; 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)ethanol; and 2-(4-(2-(1-isopropyl-1H-1,2,4-triazol-5-yl)-5,6-dihydrobenzo[f]imidazo[1,2-d][1,4]oxazepin-9-yl)-1H-imidazol-1-yl)ethanol); U.S. Pat. No. 8,227,462 to Fairhurst et al. (pyrrolidine-1,2-dicarboxamides, including (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) and (S)-pyrrolidine-1,2-dicarboxylic acid 2-amide 1-({4-methyl-5-[2-(1-methyl-cyclopropyl)-pyridin-4-yl]-thiazol-2-yl}-amide)); U.S. Pat. No. 8,217,036 to Venkatesan et al. (triazines); U.S. Pat. No. 8,217,035 to Burger et al. (pyrimidine derivatives, including 4-(trifluoromethyl)-5-(2,6-dimorpholinopyrimidin-4-yl)pyridin-2-amine); U.S. Pat. No. 8,207,153 to Fowler et al. (quinazolinones); U.S. Pat. No. 8,202,883 to Gerlach et al. (substituted pyrido[2,3-b]pyrazine compounds); U.S. Pat. No. 8,173,647 to Atallah et al. (5-(4-morpholino-6-(tetrahydro-2H-pyran-4-yloxy)pyrimidin-2-yl)-4-(trifluoromethyl)pyridin-2-amine, 4-morpholino-6-(tetrahydro-2H-pyran-4-yloxy)-4'-(trifluoromethyl)-2,5'-bipyrimidin-2'-amine, 4-morpholino-6-(tetrahydro-2H-pyran-4-yloxy)-2,5'-bipyrimidine-2',4'-diamine, 2-amino-5-(4-morpholino-6-(tetrahydro-2H-pyran-4-yloxy)pyrimidin-2-yl)pyrimidin-4(3H)-one, 2-(6-amino-4-(trifluoromethyl)pyridin-3-yl)-N-(6-methoxy-pyridin-3-yl)-6-morpholinopyrimidin-4-amine, N4-(6-methoxypyridin-3-yl)-6-morpholino-4'-(trifluoromethyl)-2,5'-bipyrimidine-2',4-diamine, N4-(6-methoxypyridin-3-yl)-6-morpholino-2,5'-bipyrimidine-2',4,4'-triamine, 2-amino-5-(4-(6-methoxypyridin-3-ylamino)-6-morpholinopyrimidin-2-yl)pyrimidin-4(3H)-one, 5-(4,6-dimorpholinopyrimidin-2-yl)-4-(trifluoromethyl)pyridin-2-amine, 4,6-dimorpholino-4'-(trifluoro-methyl)-2,5'-bipyrimidin-2'-amine, 4,6-dimorpholino-2,5'-bipyrimidine-2',4'-diamine); U.S. Pat. No. 8,163,743 to Baldwin et al. (4-carboxamide indazole derivatives); U.S. Pat. No. 8,158,626 to Castanedo et al. (thiazolopyrimidine compounds); U.S. Pat. No. 8,158,625 to Castanedo et al. (bicyclic indole-pyrimidines, including 4-(1-((2-(1H-indol-3-yl)-9-methyl-6-morpholino-9H-purin-8-yl)methyl)piperidin-4-yl)morpholine; 2-(1-((9-(2-hydroxyethyl)-2-(1H-indol-3-yl)-6-morpholino-9H-purin-8-yl)methyl)piperidin-4-yl)propan-2-ol; 4-(2-(1H-indol-3-yl)-9-methyl-8-((4-(tetrahydro-2H-1,1-dioxo-thiopyran-4-yl)piperazin-1-yl)methyl)-9H-purin-6-yl)morpholine; 1-(1-((9-ethyl-2-(5-fluoro-1H-indol-1-yl)-6-morpholino-9H-purin-8-yl)methyl)piperidin-4-yl)pyrrolidin-2-one; 1-((2-(1H-indol-3-yl)-9-methyl-6-morpholino-9H-purin-8-yl)methyl)-N,N-dimethylpiperidin-4-amine; 4-(2-(1H-indol-3-yl)-9-methyl-8-((4-(tetrahydro-2H-pyran-4-yl)piperazin-1-yl)methyl)-9H-purin-6-yl)morpholine; 2-(1-((2-(1H-indol-3-yl)-9-methyl-6-morpholino-9H-purin-8-yl)methyl)piperidin-4-yl)propan-2-ol; (3S,4R)-1-((2-(1H-indol-3-yl)-9-methyl-6-morpholino-9H-purin-8-yl)methyl)-3-fluoro-N,N-dimethylpiperidin-4-amine; (3R,4S)-1-((2-(1H-indol-3-yl)-9-methyl-6-morpholino-9H-purin-8-yl)methyl)-3-fluoro-N,N-dimethylpiperidin-4-amine; 2-(1-((2-(6-fluoro-1H-indol-3-yl)-9-methyl-6-morpholino-9H-purin-8-yl)methyl)piperidin-4-yl)propan-2-ol; 2-(1-((2-(2-(methoxymethyl)-1H-indol-1-yl)-9-methyl-6-morpholino-9H-purin-8-yl)methyl)piperidin-4-yl)propan-2-ol; 2-(1-((9-methyl-2-(2-methyl-1H-indol-1-yl)-6-morpholino-9H-purin-8-yl)methyl)piperidin-4-yl)propan-2-ol; 4-(2-(1H-indol-3-yl)-8-((4-(2-methoxypropan-2-yl)piperidin-1-yl)methyl)-9-methyl-9H-purin-6-yl)morpholine; 4-(8-((4-(2-methoxypropan-2-yl)piperidin-1-yl)methyl)-9-methyl-2-(2-methyl-1H-indol-1-yl)-9H-purin-6-yl)morpholine; 3-(8-((4-(2-hydroxypropan-2-yl)piperidin-1-yl)methyl)-9-methyl-6-morpholino-9H-purin-2-yl)-1H-indole-2-carbonitrile; and 1-(8-((4-(2-hydroxypropan-2-yl)piperidin-1-yl)methyl)-9-methyl-6-morpholino-9H-purin-2-yl)-1H-indole-2-carbonitrile); U.S. Pat. No. 8,158,624 to Castanedo et al. (purines); U.S. Pat. No. 8,138,147 to Knight et al. (quinolines, including, 4-difluoro-N-{2-(methyloxy)-5-[4-(4-pyridazinyl)-6-quinolinyl]-3-pyridinyl}benzenesulfonamide); U.S. Pat. No. 8,138,195 to Sadhu et al.; U.S. Pat. No. 8,106,039 to Meggers et al. (organometallic compounds); U.S. Pat. No. 8,097,622 to Nakayama et al. (morpholinopurine derivatives); U.S. Pat. No. 8,067,586 to Hayakawa et al. (fused heteroaryl derivatives); U.S. Pat. No. 8,044,062 to Baik et al. (substituted pyrido[2,3-d]pyrimidin-7(8H)-one compounds); U.S. Pat. No. 8,039,469 to Venkatesan et al. (triazines, including 1-(4-{[4-(dimethylamino)piperidin-1-yl]carbonyl}phenyl)-3-[4-(4,6-dimorpholin-4-yl-1,3,5-triazin-2-yl)phenyl]urea); U.S. Pat. No. 8,022,205 to Shima et al. (pyrimidine derivatives); U.S. Pat. No. 7,994,170 to Garcia-Echeverria et al. (1,3-dihydro-imidazo[4,5-c]quinolin-2-ones); U.S. Pat. No. 7,989,622 to Bajjalieh et al.; U.S. Pat. No. 7,928,248 to Do et al. (benzopyrans and benzoxepines); U.S. Pat. No. 7,928,140 to Booker et al. (benzothiazoles); U.S. Pat. No. 7,893,059 to Castanedo et al. (thiazolopyrimidines); U.S. Pat. No. 7,888,344 to Alexander et al. (fused thiazole derivatives); U.S. Pat. No. 7,820,665 to Booker et al. (imidazopyridazine compounds, including N-(6-(6-chloro-5-(3-(difluoromethoxy)phenylsulfonamido)pyridin-3-yl)-3-(pyridin-4-yl)imidazo[1,2-b]pyridazin-2-acetamide; N-(5-(2-amino-3-(pyridin-4-yl)imidazo[1,2-b]pyridazin-6-yl)-2-chloropyridin-3-yl)-3-(difluoromethoxy)benzenesulfonamide; N-(6-(6-chloro-5-(3-(difluoromethoxy)phenylsulfonamido)pyridin-3-yl)-3-(2-methylpyridin-4-yl)imidazo[1,2-b]pyridazin-2-yl)acetamide; N-(5-(2-amino-3-(2-methylpyridin-4-yl)imidazo[1,2-b]pyridazin-6-yl)-2-chloropyridin-3-yl)-3-(difluoromethoxy)benzenesulfonamide; N-(6-(6-chloro-5-(3-(difluoromethoxy)phenylsulfonamido)pyridin-3-yl)-3-(pyridin-3-yl)imidazo[1,2-b]pyridazin-2-yl)acetamide; N-(5-(2-amino-3-(pyridin-3-yl)imidazo[1,2-b]pyridazin-6-yl)-2-chloropyridin-3-yl)-3-(difluoromethoxy)benzenesulfonamide; or N-(5-(2-amino-3-(1,2,3,6-tetrahydropyridin-4-yl)imidazo[1,2-b]pyridazin-6-yl)-2-chloropyridin-3-yl)-3-(difluoromethoxy)benzenesulfonamide; U.S. Pat. No. 7,767,699 to Nuss et al.; U.S. Pat. No. 7,667,039 to Garcia-Echeverria et al. (1,3-dihydro-imidazo [4,5-c]quinolin-2-ones, including 2-methyl-2-[4-(3-methyl-2-oxo-8-quinolin-3-yl,2,3-dihydro-imidazo[4,5-c]quinolin-1-yl)-phenyl]-propionitrile and 4-toluenesulfonic acid 2-methyl-2-[4-(3- methyl-2-oxo-8-quinolin-3-yl,2,3-dihydro-imidazo[4,5-c]quinolin-1-yl)-phenyl]-propionitrile salt); U.S. Pat. No. 7,666,091 to Zask et al. (analogs of 17-hydroxywortmannin); U.S. Pat. No. 7,598,377 to Jackson et al. ((±)-7-methyl-2-morpholin-4-yl-9-(1-phenylaminoethyl)-pyrido[1,2-a]pyrimidin-4-one, (±)-2 ({1-[7 methyl 2 (morpholin-4-yl)-4-oxo pyrido[1,2-a]pyrimidin 9-yl]ethyl}amino)benzoic acid, (±)-2-({1-[7-methyl-2-(morpholin-4-yl)-4-oxo-pyrido[1,2-a]pyrimidin-9-yl]ethyl}amino)benzonitrile, (±) methyl 2-({1-[7-methyl-2-(morpholin-4-yl)-4-oxo-pyrido[1,2-a]pyrimidin-9-yl]ethyl}amino)benzoate, and (±)-7-methyl-2-(morpholin-4-yl)-9-(1-{[2-(2H-tetrazol-5-yl)phenyl]amino}ethyl)-pyrido[,2-a]pyrimid-4-one); U.S. Pat. No. 7,592,342 to Feng et al. (quinoxaline derivatives, including N-{2-(methyloxy)-5-[3-(1-methyl-1H-pyrazol-4-yl)-6-quinoxalinyl]-3-pyridinyl}benzenesulfonamide, 2,4-difluoro-N-{5-[3-(1-methyl-1H-pyrazol-4-yl)-6-quinoxalinyl]-3-pyridinyl}benzenesulfonamide, 2,6-difluoro-N-{5-[3-(1-methyl-1H-pyrazol-4-yl)-6-quinoxalinyl]-3-pyridinyl}ben- zenesulfonamide, 2,4-difluoro-N-{2-(methyloxy)-5-[3-(1-methyl-1H-pyrazol-4-yl)-6-quinoxalinyl]-3-pyridinyl}benze- nesulfonamide, and N-[5-(3-{1-[2-(dimethylamino)ethyl]-1H-pyrazol-4-yl}-6-quinoxalinyl)-3-pyridinyl]benzenesulfonamide); U.S. Pat. No. 7,585,868 to Knight et al. (substituted pyrazolo[3,4-d]pyrimidines); U.S. Pat. No. 7,511,041 to Shimada et al. (fused azole-pyrimidine derivatives); U.S. Pat. No. 7,423,148 to Nuss et al.; U.S. Pat. No. 7,173,029 to Hayakawa et al. (fused heteroaryl derivatives); U.S. Pat. No. 7,039,915 to Hayakawa et al. (fused heteroaryl derivatives); U.S. Pat. No. 6,949,535 to Sadhu et al.; U.S. Pat. No. 6,908,932 to Melese et al.; U.S. Pat. No. 6,894,055 to Melese et al. (thieno-2',3': 5,6-pyrimido[3,4-a]-1,2,4-triazole derivatives); U.S. Pat. No. 6,838,457 to Hayakawa et al. (fused heteroaryl derivatives); U.S. Pat. No. 6,800,620 to Sadhu et al.; U.S. Pat. No. 6,770,641 to Hayakawa et al. (fused heteroaryl derivatives); U.S. Pat. No. 6,667,300 to Sadhu et al.; U.S. Pat. No. 6,653,320 to Hayakawa et al. (imidazopyridine derivatives, including 3-(6-bromo-2-methylimidazo[1,2-a]pyridin-3-yl)-1H-pyrazol-1-yl 2-methyl-5-nitrophenyl sulfone; 3-(6-bromoimidazo[1,2-a]pyridin-3-yl)-1H-pyrazol-1-yl 2-methyl-5-nitrophenyl sulfone; and 6-chloro-3-[2-(2-methyl-5-nitrobenzenesulfonyl)thiazol-4-yl]imidazo[1,2-a] pyridine); U.S. Pat. No. 6,608,056 to Hayakawa et al. (fused heteroaryl derivatives, including 3-(4-morpholinopyrido[4,3-d]pyrimidin-2-y])phenol, 3-(4-morpholinopyrido[3,2-d]pyrimidin-2-yl)phenol, and 3-(4-morpholinopyrido[3,4-d]pyrimidin-2-y])phenol); U.S. Pat. No. 6,608,053 to Hayakawa et al. (fused heteroaryl derivatives, including 6-amino-3'-(4-morpholinopyrido[3',2':4,5]furo[3,2-d]pyrimidin-2-yl)nicotinanilide; 4-(4-morpholinopyrido[3',2':4,5]furo[3,2-d]pyrimidin-2-yl)aniline; 3-(4-morpholinopyrido[3',2':4,5]furo[3,2-d]pyrimidin-2-yl)phenol; 4-morpholino-2-[3-(2-piperazin-1-ylethoxy)phenyl]pyrido[3',2':4,5]furo[3,2-d]pyrimidine; and 3'-(4-morpholinopyrido[3',2':4,5]furo[3,2-d]pyrimidin-2-yl)acrylanilide); U.S. Pat. No. 6,518,277 to Sadhu et al.; U.S. Pat. No. 6,403,588 to Hayakawa et al. (imidazolidine derivatives, including 2'-[(6-bromoimidazo[1,2-a]pyridin-3-yl)methylidene]-1',2-dimethyl-5-nitrobenzenesulfonohydrazide; 2'-[(6-bromoimidazo[1,2-a]pyridin-3-yl)methyl idene]-2-ethyl-1'-methyl-5-nitrobenzenesulfonohydrazide; 3-({2-[(6-bromoimidazo[1,2-a]pyridin-3-yl)methylidene]-1-methylhydrazino}sulfonyl)-4-methylbenzonitrile; 2'-[(6-fluoroimidazo[1,2-a]pyridin-3-yl)methylidene]-1',2-dimethyl-5-nitrobenzenesulfonohydrazide; 2-amino-2'-[(6-chloroimidazo[1,2-a]pyridin-3-yl)methylidene]-1'-methyl-5-nitrobenzenesulfonohydrazide; 2'-[(6-chloroimidazo[1,2-a]pyridin-3-yl)methylidene]-1'-methyl-5-nitro-2-(2,2,2-trifluoroethoxy)benzenesulfonohydrazide; 6-bromo-3-{[(2-methyl-5-nitrobenzenesulfonyl)(2-morpholinoethyl)hydrazono]methyl}imidazo[1,2-a]pyridine; 6-chloro-3-{[(methyl)(2-methyl-5-nitrobenzenesulfonyl)hydrazono]methyl}imidazo[1,2-a]pyridine; 3-{[(methyl)(2-methyl-5-nitrobenzenesulfonyl)hydrazono]methyl}imidazo[1,2-a]pyridine-6 carbonitrile; 5-cyano-2'-[(6-fluoroimidazo[1,2-a]pyridin-3-yl)methylidene]-1',2-dimethylbenzene- sulfonohydrazide; 5-cyano-2'-[(6-cyanoimidazo[1,2-a]pyridin-3-yl)methylidene]-1',2-dimethylbenzenesulfonohydrazide; 1',2-dimethyl-2'-[(6-methylimidazo[1,2-a]pyridin-3-yl)methylidene]-5-nitrobenzenesulfonohydrazide; 2'-[(6-chloroimidazo[1,2-a]pyridin-3-yl)methylidene]-2-(1H-imidazol-1-yl)-1'-methyl-5-nitrobenzenesulfonohydrazide; 2'-[(6-chloroimidazo[1,2-a]pyridin-3-yl)methylidene]-2-dimethylamino-1'-methyl-5-nitrobenzenesulfonohydrazide); United States Patent Application Publication No. 2013/0165483 by Chau et al.; United States Patent Application Publication No. 2013/0165472 by Chau et al.; United States Patent Application Publication No. 2013/0165464 by Chau et al.; United States Patent Application Publication No. 2013/0165436 by Caravatti et al. (dihydro-benzo-oxazine and dihydro-pyrido-oxazine derivatives); United States Patent Application Publication No. 2013/0157977 by Rivero et al. (benzimidazole boronic acid derivatives); United States Patent Application Publication No. 2013/0157976 by Claus et al. (pyrido[2,3-b]pyrazine derivatives); United States Patent Application Publication No. 2013/0131080 by Hamblin et al.; United States Patent Application Publication No. 2013/0116266 by Fowler et al. (quinazolinones); United States Patent Application Publication No. 2013/0109688 by Shuttleworth et al. (naphthridines); United States Patent Application Publication No. 2013/0109670 by Venkatesan et al. (triazines); United States Patent Application Publication No. 2013/0090355 by Cai et al. (compounds with zinc binding moieties); United States Patent Application Publication No. 2013/0059835 by Li et al. (heterocyclylamine derivatives, including 4-{3-[1-(4-amino-3-methyl-1H-pyrazolo[3,4-d]pyrimidin-1-yl)ethyl]-5-chloro-2-ethoxy-6-methylphenyl}pyrrolidin-2-one; 4-[1-(4-amino-3-methyl-1H-pyrazolo[3,4-d]pyrimidin-1-yl)ethyl]-6-chloro-3-ethoxy-2-(2-oxo-1,3-oxazolidin-5-yl)benzonitrile; 6-{3-[1-(4-amino-3-methyl-1H-pyrazolo[3,4-d]pyrimidin-1-yl)ethyl]-5-chloro-2-methoxy-6-methylphenyl}morpholin-3-one; 5-{3-[1-(4-amino-3-methyl-1H-pyrazolo[3,4-d]pyrimidin-1-yl)ethyl]-5-chloro-2-methoxy-6-methylphenyl}-1,3-oxazolidin-2-one; 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one; 4-[1-(4-amino-3-methyl-1H-pyrazolo[3,4-d]pyrimidin-1-yl)ethyl]-6-chloro-3-ethoxy-2-(5-oxopyrrolidin-3-yl)benzonitrile; 4-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one; and 5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one); United States Patent Application Publication No. 2013/0029984 by Castro et al.; United States Patent Application Publication No. 2013/0029982 by Castro et al.; United States Patent Application Publication No. 2013/0018057 by Burli et al. (quinoline and quinoxaline derivatives, substituted by a fused bicyclic pyridine or pyrimidine moiety attached via an alkylene chain optionally linked to a heteroatom); United States Patent Application Publication No. 2013/0012517 by Allen et al. (quinoline and quinoxaline derivatives, substituted by an optionally substituted bicyclic heteroaryl moiety consisting of two fused six-membered aromatic rings attached via an alkylene chain optionally linked to a heteroatom); United States Patent Application Publication No. 2012/0263712 by Fairhurst et al. (pyrrolidine-1,2-dicarboxamide derivatives); United States Patent Application Publication No. 2012/0252802 by Brown et al. ((alpha-substituted aralkylamino or heteroarylalkylamino) pyrimidinyl and 1,3,5-triazinyl benzimidazoles); United States Patent Application Publication No. 2012/0245171 by Baldwin et al. (benzpyrazole derivatives); United States Patent Application Publication No. 2012/0245144 by Heffron et al. (benzoxazepine compounds); United States Patent Application Publication No. 2012/0238587 by Lee et al. (pyridopyrimidines); United States Patent Application Publication No. 2012/0238571 by Baldwin et al. (indazole derivatives); United States Patent Application Publication No. 2012/0232072 by Kumar et al. (imidazopyridine derivatives); United States Patent Application Publication No. 2012/0225859 by Burger et al. (pyrimidine derivatives); United States Patent Application Publication No. 2012/0220587 by Emde et al. (pyridinylimidazolone derivatives); United States Patent Application Publication No. 2012/0202805 by Liang (6-(2-difluoromethyl-benzoimidazol-1-yl)-9-[2-(4-methanesulfonyl-piperazin-1-yl)-ethyl]-2-morpholin-4-yl-9H-purine; 2-{6-[2-(difluoromethyl)benzimidazol-1-yl]-2-morpholin-4-ylpurin-9-yl}ethan-1-ol; 6-(2-difluoromethyl-benzoimidazol-1-yl)-2-morpholin-4-yl-9-(tetrahydro-pyran-4-yl)-9H-purine; 9-sec-butyl-6-(2-difluoromethyl-benzoimidazol-1-yl)-2-morpholin-4-yl-9H-purine; 2-[6-(2-difluoromethyl-benzoimidazol-1-yl)-2-morpholin-4-yl-purin-9-yl]-propan-1-ol; 2-[6-(2-difluoromethyl-benzoimidazol-1-yl)-2-(8-oxa-3-aza-bicyclo[3.2.1]oct-3-yl)-purin-9-yl]-propan-1-ol; 4-{1-(2H-3,4,5,6-tetrahydropyran-4-yl)-4-[2-(difluoromethyl)benzimidazolyl]pyrazolo[5,4-d]pyrimidin-6-yl}morpholine; and 4-{4-[2-(difluoromethyl)benzimidazolyl]-6-morpholin-4-ylpyrazolo[5,4-d]pyrimidinyl}piperidyl 4-methylpiperazinyl ketone); United States Patent Application Publication No. 2012/0190738 by Bandyopadhyay et al. (4-allyl-benzene-1,2-diol (hydroxychavicol); 4,5-diallylbenzene-1,2-diol; 3,4-diallylbenzene-1,2-diol; 4-allyl-5-propylbenzene-1,2-diol; 4,5-diallyl-1,2-phenylene diacetate; 4-allyl-1,2-phenylene diacetate; 4-allyl-5-propyl-1,2-phenylene diacetate; (E)-ethyl 4-(3,4-dihydroxyphenyl)-4-methylpent-2-enoate; (E)-4-(5-ethoxy-2-methyl-5-oxopent-3-en-2-yl)-1,2-phenylene diacetate; 3-allyl-benzene-1,2-diol; and 3-allyl-1,2-phenylene diacetate); United States Patent Application Publication No. 2012/0178736 by Castanedo et al. (bicyclic pyrimidines); United States Patent Application Publication No. 2012/0171199 by Dotson et al. (tricyclic compounds); United States Patent Application Publication No. 2012/0165321 by Adams et al. (quinoline derivatives); United States Patent Application Publication No. 2012/0157430 by Li et al. (N-(1-(substituted-phenyl)ethyl)-9H-purin-6-amine derivatives); United States Patent Application Publication No. 2012/0129848 by Shuttleworth et al. (benzo [E] [1,3] oxazin-4-one derivatives); United States Patent Application Publication No. 2012/0108627 by Kumar et al. (imidazo [4,5-c]quinoline derivatives); United States Patent Application Publication No. 2012/0077815 by Allen et al. (amino-substituted fused pyridine and pyrazine derivatives); United States Patent Application Publication No. 2012/0071475 by Taniyama et al. (urea derivatives); United States Patent Application Publication No. 2012/0053167 by Allen et al. (substituted [1,3,5]triazin-2-yl derivatives); United States Patent Application Publication No. 2012/0053166 by Hamblin et al. (4-oxadiazol-2-yl-indazoles); United States Patent Application Publication No. 2012/0035208 by Dotson et al. (pyrazolopyridines); and United States Patent Application Publication No. 2012/0015964 by Fowler et al. (3-(2,6-difluoro-phenyl)-2-[1-(9H-purin-6-ylamino)-ethyl]-3H-quinazolin-4-one).

Directed antibody conjugates, also known as antibody-drug conjugates, are well known in the art. Examples include brentuximab vedotin and trastuzumab emtansine. Directed antibody conjugates (antibody-drug conjugates or ADC) are described in U.S. Pat. No. 8,470,329 to Oflazoglu et al., U.S. Pat. No. 8,466,260 to Elkins et al., U.S. Pat. No. 8,461,117 to Sufi et al., U.S. Pat. No. 8,436,147 to Dennis et al., U.S. Pat. No. 8,420,086 to Govindan et al., and U.S. Pat. No. 8,394,967 to Ebens, Jr. et al., all of which are incorporated by this reference. In a directed antibody conjugate (antibody-drug conjugate), typically, the therapeutic agent and antibody are covalently joined by a cleavable linker. A number of cleavable linkers are known in the art.

Adjuvants are well known in the art and are described above.

Kinase inhibitors are well known in the art. Kinase inhibitors block the phosphorylation of one or more serine, threonine, tyrosine, or in some cases, histidine residues in proteins that are the substrates of kinases. Many kinases regulate cell proliferation and represent targets for chemotherapy. Kinase inhibitors can be either small molecules, monoclonal antibodies, or RNA aptamers. Small-molecule kinase inhibitors include, but are not limited to, afatinib, axitinib, bosutinib, crizotinib, dasatinib, erlotinib, fostamatinib, gefitinib, ibrutinib, lapatinib, lenvatinib, mubritinib, nilotinib, pazopanib, ruxolitinib, sorafenib, sunitinib, SU6656 ((3Z)—N,N-dimethyl-2-oxo-3-(4,5,6,7-tetrahydro-1H-indol-2-ylmethylidene)-2,3-dihydro-1H-indole-5-sulfonamide)), tofacitinib, vandetanib, and vemurafenib. Monoclonal antibody kinase inhibitors include, but are not limited to, bevacizumab, cetuximab, panitumumab, ranibizumab, and trastuzumab. RNA aptamer kinase inhibitors include, but are not limited to, pegaptinib.

Another aspect of the present invention is a composition to improve the efficacy and/or reduce the side effects of suboptimally administered drug therapy comprising an alternative selected from the group consisting of:

(i) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;

(ii) a composition comprising:
  (a) a therapeutically effective quantity of a therapeutic agent, a modified therapeutic agent or a derivative, analog, or prodrug of a therapeutic agent or modified therapeutic agent; and
  (b) at least one additional therapeutic agent, therapeutic agent subject to chemosensitization, therapeutic agent subject to chemopotentiation, diluent, excipient, solvent system, drug delivery system, or agent for enhancing the activity or efficacy of the therapeutic agent, the modified therapeutic agent or the derivative, analog, or prodrug of a therapeutic agent or modified therapeutic agent of (a), wherein the composition possesses increased therapeutic efficacy or reduced side effects as compared with an unmodified therapeutic agent;

(iii) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;

(iv) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and (v) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent;

(vi) a therapeutically effective quantity of a therapeutic agent or a derivative, analog, or prodrug of a therapeutic agent, wherein the therapeutic agent or the derivative, analog, or prodrug of the therapeutic agent is optimized for increasing an immunologic response; and (vii) a composition comprising:
(a) a therapeutically effective quantity of a therapeutic agent or a derivative, analog, or prodrug of a therapeutic agent; and
(b) at least one immune adjuvant for stimulating an immune response;

wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent; wherein the unmodified therapeutic agent is bisantrene or a derivative or analog of bisantrene, the modified therapeutic agent is a modification of bisantrene or a derivative or analog of bisantrene, and the derivative, analog, or prodrug is a derivative, analog, or prodrug of bisantrene or of a derivative or analog of bisantrene.

In one alternative, the composition comprises a composition to improve the efficacy and/or reduce the side effects of suboptimally administered drug therapy comprising a therapeutically effective quantity of a therapeutic agent or modified therapeutic agent or a derivative, analog, or prodrug of a therapeutic agent or modified therapeutic agent, wherein the therapeutic agent or modified therapeutic agent or the derivative, analog or prodrug of the therapeutic agent or modified therapeutic agent possesses increased therapeutic efficacy or reduced side effects, wherein the composition:

(a) includes at least one bulk drug product improvement;
(b) is produced in a specified dosage form;
(c) includes a drug conjugate form;
(d) includes a compound analog; or
(e) includes a prodrug;

wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent; wherein the unmodified therapeutic agent is bisantrene or a derivative or analog of bisantrene, the modified therapeutic agent is a modification of bisantrene or a derivative or analog of bisantrene, and the derivative, analog, or prodrug is a derivative, analog, or prodrug of bisantrene or of a derivative or analog of bisantrene.

In another alternative, the composition comprises a composition to improve the efficacy and/or reduce the side effects of suboptimally administered drug therapy comprising a therapeutically effective quantity of a therapeutic agent or modified therapeutic agent, wherein the composition:

(a) is formulated for use in a program of dose modification;
(b) is formulated for use in a program of alteration or modification of route of administration;
(c) is formulated for use in a program of alteration or modification of schedule of administration;
(d) is formulated for use in a program of selecting appropriate indications for use;
(e) is formulated for use in a program of selecting appropriate disease stages for use;
(f) is formulated for use in a program of selecting appropriate additional indications for use;
(g) is formulated for use in a program of selecting appropriate patients for use of the composition;
(h) is formulated for use in a program of selecting appropriate patient or disease phenotypes for use of the composition;
(i) is formulated for use in a program of selecting appropriate patient or disease genotypes for use of the composition;
(j) is formulated for use in a program of pre/post-treatment preparation;
(k) is formulated for use in a program of alternative medicine/therapeutic support;
(l) is formulated for use in a program of biotherapeutic enhancement;
(m) is formulated for use in a program of biotherapeutic resistance modulation;
(n) is formulated for use in a program of radiation therapy enhancement;
(o) is formulated for use to employ novel mechanisms of action in its therapeutic activity;
(p) is formulated for use in a program of selective target cell population therapeutics;
(q) is formulated for use in a program of modulating DNA methylation;
(r) is formulated for use in a program of inhibiting telomerase or inducing telomere dysfunction;
(s) is formulated for use in a program of inhibiting survivin;
(t) further comprises a diluent;
(u) further comprises a solvent system;
(v) further comprises an excipient;
(w) is incorporated into a dosage kit and packaging;
(x) comprises a drug delivery system; or
(y) is formulated to optimize an immunological response;

wherein the therapeutic agent or the modified therapeutic agent in the composition possesses increased therapeutic efficacy or reduced side effects as compared with the therapeutic agent or unmodified therapeutic agent as administered individually and not in the composition, wherein the unmodified therapeutic agent is bisantrene or a derivative or analog of bisantrene, and the modified therapeutic agent is a modification of bisantrene or a derivative or analog of bisantrene.

In yet another alternative, the composition comprises a composition to improve the efficacy and/or reduce the side effects of suboptimally administered drug therapy comprising a therapeutically effective quantity of a therapeutic agent or modified therapeutic agent, wherein the composition further comprises:

(a) an additional therapeutic agent;
(b) a therapeutic agent subject to chemosensitization;
(c) a therapeutic agent subject to chemopotentiation;
(d) a second therapeutic agent that forms a multiple drug system;
(e) an agent that enhances the activity of the therapeutic agent or modified therapeutic agent;
(f) at least one survivin modulator or inhibitor;
(g) at least one multidrug resistance reversal agent;
(h) at least one directed antibody conjugate;
(i) at least one adjuvant; or
(j) an additional therapeutic agent suitable for use with the therapeutic agent in a combinatorial regime, wherein the quantities of the therapeutic agent and the additional therapeutic agent are chosen to provide effective activity of both the therapeutic agent and the additional therapeutic agent; wherein the therapeutic agent or the modified therapeutic agent in the composition possesses increased therapeutic efficacy or reduced side effects as compared with the therapeutic agent or unmodified therapeutic agent as administered individually and not in the composition, wherein the unmodified therapeutic agent is bisantrene or a derivative or analog of bisantrene, and the modified therapeutic agent is a modification of bisantrene or a derivative or analog of bisantrene.

When the composition is formulated for use in a program of dose modification or in a program of alteration or modification of schedule of administration, one of ordinary skill in the art would be able to formulate the composition according to the intended dosage or range of dosages or the intended schedule of administration, taking into account such variables as the status or progress of the disease or condition for which the composition is to be used, other therapeutic agents the sex, age, and weight of the patient, and pharmacokinetic considerations such as liver or kidney function. When the composition is formulated for use in a program of alteration or modification of route of administration, one of ordinary skill in the art would be able to formulate the composition according to the physical properties of the composition, such as physical form, flowability, and compatibility of the composition with the intended route of administration. When the composition is formulated for use in a program of selecting appropriate indications for use, appropriate disease stages for use, appropriate additional indications for use, or appropriate patients for use of the composition, one of ordinary skill in the art would be able to formulate the composition according to the intended requirements, including the targets of therapeutic treatment, the possibility of side effects or toxicity, and the severity or stage of disease intended to be treated. When the composition is formulated for use in a program of selecting appropriate patient or disease phenotypes or genotypes for use of the composition, one of ordinary skill in the art would be able to formulate the composition according to the intended requirements, including the particular phenotypes or genotypes involved, the possibility of somatic mutation in target cells, and the potential for the occurrence of drug resistance in target cells. When the composition is formulated for use in a program of pre/post-treatment preparation or a program of alternative medicine/therapeutic support, one of ordinary skill in the art would be able to formulate the composition according to the intended requirements, including compatibility and lack of deleterious interactions with additional agents being administered or methods being used. When the composition is formulated for use in a program of biotherapeutic enhancement or biotherapeutic resistance modulation, one of ordinary skill in the art would be able to formulate the composition according to the intended requirements, including the compatibility with the biotherapeutic agents and the lack of side effects or deleterious interactions. When the composition is formulated for use in a program of radiation therapy enhancement, one of ordinary skill in the art would be able to formulate the composition according to the intended requirements, including compatibility with the means of administering radiation and the lack of side effects or deleterious interactions. When the composition is formulated for use to employ novel mechanisms of action in its therapeutic activity, one of ordinary skill in the art would be able to formulate the composition according to the intended requirements, including the scope of the novel mechanisms of action, the targets of the novel mechanism of action, including cells, tissues, or receptors, and the lack of side effects or deleterious interactions. When the composition is formulated for use in a program of selective target cell population therapeutics, one of ordinary skill in the art would be able to formulate the composition according to the intended requirements, including the properties of the intended target cells, the ability of the therapeutic agent or agents in the composition to be delivered to the target cells in active form, and the lack of side effects or deleterious interactions. When the composition is formulated for use in a program of modulating DNA methylation, one of ordinary skill in the art would be able to formulate the composition according to the intended requirements, including the dosage required to modulate DNA methylation, the ability of the therapeutic agent or agents to be delivered to cells requiring modulation of DNA methylation, and the lack of side effects or deleterious interactions. When the composition is formulated for use in a program of inhibiting telomerase or inducing telomere dysfunction, one of ordinary skill in the art would be able to formulate the composition according to the intended requirements, including the dosage required to inhibit telomerase or induce telomere dysfunction, the ability of the therapeutic agent or agents to be delivered to cells requiring inhibition of telomerase or inducing telomere dysfunction, and the lack of side effects or deleterious interactions. When the composition is formulated for use in a program of inhibiting surviving, one of ordinary skill in the art would be able to formulate the composition according to the intended requirements, including the dosage required to inhibit survivin, the ability of the therapeutic agent or agents to be delivered to cells requiring inhibition of survivin, and the lack of side effects or deleterious interactions. Other factors or variables involved in the preparation of pharmaceutical compositions according to the present invention would be taken into account by one of ordinary skill in the art.

Manufacturing methods for compositions are well known in the art. Such manufacturing methods are disclosed in United States Patent Application Publication No. 2014/0179749 by Lorenz et al.; United States Patent Application Publication No. 2014/0179712 by Baker et al. (tablets); U.S. Pat. No. 7,094,545 to Lomryd et al. (solid dosage forms); United States Patent Application Publication No. 2014/0179768 by Bettencourt (emulsions); PCT Patent Application Publication No. WO 2007/136219 by Kim et al. (docetaxel for injection); United States Patent Application Publication No. 2014/0179738 by Singh et al. (formulations for oral administration); United States Patent Application Publication No. 2014/0179732 by Jaroskova et al.; United States Patent Application Publication No. 2014/0179624 by Gutterman et al.; PCT Patent Application Publication No. WO 2008/107452 by German et al.; United States Patent Application Publication No. 2014/0186447 by Desai (nanoparticulate compositions); United States Patent Application Publication No. 2014/0186430 by Gould-Fougerite et al. (cochleate pharmaceutical compositions); United States Patent Application Publication No. 2014/0186361 by Manning et al. (stable aqueous formulations); United States Patent Application Publication No. 2014/0186339 by Sabbadini et al. (formulations for ocular administration); and United States Patent Application Publication No. 2014/0183786 by Bittorf et al. (spray-drying methods for preparation of pharmaceutical compositions), all of which are incorporated herein by this reference.

Methods of manufacture of pharmaceutical compositions is further described in S. K. Niazi, "Handbook of Pharmaceutical Manufacturing Formulations" ($2^{nd}$ ed., Informa Healthcare USA, New York, N.Y., 2009). Volume 1 is Compressed Solid Products; Volume 2 is Uncompressed Solid Products; Volume 3 is Liquid Products; Volume 4 is Semisolid Products; Volume 5 is Over-the-Counter Products; and Volume 6 is Sterile Products.

Co-precipitation for use in the preparation of pharmaceutical compositions is disclosed in U.S. Pat. No. 5,985,326 to Butler, incorporated herein by this reference.

Use of alternative salts in the preparation of pharmaceutical compositions is disclosed in S. L. Morissette, "High-Throughput Crystallization: Polymorphs, Salts, Co-Crystals and Solvates of Pharmaceutical Solids," *Adv. Drug Deliv. Rev.* 56: 275-300 (2004), incorporated herein by this reference. When a therapeutically active component present in a composition or used in a method according to the present invention exists in crystalline form, one or more polymorphic forms of the crystalline component may exist or be prepared. These polymorphic forms may differ in bioavailability or other properties and may result from, for example, differences in the solvent used for crystallization, the temperature or rate of cooling, or other factors in the crystallization process.

Typically, the composition possesses increased efficacy or reduced side effects for cancer therapy. Typically, the unmodified therapeutic agent is bisantrene or a derivative or analog or bisantrene, as described above, the modified therapeutic agent is a modification of bisantrene or a derivative or analog of bisantrene, and the derivative, analog, or prodrug is a derivative, analog, or prodrug of bisantrene or of a derivative or analog of bisantrene.

In one alternative, the composition comprises a drug combination comprising:
 (i) bisantrene or a derivative or analog of bisantrene; and
 (ii) an additional therapeutic agent selected from the group consisting of:
  (a) fraudulent nucleosides;
  (b) fraudulent nucleotides;
  (c) thymidylate synthetase inhibitors;
  (d) signal transduction inhibitors;
  (e) cisplatin or platinum analogs;
  (f) alkylating agents;
  (g) anti-tubulin agents;
  (h) antimetabolites;
  (i) berberine;
  (j) apigenin;
  (k) colchicine or an analog thereof;
  (l) genistein;
  (m) etoposide;
  (n) cytarabine;
  (o) camptothecins;
  (p) vinca alkaloids;
  (q) topoisomerase inhibitors;
  (r) 5-fluorouracil;
  (s) curcumin;
  (t) rosmarinic acid;
  (u) mitoguazone;
  (v) meisoindigo;
  (w) imatinib;
  (x) dasatinib;
  (y) nilotinib;
  (z) epigenetic modulators;
  (aa) transcription factor inhibitors;
  (ab) taxol;
  (ac) homoharringtonine;
  (ad) pyridoxal;
  (ae) spirogermanium;
  (af) caffeine;
  (ag) nicotinamide;
  (ah) methylglyoxalbisguanylhydrazone;
  (ai) PARP inhibitors;
  (aj) EGFR inhibitors;
  (ak) Bruton's tyrosine kinase (BTK) inhibitors;
  (al) bis-[thio-hydrazide] amides;
  (am) succinimide or maleimide derivatives as inhibitors of topoisomerase II;
  (an) histone deacetylase (HDAC) inhibitors;
  (ao) immunostimulants;
  (ap) telomerase inhibitors;
  (aq) inhibitors of the expression or activity of Her2;
  (at) inhibitors of the expression of activity of estrogen receptors;
  (as) inhibitors of the expression or activity of an antigen associated with a specific tumor targets;
  (at) G-quadruplex ligands;
  (au) polycyclic lysophosphatidic receptor antagonists;
  (av) anti-CTGF agents;
  (aw) myeloid differentiation inducing agents;
  (ax) covalent diabodies binding to a tumor-associated antigen;
  (ay) bispecific antibodies that have a cell-penetrating determinant and an intracellular target-binding determinant;
  (az) multidomain molecules that comprise a cell binding ligand that binds to cells in the tumor stroma such as endothelial cells, fibroblasts, or immune cells and an oligonucleotide that inhibits the nonsense-mediated decay pathway;
  (ba) tumor-specific antibodies binding to a portion of the CD44 protein or a binding protein derived from the light-chain or heavy-chain complementary-determining regions of such antibodies;
  (bb) inhibitors of CXCR4;
  (bc) pyruvate dehydrogenase kinase (PDK1) inhibitors;
  (bd) epherin receptor targeting agents;
  (be) binding proteins for Axl;
  (bf) Wnt pathway inhibitors together with MAPK pathway inhibitors;
  (bg) TEC family kinase inhibitors;
  (bh) substituted macrocyclic compounds with proteasome activity;
  (bi) peptide-based PACE4 inhibitors;

(bj) azaindole derivatives as JAK3 inhibitors;
(bk) inhibitors of Myc;
(bl) inhibitors of furin and other pro-protein convertases;
(bm) GPBP-1 inhibitors, optionally together with a p21 inhibitor; and
(bn) $PGE_2$ inhibitors.

Typically, in this composition, the bisantrene or a derivative or analog of bisantrene is bisantrene.

In another alternative, the composition comprises:
(i) bisantrene or a derivative or analog of bisantrene and
(ii) a therapeutic agent subject to chemosensitization selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) colchicine or an analog of colchicine;
(m) genistein;
(n) etoposide;
(o) cytarabine;
(p) camptothecin;
(q) vinca alkaloids;
(r) 5-fluorouracil;
(s) curcumin;
(t) rosmarinic acid; and
(u) mitoguazone.

Typically, in this composition, the bisantrene or a derivative or analog of bisantrene is bisantrene.

In another alternative, the composition comprises:
(i) bisantrene or a derivative or analog of bisantrene and
(ii) a therapeutic agent subject to chemopotentiation selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) colchicine or an analog of colchicine;
(m) genistein;
(n) etoposide;
(o) cytarabine;
(p) camptothecin;
(q) vinca alkaloids;
(r) 5-fluorouracil;
(s) curcumin;
(t) rosmarinic acid; and
(u) mitoguazone.

Typically, in this composition, the bisantrene or a derivative or analog of bisantrene is bisantrene.

In yet another alternative, the therapeutic agent is bisantrene or a derivative or analog of bisantrene, and the amonafide or derivative or analog of bisantrene is subjected to a bulk drug product improvement, wherein the bulk drug product improvement is selected from the group consisting of:
(a) preparation as a free base form;
(b) salt formation;
(c) preparation as a homogeneous crystalline structure;
(d) amorphous structure;
(e) preparation as a pure isomer;
(f) increased purity;
(g) preparation with lower residual solvent content; and
(h) preparation with lower residual heavy metal content.

Typically, in this composition, the bisantrene or a derivative or analog of bisantrene is bisantrene.

In still another alternative, the therapeutic agent is bisantrene or a derivative or analog of bisantrene and the composition comprises a diluent, wherein the diluent is selected from the group consisting of:
(a) an emulsion;
(b) dimethylsulfoxide (DMSO);
(c) N-methylformamide (NMF);
(d) dimethylformamide (DMF)
(e) dimethylacetamide (DMA);
(f) ethanol;
(g) benzyl alcohol;
(h) dextrose-containing water for injection;
(i) Cremophor;
(j) cyclodextrins; and
(k) PEG.

Typically, in this composition, the bisantrene or a derivative or analog of bisantrene is bisantrene.

In still another alternative, the therapeutic agent is bisantrene or a derivative or analog of bisantrene and the composition comprises a solvent system, wherein the solvent system is selected from the group consisting of:
(a) an emulsion;
(b) DMSO;
(c) NMF;
(d) DMF;
(e) DMA;
(f) ethanol;
(g) benzyl alcohol;
(h) dextrose-containing water for injection;
(i) Cremophor;
(j) PEG; and
(k) salt systems.

Typically, in this composition, the bisantrene or a derivative or analog of bisantrene is bisantrene.

In yet another alternative, the therapeutic agent is bisantrene or a derivative or analog of bisantrene and the composition comprises an excipient, wherein the excipient is selected from the group consisting of:
(a) mannitol;
(b) albumin;
(c) EDTA;
(d) sodium bisulfite;
(e) benzyl alcohol;
(f) carbonate buffers;
(g) phosphate buffers;
(h) PEG;
(i) vitamin A;
(j) vitamin D;
(k) vitamin E;
(l) esterase inhibitors;
(m) cytochrome P450 inhibitors;
(n) multi-drug resistance (MDR) inhibitors;
(o) organic resins; and
(p) detergents.

Typically, in this composition, the bisantrene or derivative or analog of bisantrene is bisantrene.

In yet another alternative, the therapeutic agent is bisantrene or a derivative or analog of bisantrene, and the bisantrene or derivative or analog of bisantrene is incorporated into a dosage form selected from the group consisting of:
 (a) tablets;
 (b) capsules;
 (c) topical gels;
 (d) topical creams;
 (e) patches;
 (f) suppositories;
 (g) lyophilized dosage fills;
 (h) immediate-release formulations;
 (i) slow-release formulations;
 (j) controlled-release formulations;
 (k) liquid in capsules; and
 (l) liposomal formulations.

Typically, in this composition, the bisantrene or derivative or analog of bisantrene is bisantrene.

In yet another alternative, the therapeutic agent is bisantrene or a derivative or analog of bisantrene and the bisantrene or derivative or analog of bisantrene is incorporated into a dosage kit and packaging selected from the group consisting of amber vials to protect from light and stoppers with specialized coatings to improve shelf-life stability.

Typically, in this composition, the bisantrene or derivative or analog of bisantrene is bisantrene.

In still another alternative, the therapeutic agent is bisantrene or a derivative or analog of bisantrene and the composition comprises a drug delivery system selected from the group consisting of:
 (a) oral dosage forms;
 (b) nanocrystals;
 (c) nanoparticles;
 (d) cosolvents;
 (e) slurries;
 (f) syrups;
 (g) bioerodible polymers;
 (h) liposomes;
 (i) slow-release injectable gels;
 (j) microspheres;
 (k) amphiphilic block copolymer systems;
 (l) emulsion vehicles comprising an emulsion of α-tocopherol stabilized by biocompatible surfactants;
 (m) biodegradable polymer compositions containing phosphorus and desaminotyrosyl L-tyrosine linkages in the polymer backbone;
 (n) substantially anhydrous injectable semi-solid compositions comprising a water immiscible fatty acid matrix and a cytostatic agent;
 (o) lipophilic vehicles;
 (p) pH-dependent carriers that include a compound that includes at least one ionizable group;
 (q) pH-dependent carriers that include a monocarboxylic acid having at least 8 carbons and less than about 10% by weight of zwitterionic phospholipids; and
 (r) liposomes comprising the bisantrene or the derivative or analog thereof followed, in use of the composition, by administration of a lipid nanoparticle comprising a triggering agent.

Typically, in this composition, the bisantrene or derivative or analog of bisantrene is bisantrene.

In yet another alternative, the therapeutic agent is bisantrene or a derivative or analog of bisantrene and the bisantrene or derivative or analog of bisantrene is present in the composition in a drug conjugate form selected from the group consisting of:
 (a) a polymer system;
 (b) polylactides;
 (c) polyglycolides;
 (d) amino acids;
 (e) peptides;
 (f) multivalent linkers;
 (g) conjugates to fatty acids;
 (h) conjugates to fatty alcohols;
 (i) conjugates to elastin-like peptide;
 (j) conjugates with polyclonal or monoclonal antibodies, proteins, or peptides;
 (k) conjugates with cell-binding agents through a charged or pro-charged cross-linker;
 (l) conjugates to antibodies targeted to tumor markers;
 (m) biodegradable polymer-bioactive moiety conjugates;
 (n) conjugates with 2-nitroimidazole compounds with a secondary basic nitrogen atom and a linker;
 (o) conjugates with ladder frame polyether compounds, including those derived from brevenal, brevisin, tamulamide, brevetoxins, hemibrevetoxins, gambierols, and gambieric acids;
 (p) conjugates to antibodies having one or more non-natural amino acid residues at specific positions in the heavy or light chains;
 (q) conjugates to a sialoadhesin binding moiety;
 (r) pheophorbide-α conjugates;
 (s) conjugates to multi-component nanochains;
 (t) conjugates to activatable antibodies that include a masking moiety, a cleavable moiety, and an antibody binding specifically to interleukin-6;
 (u) conjugates including hydrophilic linkers;
 (v) conjugates to antibodies specific for p97;
 (w) conjugates including a modified amino acid incorporating an azido group;
 (x) conjugates to albumin; and
 (y) conjugates to folate.

Typically, in this composition, the bisantrene or derivative or analog of bisantrene is bisantrene.

In yet another alternative, the therapeutic agent is a modified bisantrene or a modified derivative or analog of bisantrene and the modification is selected from the group consisting of:
 (a) alteration of side chains to increase or decrease lipophilicity;
 (b) addition of an additional chemical functionality to alter a property selected from the group consisting of reactivity, electron affinity, and binding capacity; and
 (c) alteration of salt form.

Typically, in this composition, the modified bisantrene or modified derivative or analog of bisantrene is a modified bisantrene.

In still another alternative of a composition according to the present invention, the therapeutic agent is bisantrene or a derivative or analog of bisantrene and the bisantrene or derivative or analog of bisantrene is in the form of a prodrug system, wherein the prodrug system is selected from the group consisting of:
 (a) enzyme sensitive esters;
 (b) dimers;
 (c) Schiff bases;
 (d) pyridoxal complexes;
 (e) caffeine complexes;
 (f) plasmin-activated prodrugs; and (g) drug targeting complexes comprising a targeting carrier molecule that is selectively distributed to a specific cell type or tissue containing the specific cell type; a linker which is acted upon by a molecule that is present at an effective concentration in the environs of the specific cell type; and a therapeutically active agent to be delivered to the specific cell type; and (h) a prodrug molecule comprising a conjugate of bisantrene or a derivative or analog of bisantrene, a protease-specific cleavable peptide, and optionally, a targeting peptide, with the prodrug molecule being substantially inactive prior to degradation of the protease-specific cleavable peptide by a proteolytic enzyme within or in close proximity to the cancer cell.

Typically, in this composition, the bisantrene or derivative or analog of bisantrene is bisantrene.

In yet another alternative, the therapeutic agent is bisantrene or a derivative or analog of bisantrene and the composition further comprises at least one additional therapeutic agent to form a multiple drug system, wherein the at least one additional therapeutic agent is selected from the group consisting of:

(a) inhibitors of multi-drug resistance;
(b) specific drug resistance inhibitors;
(c) specific inhibitors of selective enzymes;
(d) signal transduction inhibitors;
(e) meisoindigo;
(f) imatinib;
(g) hydroxyurea;
(h) dasatinib;
(i) capecitabine;
(j) nilotinib;
(k) repair inhibition agents;
(l) topoisomerase inhibitors with non-overlapping side effects;
(m) PARP inhibitors;
(n) a taxane;
(o) cytarabine;
(p) microtubule inhibitors;
(q) EGFR inhibitors; and
(r) HDAC inhibitors.

Typically, in this composition, the bisantrene or derivative or analog of bisantrene is bisantrene.

In still another alternative, the therapeutic agent is bisantrene or a derivative or analog of bisantrene and the composition further comprises at least one agent for enhancing the activity or efficacy of the bisantrene or derivative or analog of bisantrene, wherein the at least one agent for enhancing the activity or efficacy of the bisantrene or derivative or analog of bisantrene is selected from the group consisting of:

(i) nicotinamide;
(ii) caffeine;
(iii) tetandrine; and
(iv) berberine.

Typically, in this composition, the bisantrene or derivative or analog of bisantrene is bisantrene.

In still another alternative, the composition comprises a therapeutically effective quantity of bisantrene or a derivative, analog, or prodrug of bisantrene, wherein the bisantrene or the derivative, analog, or prodrug of bisantrene is optimized for increasing an immunologic response.

Typically, in this composition, the bisantrene or derivative or analog of bisantrene is bisantrene.

In still another alternative, the composition comprises:
(a) a therapeutically effective quantity of bisantrene or a derivative, analog, or prodrug of bisantrene; and
(b) at least one immune adjuvant for stimulating an immune response.

Suitable immune adjuvants are as described above.

Typically, in this composition, the bisantrene or derivative or analog of bisantrene is bisantrene.

In still another alternative, the composition comprises:
(a) a therapeutically effective quantity of bisantrene or a derivative or analog of bisantrene; and
(b) a multidrug resistance reversal agent.

Typically, the multidrug resistance reversal agent is verapamil.

Typically, in this composition, the bisantrene or derivative or analog of bisantrene is bisantrene.

In yet another alternative, the composition comprises:
(a) a therapeutically effective quantity of bisantrene or a derivative or analog of bisantrene; and
(b) an additional therapeutic agent suitable for use with the bisantrene or the derivative or analog of bisantrene in a combinatorial regime;
wherein the quantities of the bisantrene or the derivative or analog of bisantrene and the additional therapeutic agent are chosen to provide effective activity of both the bisantrene or the derivative or analog of bisantrene and the additional therapeutic agent.

Typically, in this composition, the bisantrene or derivative or analog of bisantrene is bisantrene.

Typically, in this composition, the additional therapeutic agent is selected from the group consisting of:

(a) an agent inducing immunoactivity, wherein the bisantrene or derivative or analog thereof acts as a chemotherapeutic agent;
(b) an agent inducing macrophage activation, wherein the bisantrene or derivative or analog thereof acts as a chemotherapeutic agent;
(c) a cytokine, wherein the bisantrene or derivative or analog thereof acts as a chemotherapeutic agent;
(d) an agent inhibiting telomerase, wherein the bisantrene or derivative or analog thereof acts as a chemotherapeutic agent;
(e) an agent inhibiting surviving, wherein the bisantrene or derivative or analog thereof acts as a chemotherapeutic agent;
(f) an agent inducing demethylation, wherein the bisantrene or derivative or analog thereof acts as a chemotherapeutic agent;
(g) an adjuvant, wherein the bisantrene or derivative or analog thereof acts as a chemotherapeutic agent;
(h) an antibody, wherein the bisantrene or derivative or analog thereof acts as a chemotherapeutic agent;
(i) an innate or adaptive immune stimulator, wherein the bisantrene or derivative or analog thereof acts as a chemotherapeutic agent;
(j) a checkpoint inhibitor, wherein the bisantrene or derivative or analog thereof acts as a chemotherapeutic agent;
(k) an mTOR antagonist, wherein the bisantrene or derivative or analog thereof acts as a chemotherapeutic agent;
(l) an Akt inhibitor, wherein the bisantrene or derivative or analog thereof acts as a chemotherapeutic agent;
(m) a notch inhibitor, wherein the bisantrene or derivative or analog thereof acts as a chemotherapeutic agent;
(n) an HSP inhibitor, wherein the bisantrene or derivative or analog thereof acts as a chemotherapeutic agent;
(o) a phosphatidylinositide 3-kinase inhibitor, wherein the bisantrene or derivative or analog thereof acts as a chemotherapeutic agent;

(p) a kinase inhibitor, wherein the bisantrene or derivative or analog thereof acts as a chemotherapeutic agent;

(q) an agent inducing telomerase inhibition, wherein the bisantrene or derivative or analog thereof acts as an agent inducing macrophage activation;

(r) a cytokine, wherein the bisantrene or derivative or analog thereof acts as an agent inducing macrophage activation;

(s) an agent inhibiting survivin, wherein the bisantrene or derivative or analog thereof acts as an agent inducing macrophage activation;

(t) an agent inducing demethylation, wherein the bisantrene or derivative or analog thereof acts as an agent inducing macrophage activation;

(u) an adjuvant, wherein the bisantrene or derivative or analog thereof acts as an agent inducing macrophage activation;

(v) an antibody, wherein the bisantrene or derivative or analog thereof acts as an agent inducing macrophage activation;

(w) an innate or adaptive immune stimulator, wherein the bisantrene or derivative or analog thereof acts as an agent inducing macrophage activation;

(x) a checkpoint inhibitor, wherein the bisantrene or derivative or analog thereof acts as an agent inducing macrophage activation;

(y) an mTOR antagonist, wherein the bisantrene or derivative or analog thereof acts as an agent inducing macrophage activation;

(z) an Akt inhibitor, wherein the bisantrene or derivative or analog thereof acts as an agent inducing macrophage activation;

(aa) a notch inhibitor, wherein the bisantrene or derivative or analog thereof acts as an agent inducing macrophage activation;

(ab) an HSP inhibitor; wherein the bisantrene or derivative or analog thereof acts as an agent inducing macrophage activation;

(ac) a phosphatidylinositide 3-kinase inhibitor, wherein the bisantrene or derivative or analog thereof acts as an agent inducing macrophage activation; and (ad) a kinase inhibitor, wherein the bisantrene or derivative or analog thereof acts as an agent inducing macrophage activation.

Typically, the composition is optimized to treat a hyperproliferative disease. Typically, the hyperproliferative disease is cancer. Typically, the cancer is a form of cancer selected from the group consisting of breast cancer, (including refractory and triple-negative breast cancer), acute myelocytic leukemia, acute leukemias of childhood, lymphoma and ovarian cancer.

In one alternative, the composition is formulated for intravenous, intraperitoneal, or subcutaneous administration. The composition can alternatively be formulated for other routes of administration, such as, but not limited to, central or peripheral venous administration, intravesicular administration (particularly for use in treating bladder cancer), intrathecal administration, and intra-arterial administration.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992), all incorporated herein by this reference.

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent that is included in a unit dose of a pharmaceutical composition according to the present invention will vary depending upon factors such as the particular compound, disease condition and its severity, the identity (e.g., weight or surface area) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., *Remington: The Science and Practice of Pharmacy*, Mack Publishing Co., $20^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Methods and compositions according to the present invention are suitable for use in treating diseases and conditions of both humans and non-humans, including treatment of socially and economically important animals such as dogs, cats, cows, horses, sheep, pigs, goats, and other species. Unless specified, methods and compositions according to the present invention are not limited to treatment of humans.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg. In particular, for bisantrene or derivatives or analogs thereof, suitable doses typically are from about 50 mg/m$^2$ to about 500 mg/m$^2$ or from about 0.1 mg/kg to about 10 mg/kg. These doses are particularly suitable for bisantrene.

Plasma concentrations in the subjects may be between about 1 µM to about 1000 µM. In some embodiments, the plasma concentration may be between about 200 µM to about 800 µM. In other embodiments, the concentration is about 300 µM to about 600 µM. In still other embodiments the plasma concentration may be between about 400 to about 800 µM. In one typical alternative, dosages of bisantrene or a derivative or analog of bisantrene are from about 1 mg/m$^2$/day to about 600 mg/m$^2$/day. Administration of prodrugs is typically dosed at weight levels which are chemically equivalent to the weight levels of the fully active form.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-α-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, peripheral intravenous, central intravenous, parenteral, intraperitoneal, transcutaneous, subcutaneous, intramuscular, intra-urethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing adverse events or one or more of the improving symptoms associated with the disease, disorder, or condition being treated, or by observing one or more of the improving clinical parameters associated with the disease, disorder, or condition being treated, as described above.

Sustained-release formulations or controlled-release formulations are well-known in the art.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

Advantages of the Invention

The present invention provides more effective and efficient methods of using therapeutic drugs that have previously been evaluated for treatment of a number of diseases and conditions, especially hyperproliferative disorders, but whose evaluations resulted in a premature conclusion of lack of sufficient efficacy or of occurrence of side effects sufficient to prevent the use of the therapeutic drug. Such more effective and efficient methods of therapeutic drugs will improve efficacy, prevent or reduce the occurrence of significant side effects, and will identify categories of patients and situations in which such drugs can be effectively employed. Such drugs particularly include bisantrene and derivatives and analogs thereof.

Methods according to the present invention possess industrial applicability for the preparation of a medicament for the treatment of a number of diseases and conditions, especially hyperproliferative diseases, and compositions according to the present invention possess industrial applicability as pharmaceutical compositions.

Where methods are referred to, the methods of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method to improve the efficacy and/or reduce the side effects of suboptimally administered drug therapy comprising the steps of:
   (a) identifying at least one factor or parameter associated with the efficacy and/or occurrence of side effects of the drug therapy; and
   (b) modifying the factor or parameter to improve the efficacy and/or reduce the side effects of the drug therapy;
wherein the drug therapy comprises administration of bisantrene or a derivative or analog thereof;
and wherein the factor or parameter is use of bisantrene or a derivative or analog thereof in a combinatorial regime;
wherein, when the use in a combinatorial regime is a use of a derivative or analog of bisantrene, the derivative or analog of bisantrene is selected from the group consisting of:
   (a) the analog of Formula (II)

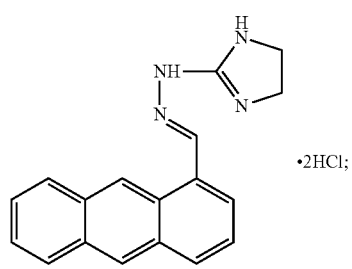

(b) the bisantrene analog of Formula (III)

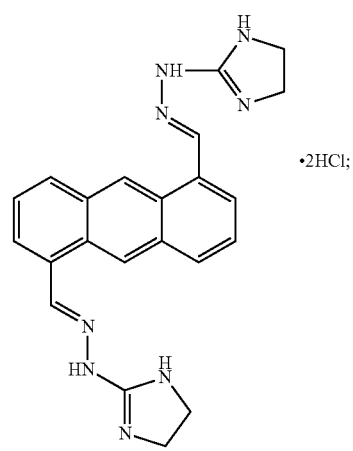

(c) the bisantrene analog of Formula (IV)

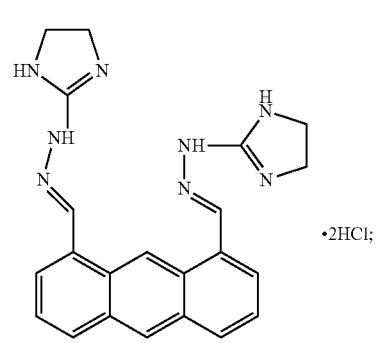

(d) the bisantrene analog of Formula (V)

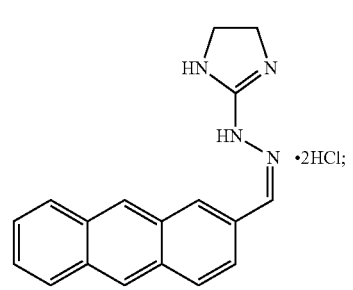

(e) the bisantrene analog of Formula (VI)

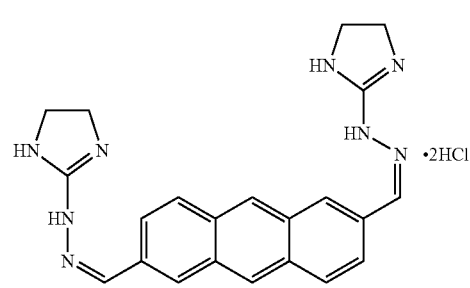

(f) the bisantrene analog of Formula (VII)

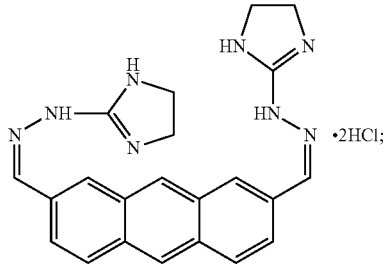

(g) the bisantrene analog of Formula (VIII)

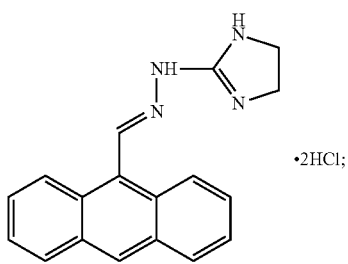

(h) the bisantrene analog anthracen-9-ylmethylene-[2-methoxyethoxymethylsulfanyl]-5-pyridin-3-yl-[1,2,4]triazol-4-amine;

(i) the bisantrene analog of Formula (X)

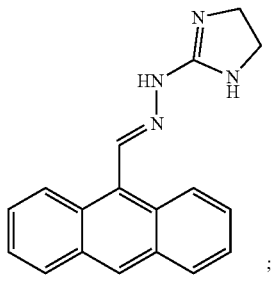

(j) the bisantrene analog of Formula (XI)

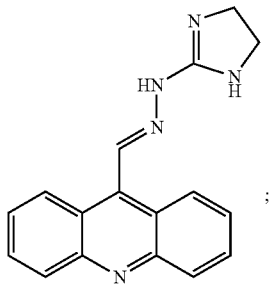

(k) the bisantrene analog of Formula (XII)

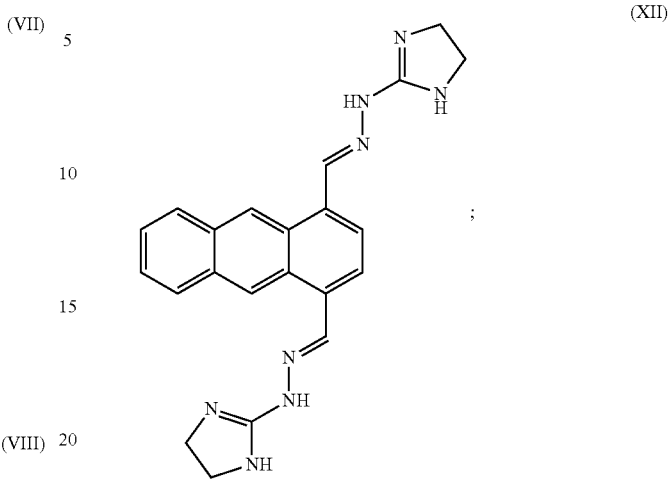

(l) the bisantrene analog of Formula (XIII)

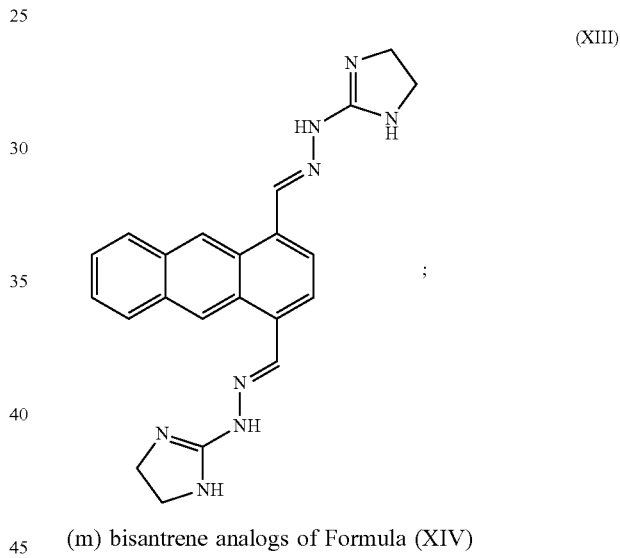

(m) bisantrene analogs of Formula (XIV)

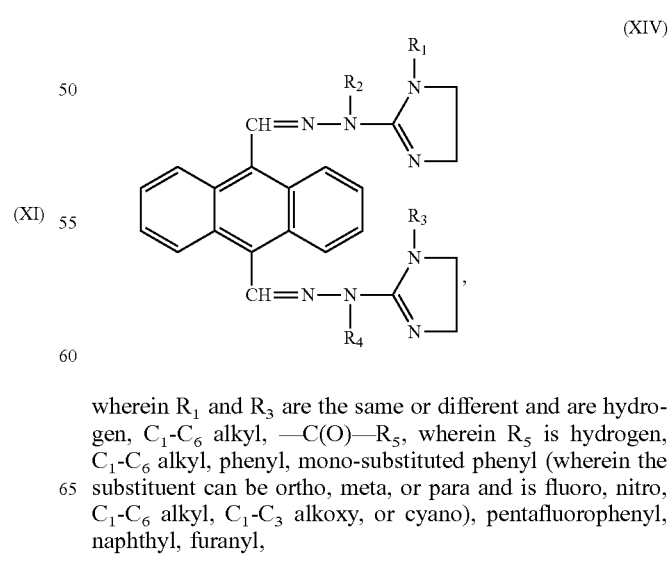

wherein $R_1$ and $R_3$ are the same or different and are hydrogen, $C_1$-$C_6$ alkyl, —C(O)—$R_5$, wherein $R_5$ is hydrogen, $C_1$-$C_6$ alkyl, phenyl, mono-substituted phenyl (wherein the substituent can be ortho, meta, or para and is fluoro, nitro, $C_1$-$C_6$ alkyl, $C_1$-$C_3$ alkoxy, or cyano), pentafluorophenyl, naphthyl, furanyl,

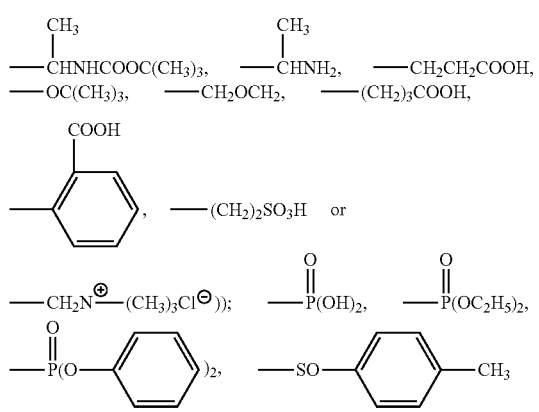

or
—SO₃H; wherein only one of $R_1$ and $R_3$ may be hydrogen or $C_1$-$C_6$ alkyl; $R_2$ and $R_4$ are the same or different and are: hydrogen, $C_1$-$C_4$ alkyl or —C(O)—$R_6$, where $R_6$ is hydrogen, $C_1$-$C_6$ alkyl, phenyl, mono-substituted phenyl (wherein the substituent may be in the ortho, meta, or para position and is fluoro, nitro, $C_1$-$C_6$ alkyl, $C_1$-$C_3$ alkoxy, or cyano), pentafluorophenyl, naphthyl, furanyl, or —CH₂OCH₃, and wherein the compounds can have the schematic structure $B(Q)_n$, wherein B is the residue formed by removal of a hydrogen atom from one or more basic nitrogen atoms of an amine, amidine, guanidine, isourea, isothiourea, or biguanide-containing pharmaceutically active compound, and Q is hydrogen or A, wherein A is

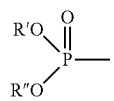

such that R' and R" are the same or different and are R (where R is $C_1$-$C_6$ alkyl, aryl, aralkyl, heteroalkyl, NC—CH₂CH₂—,

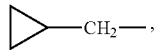

Cl₃C—CH₂—, or $R_7$OCH₂CH₂—, where $R_7$ is hydrogen or $C_1$-$C_6$ alkyl, hydrogen, or a pharmaceutically acceptable cation or R' and R" are linked to form a —CH₂CH₂— group or a

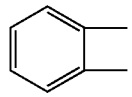

group, and n is an integer representing the number of primary or secondary basic nitrogen atoms in the compound such that at least one Q is A;
  (n) the bisantrene analog 9,10-bis[(2-hydroxyethyl)iminomethyl]anthracene;
  (o) the bisantrene analog 9,10-bis{[2-(-2-hydroxyethylamino)ethyl]iminomethyl anthracene;
  (p) the bisantrene analog 9,10-bis{[2-(-2-hydroxyethylamino)ethyl]iminomethyl anthracene;
  (q) the bisantrene analog 9,10-bis{[2-(morpholin-4-yl)ethyl]iminomethyl anthracene;
  (r) the bisantrene analog 9,10-bis[(2-hydroxyethyl)aminomethyl]anthracene;
  (s) the bisantrene analog 9,10-bis{[2-(2-hydroxyethylamino)ethyl]aminomethyl}anthracene tetrahydrochloride;
  (t) the bisantrene analog 9,10-bis{[2-(piperazin-1-yl)ethyl]aminomethyl}anthracene hexahydrochloride;
  (u) the bisantrene analog 9,10-bis{[2-(morpholin-4-yl)ethyl]aminomethyl}anthracene tetrahydrochloride;
  (v) N,N'-bis[2-(dimethylamino)ethyl]-9,10-anthracene-bis(methylamine);
  (w) N,N'-bis(1-ethyl-3-piperidinyl)-9,10-anthracene-bis(methylamine); and
  (x) salt forms of the compounds of (a)-(w); and
wherein the drug therapy is administered to treat a form of cancer selected from the group consisting of refractory breast cancer, triple-negative breast cancer, acute myelocytic leukemia, and acute leukemias of childhood.

2. The method of claim 1 wherein the drug therapy comprises administration of bisantrene.

3. The method of claim 1 wherein the drug therapy comprises administration of a derivative or analog of bisantrene selected from the group consisting of:
  (a) the analog of Formula (II)

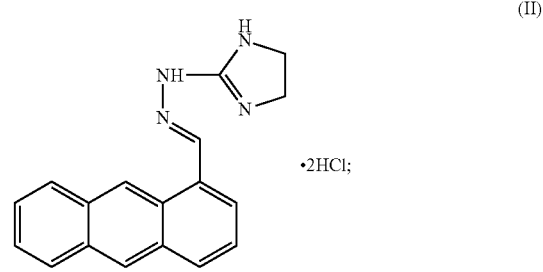 [SMILES: C(=N\NC1=NCCN1)/c1cccc2cc3ccccc3cc12]

(II)

(b) the bisantrene analog of Formula (III)

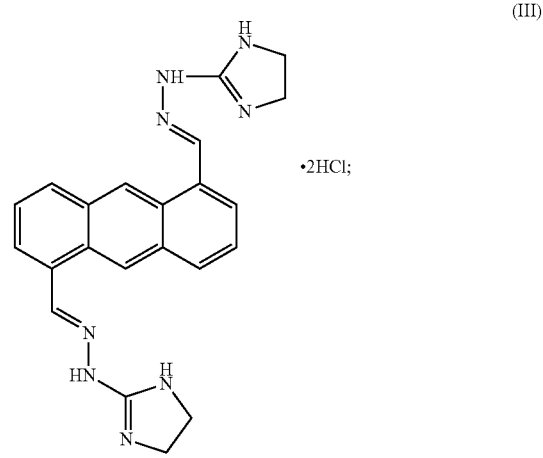 [SMILES: C(=N\NC1=NCCN1)/c1cccc2cc3c(/C=N/NC4=NCCN4)cccc3cc12]

(III)

(c) the bisantrene analog of Formula (IV)

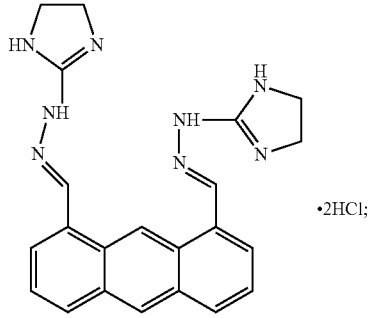

(d) the bisantrene analog of Formula (V)

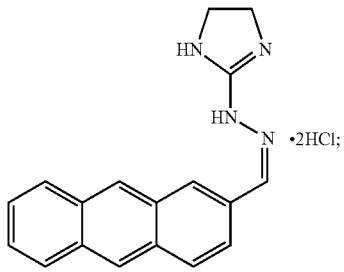

(e) the bisantrene analog of Formula (VI)

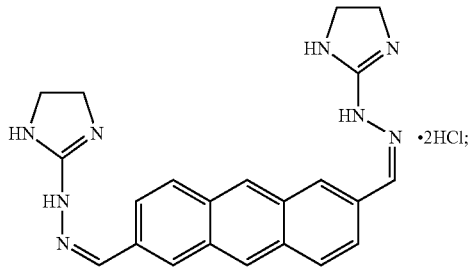

(f) the bisantrene analog of Formula (VII)

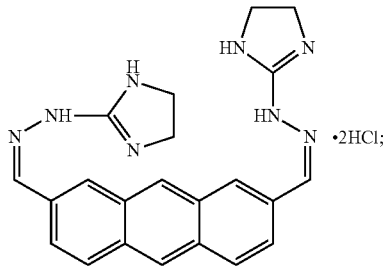

(g) the bisantrene analog of Formula (VIII)

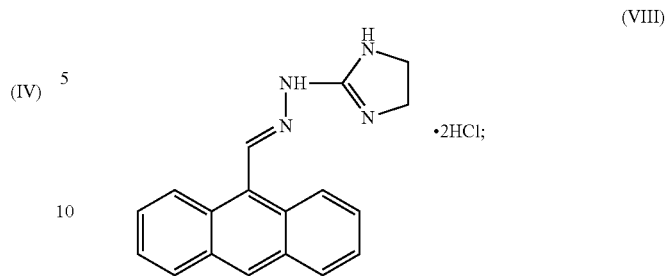

(h) the bisantrene analog anthracen-9-ylmethylene-[2-methoxyethoxymethylsulfanyl]-5-pyridin-3-yl-[1,2,4]triazol-4-amine;

(i) the bisantrene analog of Formula (X)

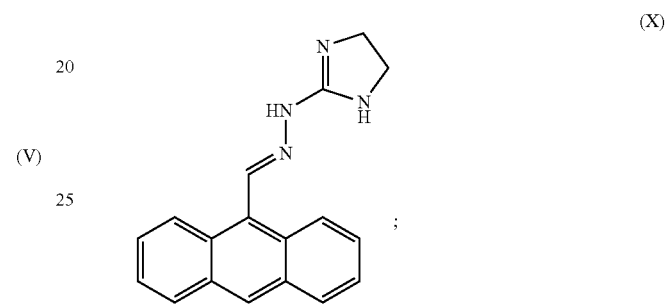

(j) the bisantrene analog of Formula (XI)

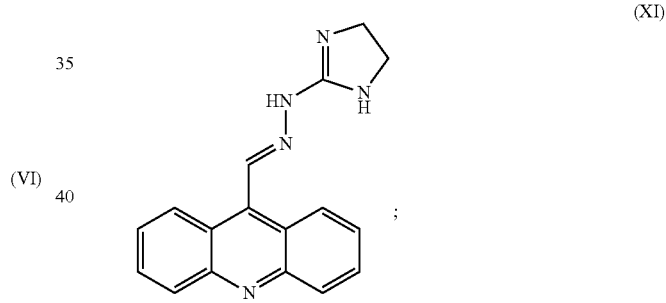

(k) the bisantrene analog of Formula (XII)

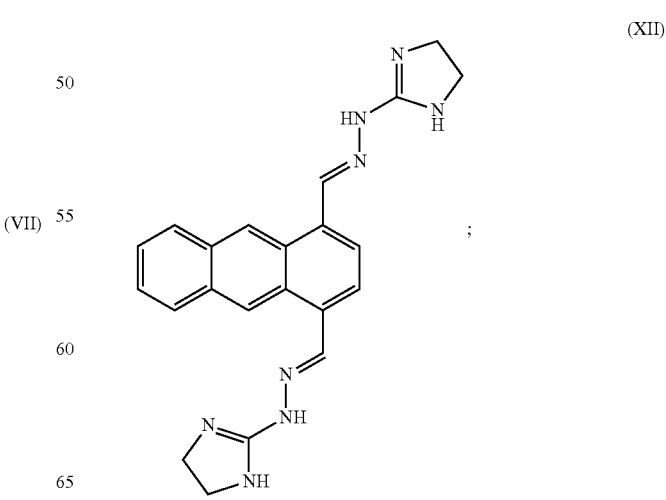

(l) the bisantrene analog of Formula (XIII)

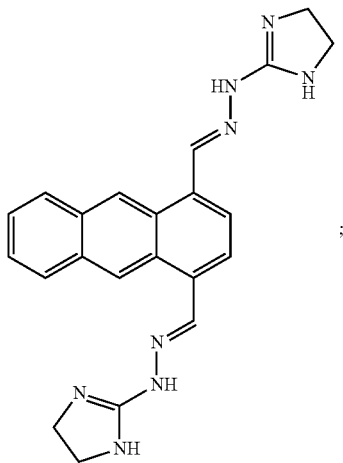

(XIII)

;

(m) bisantrene analogs of Formula (XIV)

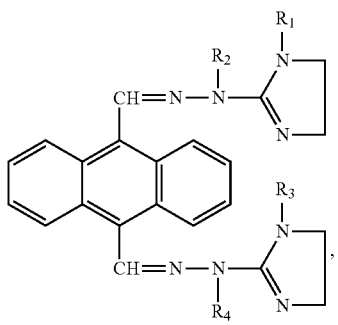

(XIV)

wherein $R_1$ and $R_3$ are the same or different and are hydrogen, $C_1$-$C_6$ alkyl, —C(O)—$R_5$, wherein $R_5$ is hydrogen, $C_1$-$C_6$ alkyl, phenyl, mono-substituted phenyl (wherein the substituent can be ortho, meta, or para and is fluoro, nitro, $C_1$-$C_6$ alkyl, $C_1$-$C_3$ alkoxy, or cyano), pentafluorophenyl, naphthyl, furanyl,

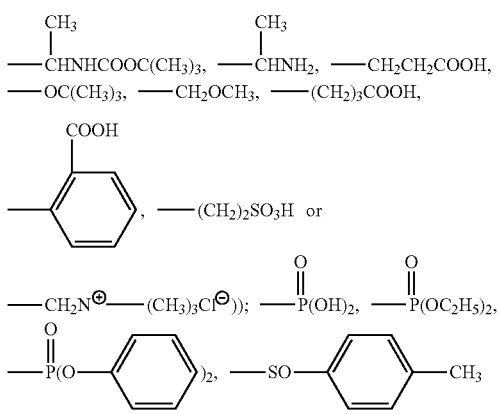

or
—SO$_3$H; wherein only one of $R_1$ and $R_3$ may be hydrogen or $C_1$-$C_6$ alkyl; $R_2$ and $R_4$ are the same or different and are:
hydrogen, $C_1$-$C_4$ alkyl or —C(O)—$R_6$, where $R_6$ is hydrogen, $C_1$-$C_6$ alkyl, phenyl, mono-substituted phenyl (wherein the substituent may be in the ortho, meta, or para position and is fluoro, nitro, $C_1$-$C_6$ alkyl, $C_1$-$C_3$ alkoxy, or cyano), pentafluorophenyl, naphthyl, furanyl, or —CH$_2$OCH$_3$, wherein the compounds can have the schematic structure $B(Q)_n$, wherein B is the residue formed by removal of a hydrogen atom from one or more basic nitrogen atoms of an amine, amidine, guanidine, isourea, isothiourea, or biguanide-containing pharmaceutically active compound, and Q is hydrogen or A, wherein A is

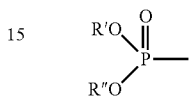

such that R' and R" are the same or different and are R (where R is $C_1$-$C_6$ alkyl, aryl, aralkyl, heteroalkyl, NC—CH$_2$CH$_2$—,

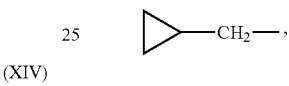

Cl$_3$C—CH$_2$—, or $R_7$OCH$_2$CH$_2$—, where $R_7$ is hydrogen or $C_1$-$C_6$ alkyl, hydrogen, or a pharmaceutically acceptable cation or R' and R" are linked to form a —CH$_2$CH$_2$— group or a

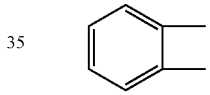

group, and n is an integer representing the number of primary or secondary basic nitrogen atoms in the compound such that at least one Q is A;
(n) the bisantrene analog 9,10-bis[(2-hydroxyethyl)iminomethyl]anthracene;
(o) the bisantrene analog 9,10-bis{[2-(-2-hydroxyethylamino)ethyl]iminomethyl}anthracene;
(p) the bisantrene analog 9,10-bis{[2-(-2-hydroxyethylamino)ethyl]iminomethyl}anthracene;
(q) the bisantrene analog 9,10-bis{[2-(morpholin-4-yl)ethyl]iminomethyl}anthracene;
(r) the bisantrene analog 9,10-bis[(2-hydroxyethyl)aminomethyl]anthracene;
(s) the bisantrene analog 9,10-bis{[2-(2-hydroxyethylamino)ethyl]aminomethyl}anthracene tetrahydrochloride;
(t) the bisantrene analog 9,10-bis{[2-(piperazin-1-yl)ethyl]aminomethyl}anthracene hexahydrochloride;
(u) the bisantrene analog 9,10-bis{[2-(morpholin-4-yl)ethyl]aminomethyl}anthracene tetrahydrochloride;
(v) N,N'-bis[2-(dimethylamino)ethyl]-9,10-anthracene-bis(methylamine);
(w) N,N'-bis(1-ethyl-3-piperidinyl)-9,10-anthracene-bis(methylamine); and
(x) salt forms of the compounds of (a)-(w).
4. The method of claim 1 wherein the drug therapy is administered to treat cancer, and wherein the cancer is a form of cancer selected from the group consisting of refractory breast cancer and triple-negative breast cancer.

5. The method of claim 1 wherein the combinatorial regime is a combinatorial regime selected from the group consisting of:
(a) use in a combinatorial regime as a chemotherapeutic agent with at least one agent inducing immunoactivity;
(b) use in a combinatorial regime as a chemotherapeutic agent with at least one agent inducing macrophage activation;
(c) use in a combinatorial regime as a chemotherapeutic agent with at least one cytokine;
(d) use in a combinatorial regime as a chemotherapeutic agent with at least one agent inhibiting telomerase;
(e) use in a combinatorial regime as a chemotherapeutic agent with at least one agent inhibiting survivin;
(f) use in a combinatorial regime as a chemotherapeutic agent with at least one agent inducing demethylation;
(g) use in a combinatorial regime as a chemotherapeutic agent with at least one adjuvant;
(h) use in a combinatorial regime as a chemotherapeutic agent with at least one antibody;
(i) use in a combinatorial regime as a chemotherapeutic agent with at least one innate or adaptive immune stimulator;
(j) use in a combinatorial regime as a chemotherapeutic agent with at least one checkpoint inhibitor;
(k) use in a combinatorial regime as a chemotherapeutic agent with at least one mTOR antagonist;
(l) use in a combinatorial regime as a chemotherapeutic agent with at least one Akt inhibitor;
(m) use in a combinatorial regime as a chemotherapeutic agent with at least one notch inhibitor;
(n) use in a combinatorial regime as a chemotherapeutic agent with at least one HSP inhibitor;
(o) use in a combinatorial regime as a chemotherapeutic agent with at least one phosphatidylinositide 3-kinase inhibitor;
(p) use in a combinatorial regime as a chemotherapeutic agent with at least one kinase inhibitor;
(q) use in a combinatorial regime as a chemotherapeutic agent with cytarabine;
(r) use in a combinatorial regime as a chemotherapeutic agent with taxane;
(s) use in a combinatorial regime as a chemotherapeutic agent with taxol;
(t) use in a combinatorial regime as an agent inducing macrophage activation with at least one agent inducing telomerase inhibition;
(u) use in a combinatorial regime as an agent inducing macrophage activation with at least one cytokine;
(v) use in a combinatorial regime as an agent inducing macrophage activation with at least one agent inhibiting survivin;
(w) use in a combinatorial regime as an agent inducing macrophage activation with at least one agent inducing demethylation;
(x) use in a combinatorial regime as an agent inducing macrophage activation with at least one adjuvant;
(y) use in a combinatorial regime as an agent inducing macrophage activation with at least one antibody;
(z) use in a combinatorial regime as an agent inducing macrophage activation with at least one innate or adaptive immune stimulator;
(aa) use in a combinatorial regime as an agent inducing macrophage activation with at least one checkpoint inhibitor;
(ab) use in a combinatorial regime as an agent inducing macrophage activation with at least one mTOR antagonist;
(ac) use in a combinatorial regime as an agent inducing macrophage activation with at least one Akt inhibitor;
(ad) use in a combinatorial regime as an agent inducing macrophage activation with at least one notch inhibitor;
(ae) use in a combinatorial regime as an agent inducing macrophage activation with at least one HSP inhibitor;
(af) use in a combinatorial regime as an agent inducing macrophage activation with at least one phosphatidylinositide 3-kinase inhibitor;
(ag) use in a combinatorial regime as an agent inducing macrophage activation with at least one kinase inhibitor;
(ah) use in a combinatorial regime as an agent inducing macrophage activation with cytarabine;
(aj) use in a combinatorial regime as an agent inducing macrophage activation with taxane; and
(ak) use in a combinatorial regime as an agent inducing macrophage activation with taxol.

* * * * *